(12) United States Patent
Kamen et al.

(10) Patent No.: US 10,563,681 B2
(45) Date of Patent: *Feb. 18, 2020

(54) SYSTEM, METHOD, AND APPARATUS FOR CLAMPING

(71) Applicant: DEKA Products Limited Partnership, Manchester, NH (US)

(72) Inventors: Dean Kamen, Bedford, NH (US); Stephen L. Fichera, Salem, NH (US); Larry B. Gray, Merrimack, NH (US); Thomas A. Friedrich, Loudon, NH (US); Erik N. Sabin, Manchester, NH (US); Richard J. Lanigan, Concord, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 474 days.

This patent is subject to a terminal disclaimer.

(21) Appl. No.: 15/205,538

(22) Filed: Jul. 8, 2016

(65) Prior Publication Data

US 2016/0319850 A1    Nov. 3, 2016

Related U.S. Application Data

(63) Continuation of application No. 13/833,712, filed on Mar. 15, 2013, now Pat. No. 9,488,200, and a
(Continued)

(51) Int. Cl.
*F16B 2/02* (2006.01)
*A61M 5/14* (2006.01)

(52) U.S. Cl.
CPC .............. *F16B 2/02* (2013.01); *A61M 5/1415* (2013.01); *Y10T 292/1047* (2015.04); *Y10T 292/1082* (2015.04)

(58) Field of Classification Search
CPC ........ Y10T 292/1047; Y10T 292/1082; A61M 5/1415
(Continued)

(56) References Cited

U.S. PATENT DOCUMENTS 3,066,965 A    12/1962    Jeavons
4,241,906 A    12/1980    Cole
(Continued)

FOREIGN PATENT DOCUMENTS

DE    4030368 C1    9/1990
EP    966944 A2    12/1999
(Continued)

OTHER PUBLICATIONS

International Search Report & Written Opinion dated Jun. 26, 2014, received in International patent application No. PCT/US2013/077270, 17 pgs.
(Continued)

*Primary Examiner* — Monica S Carter
*Assistant Examiner* — Mahdi H Nejad
(74) *Attorney, Agent, or Firm* — James D. Wyninegar, Jr.

(57) ABSTRACT

A protective mechanism for use when gripping a medical device to a rack is provided. A related system and method are also provided. The protective mechanism includes a guide member, a connector, an actuation member configured to have a first end portion and a second end portion. The first end portion of the actuation member is pivotally coupled to the guide member. The cover member is pivotally coupled to the guide member and is configured to interact with the actuation member so as to pivot to uncover the connector when the actuation member pivots in a first direction and to pivot to cover the connector when the actuation member pivots in a second direction.

25 Claims, 65 Drawing Sheets

Related U.S. Application Data continuation-in-part of application No. 13/333,574, filed on Dec. 21, 2011, now Pat. No. 10,453,157, which is a continuation-in-part of application No. PCT/US2011/066588, filed on Dec. 21, 2011, said application No. 13/833,712 is a continuation-in-part of application No. 13/723,238, filed on Dec. 21, 2012, now Pat. No. 9,759,369, and a continuation-in-part of application No. 13/333,574, filed on Dec. 21, 2011, now Pat. No. 10,453,157, and a continuation-in-part of application No. PCT/US2011/006588, filed on Dec. 21, 2011, said application No. 13/833,712 is a continuation-in-part of application No. 13/723,235, filed on Dec. 21, 2012, now Pat. No. 9,400,873, and a continuation-in-part of application No. 13/333,574, filed on Dec. 21, 2011, now Pat. No. 10,453,157, which is a continuation-in-part of application No. PCT/US2011/066588, filed on Dec. 21, 2011, said application No. 13/833,712 is a continuation-in-part of application No. PCT/US2012/071131, filed on Dec. 21, 2012, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. 13/724,568, filed on Dec. 21, 2012, now Pat. No. 9,295,778, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. 13/725,790, filed on Dec. 21, 2012, now Pat. No. 9,677,555, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. PCT/US2012/071490, filed on Dec. 21, 2012, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. 13/723,239, filed on Dec. 21, 2012, now Pat. No. 10,108,785, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. 13/723,242, filed on Dec. 21, 2012, said application No. 13/833,712 is a continuation-in-part of application No. 13/723,244, filed on Dec. 21, 2012, now Pat. No. 9,151,646, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. PCT/US2012/071142, filed on Dec. 21, 2012, and a continuation-in-part of application No. PCT/US2011/066588, filed on Dec. 21, 2011, and a continuation-in-part of application No. 13/333,574, filed on Dec. 21, 2011, now Pat. No. 10,453,157, said application No. 13/833,712 is a continuation-in-part of application No. 13/723,251, filed on Dec. 21, 2012, now Pat. No. 9,636,455, and a continuation-in-part of application No. 13/333,574, filed on Dec. 21, 2011, now Pat. No. 10,453,157, which is a continuation-in-part of application No. PCT/US2011/066588, filed on Dec. 21, 2011, said application No. 13/833,712 is a continuation-in-part of application No. PCT/US2012/071112, filed on Dec. 21, 2012, and a continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/833,712 is a continuation-in-part of application No. 13/723,253, filed on Dec. 21, 2012, and a continuation-in-part of application No. 13/333,574, filed on Dec. 21, 2011, now Pat. No. 10,453,157, and a continuation-in-part of application No. PCT/US2011/066588, filed on Dec. 21, 2011.

(60) Provisional application No. 61/679,117, filed on Aug. 3, 2012, provisional application No. 61/651,322, filed on May 24, 2012, provisional application No. 61/578,649, filed on Dec. 21, 2011, provisional application No. 61/578,658, filed on Dec. 21, 2011, provisional application No. 61/578,674, filed on Dec. 21, 2011.

(58) Field of Classification Search
USPC .......................................................... 292/216
See application file for complete search history.

(56) References Cited

U.S. PATENT DOCUMENTS

| | | | |
|---|---|---|---|
| D288,405 S | 2/1987 | Klapperich | |
| D289,395 S | 4/1987 | Bowers | |
| D295,825 S | 5/1988 | Persson | |
| 4,978,153 A * | 12/1990 | Hirsch | B04B 7/06 292/201 |
| 5,044,678 A * | 9/1991 | Detweiler | E05B 47/026 292/144 |
| 5,052,730 A | 10/1991 | Frank | |
| D342,005 S | 12/1993 | Forsberg | |
| D344,529 S | 2/1994 | Gowdy | |
| 5,332,184 A | 7/1994 | Davis | |
| 5,413,391 A | 5/1995 | Clavin et al. | |
| 5,722,704 A | 3/1998 | Chaput | |
| 5,820,175 A | 10/1998 | Clavin | |
| 5,833,191 A | 11/1998 | Gennep | |
| 5,884,958 A * | 3/1999 | Oddenino | B60K 15/04 296/97.22 |
| D415,410 S | 10/1999 | An | |
| 5,983,474 A | 11/1999 | Koppe | |
| 6,012,712 A | 1/2000 | Bernstein | |
| 6,017,026 A | 1/2000 | Durfee | |
| D425,017 S | 5/2000 | Leung | |
| D437,547 S | 2/2001 | Moubayed | |
| 6,244,580 B1 | 6/2001 | Durfee, Jr. | |
| 6,253,634 B1 | 7/2001 | Nakagome | |
| 6,464,184 B1 | 10/2002 | Lytle | |
| 6,572,390 B2 | 6/2003 | Ladin | |
| D491,523 S | 6/2004 | Chi et al. | |
| 6,832,416 B2 | 12/2004 | Dixon | |
| 6,896,232 B2 | 5/2005 | Crowell et al. | |
| 7,040,783 B1 | 5/2006 | Christianson | |
| 7,272,878 B2 | 9/2007 | Dixon | |
| 7,290,898 B2 | 11/2007 | Martin et al. | |
| 7,313,937 B2 | 1/2008 | Straka, Jr. | |
| D568,814 S | 5/2008 | Hung | |
| 7,523,535 B2 | 4/2009 | Coleman | |
| 7,566,038 B2 | 7/2009 | Scott et al. | |
| 7,731,141 B2 | 6/2010 | Schuerch | |

(56) References Cited

U.S. PATENT DOCUMENTS

| | | |
|---|---|---|
| D622,583 S | 8/2010 | Parks |
| 7,883,137 B2 | 2/2011 | Bar |
| 7,980,521 B2 | 7/2011 | Harr et al. |
| 8,051,515 B1 | 11/2011 | Kring |
| 8,167,259 B2 | 5/2012 | Spang, Jr. et al. |
| D662,051 S | 6/2012 | Saunders et al. |
| 8,235,402 B2 | 8/2012 | Knappe |
| 8,276,895 B2 | 10/2012 | Brown et al. |
| D681,436 S | 5/2013 | Jebara |
| D692,378 S | 10/2013 | Esses |
| 8,631,544 B1 | 1/2014 | Shotey et al. |
| 8,814,094 B2 | 8/2014 | Tran |
| D728,779 S | 5/2015 | Sabin et al. |
| 9,022,374 B1 | 5/2015 | Baryam |
| D735,319 S | 7/2015 | Sabin et al. |
| D736,370 S | 8/2015 | Sabin et al. |
| D736,586 S | 8/2015 | Fukui |
| 9,132,515 B2 | 9/2015 | Spillane |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| 10,082,241 B2 * | 9/2018 | Janway ............. A61M 39/28 |
| 2003/0071402 A1 | 4/2003 | Martinez |
| 2005/0230444 A1 | 10/2005 | Alling et al. |
| 2006/0049566 A1 | 3/2006 | Bernstein |
| 2006/0237974 A1 | 10/2006 | Hamm et al. |
| 2006/0289083 A1 * | 12/2006 | Bar ............. B60K 15/04 141/350 |
| 2007/0190826 A1 | 8/2007 | Knappe et al. |
| 2008/0116157 A1 | 5/2008 | Fulbrook et al. |
| 2008/0149788 A1 | 6/2008 | Wong et al. |
| 2009/0212580 A1 * | 8/2009 | Ballhause ............. B04B 7/06 292/341.16 |
| 2010/0265679 A1 * | 10/2010 | Van Der Mee ...... H05K 7/1407 361/759 |
| 2011/0037277 A1 * | 2/2011 | Visenzi ............. B62J 9/00 292/58 |
| 2011/0313789 A1 | 12/2011 | Kamen et al. |
| 2012/0049580 A1 | 3/2012 | Konchan |
| 2012/0056065 A1 | 3/2012 | Andersson |
| 2012/0185267 A1 | 7/2012 | Kamen et al. |
| 2013/0177455 A1 | 7/2013 | Kamen et al. |
| 2013/0182381 A1 | 7/2013 | Gray et al. |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen et al. |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen et al. |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen et al. |
| 2014/0318639 A1 | 10/2014 | Peret |
| 2014/0343492 A1 | 11/2014 | Kamen |
| 2014/0345787 A1 | 11/2014 | Zaborowski et al. |
| 2014/0373580 A1 | 12/2014 | Le |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0041419 A1 | 2/2015 | Hasegawa |
| 2015/0314083 A1 | 4/2015 | Blumberg, Jr. et al. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0221814 A1 | 8/2016 | Kent |
| 2016/0262977 A1 | 9/2016 | Demers et al. |
| 2016/0319850 A1 | 11/2016 | Kamen et al. |

FOREIGN PATENT DOCUMENTS

| | | |
|---|---|---|
| EP | 1690517 A2 | 8/2006 |
| EP | 2532901 A1 | 12/2012 |
| JP | 3048970 B2 | 6/2000 |
| WO | WO2001036027 A1 | 5/2001 |
| WO | WO2010128929 A1 | 11/2010 |
| WO | WO2013095459 A9 | 6/2013 |
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013102494 A1 | 7/2013 |
| WO | WO2013161709 A1 | 10/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

OTHER PUBLICATIONS

International Preliminary Report on Patentability dated Jun. 23, 2015, received in International patent application No. PCT/US2013/077270, 11 pgs.
Invitation to Pay Additional Fees and, Where Applicable, Protest Fee dated Apr. 25, 2016, received in International patent application No. PCT/US2015/063359, 7 pgs.
U.S. Appl. No. 61/297,544, filed Jan. 22, 2010.
U.S. Appl. No. 13/011,543, filed Jan. 21, 2011, US20110313789A1.
U.S. Appl. No. 13/333,574, filed Dec. 21, 2011, US20120185267A1.
PCT/US11/66588, filed Dec. 21, 2011, WO2013095459A1.
U.S. Appl. No. 61/578,649, filed Dec. 21, 2011.
U.S. Appl. No. 61/578,658, filed Dec. 21, 2011.

(56) References Cited

OTHER PUBLICATIONS

U.S. Appl. No. 61/578,674, filed Dec. 21, 2011.
U.S. Appl. No. 61/651,322, filed May 24, 2012.
U.S. Appl. No. 61/679,117, filed Aug. 3, 2012.
U.S. Appl. No. 61/738,447, filed Dec. 18, 2012.
U.S. Appl. No. 61/740,474, filed Dec. 21, 2012.
U.S. Appl. No. 13/723,253, filed Dec. 21, 2012, US20130191513A1.
U.S. Appl. No. 13/723,251, filed Dec. 21, 2012, US20130204188A1.
PCT/US12/71142, filed Dec. 21, 2012, WO2013096722A1.
U.S. Appl. No. 13/723,244, filed Dec. 21, 2012, US20130188040A1.
U.S. Appl. No. 13/723,242, filed Dec. 21, 2012, US20130317753A1.
U.S. Appl. No. 13/723,239, filed Dec. 21, 2012, US20130297330A1.
U.S. Appl. No. 13/725,790, filed Dec. 21, 2012, US20130177455A1.
U.S. Appl. No. 13/724,568, filed Dec. 21, 2012, US20130184676A1.
PCT/US12/71131, filed Dec. 21, 2012, WO2013096718A1.
U.S. Appl. No. 13/723,235, filed Dec. 21, 2012, US20130197693A1.
U.S. Appl. No. 13/723,238, filed Dec. 21, 2012, US20130182381A1.
PCT/US12/71490, filed Dec. 21, 2012, WO2013096909A1.
PCT/US12/71112, filed Dec. 21, 2012, WO2013096713A1.
U.S. Appl. No. 13/840,339, filed Mar. 15, 2013, US20130336814A1.
U.S. Appl. No. 13/833,712, filed Mar. 15, 2013, US20130272773A1.
U.S. Appl. No. 13/836,497, filed Mar. 15, 2013, US20130346108A1.
PCT/US13/32445, filed Mar. 15, 2013, WO2013176770A1.
U.S. Appl. No. 13/834,030, filed Mar. 15, 2013, US20130310990A1.
U.S. Appl. No. 13/833,432, filed Mar. 15, 2013, US20130281965A1.
U.S. Appl. No. 13/900,655, filed May 23, 2013, US20130317837A1.
PCT/US13/42350, filed May 23, 2013, WO/2013/177357A1.
U.S. Appl. No. 29/457,516, filed Jun. 11, 2013, U.S. Pat. No. D 728,779S.
U.S. Appl. No. 29/457,520, filed Jun. 11, 2013, U.S. Pat. No. D 735,319S.
U.S. Appl. No. 29/457,522, filed Jun. 11, 2013, U.S. Pat. No. D 736,370S.
U.S. Appl. No. 29/457,521, filed Jun. 11, 2013.
U.S. Appl. No. 61/843,574, filed Jul. 8, 2013.
U.S. Appl. No. 61/860,398, filed Jul. 31, 2013.
U.S. Appl. No. 13/971,258, filed Aug. 20, 2013, US20130339049A1.
U.S. Appl. No. 61/894,801, filed Oct. 23, 2013.
U.S. Appl. No. 29/471,856, filed Nov. 6, 2013, U.S. Pat. No. D 751,689S.
U.S. Appl. No. 61/900,431, filed Nov. 6, 2013.
U.S. Appl. No. 29/471,864, filed Nov. 6, 2013, U.S. Pat. No. D 752,209S.
U.S. Appl. No. 29/471,861, filed Nov. 6, 2013, U.S. Pat. No. D 749,206S.
U.S. Appl. No. 29/471,859, filed Nov. 6, 2013, U.S. Pat. No. D 745,661S.
U.S. Appl. No. 29/471,858, filed Nov. 6, 2013, U.S. Pat. No. D 751,690S.
U.S. Appl. No. 61/904,123, filed Nov. 14, 2013.
U.S. Appl. No. 14/101,848, filed Dec. 10, 2013, US20140165703A1.
U.S. Appl. No. 14/137,562, filed Dec. 20, 2013, US20140227021A1.
U.S. Appl. No. 29/477,232, filed Dec. 20, 2013.
U.S. Appl. No. 29/477,233, filed Dec. 20, 2013.
PCT/US13/77135, filed Dec. 20, 2013, WO/2014/100687A1.
U.S. Appl. No. 29/477,242, filed Dec. 20, 2013, U.S. Pat. No. D 756,386S.
U.S. Appl. No. 14/136,243, filed Dec. 20, 2013, US20140188516A1.
PCT/US13/77270, filed Dec. 20, 2013, WO/2014/100744A1.
U.S. Appl. No. 29/477,231, filed Dec. 20, 2013.
PCT/US13/77077, filed Dec. 20, 2013, WO/2014/100658A1.
U.S. Appl. No. 14/135,784, filed Dec. 20, 2013, US20140188076A1.
PCT/US13/76886, filed Dec. 20, 2013, WO/2014/100571A1.
U.S. Appl. No. 29/477,249, filed Dec. 20, 2013.
PCT/US13/76851, filed Dec. 20, 2013, WO2014100557A1.
U.S. Appl. No. 29/477,236, filed Dec. 20, 2013.
U.S. Appl. No. 14/137,421, filed Dec. 20, 2013, US20140180711A1.
PCT/US13/77258, filed Dec. 20, 2013, WO2014100736A1.
U.S. Appl. No. 14/135,809, filed Dec. 20, 2013, US20140195639A1.
U.S. Appl. No. 61/942,986, filed Feb. 21, 2014.
U.S. Appl. No. 14/191,827, filed Feb. 27, 2014, US20150238228A1.
U.S. Appl. No. 14/213,373, filed Mar. 14, 2014, US20140318639A1.
U.S. Appl. No. 61/953,036, filed Mar. 14, 2014.
PCT/US14/29020, filed Mar. 14, 2014, WO/2014/144557A1.
U.S. Appl. No. 61/987,742, filed May 2, 2014.
U.S. Appl. No. 61/990,330, filed May 8, 2014.
U.S. Appl. No. 14/341,207, filed Jul. 25, 2014, US20150033823A1.
PCT/US2014/48227, filed Jul. 25, 2014, WO2015017275A1.
U.S. Appl. No. 14/451,904, filed Aug. 5, 2014, US20140343492A1.
U.S. Appl. No. 62/052,008, filed Sep. 18, 2014.
U.S. Appl. No. 14/491,161, filed Sep. 19, 2014, US20150002677A1.
U.S. Appl. No. 14/491,143, filed Sep. 19, 2014, US20150002668A1.
U.S. Appl. No. 14/491,128, filed Sep. 19, 2014, US20150002667A1.
U.S. Appl. No. 62/086,356, filed Dec. 2, 2014.
U.S. Appl. No. 14/616,079, filed Feb. 6, 2015, US20150154364A1.
U.S. Appl. No. 29/517,096, filed Feb. 10, 2015.
U.S. Appl. No. 29/517,101, filed Feb. 10, 2015.
U.S. Appl. No. 29/517,100, filed Feb. 10, 2015.
U.S. Appl. No. 29/517,099, filed Feb. 10, 2015.
U.S. Appl. No. 29/517,097, filed Feb. 10, 2015.
U.S. Appl. No. 29/517,095, filed Feb. 10, 2015.
U.S. Appl. No. 29/517,098, filed Feb. 10, 2015, U.S. Pat. No. D 754,065S.
U.S. Appl. No. 14/627,287, filed Feb. 20, 2015, US20150157791A1.
PCT/US15/16796, filed Feb. 27, 2015.
U.S. Appl. No. 14/656,945, filed Mar. 13, 2015, US20150257974A1.
U.S. Appl. No. 14/679,364, filed Apr. 6, 2015, US20150314083A1.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 14/812,149, filed Jul. 29, 2015, US20150332009A1.
U.S. Appl. No. 29/538,153, filed Sep. 1, 2015.
U.S. Appl. No. 62/212,871, filed Sep. 1, 2015.
U.S. Appl. No. 14/853,300, filed Sep. 14, 2015.
PCT/US15/49952, filed Sep. 14, 2015.
U.S. Appl. No. 14/873,515, filed Oct. 2, 2015, US20160097382A1.
U.S. Appl. No. 14/931,928, filed Nov. 4, 2015, US20160055397A1.
U.S. Appl. No. 14/932,291, filed Nov. 4, 2015, US20160055649A1.
U.S. Appl. No. 14/938,083, filed Nov. 11, 2015, US20160073063A1.
U.S. Appl. No. 14/938,368, filed Nov. 11, 2015, US20160061641A1.
U.S. Appl. No. 14/939,586, filed Nov. 12, 2015, US20160131272A1.
U.S. Appl. No. 14/939,015, filed Nov. 12, 2015, US20160063353A1.
U.S. Appl. No. 14/956,648, filed Dec. 2, 2015 US20160084434A1.
PCT/US2015/63359, filed Dec. 2, 2015.
U.S. Appl. No. 29/547,405, filed Dec. 3, 2015.
U.S. Appl. No. 29/547,402, filed Dec. 3, 2015.
U.S. Appl. No. 29/548,225, filed Dec. 11, 2015.
U.S. Appl. No. 29/552,303, filed Jan. 21, 2016.
U.S. Appl. No. 29/552,942, filed Jan. 27, 2016.
U.S. Appl. No. 29/552,943, filed Jan. 27, 2016.
U.S. Appl. No. 29/553,094, filed Jan. 28, 2016.
U.S. Appl. No. 62/288,132, filed Jan. 28, 2016.
U.S. Appl. No. 29/556,048, filed Feb. 26, 2016.
U.S. Appl. No. 15/055,941, filed Feb. 29, 2016.
U.S. Appl. No. 15/059,394, filed Mar. 3, 2016.
U.S. Appl. No. 15/077,389, filed Mar. 22, 2016.
U.S. Appl. No. 29/561,572, filed Apr. 18, 2016.
U.S. Appl. No. 29/564,750, filed May 16, 2016.
U.S. Appl. No. 15/161,876, filed May 23, 2016.
U.S. Appl. No. 62/341,396, filed May 25, 2016.
U.S. Appl. No. 29/565,908, filed May 25, 2016.
U.S. Appl. No. 15/163,906, filed May 25, 2016.
U.S. Appl. No. 29/569,450, filed Jun. 28, 2016.
U.S. Appl. No. 29/569,640, filed Jun. 28, 2016.
U.S. Appl. No. 13/833,712, filed Mar. 15, 2013.
U.S. Appl. No. 13/833,712.
JP3048970B2, English Abstract.
First Examination Report dated Jan. 18, 2017, received in New Zealand patent application No. 709299, 4 pgs.
Office Action dated Dec. 9, 2016, notified/published on Dec. 12, 2016, received in Colombian patent application No. 15.302.333, 26 pgs. with English translation attached. Received by Applicant's US representative on Jan. 19, 2017.

(56) References Cited

OTHER PUBLICATIONS

Office Action dated Dec. 15, 2016, notified/published on Dec. 16, 2016, received in Colombian patent application No. 15.302.359, 26 pgs. with English translation attached. Received by Applicant's US representative on Jan. 25, 2017.
Office Action received in Colombian patent application No. 15.167.448, 12 pgs., English Translation is 18 pgs. Office Action notified to wrong party dated Dec. 12, 2016. Received by Applicant's US representative on Mar. 29, 2017.
Communication pursuant to Article 94(3) EPC dated Feb. 28, 2017, from the European Patent Office for application 13 828 963.2-1664, 3pgs.
U.S. Appl. No. 15/418,096, filed Jan. 27, 2017.
PCT/US2017/15382, filed Jan. 27, 2017.
U.S. Appl. No. 15/467,196, filed Mar. 23, 2017.
Office Action received in Colombian patent application No. 15.167.448, 12 pgs., English Translation is 18 pgs. Office Action notified to wrong party dated Dec. 12, 2016.
International Search Report & Written Opinion dated Jul. 4, 2016, received in International patent application No. PCT/US2015/063359, 18 pgs.
Written Opinion from The Intellectual Property Office of Singapore for Application 11201504885X, dated Apr. 13, 2016, 14 pgs.
Invitation to Pay Additional Fees and, Where Applicable, Protest Fee dated May 9, 2014, received in International patent application No. PCT/US2013/077270, 5 pgs.
Report of substantive examination from Superintendent of Industry and Commerce of Colombia for Patent Application 15-167448-1, dated Aug. 8, 2015.
Report of substantive examination from Superintendent of Industry and Commerce of Colombia for Patent Application 15-167448-1, dated Feb. 11, 2016.
U.S. Appl. No. 29/570,648, filed Jul. 11, 2016.
U.S. Appl. No. 29/571,387, filed Jul. 18, 2016.
DE4030368C1, Machine Translation.
WO2013161709A1, (See US2015/0041419A1).
Report of substantive examination from Superintendent of Industry and Commerce of Colombia for Patent Application 15-167448-1, dated Aug. 8, 2015, Machine Translation.
Report of substantive examination from Superintendent of Industry and Commerce of Colombia for Patent Application 15-167448-1, dated Feb. 11, 2016, Machine Translation.
Second Written Opinion from The Intellectual Property Office of Singapore for Application 11201504885X, dated Oct. 24, 2016, 8 pgs.
U.S. Appl. No. 29/575,331, filed Aug. 24, 2016.
U.S. Appl. No. 29/575,316, filed Aug. 24, 2016.
U.S. Appl. No. 15/248,200, filed Aug. 26, 2016.
U.S. Appl. No. 15/270,321, filed Sep. 20, 2016.
U.S. Appl. No. 15/341,611, filed Nov. 2, 2016.

* cited by examiner

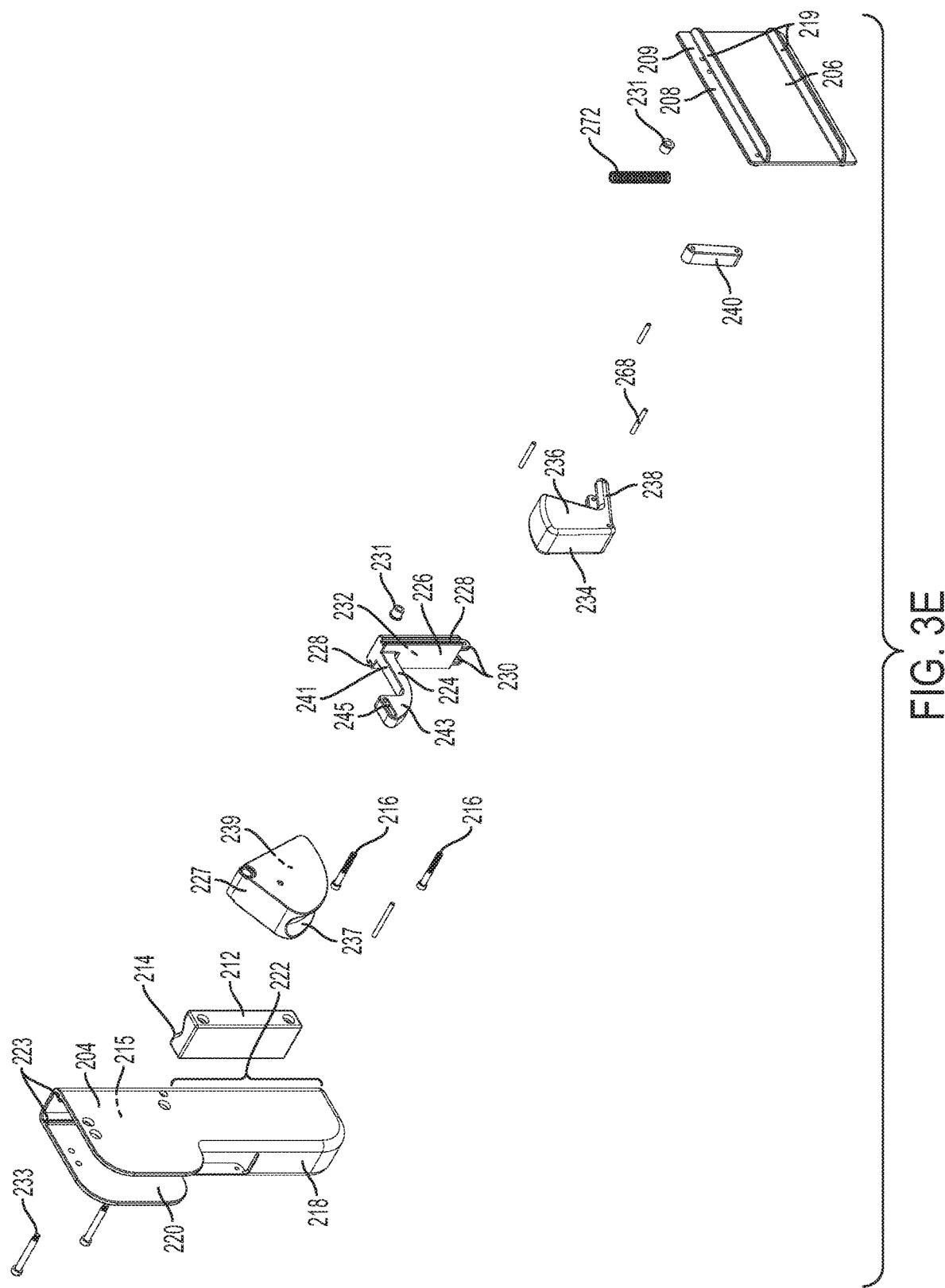

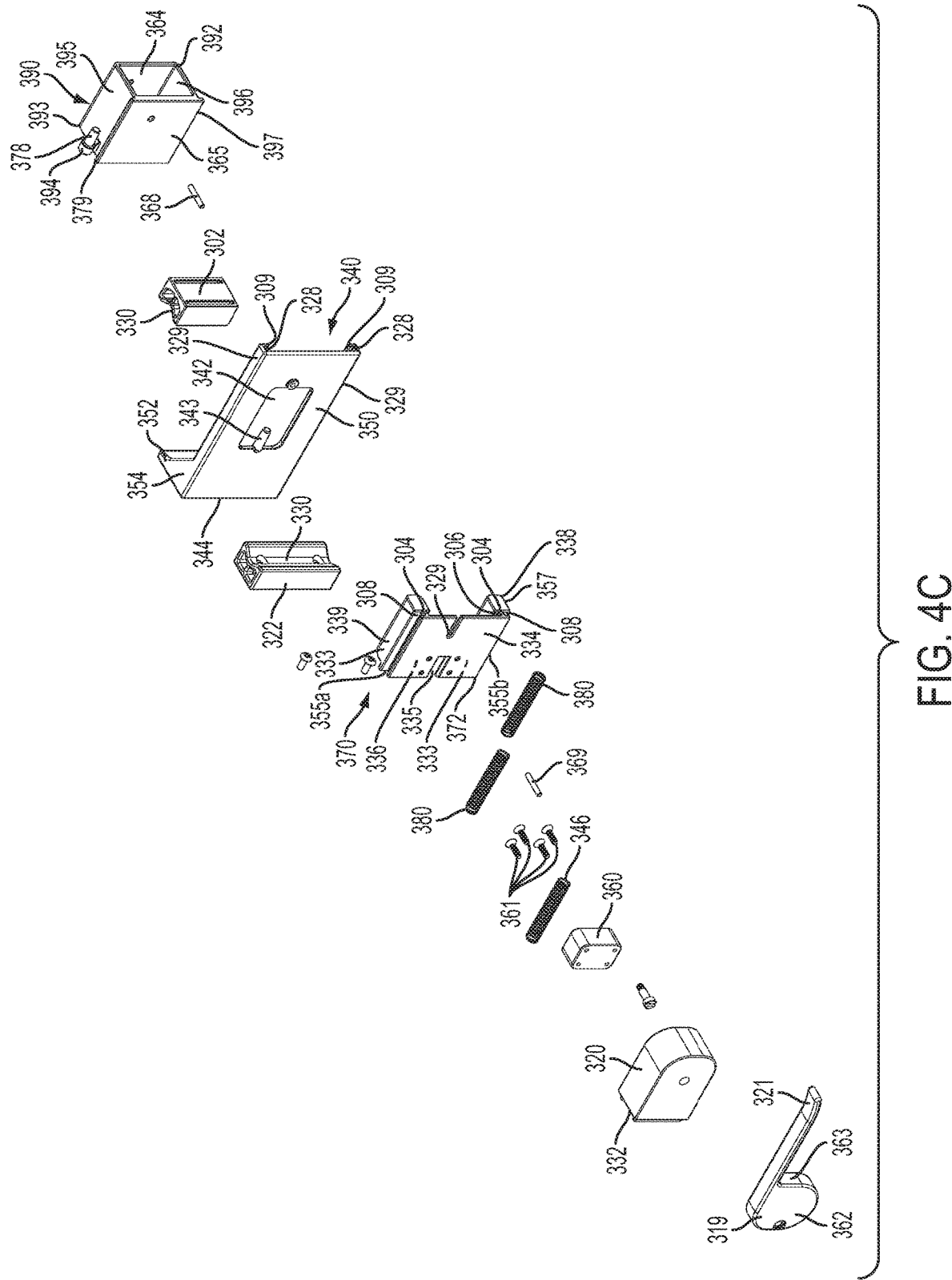

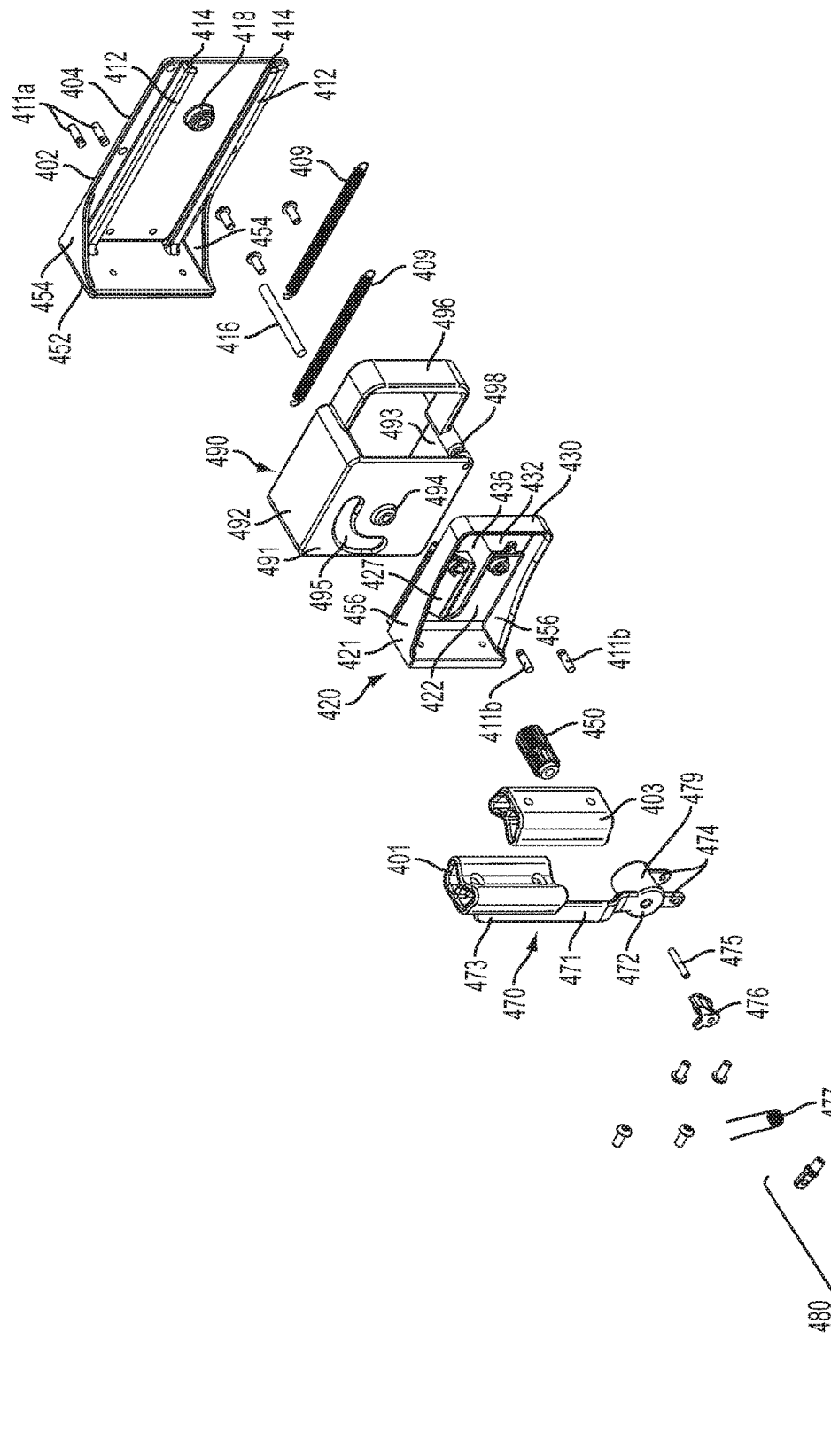

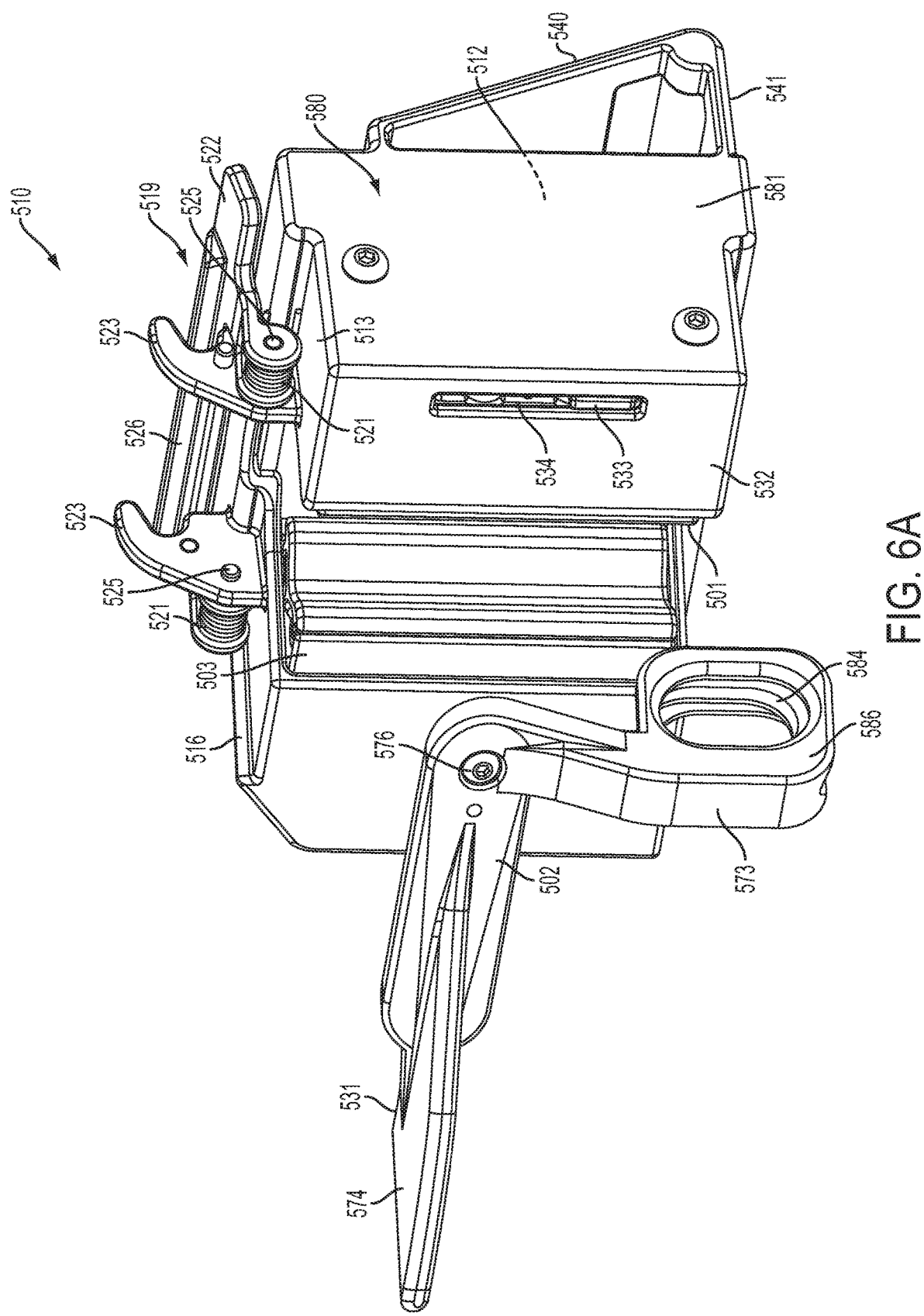

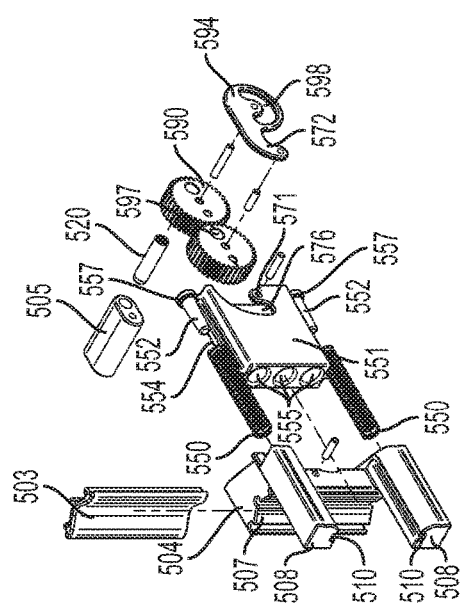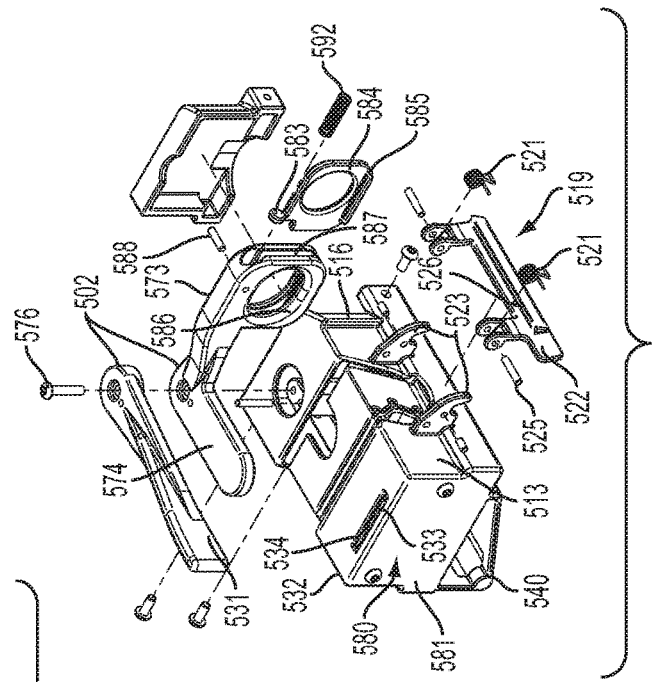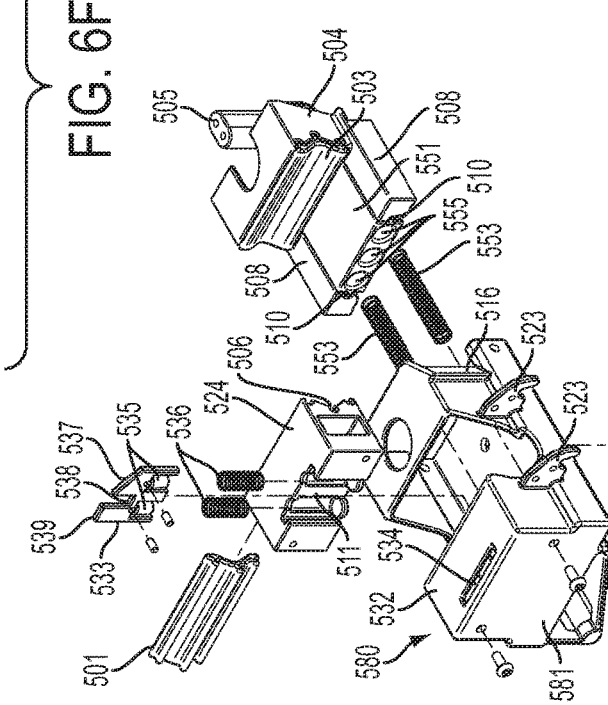

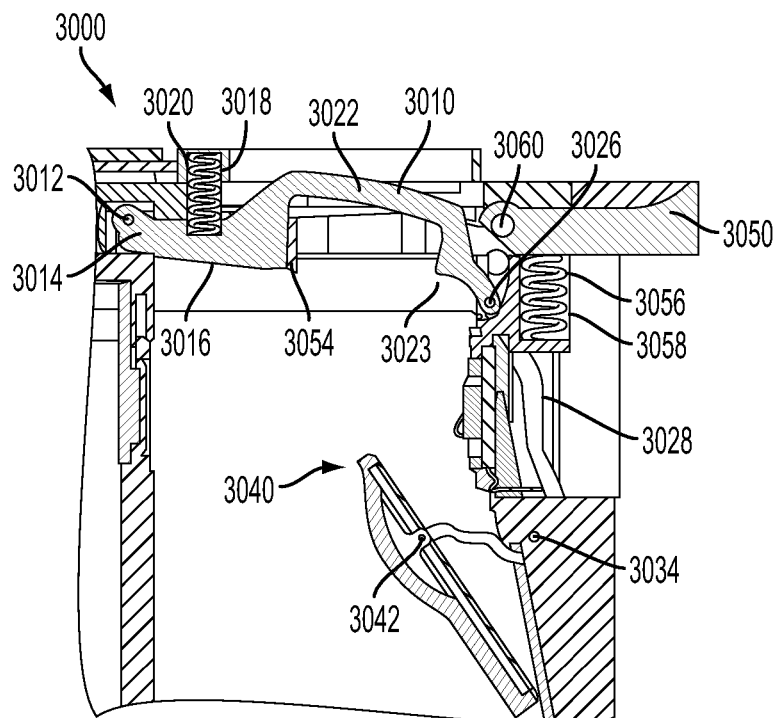
FIG. 12F
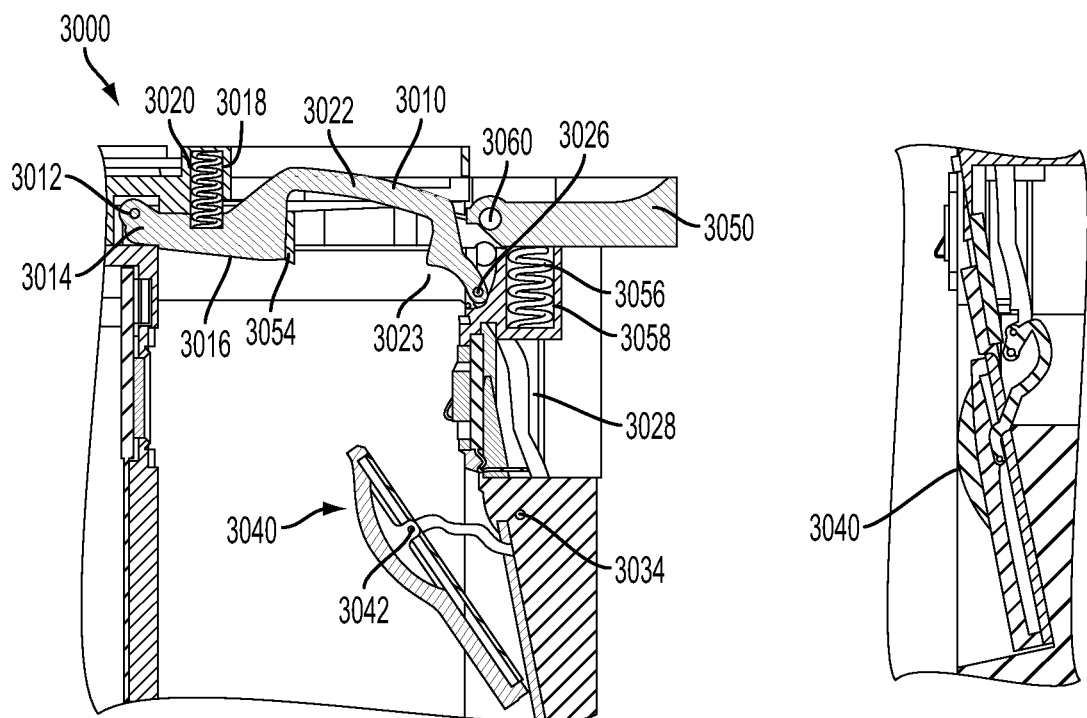
FIG. 12G
FIG. 12H

SYSTEM, METHOD, AND APPARATUS FOR CLAMPING

CROSS REFERENCE TO RELATED APPLICATIONS

The present application is a continuation application of U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and the benefit of the following:

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and the benefit of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-in-Part application of U.S. patent application Ser. No. 13/723,238, filed Dec. 21, 2012 and entitled System, Method, and Apparatus for Clamping, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,238 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-in-Part application of U.S. patent application Ser. No. 13/723,235, filed Dec. 21, 2012 and entitled System, Method, and Apparatus for Dispensing Oral Medications, which claims priority to and benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,235 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of PCT Application Serial No. PCT/US12/71131, filed Dec. 21, 2012 and entitled System, Method, and Apparatus for Dispensing Oral Medications, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US 12/71131 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/724,568, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/724,568 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/725,790, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/725,790 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of PCT Application Serial No. PCT/US 12/71490, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

PCT Application Serial No. PCT/US 12/71490 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/723,239, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/723,242, filed Dec. 21, 2012 and entitled System, Method, and Apparatus for Electronic Patient Care, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/723,244, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,244 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of PCT Application Serial No. PCT/US 12/71142, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US 12/71142 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/723,251, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,251 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of PCT Application Serial No. PCT/US 12/71112, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US 12/71112 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and is also a Continuation-In-Part Applications of U.S. patent application Ser. No. 13/723,253, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253 claims priority to and is a Continuation-In-Part Applications of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US 11/66588, filed Dec. 21, 2011 and entitled System, Method, and Apparatus for Electronic Patient Care, both of which are hereby incorporated herein by reference in their entireties.

U.S. patent application Ser. No. 13/833,712, entitled System, Method, and Apparatus for Clamping, filed on Mar. 15, 2013, now U.S. Publication No. US 2013-0272773-A1, published on Oct. 17, 2013, which claims priority to and may also be related to one or more of the following U.S. patent Applications filed on Mar. 15, 2013, all of which are hereby incorporated herein by reference in their entireties:

U.S. patent application Ser. No. 13/840,339, and entitled Apparatus for Infusing Fluid;

PCT Application serial No. PCT/US 13/32445, and entitled Apparatus for Infusing Fluid;

U.S. patent application Ser. No. 13/833,432, and entitled Syringe Pump and Related Method;

U.S. patent application Ser. No. 13/836,497, and entitled System and Apparatus for Electronic Patient Care; and U.S. patent application Ser. No. 13/834,030, and entitled System, Method, and Apparatus for Monitoring, Regulating, or Controlling Fluid Flow.

BACKGROUND

Field of Disclosure

The present disclosure relates generally to releasably attaching an object to another object (e.g., clamping a medical device onto a pole). More particularly, the present disclosure relates to a system, method, and apparatus for mounting an object onto a pole or other support structure.

Description of Related Art

Patient care generally involves a number of medical devices and systems that are used to monitor and treat a patient. The specific medical devices required vary with each patient and may change during the course of treatment. Medical devices often require monitoring by health care providers and so need to be easily accessible. They are often expensive, so redundancy is rarely possible, and a given device will often need to be moved to a different patient after a treatment is completed. Given their expense, medical devices need to be firmly and safely attached to a location to prevent either their damage or an interruption to patient care should they come unattached.

Medical devices are typically attached to a vertical pole located near the bedside of their assigned patient. This arrangement facilitates: the attached equipment to be customized according to patient's treatment, convenient monitoring by health care providers, minimizing the length of tubing or other connections between the patient and the device, and moving the pole and the attached equipment to follow movement of the patient. A typical attachment involves a brace fixed to the medical device and a threaded screw that can be tightened to squeeze a section of the support pole positioned between the brace and the screw. Typically, turning the screw clockwise advances the screw into the interior of the brace and attaches the medical device to the pole; counterclockwise rotation retracts the screw and allows the device to be removed. Once the advancing screw contacts the support pole, it exerts a predominantly compression-based force into the pole which holds the medical device in position against the downward pull of gravity. The user manually adjusts the clamp to poles of different diameter by varying the number of screw rotations and rotational direction of screw rotations thus controlling how far into the brace interior the screw is extended. Such positioning and adjustment faces a number of constraints, for example, it can be time consuming, there is risk of cross-threading, there is risk of human error (i.e. not tightening enough) etc.

SUMMARY

Clamp Mechanisms

In accordance with an embodiment of the present disclosure a clamp comprises a housing. The clamp may also include at least one pawl. The at least one pawl may be pivotally coupled to a pivot point. The clamp may also include a lift bar. The lift bar may be operatively coupled to the at least one pawl. The lift bar may be configured to control the at least one pawl. The clamp may also include at least one bias member operatively coupled to the housing. The at least one bias member may be configured to bias the at least one pawl toward a first position. The clamp may additionally include an actuator operatively coupled to the lift bar. The actuator may be configured move the lift bar to thereby move the at least one pawl to a second position.

In some embodiments, the said housing may include a means of coupling the clamp to a load. In some embodiments, the clamp may be configured to couple to a medical device. In some embodiments, the medical device may be an infusion pump. In some embodiments, the medical device may be a peristaltic infusion pump.

In some embodiments, the clamp may be configured such that a downward pull of gravity on the clamp causes the at least one pawl to amplify the clamping force exerted on a clamped object.

In some embodiments, the housing further comprises at least one track. In some embodiments, the housing has at least one handle.

In some embodiments, at least one of the at least one pawl further comprises a gripping surface configured to engage a clamped object. The gripping surface may be made of a material which will firmly grip, but not deform, a clamped object.

In some embodiments, at least one of the at least one bias member may be a coil spring. At least one of the at least one bias member may be a gas spring. At least one of the at least one bias member may be a torsion spring. At least one of the at least one bias member may made of a springy, compressible material. At least one of the at least one bias member may be a constant force spring.

In some embodiments, said housing includes a back plate with at least one handle coupled thereto.

The clamp may further comprise at least one track, wherein the at least one track is inclined and offset from the housing.

In still other embodiments, the clamp may further comprise at least one pawl assembly. The at least one pawl assembly may include a pawl of the at least one pawl, and the pawl may be pivotally coupled to the pawl assembly.

In some embodiments the at least one pawl assembly may further comprise a sliding wedge and the pawl may be pivotally coupled to the sliding wedge. The sliding wedge comprises an engagement surface configured for movement along the at least one track. In some embodiments the at least one pawl assembly may be slidingly coupled to the lift bar. The lift bar may be configured such that all of the at least pawl move in unison with each other.

In some embodiments, the housing may comprise a vertical groove configured for engaging with an engagement surface of the lift bar to thereby guide the movement of the lift bar.

In some embodiments, the at least one pawl may be configured to engage with a girth a variety of different clamped objects.

In some embodiments, the actuator may comprise a pull handle. The pull handle may be configured for being operated by a user so as to overcome the at least one bias member and move the at least one pawl from the first position to the second position.

In some embodiments, the housing may include at least one catch. The at least one catch may be configured to engage the actuator and hold it in one of the first and second positions.

In some embodiments, the clamp the housing may comprise a first and a second inclined track offset from a back plate. The at least one pawl may comprise a first pawl pivotally coupled to a first sliding wedge. The first sliding wedge may be configured to ride along the first track. A second pawl may be pivotally coupled to a second sliding wedge. The second sliding wedge may be configured to ride along the second track. The lift bar may be configured to slidingly couple to the first and second sliding wedges such that the lift bar thereby ensures the first and second pawls move in unison with one another. The at least one bias member may be configured to bias the lift bar to the first position. A handle may be coupled to the lift bar and configured for being operated by a user so as to overcome the at least one bias member to thereby move the first and second pawls to the second position. Additionally, a catch, may be configured to engage a notch in said handle and when engaged holds the handle in one of the first and second positions.

In some embodiments, the housing may comprises at least one vertical track. In some embodiments at least one pair of pawls may be pivotally coupled to the housing. The at least one pair of pawls may be coupled together by the lift bar. The lift bar may ensure that the at least one pair of pawls move in unison.

In some embodiments, the said lift bar may comprise an engagement surface for movement along said track in said housing.

In some embodiments, the actuator may be a pivotal actuator handle. The pivotal actuator handle may be configured to be pulled by the user in order to move the clamp between the first position and the second position.

In some embodiments, the housing of the clamp may comprise at least one vertical track. The at least one pawl may comprise first and second pawls each pivotally coupled to the housing. The lift bar may be coupled to the first and second pawls. The lift bar may be configured to ensure the first and second pawls pivot in unison with each another. The at least one bias member may configured to bias the lift bar towards the first position. The actuator handle may be configured for being operated by a user so as to overcome the at least one bias member to move the lift bar towards the second position.

In some embodiments, the housing may comprise at least one track located on an interior surface of the housing along at least one wall of at least one hollow cavity in the housing. The at least one track may be vertical.

In some embodiments, the housing may further comprise at least one fixed gripping surface. The said housing may comprise a back plate to which the at least one fixed gripping surface is coupled. The at least one fixed gripping surface may formed of a material which will firmly grip, but not deform a clamped object.

In some embodiments, the at least one pawl may comprise only a single pawl. Opposite said single pawl may be a fixed gripping surface. The first pawl and opposite fixed gripping surface may be configured to automatically mimic the girth of a clamped object.

In some embodiments, the lift bar may comprise an engagement surface for movement along the at least one vertical track. The lift bar may couple to a single pawl. Movement of the lift bar may cause the single pawl to pivot about the single pawl's pivot point.

In some embodiments the said actuator may be a depressible trigger.

In some embodiments, the housing of the clamp may comprise at least one hollow cavity with at least one vertical track running along at least a part of an interior wall of the hollow cavity. The clamp may comprise at least one fixed gripping surface. The at least one pawl may comprise a single pawl pivotally coupled to the housing. The lift bar may comprise an engagement surface for engaging the at least one vertical track on at least a part of the interior wall of the housing. The lift bar may couple to the single pawl thereby causing it to pivot about its pivot point as the lift bar move along the at least one vertical track. The at least one bias member may be configured to bias the lift bar to the first position. The actuator may be configured for being operated by a user so as to overcome the at least one bias member thereby move the lift bar to the second position.

In accordance with an embodiment of the present disclosure, a method of making a clamp may comprise providing a housing such that the housing comprises at least one track. The method may also comprise providing at least one pawl configured for engaging a clamped object such that the at least one pawl is pivotally coupled to a pivot point. The method may also comprise providing a lift bar such that the lift bar may be coupled to the at least one pawl and such that the lift bar may be capable of controlling the movement of the at least one pawl. The method may also comprise providing at least one bias member such that the at least one bias member may be configured to bias the at least one pawl to a first position. The method may also comprise providing an actuator such that the actuator may be configured for being operated by a user so as to overcome the at least one bias member to move the at least one pawl to a second position.

In some embodiments, providing the said clamp comprises providing the said clamp for use with medical devices and accessories.

In some embodiments, providing said housing comprises providing a means of coupling to a load.

In some embodiments, providing the means of coupling to the load comprises providing the means of coupling to a load which is one of a medical device and a medical accessory.

In some embodiments, providing one of the medical device and medical accessory may comprise providing an infusion pump.

In some embodiments, providing the infusion pump may comprise providing a peristaltic infusion pump.

In some embodiments, providing said housing may comprise providing at least one handle on the housing.

In some embodiments, providing said at least one pawls may further comprise providing a gripping surface to engage a clamped object on at least a part of a surface of the at least one pawl. Providing said gripping surface may comprise providing said gripping surface being of a material which will firmly grip, but not deform the clamped object.

In some embodiments, providing the said at least one bias member may comprise providing at least one coil spring. Providing the said at least one bias member may comprise providing at least one gas spring. Providing the said at least one bias member may comprise providing at least one torsion spring. Providing the said at least one bias member may comprise providing at least one springy, compressible material.

In some embodiments, providing the housing may comprise providing a back plate with at least one handle.

In some embodiments, providing the at least one track may comprise providing the at least one track such that the at least one track is inclined and offset from the housing.

In some embodiments, providing at least one pawl may comprise providing the at least one pawl such that the at least one pawl is pivotally coupled on a pawl assembly.

In some embodiments, providing the clamp may comprise providing the at least one pawl such that the at least one pawl is pivotally coupled to a sliding wedge. Providing the sliding wedge may comprise providing the sliding wedge with an engagement surface for movement along the at least one track.

In some embodiments, providing the pawl assembly may comprise providing the pawl assembly such that the pawl assembly may be slidably coupled to the lift bar. Providing the lift bar may comprise providing the lift bar such that the lift bar is capable of moving the pawl assembly.

In some embodiments, providing the housing may comprise providing a vertical groove on the housing which engages an engagement surface on the lift bar thereby guiding the movement of the lift bar.

In some embodiments, providing the clamp may comprise providing the clamp such that the clamp is capable of automatically mimicking the girth of a variety of different clamped objects.

In some embodiments, providing the actuator may comprise providing a pull handle. Providing the pull handle may comprise providing the pull handle such that the pull handle is capable of being operated by a user so as to overcome the bias members and move the clamp from a first position to a second position.

In some embodiments, providing the housing may comprise providing at least one catch.

In some embodiments, providing the at least one bias member may comprise providing a constant force spring.

In some embodiments, providing the at least one catch may comprise providing the at least one catch such that the at least one catch is able to engage the actuator and hold the actuator in one of the first position and the second position.

In some embodiments, providing the clamp may comprise providing the housing, such that the housing comprises two inclined track offset from a back plate. Providing a first pawl assembly such that a pawl is pivotally coupled to a sliding wedge. Providing the sliding wedge may comprise providing the sliding wedge such that the sliding wedge may be able to ride along one of the inclined tracks. Providing a second pawl assembly opposite and symmetrical to the first pawl assembly such a second pawl is pivotally coupled to a second sliding wedge, and such that the second sliding wedge may able to ride along the other of the inclined tracks. Providing the lift bar such that a crosspiece of the lift bar couples to the two pawl assemblies and such that the lift bar ensures the pawl assemblies move in unison with one another. Providing the at least one bias member such that the at least one bias member biases the said clamp to a first position. Providing a handle, said handle capable of being operated by a user so as to overcome the at least one bias member and move the clamp to a second position. Providing a catch such that said catch may be capable of engaging a notch in said handle and when engaged holds clamp in either the first or second position. Providing the clamp such that the downward pull of gravity on the clamp causes the sliding wedges to move toward each other.

In some embodiments, providing the at least one track may comprise providing at least one vertical track.

In some embodiments, providing at least one pawl may comprise providing at least one pair of pawls pivotally coupled to the housing.

In some embodiments, providing the at least one pair of pawls may comprise providing the at least one pair of pawls such that the at least one pair of pawls are coupled together by the lift bar and wherein the lift bar ensures that the at least one pair of pawls move in unison.

In some embodiments, providing the lift bar may comprise providing the lift bar with an engagement surface for movement along the at least one track in the housing.

In some embodiments, providing the actuator may comprise providing a pivotal actuator handle.

In some embodiments, providing the pivotal actuator handle may comprise supporting the pivotal actuator handle such that the pivotal actuator handle may be pulled by the user toward at least one handle on the housing in order to move the clamp from the first position to the second position.

In some embodiments, providing the clamp may comprise providing the housing, such that the housing may comprise at least one pair of vertical tracks. Providing at least one pair of pawls pivotally coupled to the housing. Providing the lift bar such that the said lift bar couples to the at least one pair of pawls and wherein the lift bar ensures the at least one pair of pawls pivot in unison with one another. Providing the at least one bias member such that the at least one bias member biases the said clamp to the first position. Providing the actuator handle, said actuator handle capable of being operated by a user so as to overcome the at least one bias member and move the clamp to the second position. And providing the clamp such that the downward pull of gravity on the clamp causes the pawls of the at least one pair of pawls to pivot toward each other.

In some embodiments, providing the at least one track may comprise locating the at least one track on the interior of the housing along at least one wall of at least one hollow cavity.

In some embodiments, providing the at least one track may comprise providing the at least one track such that the at least one track is vertical.

In some embodiments, providing the housing may further comprise providing at least one fixed gripping surface on the housing.

In some embodiments, providing the housing may comprise providing a back plate to which the at least one fixed gripping surface is coupled.

In some embodiments, providing the at least one fixed gripping surface may comprise providing the at least one fixed gripping surface such that the at least one fixed gripping surface is of a material which will firmly grip, but not deform a clamped object.

In some embodiments, providing the at least one pawl may comprise providing only a single pawl.

In some embodiments, providing the single pawl may comprise providing a fixed gripping surface opposite the single pawl.

In some embodiments, providing the single pawl and opposite fixed gripping surface may comprise providing the single pawl and the opposite fixed gripping surface such that the single pawl and the opposite fixed gripping surface are capable of automatically mimicking the girth of a clamped object.

In some embodiments, providing the lift bar may comprise providing an engagement surface on the lift bar for movement along the at least one track.

In some embodiments, providing the lift bar may comprise providing the lift bar such that the lift bar couples to a single pawl and wherein movement of the lift bar causes the single pawl to pivot about the pivot point.

In some embodiments, providing the actuator may comprise providing a depressible trigger.

In some embodiments, providing the clamp may comprise providing the housing such that said housing may comprise at least one hollow cavity with at least one vertical track running along at least a part of the hollow cavity. Providing at least one fixed gripping surface. Providing the at least one pawl wherein providing the at least one pawl comprises providing a single pawl pivotally coupled to the housing. Providing the lift bar such that the said lift bar has an engagement surface for engaging the at least one vertical track, and such that the lift bar couples to the single pawl, causing it to pivot about the pivot point as the lift bar moves along the said track. Providing the least one bias member such that the at least one bias member biases the said clamp to the first position. Providing the actuator, such that said actuator is capable of being operated by a user so as to overcome the at least one bias member and move the clamp to the second position. And providing the clamp such that the downward pull of gravity on the clamp causes the single pawl to rotate toward the at least one fixed gripping surface.

In accordance with another embodiment of the disclosure, a clamp may comprise a guide plate having a first end, a second end, and a plurality of surfaces, first gripper mounted on one of the plurality of surfaces, and a second gripper slidingly coupled to one of the plurality of surfaces, said second gripper located between said first gripper and said second end. The clamp may also comprise an actuator, said actuator rotatably attached to said guide plate, the actuator configured and positioned on said guide plate such that rotation of said actuator moves said second gripper towards said first gripper. The clamp may also comprise at least one bias member configured to bias the second gripper to a first position.

In some embodiments, the at least one bias member may be a compression spring.

In some embodiments, said second gripper is mounted to a slider sled, said slider sled being in sliding connection with said guide plate and configured to allow said second gripper to move between the first position and a second position.

In some embodiments, the clamp may further comprise at least one spring support mounted to said slider sled. Said at least one spring support may comprise at least one portion with a diameter less than a diameter of said at least one compression spring. Said portion of said at least one spring support may be positioned to fit inside the diameter of said at least one compression spring.

In some embodiments, the at least one spring support may further comprise an expanded end, wherein said expanded end is an end nearest to said first gripper, and wherein said end has a diameter greater than the diameter of said at least one compression spring.

In some embodiments, the clamp may further comprise a pressure plate, said pressure plate slidingly coupled to both said slider sled and to said guide plate, and may further comprise a projection, said projection located adjacent to said actuator and positioned such that rotation of said actuator moves said projection towards said first gripper.

In some embodiments, the clamp may further comprise at least one bias member housing attached to said pressure plate. Said at least one bias member housing may be hollow and may comprise a sealed end. Said at least one bias member housing may comprise a diameter greater than the diameter of said at least one bias member.

In some embodiments, the clamp may further comprise a bias member located on said guide plate and oriented such that movement of said second gripper towards said first gripper stores mechanical energy in said bias member.

In some embodiments, the guide plate may further comprise a bias member support, said bias member support coupled to said guide plate and sized to support said bias member.

In some embodiments, at least one of said second gripper or said first gripper may be comprised of a material which will firmly grip, but not deform a clamped object.

In some embodiments, at least a part of at least one of the first gripper or second gripper may be comprised of polyurethane.

In some embodiments, at least one of said second gripper or said first gripper may be at least partially covered by a removable surface.

In some embodiments, at least one of said second gripper or said first gripper may comprise at least one approximately semi-circular or contoured face.

In some embodiments, one of the plurality of surfaces of said guide plate may comprise a support wall, said support wall supporting said first gripper. In some embodiments, the support structure may further comprise one or more buttresses, said buttresses extending from support wall to said guide plate.

In some embodiments, said actuator may comprise a handle.

In some embodiments said actuator may comprise a cam with at least one flat segment.

In accordance with another embodiment of the present disclosure, a clamp may comprise a guide plate having a first end, a second end, and a plurality of surfaces, a first gripper coupled to one of the plurality of surfaces, a second plate slidingly coupled to one of the plurality of surfaces of the guide plate, a second gripper coupled to the second plate, and at least one bias member, said bias member coupled to both said guide plate and said second plate.

In some embodiments, the guide plate may further comprise a member adapted as a palm support. Said member may be U-shaped.

In some embodiments, the second plate may further comprise a rack. Said second plate may further comprise a second member, said second member adapted as a handle. Said handle may be U-shaped.

In some embodiments, at least one of said second gripper or said first gripper may be comprised of a material which will firmly grip, but not deform a clamped object.

In some embodiments at least one of said second gripper or said first gripper may be at least partially covered by a removable surface.

In some embodiments at least one of said second gripper or said first gripper may comprise at least one approximately semi-circular or contoured face.

In some embodiments, one of said plurality of surfaces of said guide plate may comprise a support wall, said support wall supporting said first gripper.

In some embodiments, the clamp may further comprise one or more buttresses, said buttresses extending from said support wall to said guide plate.

In some embodiments, said second plate may comprise a support wall, said support wall supporting said second gripper.

In some embodiments, the second plate may further comprise one or more buttresses, said buttresses extending from said second plate support wall to said second plate.

In some embodiments, the clamp may further comprise a pinion gear in operative engagement with said rack of said second plate.

In some embodiments, said second plate comprises an aperture through which the pinion gear project. In some embodiments, at least one edge of said aperture may comprise the teeth of said rack.

In some embodiments, the clamp may further comprise a gear shaft, said gear shaft coupled to said guide plate. Said pinion gear may rotate about the axis of said gear shaft.

In some embodiments, the clamp may further comprise a ratcheter.

In some embodiments, said ratcheter may comprise a ratcheting lever, said ratcheting lever may comprise, a ratcheting lever input structure, a ratcheting lever output structure and, a ratcheting lever hub rotatable about the axis of the gear shaft and to which the ratcheting lever input structure and output structure are coupled.

In some embodiments the input structure of the ratcheting lever may comprise a ratcheting lever handle.

In some embodiments, the output structure of the ratcheting lever may comprise one or more members. The members of the output structure may support at least one pawl.

In some embodiments, actuation of the ratcheting lever may cause the pawl to operatively engage the pinion gear through an orifice in the ratcheting lever hub.

In some embodiments, actuation of the ratcheting lever may cause the second gripper to displace from the first position toward a second position.

In some embodiments, the clamp may further comprise an over-center linkage wherein the over-center linkage is in an over-center position when the second gripper is in one of the first position and second position.

In some embodiments, the clamp may be for use with medical devices.

In some embodiments, the at least one bias member may be an extension spring.

In some embodiments, the untensioned length of said extension spring may be slightly less than the distance between an extension spring coupling point on the guide plate and an extension spring coupling point on the second plate.

In accordance with another embodiment of the present disclosure a clamp may comprise a housing having a first end, a second end, and a plurality of surfaces. The clamp may comprise a first gripper base coupled to one of said plurality of surfaces. The clamp may comprise a second gripper base slidable about one of the said plurality of surfaces, said second gripper base located between said first gripper base and said second end. The clamp may also comprise at least one bias member, an actuator, said actuator rotatably coupled to said housing, and at least one gear.

In some embodiments, the at least one of the at least one gear may be an eccentric cam gear.

In some embodiments, the first gripper may be coupled to the first gripper base and a second gripper may be coupled to the second gripper base.

In some embodiments, at least one of said mobile gripper or said fixed gripper may be comprised of a material which will firmly grip, but not deform a clamped object.

In some embodiments, at least one of said first gripper or said second gripper may be at least partially covered by a removable surface.

In some embodiments, at least one of said first gripper or said second gripper may comprise at least one approximately semi-circular or contoured face.

In some embodiments, said actuator may be a handle. The handle may be roughly L-shaped comprising a horizontal arm and a vertical arm. Said vertical arm may comprise a latch housing sized to accommodate an actuator handle latch.

In some embodiments, the latch housing comprises at least one bias member, said bias member positioned to bias said actuator handle latch to a first position.

In some embodiments, the said actuator handle latch may catch on a structure of the housing when in the first position disallowing any rotation of the actuator.

In some embodiments, the clamp may further comprise a slider sled.

In some embodiments, said slider sled may comprise at least one guide recess sized to fit a guide projection on said second gripper base.

In some embodiments, the clamp may further comprise a slider sled, said slider sled may comprise a means for a slidably coupling to said second gripper base.

In some embodiments, the clamp may further comprise at least one bias member support coupled to at least one face of said slider sled.

In some embodiments, the at least one of the at least one bias member may be a coil spring.

In some embodiments, said bias member support may comprise a projection sized to fit within a coil diameter of a compression spring.

In some embodiments, the bias member support may further comprise an end, said end may be attached to said bias member support and may have a diameter greater than said coil diameter of said compression spring.

In some embodiments, at least one of the at least one gear may be eccentrically and rotatably coupled to a gear shaft.

In some embodiments, a gear shaft may rotate when the actuator is actuated.

In some embodiments, the clamp may further comprise at least one additional cam gear, said additional cam gear may be positioned to be rotated by said gear on said gear shaft.

In some embodiments, said additional cam gear may be eccentrically and rotatably attached to said second gripper.

In some embodiments, an additional cam gear may eccentrically and rotatably attached to said slider sled.

In some embodiments, said additional cam gear may be rotatably connected to said gear by a linkage.

In some embodiments, said linkage may be a roughly claw-shaped body, said linkage may be configured to restrict the arc through which the gear and additional cam gear are capable of rotating.

In some embodiments, the clamp may further comprise a latch, said latch may be an operatively displaceable body secured to said first gripper base.

In some embodiments, said latch may comprise at least one surface that defines a catch.

In some embodiments, the latch may catch at least one portion of the actuator, disallowing further actuation of the actuator.

In some embodiments, the clamp may further comprise a latch, said latch may be an operatively displaceable body secured to said first gripper base. Said latch may comprise at least one surface defining a catch, said catch capable of engaging a portion of the horizontal arm of the handle and thereby disallowing further actuation of said handle.

In some embodiments, said latch may comprise a trough flanked by at least one sloped surface.

In some embodiments, the latch may further comprise at least one bias member configured to bias the latch to a first position.

In some embodiments, the latch may assume a second position during at least a part of actuation of the actuator.

In some embodiments, the latch may be in the first position after full actuation of the actuator and operatively engage the actuator to prevent further actuation of the actuator.

In accordance with another embodiment of the present disclosure a clip may comprise a torsion latch, said torsion latch comprising a beam having a front, a back, and a bottom. The clip may further comprise at least one spring holder, said spring holder comprising a pair of approximately circular projections attached to said bottom of said torsion latch. The clip may further comprise at least one torsion spring, said torsion spring sized to fit between said pair of approximately circular projections. The clip may further comprise at least one latch hook. The at least one latch hook may comprise a notch. The torsion latch may further be configured to pivot between a first position and a second position.

In some embodiments, the clip may be configured to attach a medical device to a support structure.

In some embodiments, the clip may further comprise a latch wedge, said latch wedge may be a triangular prism projecting from at least a portion of said front of said torsion latch.

In some embodiments, the latch may further comprise at least two latch hooks.

In accordance with another embodiment of the present disclosure a clamp may comprise a housing, first and second gripper jaws, both of said gripper jaws at least partially contained within said housing, a first bracket comprising part of said first gripper jaw, and a second bracket comprising part of said second gripper jaw, a first gripping surface coupled to at least one surface of the first bracket, a second gripping surface coupled to at least one surface of the second bracket, at least one gear, said gear operatively coupled to said first gripper jaw and said second gripper jaw, and at least one bias member attached to said housing and to at least one of the first and second gripper jaws.

In some embodiments, the at least one bias member may comprise two bias members, one of said bias members extending from said first gripper jaw to said housing, the other of said bias members extending from said second gripper jaw to said housing.

In some embodiments, the bias members may be extension springs.

In some embodiments, the first and second gripper jaws may comprise at least one toothed surface.

In some embodiments, said at least one gear is a pinion gear may operatively engage with at least one of said toothed surfaces of said first or said second gripper jaw.

In some embodiments, the clamp may further comprise a handle, said handle pivotally attached to said first gripper jaw. Said handle may be moveable between a first and a second position.

In some embodiments, the clamp may further comprise at least one linkage, said linkage may extend from said handle to said first gripper jaw.

In some embodiments, at least one of the at least one linkages may be an over-center linkage.

In some embodiments, at least one of the at least one linkages may operatively couple the handle to a cam, such that when said handle is moved to said second position, said cam pushes said first gripper jaw and said second gripper jaw closer together.

In some embodiments, the over-center linkage may be in an over-center position when the handle is in the second position.

In accordance with another embodiment of the present disclosure a clamp may comprise a base for attaching an object, said base having a centerline. The clamp may also comprise a pair of grippers, said pair of grippers oriented obliquely to said centerline of said base.

In some embodiments, the object may be a medical device.

In accordance with another embodiment of the present disclosure a clamp may comprise a housing, first gripper and second gripper, at least one of the first and second grippers being moveable, and and actuator. The actuator may be configured to actuate the moveable gripper of the first and second grippers between a first position and a second position. The clamp may further comprise at least one linkage. The at least one linkage may operatively couple the actuator to the mobile gripper. The clamp may further comprise at least one bias member configured and positioned so as to supply a clamping force when the moveable gripper of the first and second grippers is in one of the first and second positions.

In some embodiments, said at least one linkage may be an over-center linkage. The over-center linkage may be in an over-center orientation when the mobile gripper is in one of the first position and second position.

In some embodiments, said first gripper and second gripper may be oriented obliquely to a centerline of said clamp.

In some embodiments, said moveable gripper may be slidingly coupled to a driven member.

In some embodiments, said driven member may be slidingly coupled to the housing.

In some embodiments, at least two of the bias members may be compression springs, said compression springs may be positioned such that when compressed the compression springs are configured to exert a clamping force on a clamped object.

In some embodiments, at least one bias member may be a constant force spring, said at least one constant force spring may be positioned such that when unwound a clamping force is exerted against a clamped object.

In some embodiments, the actuator may be a handle.

In some embodiments, at least one of the at least one bias members may be an extension spring said extension spring attached to said handle at a first end and to said housing at a second end.

In some embodiments, said at least one extension spring may be an over-center spring and may be in an over-center orientation when the moveable gripper is in one of first position and second position.

In some embodiments the clamp may further comprise a latch, said latch may be pivotally coupled to said actuator and comprising a latch projection.

In some embodiments, said latch may be pivotable between a first position and a second position. Said latch may comprise a latch body with a plurality of faces at least one of which may further comprise at least one ergonomic feature.

In some embodiments, the latch may be biased to the first position by at least one torsion spring.

In some embodiments the clamp may further comprise a latch catch, said latch catch may be a part of one of the first gripper jaw and second gripper jaw.

In some embodiments, said latch catch may be configured to retain said latch projection when said actuator has actuated the moveable gripper to one of the first position and second position.

In some embodiments, pivoting the latch from the first position to the second position may release the latch projection from said latch catch.

In some embodiments, the clamp may be for use with medical devices and medical accessories.

In some embodiments, the housing may include a means of coupling the clamp to a load. The load may be a medical device. In some embodiments, the medical device may be a peristaltic infusion pump or syringe pump infusion pump.

In some embodiments, at least at part of at least one of the grippers may comprise a gripping surface being of a material which may firmly grip, but not deform a clamped object.

In some embodiments, the said gripping surface may be removable and/or replaceable.

In some embodiments, the said gripping surface may comprise a semi-circular or contoured face.

In one embodiment of the present disclosure, a clamp includes a housing, a fixed gripper, a driven member, a moveable gripper and an actuator. The housing includes first and second tracks. The fixed gripper is coupled to the housing. The driven member is configured to slide within the first and second tracks of the housing. The moveable gripper is operatively coupled to the driven member. The actuator is configured to move the driven member towards a first position to thereby move the moveable gripper towards the fixed gripper. The actuator is further configured to move the driven member towards a second position to thereby move the moveable gripper away from the fixed gripper. The actuator may be a handle pivotally coupled to the housing. The clamp may further include first and second linkages. The first linkage may be coupled a first side of the handle and a first side of the driven member, and the second linkage may be coupled to a second side of the handle and to a second side of the driven member.

The clamp may further comprise a gripper sled slidably coupled to the driven member. A bias member may be configured to bias the gripper sled within the driven member towards the fixed gripper.

The driven member may include a stop member configured to prevent movement of the gripper sled relative to the driven member beyond a predetermined location of the driven member. The moveable gripper may be coupled to the gripper sled.

The bias member may be a constant force spring, a compression spring, or other compressible or expandable spring.

The clamp may be configured to allow the gripper sled to stop when abutting against an object while allowing the driven member to continue to move as the actuator is further actuated.

The gripper sled may be rigidly coupled to the moveable gripper, and the clamp may further include a bias member configured to bias the gripper sled within the driven member towards the fixed gripper.

In yet another embodiment, a clamp includes a housing, a fixed gripping means, and a moveable gripping means. The fixed gripping means is for rigidly being coupled to the housing. The moveable gripping means is for gripping the clamp onto an object.

Rack Apparatus and Rack System

In the present disclosure, a rack may include a support member that has a first end portion and a second end portion that is opposite to the first end portion. The rack may also include at least one mount. The at least one mount may be coupled to the support member and may be disposed on the support member between the first end portion and the second end portion of the support member. In addition, a clamp may be coupled to the support member, and the clamp may be configured to have a clamped position and an unclamped position.

In an exemplary embodiment, the support member may be a cylindrically shaped object, such as a pole. In certain embodiments, the at least one mount may be approximately perpendicular to the support member. The at least one mount may also be elongated in a first direction, wherein the first direction is approximately perpendicular to the support member. The at least one mount may also include a substantially planar surface. Similarly, each of the at least one mount may be a plate. Additionally, the at least one mount may be pivotally connected to the support member. The at least one mount may also be configured to rotate about a longitudinal axis of the support member. Furthermore, the at least one mount may be hingably coupled to the support member. In certain embodiments, the hinge may be configured to have an axis of rotation in a transverse plane of the support member. In other embodiments, the hinge may be configured to have an axis of rotation in a longitudinal plane of the support member. In addition, the at least one mount may be removably coupled to the support member. Alternatively, the at least one mount may be fixedly coupled to the support member. The at least one mount may also include a flange that extends upwardly from a second end of the at least one mount, wherein the second end of the at least one mount is opposite to a first end of the at least one mount.

In a preferred embodiment, the at least one mount may be configured to receive a medical device. The medical device may be attachable to any one of the at least one mount. Likewise, the medical device may be detachable from any one of the at least one mount.

The rack may further comprise a base member that may be coupled to the support member. The base member may be positioned in spaced relation to the support member and may be configured to provide a moment of force that is sufficient to counteract a moment of force about the clamp of the rack. In a preferred embodiment, the base member may be configured to abut a support structure at a resting point and thereby position the support member at a distance away from the support structure. The base member may include a notch at the resting point where the base member abuts the support structure, and the notch may have a radius of curvature. Alternatively, the base member may include a clamp that is configured to clamp onto a support structure. In a preferred embodiment, the base member may be operatively coupled to the second end portion of the support member. In embodiments where the base member is coupled to the second end portion of the support member, two or more wheels may be coupled to the base member. In certain embodiments the at least two wheels may be removably coupled to the base member. In other embodiments, a wheel assembly may couple at least two wheels to the base member. The wheel assembly may likewise be removably coupled to the base member. Furthermore, the base member may itself be configured to receive a medical device.

The clamp of the rack may include a fixed gripper and a mobile gripper. In a preferred embodiment, the clamp may be operatively coupled to the first end portion of the support member. To couple with a support structure, the mobile gripper may move in a first direction towards the fixed gripper. To decouple from the support structure, the mobile gripper may move in a second direction away from the fixed gripper. The fixed gripper and the mobile gripper may be shaped to couple with a range of different support structures. Thus, the clamp may be configured to removably couple with a support structure when the clamp is in clamped position.

To enable the at least one mount, the support member, and the clamp to be carried as a group, the rack may further comprise a handle that may be coupled to the first end portion of the support member and that may be disposed above the at least one mount. The handle may approximate the shape of a "U" and may be configured to extend in an approximately perpendicular direction to the support member.

Each of the at least one mount may also include a respective connector. The connector may be configured to interface with a medical device, such as a monitoring client. In a preferred embodiment, the respective connector of the at least mount may be configured to receive power. The power may be supplied by a power system that is configured to supply power to the respective connector of the at least one mount. The power system may be configured to receive balanced alternating-current power and to supply direct-current power to the respective connector of the at least one mount. Similarly, the power system may be configured to receive unbalanced alternating-current power and to supply direct-current power to the respective connector of the at least one mount. The power system may include a power-supply system that is operatively coupled to the support member, and each of the at least one mount may include a respective power-transmission system that is configured to provide power to the respective connector of the at least one mount. The base member may operatively include elements of the aforementioned power system.

In certain embodiments, the respective connector of the at least one mount may be configured to carry signals. To carry signals between respective connectors, each of the at least one mount may include a respective support-plate bus that is connected to the respective connector therein, and the respective support-plate bus may interface with a central bus that is operatively coupled to the support member.

Substantially rigid materials such as aluminum alloys, stainless steel alloys, steel alloys, and engineering polymers may be used to construct the rack and components like the at least one mount, the support member, the base member, and the clamp. In addition, at least a portion of the support member, the at least one mount, the base member, and the clamp may include an antibacterial, an antimicrobial, or an antiviral coating.

A rack system may include the rack described above. The rack system may further comprise at least one device that may be adapted to be received by any one of the at least one mount of the rack. The device may further include a clamp mechanism that is configured to operatively and removably couple with the support member of the rack. In addition, the device may include a connector that may be configured to electrically communicate with the respective connector of any one of the at least one mount. The clamp mechanism of the at least one device may comprise any one of the clamp mechanisms described above. In a preferred embodiment of the rack system, the device may be a medical device.

Protective Mechanisms

In some embodiments of the present disclosure, the connectors may be disposed on protective mechanisms that may be coupled to the rack. In one specific embodiment, a protective mechanism includes: a guide member; a connector that is coupled to the guide member; an actuation member having first and second end portions, wherein the first end portion of the actuation member is pivotally coupled to the guide member; and a cover member that may be pivotally coupled to the guide member. The cover member may be configured to interact with the actuation member so as to pivot to thereby uncover the connector when the actuation member pivots in a first direction and to pivot to cover the connector when the actuation member pivots in a second, opposite direction. The protective mechanism may also include a backstop member that is disposed on a guide member face. The backstop member may also have a backstop member face that is approximately perpendicular to the guide member face. The connector may be disposed on the backstop member face.

In a specific embodiment, the cover member of the protective mechanism may be adapted to uncover the connector when the actuation member pivots from a first position to a second position. The cover member may be adapted to cover the connector when the actuation member pivots in a second, opposite direction from the second position to the first position. The backstop member face may define a recess or an aperture that is configured to receive at least a portion of the cover member when the cover member is completely uncovered and the actuation member is in the second position.

In yet another embodiment of the present disclosure, the protective mechanism may further comprise a compliant gasket that may be coupled to the backstop member and configured to encompass the connector. The cover member may include a perimeter rib that may be adapted to seal against the compliant gasket when the actuation member is in the first position and the connector is covered by the cover member. In some embodiments, the compliant gasket may include a first portion, a second portion, and a transitional portion between the first and second portions of the compliant gasket; the perimeter rib may be adapted to seal against at least the first portion of the compliant gasket when the actuation member is in a first position and the connector is covered, and the perimeter rib may be adapted to seal against at least the second portion of the compliant gasket when the actuation member is in the second position and the connector is uncovered.

To receive a device, the protective mechanism may further comprise first and second rail projections. Each rail projection may have a web portion and a wider head portion such that the web portion couples the head portion to the guide member face. The first and second rail projections may be disposed on the guide member face such that they are approximately parallel and in spaced relation to one another. Between the first and second rail projections, the guide member may define an aperture that extends from a first guide member face (the aforementioned guide member face) to a second guide member face, or the guide member may define a recess that is disposed on the guide member face. Both the recess and the aperture may be adapted to receive a portion of the actuation member.

The actuation member of the protective mechanism may include a sloped face that defines a sloped portion of the actuation member. In some embodiments, due to the sloped face, the sloped portion of the actuation member may increase in cross-sectional area from the first end portion of the actuation member to a point where the sloped face ends between the first and second end portions of the actuation member. The sloped face may slope such that the sloped face protrudes from the plane of the guide member face when the actuation member is in a first position and when the actuation member is in a second position. The sloped face may lie substantially in the plane of the face guide member face. The protective mechanism may further comprise at least one actuation spring that may bias the actuation member such that the actuation member may automatically return to the first position under the force of the actuation spring. Thus, the at least one actuation spring may have a first end that is coupled to the actuation member and a second end that is coupled to the guide member.

The protective mechanism may also include a latch member that may be pivotally coupled to the guide member at a pivot point between first and second end portions of the latch member. Additionally, the latch member may define an aperture that is capable of receiving at least a portion of the actuation member, and the latch member may include a latch projection that may be disposed on the first end portion of the latch member and protrude from the face of the guide member when the latch member is in a latched position Like the actuation member, the latch member may be adapted to automatically return to the latched position under the force of one or more latch springs. Thus, each of the one or more latch springs may have a first end that is coupled to the backstop member and a second end that is coupled to the latch member at a point between the pivot point and the second end portion of the latch member. To arrest pivotal movement of the latch member under the force of the at least one latch spring, the protective mechanism may further comprise at least one arrester projection that may be coupled to the guide member and disposed in spaced relation to the pivot point of the latch member such that the at least one arrester projection may arrest pivotal movement of the latch member when the latch member pivots to the latched position.

In an embodiment of the present disclosure, the cover member is a protective member that includes a cover portion. The protective member may have a first end portion that is coupled to one of the guide member and the backstop member, and the protective member may have a second end portion that includes the cover portion. To protect the connector, the protective member may be adapted to engage with the actuation member such that pivotal movement of the actuation member in a first direction from the first position to the second position may cause the protective member to pivot from a protective position to a non-protective position, and thereby uncover the connector. Likewise, pivotal movement of the actuation member in a second, opposite direction from the second position to the first position may cause the protective member to pivot from the non-protective position to the protective position to thereby cover the connector.

The actuation member of the first embodiment may include first and second channeled projections disposed on the second end portion of the actuation member. The first and second channeled projection may be spaced apart such that a portion of the protective member may be received between them. To enable the actuation member to actuate the protective member, the protective member may include first and second actuation projections that are adapted to respectively engage the first and second channeled projections of the actuation member. Thus, the first and second channeled projections may respectively include a first channel and a second channel, wherein each channel is shaped and sized such that pivotal movement of the actuation member form the first position to the second position may cause the protective member to pivot from the protective position to the non-protective position.

In some embodiments of the present disclosure, the protective mechanism may include a latch member. Furthermore, the first embodiment of the protective mechanism may include a latch member that defines a latch aperture between the first end portion of the latch member and the pivot point of the latch member. The latch aperture may be configured such that the actuation member may pass through the latch aperture when the actuation member is in the first position, and the latch aperture may receive at least the cover portion of the protective member when actuation member is in the second position and the protective member is in the non-protective position.

The first embodiment of the protective mechanism may further comprise a compliant gasket that may be coupled to the backstop member and encompass the connector. To seal the connector within the compliant gasket, the cover portion of the protective member may include a perimeter rib that is adapted to seal against the compliant gasket when the protective member is in the protective position.

A second embodiment of the protective mechanism may differ from the first embodiment of the protective mechanism. The second embodiment of the protective mechanism may include at least one first link-member and at least one second link-member. Each of the at least one first link-member may be configured to have a respective first end portion and a respective second portion such that the respective first end portion may be pivotally coupled to the second end portion of the actuation member. Likewise, each of the at least one second link-member may have a respective first end portion and respective second portion. The respective first end portion of the at least one second link-member may be pivotally coupled to each of the backstop member at a first point and the respective second end portion of a respective at least one first link-member at a second point. The first point and the second point may be disposed in spaced relation such that pivotal and substantially translational movement of the second end portion of the actuation member may be transmitted through the at least one first link-member and thus cause the at least one second link-member to pivot about the first point.

The cover member of the second embodiment of the protective mechanism may be pivotally coupled to the respective second end portion of the at least one second link-member such that the cover member may pivot to a non-protective position, and thereby uncover the connector, when the actuation member pivots in the first direction and to pivot to a protective position, and thereby cover the connector, when the actuation member pivots in the second direction. To enable the at least one second link-member to couple with the cover member, the second embodiment of the protective mechanism may further comprise an at least one pass-thru aperture defined by the backstop member, and each of the at least one second link-member may be disposed within a respective at least one pass-thru aperture.

In yet another embodiment of the present disclosure, the protective mechanism may include a compliant gasket. The compliant gasket may be coupled to the backstop member and have a first portion, a second portion, and a transition portion between the first portion and the second portion of the compliant gasket. The first portion of the compliant gasket may be configured to encompass the connector. The transition portion of the compliant gasket may be configured to encompass each of the at least one pass-thru aperture. And the second portion of the compliant gasket may be configured to mirror the first portion of the compliant gasket.

To seal against the compliant gasket, the cover member may include a perimeter ridge. The perimeter ridge may be adapted to compress the first portion of the compliant gasket and a portion of the transition portion such that the perimeter ridge encompasses the connector and each of the at least one pass-thru apertures when the cover member is in the protective position. When the cover member is in the non-protective position, the perimeter ridge may be adapted to seal against the compliant gasket such that the perimeter ridge compresses the second portion of the compliant gasket and a portion of the transition portion such that the perimeter ridge encompasses each of the at least one pass-thru aperture.

The protective mechanism may further include a backstop member recess or a backstop member aperture defined by the backstop member face. The backstop member recess and the backstop member aperture may be configured to receive at least a portion of the cover member when the cover member is in the non-protective position.

The protective mechanism may be one embodiment of a component of a system for receiving a device. The system for receiving a device may comprise at least one protective mechanism and at least one receivable device. The at least one protective mechanism may include a guide member having a guide member face, a connector that is coupled to the guide member, an actuation member, a cover member, and at least one rigid member disposed on the guide member. The actuation member may be configured to have a first end portion and a second end portion, wherein the first end portion may be pivotally coupled to the guide member, and thus, the actuation member may pivot in a first direction from a first position to a second position and in a second direction from the second position to the first position. The cover member may be pivotally coupled to the guide member and adapted to interact with the actuation member so as to pivot to uncover the connector when that actuation member pivots in the first direction and to pivot to cover the connector when the actuation member pivots in the second, opposite direction. In any embodiment described herein, the protective mechanism may be adapted to be a protective mechanism of the system for receiving a device.

The at least one receivable device of the system for receiving a device may comprise a connector and an at least one channel. The connector may be disposed on the receivable device such that it is capable of interfacing with the connector of the at least one protective mechanism. The at least one channel may be disposed on the receivable device and configured to receive the at least one rigid member of a respective at least one protective mechanism. The at least one receivable device may further comprise a respective latch recess defined by a respective face of the at least one receivable device. The respective latch recess may be adapted to engage with a latch member projection of the at least one protective mechanism such that the at least one receivable device is securely received by the at least one protective mechanism.

BRIEF DESCRIPTION OF THE DRAWINGS

These and other aspects will become more apparent from the following detailed description of the various embodiments of the present disclosure with reference to the drawings wherein:

FIGS. 3A-3E show several views of a clamp in accordance with an embodiment of the present disclosure;

FIGS. 4A-4D show several views of a clamp in accordance with an embodiment of the present disclosure;

FIGS. 5A-5D show several views of a clamp in accordance with an embodiment of the present disclosure;

FIGS. 6A-6G show several views of a clamp in accordance with an embodiment of the present disclosure;

FIGS. 12e-h depict a number of cross-sectional views of a clamshell mechanism in accordance with an embodiment of the present disclosure;

DETAILED DESCRIPTION

Clamp Mechanisms

Figure 1A:
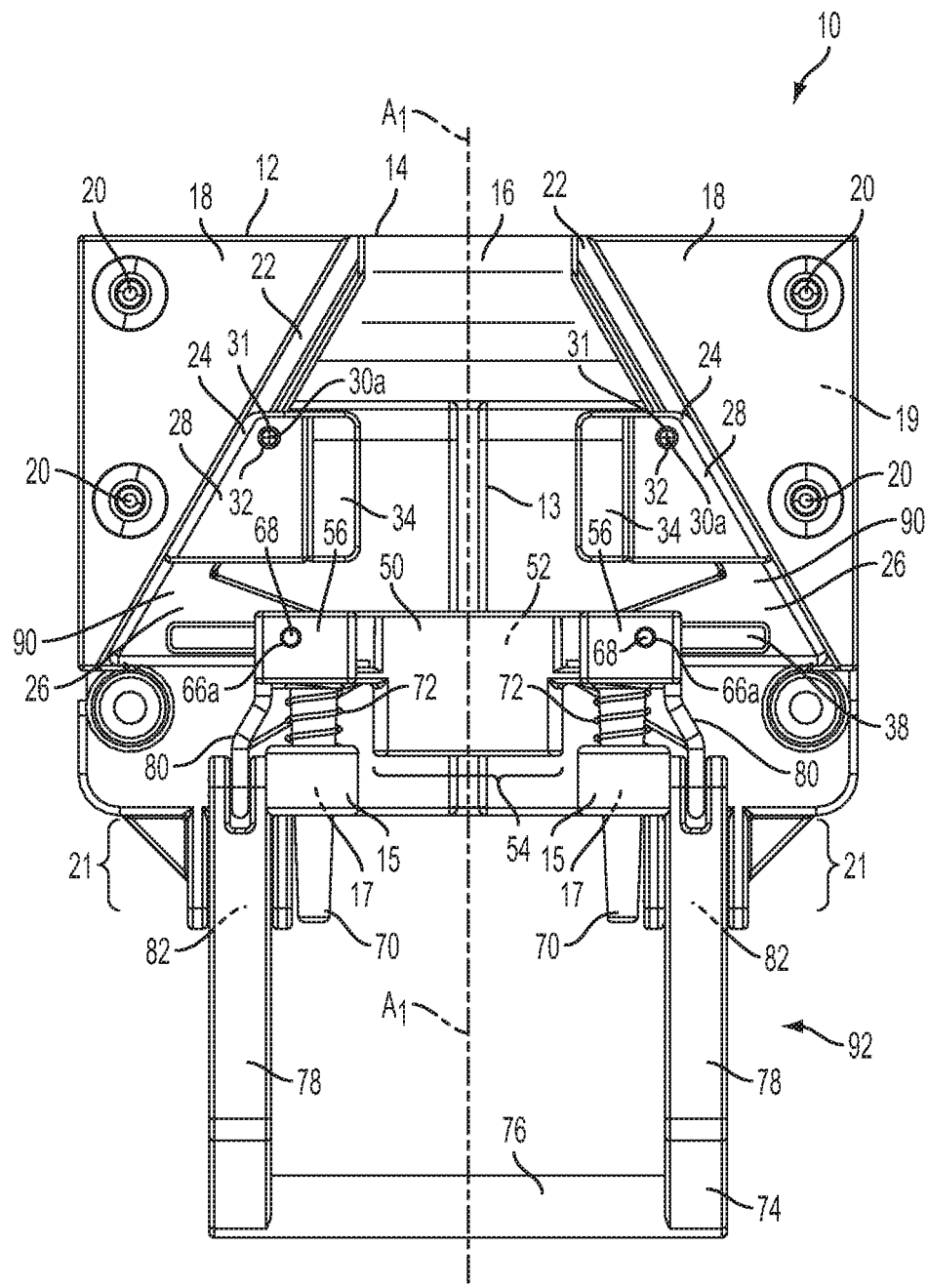
FIGS. 1A-1E show several views of a clamp in accordance with an embodiment of the present disclosure.

In one example embodiment, as shown in FIGS. 1A-1E, a clamp apparatus 10 is depicted. The clamp apparatus 10 comprises a housing 12. In the shown embodiment, the housing 12 has a back plate 14, which is generally planar. On one portion of the back plate 14 is a raised grip 16 extending away from the housing 12. The grip 16 affords the user ease of movement along a clamped object 100 generally extending along an axis A1. The grip 16 is also meant to aid in carrying. The grip 16 may be made of the same material as the rest of the housing 12, may be made of a different material, or may be made of a combination thereof. Possible materials may include, but are not limited to, rubber, polymer, composite, metal, plastic, foam, etc. Additionally, the grip 16 may comprise ergonomic finger groves, nubs, a ribbed texture, a honeycombed texture, etc.

The rear of the back plate 14 may also feature any of a variety of mechanisms 19 (not shown) to attach a load to the clamp apparatus 10. Such mechanisms 19 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

On the front portion of the back plate 14, a groove 13 runs vertically down the centerline (shown as a line of short and long dashes) of the back plate 14. The groove 13 is further described below. Two compression spring pockets 15 are coupled to the back plate 14 and are raised off the bottom of the front face of the back plate 14. The compression spring pockets 15 may be generally cylindrical and hollow much like a cup. The compression spring pockets 15 will be elaborated upon later.

Extending off the bottom edge of the back plate 14 toward the bottom of the page are two twin catch structures 21 which are symmetrical around the centerline of the back plate 14. The catch structures 21 are formed such that a first portion of the structure 21 is a member which extends toward the bottom of page in a manner substantially perpendicular to the bottom edge of the back plate 14. A second portion of the structure 21 is a member extending toward the bottom of the page in the same manner as the first portion. The first and second portions are offset from each other so as to allow a crosspiece to form a bridge between the first and second portion of the catch structure 21. The crosspiece of the catch structure 21 runs in a direction substantially parallel to the bottom edge of the back plate 14. The catch structure 21 will be further elaborated upon later.

In the example embodiment, two blocks 18 are fixedly coupled to the front of the back plate 14 by any variety of means. This could include, but is not to be limited to, screws 20 (as shown), bolts, welds, etc. The back plate 14 and blocks 18 can also be formed as a continuous part during manufacture. The blocks 18 are offset by some distance from the back plate 14.

The blocks 18 are generally right triangles with their hypotenuses facing A1. It should be appreciated, however, that the blocks 18 could take any shape so long as the interior face of the blocks 18 extends in a suitable direction. The blocks 18 also display symmetry around A1.

Along the inward facing sides of the blocks 18 there may be tracks 22. The tracks 22 may engage corresponding protrusions 24 on a surface of a sliding wedge 26. These components interact in such a way that the sliding wedges 26 are able to traverse the span of the tracks 22. In the example embodiment, the sliding wedges 26 are approximately "L" shaped, but this should not be construed as limiting the sliding wedges 26 to only an "L" shape. It should also be noted that in place of the protrusions 24 on the sliding wedge 26, any other type of suitable engagement surfaces, such as ball bearings or rollers, could be employed. In other embodiments, the track 22 may be raised off the blocks 18. In such embodiments, the protrusions 24 would be replaced by another suitable engagement surface such as a recessed groove, rollers, ball bearings, etc. In yet some additional embodiments, a track 22 comprises the rack portion of a rack and pinion, be the track 22 in a raised or recessed configuration; in place of the protrusions 24, on the sliding wedge 26, one or more pinion gears would extend so as to engage the rack track 22, in this specific embodiment.

At the top of both the sliding wedges 26, a pawl 28 may be pivotally coupled. In the embodiment shown in FIGS. 1A-1E this is accomplished by means of a pair of pins 30 (though a single pin, hinge, or other suitable arrangement could also be used) running through openings 32 which extend through both the sliding wedge 26 and the pawl 28. One pin 30a pivotally couples the pawl to the sliding wedge 26 through the front surfaces of the sliding wedge 26 and the pawl 28. Likewise, the second 30b of the pair of pins 30 (best shown in FIG. 1E) pivotally couples the pawl 28 to the sliding wedge 26 through the rear surfaces of the pawl 28 and the sliding wedge 26. Bushings 31 may also be present in some embodiments to provide a bearing surface.

On at least a portion of the pawls 28 there may be a gripping surface 34 which engages the clamped object 100. This gripping surface 34 consists of a material chosen for its gripping ability. The gripping surface 34 may be made of a high friction material, a compressible material, a material exhibiting both these qualities, or any other suitable material. The gripping surface 34 is made of a material which allows a firm grip without the deformation of a clamped object 100. Additionally, the gripping surface 34 may be contoured (as is easily seen in FIG. 1B).

Figure 1B:
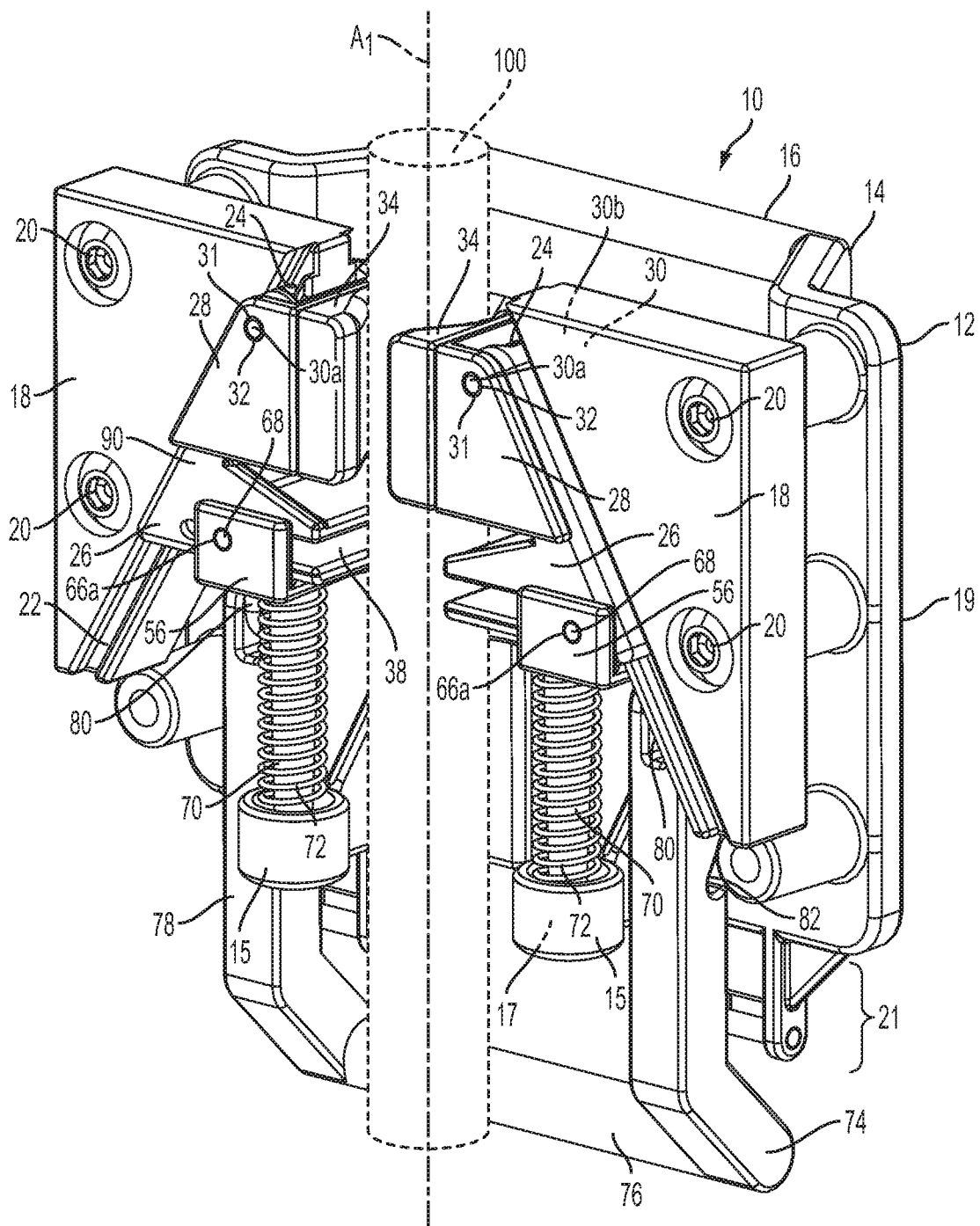
Figure 1C:
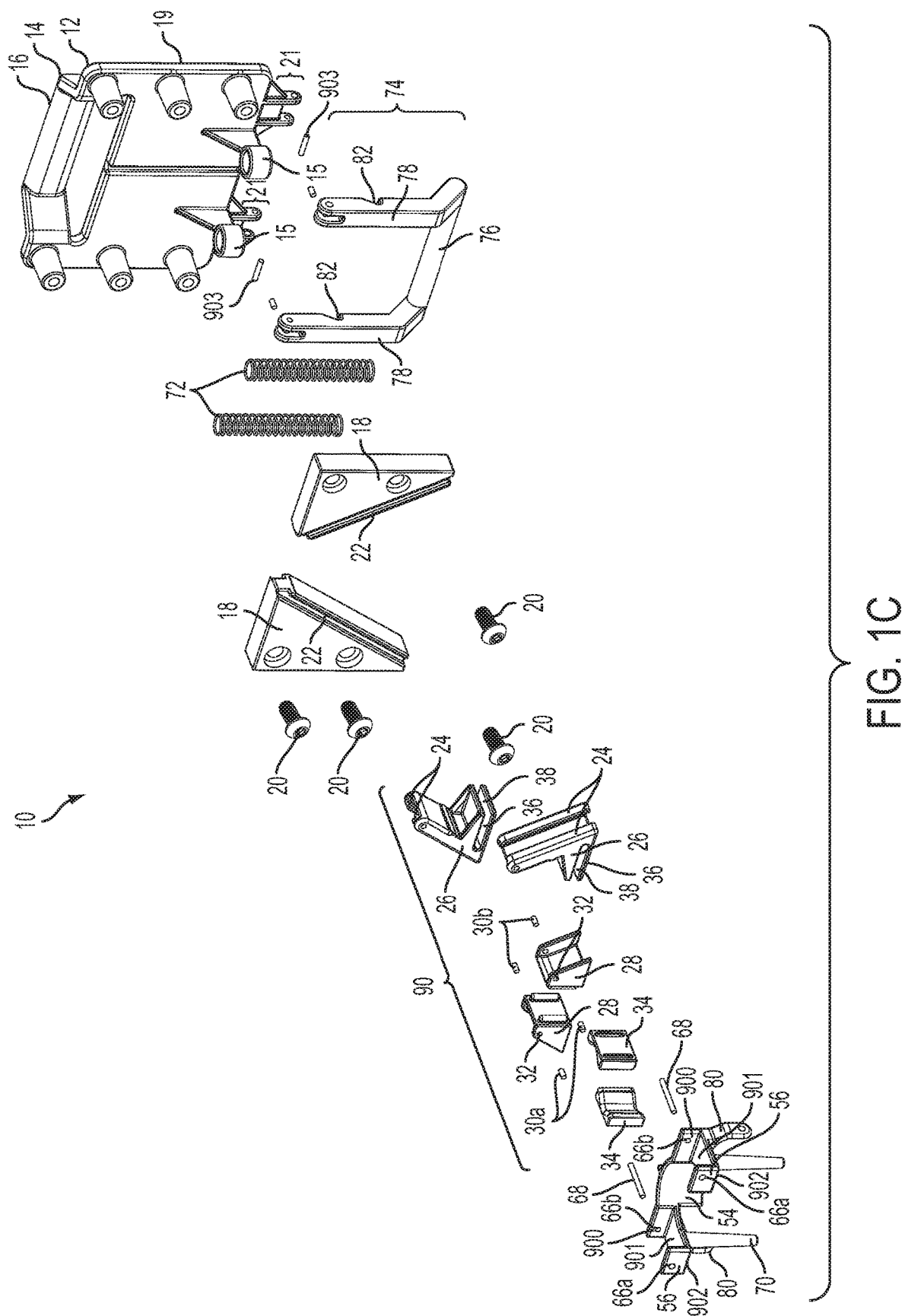
Figure 1D:
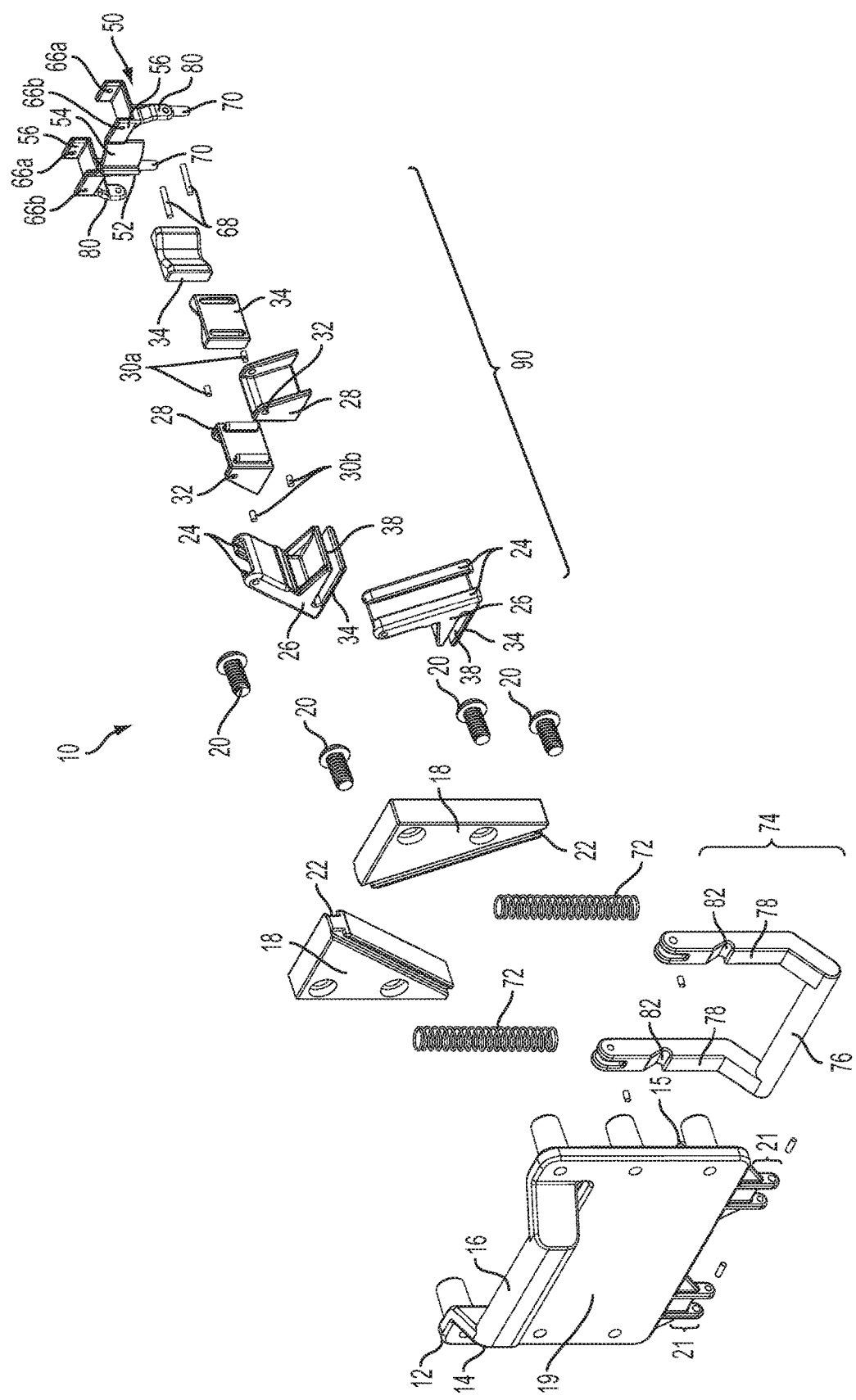
Figure 1E:
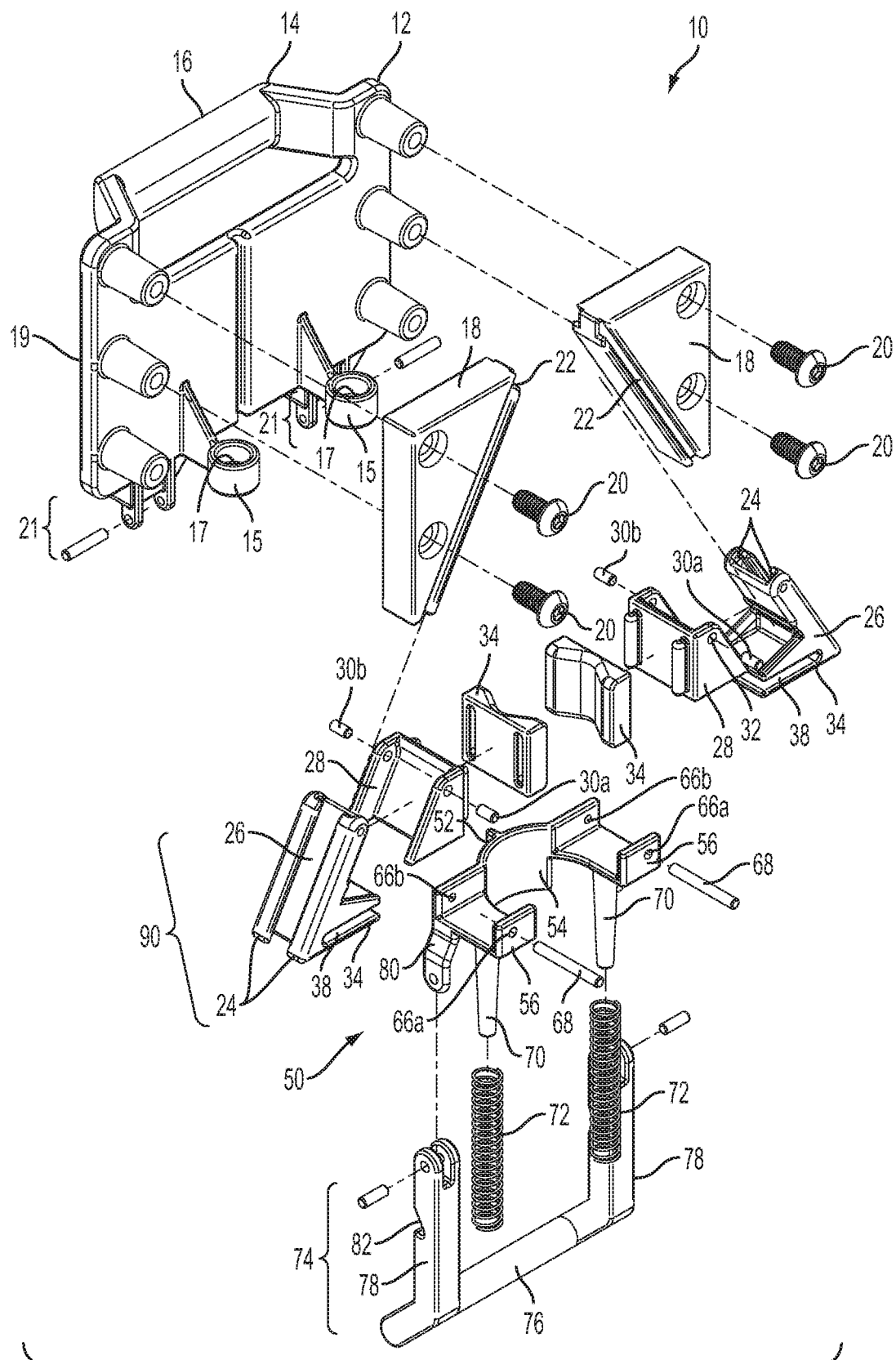

Best shown in the clamp apparatus 10 exploded views in FIGS. 1C-1E, the bottom of the sliding wedge 26 may feature a flange 36. The flange 36 extends inward, at an angle substantially perpendicular to the axial direction A1, from the portion of the sliding wedge 26 which engages the tracks 22. A slot 38 is cut into the flange 36 and will be elaborated upon later.

Together, the sliding wedge 26, the pawl 28, and the gripping surface 34 comprise a sliding wedge-pawl assembly 90. The sliding wedge-pawl assemblies 90 are capable of movement, together as a unit, up and down the track 22. This allows the clamp apparatus 10 to adjust to and grip clamped objects 100 of a variety of different girths such that the distance between the gripping surfaces 34 of the sliding wedge-pawl assemblies 90 mimics the diameter of a clamped object 100.

The clamp apparatus 10, in this exemplary embodiment, also comprises a second assembly, the spring handle assembly 92. At the top of the spring handle assembly 92 is a guided lift bar 50. The rear portion of the guided lift bar 50 has a vertical ridge 52 which engages with the vertical groove 13 in the back plate 14. This constricts the guided lift bar 50 to movement up and down in the axial direction A1.

In the embodiment shown in FIGS. 1A-1E, the center span 54 of the guided lift bar 50 arcs/curves or bends toward the back plate 14. This allows the guided lift bar 50 to better accommodate the clamped object 100.

On each the right and left side of the center span 54, a member 56 may be attached which fits around the flange 36 of the sliding wedge 26. The member 56 is formed such that a first portion 900 of the member 56 extends off the center span 54 on a plane substantially parallel to the back plate 14. Extending off the bottom of first portion 900 at an angle substantially perpendicular to the first portion is a second portion 901 of the member 56. This second portion 901 is formed such that the edge of the second portion 901 distal to A1 is straight and occupies the same vertical plane extended off the distal edge of the first portion 900. The edge of the second portion 901 of the member 56 proximal to A1 tapers toward the distal edge of the second portion 901. This taper again helps to accommodate the clamped object 100. The member 56 has a third portion 902 which is attached to the second portion 901 such that the bottom of the third portion 902 is coupled to the front edge of the second portion 901 at an angle that is substantially perpendicular. The third portion 902 extends on a plane parallel to the first portion 900. The edge of the third portion 902 distal to A1 is straight and occupies the same vertical plane extended off the distal edge of the first portion 900. The proximal edge of the third portion 902 is flush with the proximal, tapered edge of the second portion 901 and extends upwards from it in a substantially perpendicular manner.

In the example embodiment in FIGS. 1A-1E, the third portion 902 of the member 56 described above has a hole 66*a* creating a passage through the third portion 902. Likewise, the first portion 900 also has a hole 66*b* creating a passage through the first portion 900. The centers of both holes 66*a*, 66*b* extend along a common axis which is substantially perpendicular to the front face of each the first and third portions 900, 902 of the member 56. The locations of the holes 66*a* and 66*b* are selected such that they are in line with the slots 38 in the sliding wedges 26 when the clamp apparatus 10 is assembled. Placing the holes 66*a* and 66*b* at this location allows the insertion of dowels 68 through each of the holes 66*a* and 66*b* and their corresponding slots 38, thus coupling the sliding wedge-pawl assemblies 90 to the spring handle assembly 92. Though the example embodiments employ the use of a dowel 68 to couple the two assemblies together, other means of coupling the assemblies, such as but not limited to, a bar, rollers, ball bearings, etc. could be implemented.

In the example embodiment, when both assemblies 90 and 92 are coupled together, the guided lift bar 50 functions as a crossbar which ensures that the right and left sliding wedge-pawl assemblies 90 move together in unison along the tracks 22. This coupling also allows the spring handle assembly 92 to control whether the clamp apparatus 10 is in the open or closed position.

Coupled to the bottom of the second portion 901 of the members 56 a generally cylindrical shape 70 may be extended downward (in additional embodiments, other shapes may be used). As shown in the example embodiments in FIGS. 1A-1E, the generally cylindrical shape 70 may taper slightly in diameter as it extends farther away from the bottom of the second portion 901 of the member 56 toward the bottom of the page. The generally cylindrical shape 70 may be solid or hollow. A coil spring 72 surrounds the generally cylindrical shape 70. One end of the coil spring 72 abuts the bottom of the second portion 901 of the member 56 from which the generally cylindrical shape 70 extends. The other end of the coil spring 72 seats in the compression spring pocket 15 on the back plate 14 mentioned above. The bottom of the compression spring pocket 15 has a hole 17 through which the generally cylindrical shape 70 may pass as the clamp apparatus 10 is moved to/in the open position. Though the shown embodiments use a coil spring 72, other embodiments could conceivably employ any other suitable bias member. A wide variety of suitable bias members may be employed. Examples of suitable bias members include, but are not limited to, a gas spring using a bladder, a piston type arrangement, a compression spring made of a compressible, springy material such as rubber, an extension spring, a constant force spring, etc.

In the example embodiment, the coil springs 72 bias the clamp apparatus 10 toward the closed position (as shown in FIG. 1B). That is, the coil springs 72 bias the wedges 26 to slide up the tracks 22 such that the pawls 28 approach each other towards the clamped object 100 (e.g., a pole). In the closed position, the sliding wedge-pawl assemblies 90 are sufficiently at the top of the tracks 22 to clamp the pawls 28 onto the clamped object 100 (via attached gripping surfaces 34). The guided lift bar 50 is also at a higher position in the vertical groove 13 in the back plate 14. Also in this position, the coupling dowel 68, in relation to A1, is located in a more distal end of the slot 38 in the flange 36 of the sliding wedge 26.

If a clamped object 100 is present in the example embodiment, the coil springs 72 bias the clamping apparatus 10 to clamp down on the object 100. Depending on the size of the clamped object 100, the sliding wedge-pawl assemblies' 90 location on the track 22 will vary so that the distance between the sliding wedge-pawl assemblies 90 will mimic the diameter of the clamped object 100. The larger the clamped object 100 the lower the sliding wedge-pawl assemblies 90 will be on the track 22. Similarly and consequentially, the location of the guided lift bar 50 along the groove 13 will be lower with larger clamped objects 100.

The clamping apparatus 10 in the example embodiment is designed in such a way as to utilize the force of gravity to increase the clamping force. As gravity pulls on the clamp, especially when a load is attached to the back plate 14, a force is exerted on the sliding wedge-pawl assemblies 90.

This force causes the sliding wedge-pawl assemblies 90 to want to ride further up the tracks 22. Since the clamped object 100 is in the way, the sliding wedge-pawl assemblies 90 cinch up on and exert more clamping force on the clamped object 100. Additionally, because the pawls 28 are pivotally coupled to the sliding wedge 26, the pull of gravity causes the point of contact on the pawls 28 to want to swing up and into the clamped object 100. Since the clamped object 100 is in the way, the pawls 28 cinch up on and exert more clamping force on the clamped object 100.

In order to move the clamping apparatus 10 to the open position, a pull handle 74 may be pulled down. In the example embodiment, the pull handle 74 comprises a grip 76 and one or more posts 78 extending from the grip 76. The grip 76 may be made of the same material as the rest of the pull handle 74, may be made of a different material, or may be made of a combination thereof. Possible materials may include, but are not limited to, rubber, polymer, composite, metal, plastic, foam, etc. Additionally, the handle 74 may comprise ergonomic finger groves, nubs, a ribbed texture, a honeycombed texture, etc.

The one or more posts 78 of the pull handle 74 extend up to a corresponding number of arms 80 on the guided lift bar 50. The posts 78 are coupled to the arms 80 on the guided lift bar 50 through any of a variety of means. In the example embodiment, coupling is accomplished by means of a pin which runs through both the arm 80 and post 78. In other embodiments, this coupling may be accomplished in any number of suitable ways including, but not limited to, welds, bolts, screws, etc. The pull handle 74 and guided lift bar 50 could also be made as a single continuous part during manufacture. In some embodiments, the posts 78 extend straight down to the grip 76. In other embodiments, the posts 78 may be arcuated or have a bend out toward the rear of the page to allow greater ease in grasping the grip 76. Additionally, in some embodiments, including the example embodiment, the posts 78 have a notch 82 which runs across the back of the posts 78 in a direction substantially parallel to the bottom edge of the back plate 14.

As aforementioned, to move the clamping apparatus 10 from the closed position to the open position, a pull handle 74 may need to be pulled down. In the example embodiment, as the pull handle 74 is pulled down, the guided lift bar 50 is also pulled down the groove 13 in the back plate 14. This causes the compression springs 72 to become compressed and causes the generally cylindrical shape 70 to extend through the hole 17 in the compression spring pockets 15. Pulling down the pull handle 74 also causes the sliding wedge-pawl assemblies 90 to slide down the tracks 22. Due to the slope of the tracks 22, moving the clamping apparatus 10 to the open position also causes the location of the coupling dowel 68 within the slot 38 to change. When the clamp is in the fully open position, the coupling dowel 68 is at the most proximal end of the slot 38 in relation to A1.

In the example embodiment, to hold the clamping apparatus 10 in the fully open position against the restoring force of the compression springs 72, the notch 82 in the pull handle 74 may be engaged with the catch structure 21 extending off the back plate 14. When the clamping apparatus 10 is locked in the open position, the crosspiece 903 of the catch structure 21 is caught by the notch 82 of the pull handle 74 thereby disallowing the compression springs 72 to return the clamping apparatus 10 to the closed position. Other embodiments may employ other types of catch mechanisms in addition to the elbow type catch in the example embodiment. Other suitable catches may include, but are not limited to, a magnetic catch, a ball catch, a latch, a roller catch, etc.

In another embodiment, as shown in FIGS. 2A-2E, a clamp apparatus 110 is depicted. The clamp apparatus 110 comprises a housing 112. The housing 112 resembles a frame. The housing 112 comprises an upper handle 114 at the top of the housing 112. In the example embodiment, the upper handle 114 is essentially "U" shaped with the bottom, grip portion 116 of the "U" extended toward the back of the page (directions given in relation to the embodiment depicted in FIG. 2A). In other embodiments, the upper handle 114 need not take the shape of a "U", but rather any other desirable form. The grip portion 116 of the upper handle 114 may be cylindrical, planar, or take any other desired form. The grip portion 116 of the upper handle 114 may also have gentle ergonomic finger grooving, nubs, a ribbed texture, a honeycombed texture, etc. 118 (not shown) to increase ease of use. The grip portion 116 may be made of the same material as the rest of the upper handle 114, may be made of a different material, or may be made of a combination thereof. Possible materials may include, but are not limited to, rubber, polymer, composite, metal, plastic, foam, etc.

In the example embodiment, the uprights 113 of the "U" extend from the grip portion 116 toward the front of the page. The uprights 113 of the "U" each comprise a set of brackets 115 which extend substantially perpendicularly from the faces of the uprights 113 most proximal to A2 toward A2.

The housing 112 in the example embodiment also comprises one or more members 120 extending from the upper handle 114. In the embodiment shown in FIGS. 2A-2E, two substantially planar members 120 extend down in parallel fashion from the upper handle 114 at an angle that is generally perpendicular to the bottom surface of the upper handle 114. The members 120 may be coupled to the upper handle 114 with screws 122 (as shown best in FIGS. 2C-2E), bolts, welds, or by any other manner. The upper handle 114 and one or more vertical members 120 may also be formed as a single part during manufacture. The members 120 may also comprise tracks 123 on the faces of the members 120 most proximal to A2. In the example embodiment, the tracks 123 run vertically up the face of each member 120 though this need not be true of every embodiment. Additionally, in the example embodiment, the tracks 123 are cut into the members 120. In other embodiments, the tracks may be raised off the members 120.

Figure 2A:
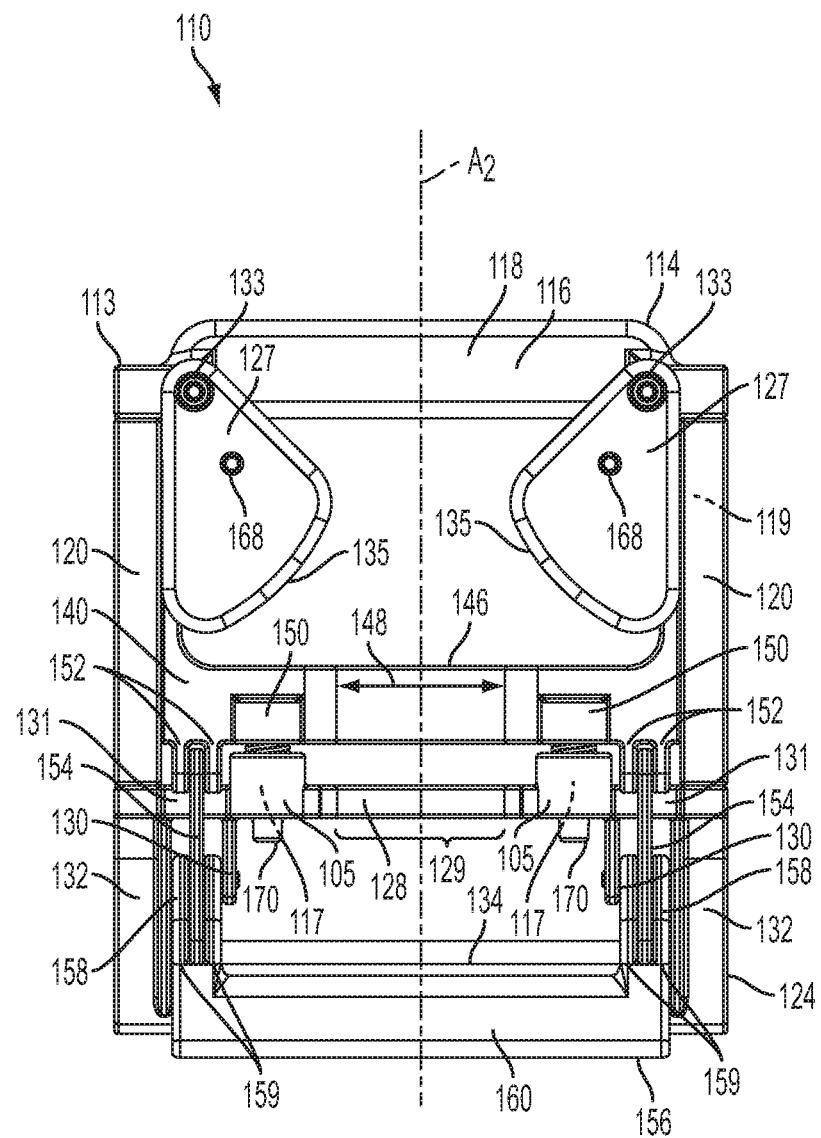
FIGS. 2A-2E show several views of a clamp in accordance with an embodiment of the present disclosure.
Figure 2B:
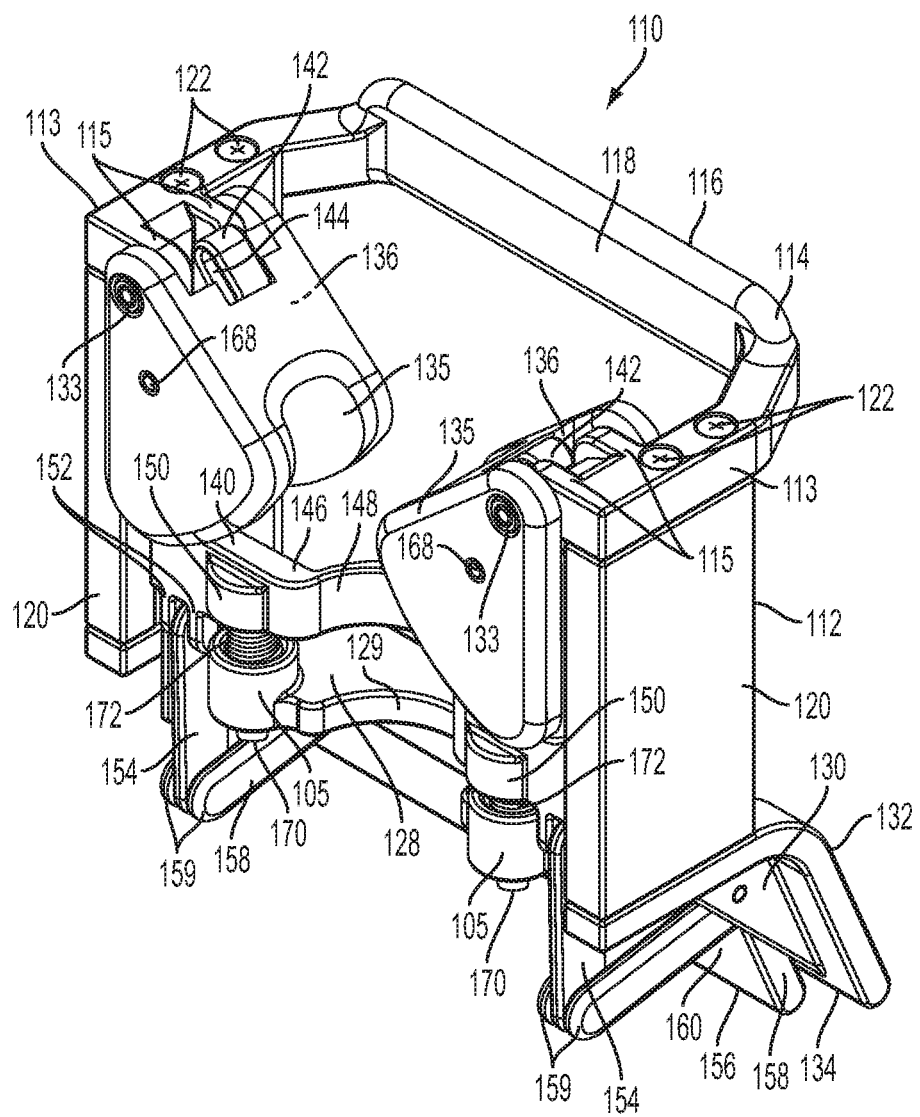
Figure 2C:
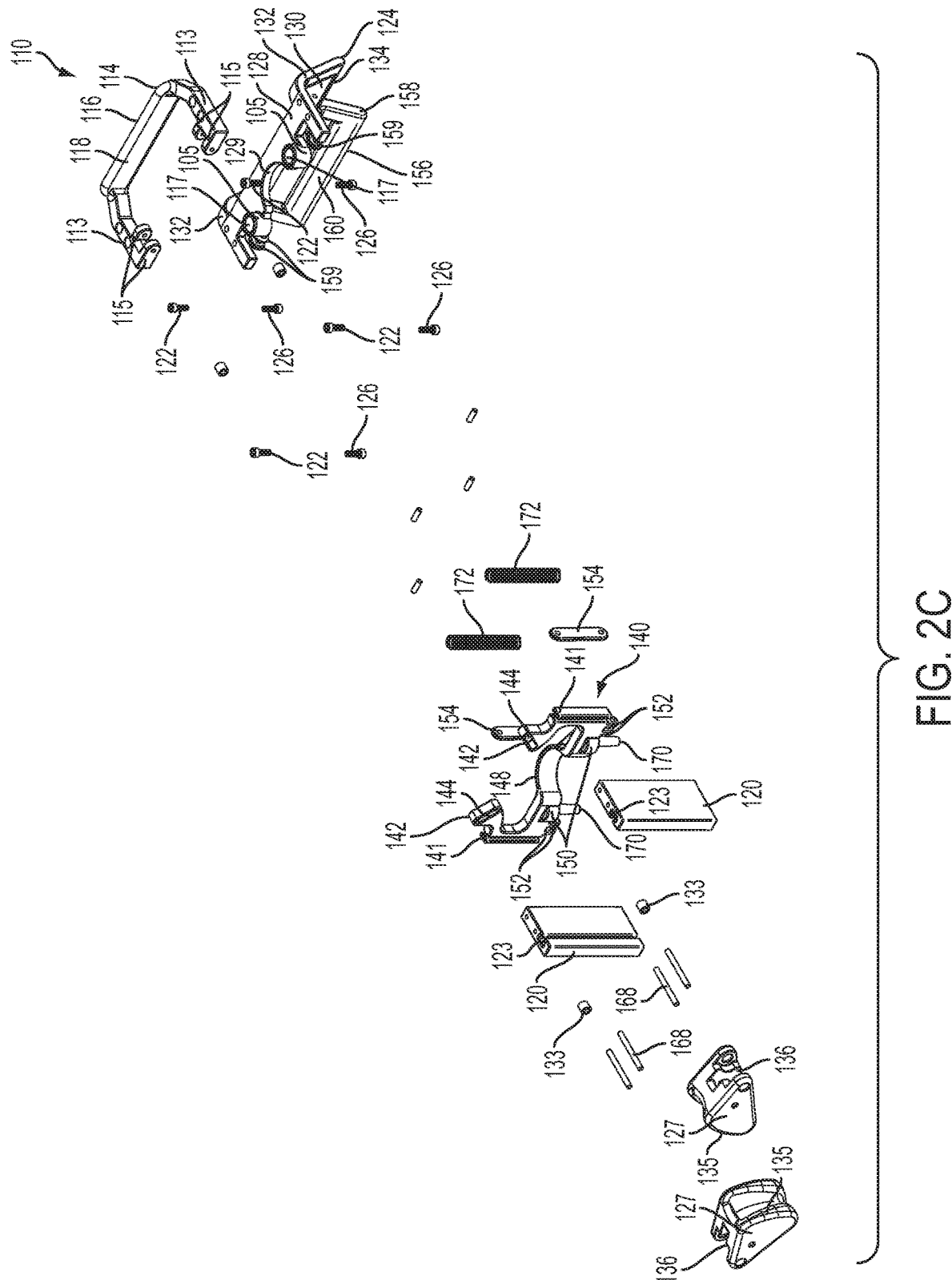
Figure 2D:
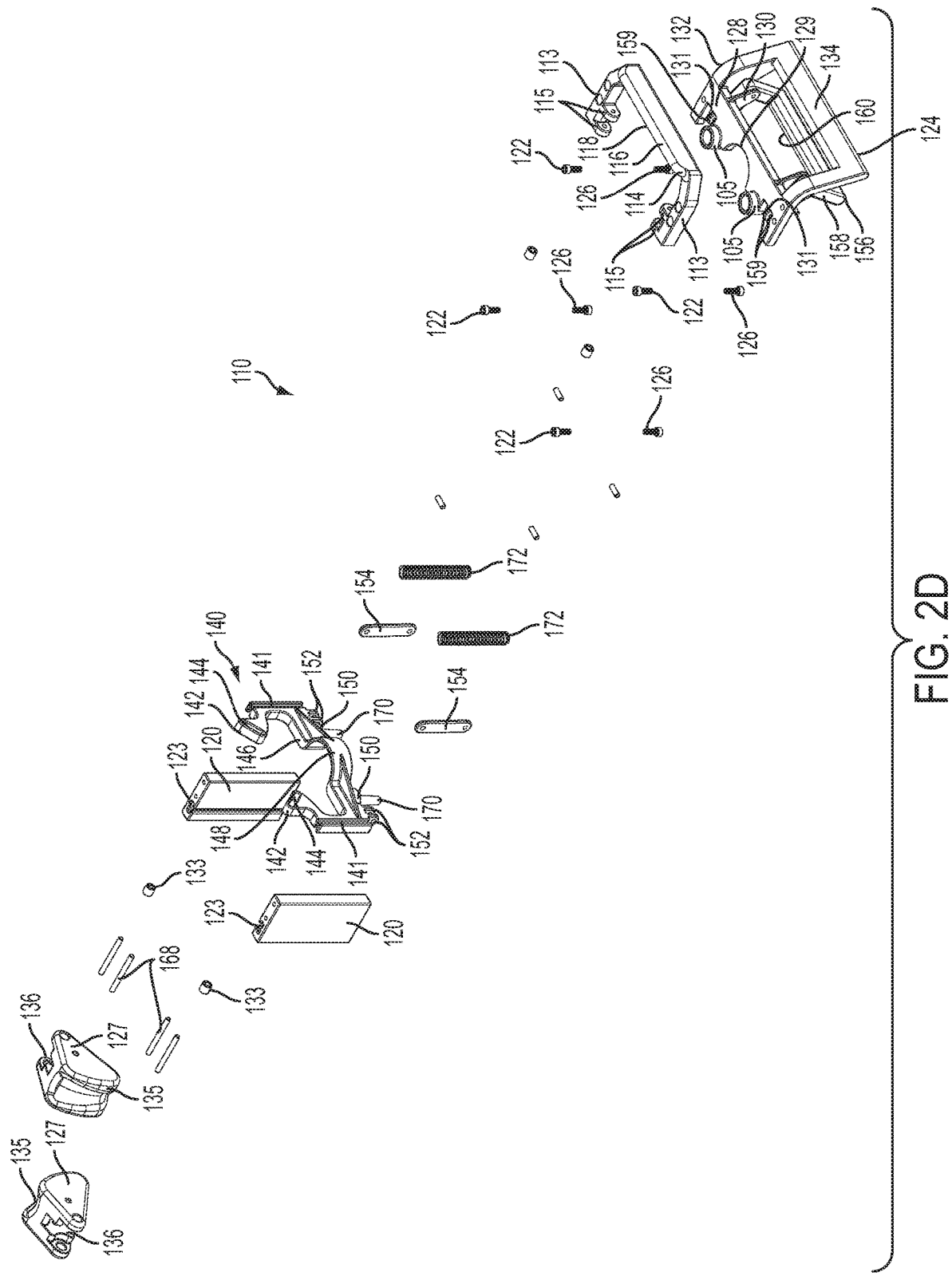
Figure 2E:
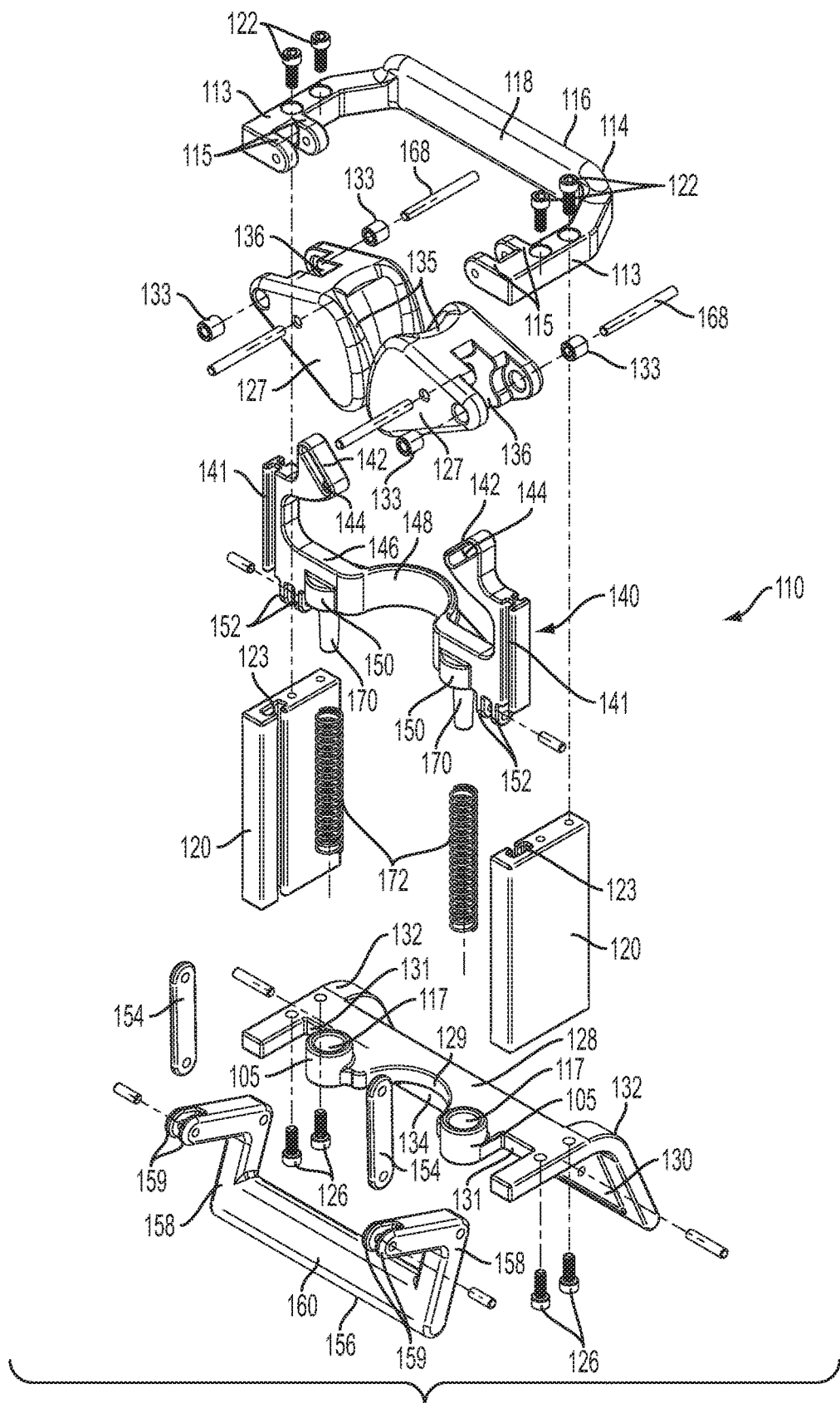

The housing 112 may also comprise a lower handle 124. In the example embodiment, the lower handle 124 is coupled to the bottom edges of the members 120. The lower handle 124 may be coupled to the members 120 in any of a variety of ways including screws 126, bolts, welds, etc (as best shown in FIGS. 2C-2E). The lower handle 124 may also be formed with the members 120 as a single continuous part during manufacture. In other embodiments, the upper handle 116, members 120, and lower handle 124 are all formed as a continuous part in manufacture. Spanning the distance between the members 120, the lower handle 124 may comprise a crosspiece 128. The center span 129 of the crosspiece 128 may arc/curve or bend toward the back of the page to better accommodate a clamped object 100. The crosspiece 128 also may comprise a pair of compression spring pockets 105. The compression spring pockets 105 are generally cylindrical and are hollow much like a cup. In the example embodiment, the bottom of the compression spring pockets 105 have an opening 117. A pair of brackets 130 extend off the bottom of the crosspiece 128 and will be elaborated upon later. The crosspiece 128 may have recessed portions 131 spanning the distance between the distal sides of the compression spring pockets 105 (in relation to A2) and the arms 132 of the lower handle 124 (elaborated upon in the following paragraph).

The lower handle 124 extends toward the back of the page in a manner similar to the upper handle 114. The arms 132 of the lower handle 124 may be arcuated or have a bend which arcs/bends the lower handle 124 toward the bottom of the page. The arms 132 of the lower handle 124 are joined by a grip 134 at the part of the handle closest to the bottom of the page.

The grip 134 may be made of the same material as the rest of the lower handle 124, may be made of a different material, or may be made of a combination thereof. Possible materials may include, but are not limited to, rubber, polymer, composite, metal, plastic, foam, etc. Additionally, the grip 134 may comprise ergonomic finger groves, nubs, a ribbed texture, a honeycombed texture, etc.

The housing 112 may also feature any of a variety of mechanisms 119 (not shown) to attach a load to the clamp apparatus 110. Such mechanisms 119 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

The clamping apparatus 110 may further comprise a set of pawls 127 which are pivotally coupled to the brackets 115 of the upper handle 116. The set of pawls 127 may be coupled to the brackets 115 of the upper handle by any of a variety of ways. Additionally, bushings 133 may be present to provide a bearing surface. The pawls 127 may have a trough 136 cut into them essentially along the center plane of the pawls 127 running parallel to the plane of the grip 116 shown in the example embodiment. The trough 136 will be elaborated upon later.

On at least a portion of the pawls 127 there may be a gripping surface 135 which engages the clamped object 100. The gripping surface 135 may consist of a material chosen for its gripping ability. The gripping surface 135 could be made of a high friction material, a compressible material, a material exhibiting both those qualities, or any other suitable material. The gripping surface 135 is made of a material which allows a firm grip without the deformation of a clamped object 100. Additionally, the gripping surface 135 may be contoured. Though the example embodiment includes a single set of pawls 127, in other embodiments, further sets of pawls 127 may be added to the clamping apparatus 110 to afford the clamping apparatus 110 added stability.

In the example embodiment, the clamping apparatus 110 also comprises a lift bar guide 140. The lift bar guide 140 comprises a set of protrusions 141 which engage with the tracks 123 in the members 120. This enables the lift bar guide 140 to travel along the track 123 in the members 120. In place of protrusions 141 some alternate embodiments employ a variety of different engagement surfaces. These surfaces include, but are not limited to, rollers, ball bearings, etc. In other embodiments, the track 123 may be raised off the members 120. In such embodiments, the protrusions 141 would be replaced by another suitable engagement surface such as a recessed groove, rollers, ball bearings, etc. It would also be conceivable for some embodiments to use a track 123, be it raised or recessed, comprising the rack portion of a rack and pinion. In place of the protrusions 141, on the lift bar guide 140, one or more pinion gears would extend so as to engage the rack track 123.

The top portion of the lift bar guide 140 may comprise a set of wings 142 which project inward toward A2. The wings 142 are shaped such that they are able to fit within the trough 136 in the pawls 127. The wings 142 have a slit 144 cut into them (best shown in FIGS. 2C-2E) similar to the slot 38 depicted in FIGS. 1A-1E. A coupling dowel 168 couples the pawls 127 to the lift bar guide 140 through the slit 144 in the wings 142. The lift bar guide 140 has a crossbar 146. This enables the lift bar guide 140 to cause the pawls 127 to move in unison. The center span 148 of the crossbar 146 may be arced/bent toward the back of the page to better accommodate a clamped object 100.

On each side of the arced center span 148, recessed compression spring pockets 150 are recessed into bottom face the lift bar guide 140. From the centers of the recessed compression spring pockets 150 a generally cylindrical shape 170 extends (though the shape need not be cylindrical in all embodiments) toward the bottom of the page. The generally cylindrical shape 170 may be solid or hollow. The generally cylindrical shape 170 may taper slightly in diameter as it extends farther away from the bottom face of the lift bar guide 140. The diameter of the generally cylindrical shape 170 is such it occupies much of the center of the recessed compression spring pocket 150, but leaves a ring surrounding the base of the generally cylindrical shape 170. One end of a coil spring 172 is seated in the ring surrounding the generally cylindrical shape 170 in the recessed compression spring pocket 150. The other end of the coil spring 172 abuts the bottom of the compression spring pocket 105 on the lower handle 124 mentioned above. The bottom of the compression spring pocket 105 has a hole 117 through which the generally cylindrical shape 170 may pass as the clamp apparatus 110 is moved to/in the open position. Though the shown embodiments use a coil spring 172, other embodiments could conceivably employ any other suitable bias member configuration. A wide variety of suitable bias members could be employed. Examples of suitable bias members include, but are not limited to, a gas spring using a bladder, piston type arrangement, a compression spring made of a compressible, springy material such as rubber, an extension spring, constant force spring, spring steel, etc.

In the shown embodiment, more distal from A2 than the recessed compression spring pockets 150, a set of brackets 152 extends downward on each side of the bottom face of the lift bar guide 140. In some embodiments, the placement of the recessed compression spring pockets 150 or other suitable bias structure and the brackets 152 may be switched. Coupled to the brackets 152 on the lift bar guide 140 there may be a link structure 154. In the example embodiments, the link structure 154 is a generally oblong disc with rounded edges. In other embodiments, the link structure 154 may take other forms and shapes. Examples of link structures 154 in other possible embodiments may include, but are not limited to, prismatic joints, any of a variety or springs, etc. It would also be conceivable to forgo the brackets 152 while coupling a camming surface to the actuator lever handle 156 (introduced in the following paragraph) thus effectively making the lift bar guide 140 a cam follower.

In the example embodiment, the other end of the link structure 154 is coupled to an actuator lever handle 156. The actuator lever handle 156 has a set of members 158. One end of the members 158 may be fitted with brackets 159 which allows the members 158 to couple to the link structure 154 as is shown in the example embodiment. From their coupling point to the link structure 154, the members 158 may extend to and are coupled to the brackets 130 projecting off the bottom face of the crosspiece 128 of the lower handle 124. In some embodiments, a torsion spring may be employed where the members 158 of the actuator lever handle 156 couple to the crosspiece 128 brackets 130. The torsion spring may be a substitute for, or used in conjunction with the coil spring 172 or other suitable bias structure. From their coupling point on the crosspiece 128 brackets 130, the members 158 arc/curve or bend steeply downward. In the example embodiments the members 158 bend at nearly a right angle, though other suitable angles may be used. A gripping portion 160 spans the distance between lowest ends of the members 158.

The gripping portion 160 may be made of the same material as the rest of the actuator lever handle 156, may be made of a different material, or may be made of a combination thereof. Possible materials may include, but are not limited to, rubber, polymer, composite, metal, plastic, foam, etc. Additionally, the gripping portion 160 may comprise ergonomic finger grooves, nubs, a ribbed texture, a honeycombed texture, etc.

In the example embodiment, the coil springs 172 bias the clamping apparatus 110 toward the closed position. In the closed position the lift bar guide 140 is at its highest point of travel along the tracks 123 in the members 120. The pawls 127 are rotated up and inward toward A2. Also in the closed position, the coupling dowel 168 is at the bottom of the slit 144 in the wings 142 of the lift bar guide 140.

If a clamped object 100 is present in the example embodiment, the coil springs 172 bias the clamp apparatus 110 to clamp down on the object 100. Depending on the size of the clamped object 100, the lift bar guide's 140 location on the track 123 will vary. The larger the clamped object 100 the lower the lift bar guide 140 will be on the track 123. Additionally, the pawls 127 will not be fully rotated up and inward toward A2. Instead the distance between the gripping surfaces 135 of the pawls 127 will mimic the diameter of the clamped object 100. This also means that the location of the coupling dowel 168 will be somewhat closer to the top of the slit 144.

The clamp apparatus 110 in the example embodiment is designed in such a way as to utilize the force of gravity to increase the clamping force. As gravity pulls on the clamp apparatus 110, especially when a load is attached to the housing 112 the force causes the pawls 127 to want to rotate further in towards A2. Since the clamped object 100 is in the way, the pressure of the pawls 127 against the clamped object 100 increases and the clamping apparatus 110 grips the clamped object 100 more vigorously.

To open the clamp apparatus 110 in the example embodiment, a user's hand may reach around the lower handle 124 and grasp the actuator lever handle 156 with their fingers. The user may then pull the actuator lever handle 156 toward the lower handle 124 of the housing 112. This causes the actuator lever handle 156 to pivot about its coupling to the brackets 130 on the cross piece 128 of the lower handle 124. This in turn pulls down on the link structure 154 which couples the actuator lever handle 156 to the lift bar guide 140. As the link structure 154 is pulled downward, the lift bar guide 140 travels down the tracks 123 in the members 120 of the housing 112. As the lift bar guide 140 travels downward, the compression springs 172 are compressed and the generally cylindrical shape 170 extends through the hole 117 in the compression spring pockets 105 on the crosspiece 128 of the lower handle 124. The downward travel of the lift bar guide 140 also causes the pawls 127 to rotate downward and away from A2. This is caused by the slit 144 in the wings 142 of the lift bar guide 140 sliding over the coupling dowel 168 until the coupling dowel 168 reaches the top of the slit 144. When the coupling dowel 168 is in this position, the pawls 127 are fully open. The clamp apparatus 110 may then be placed on a clamped object 100. Once the actuator lever handle 156 is released, the compression springs 172 will bias the clamp apparatus 110 to close and clamp down on the clamped object 100.

In another embodiment shown in FIGS. 3A-3E, a clamp apparatus 202 is depicted. The clamp apparatus 202 comprises a housing 204. The housing 204 comprises a number of portions. The first portion of the housing 204 may include a back plate 206. The back plate 206 may be substantially planar as shown in FIGS. 3A-3E.

The back plate 206 may also include a gripping handle 208 (not shown). The gripping portion 209 of the gripping handle 208 may be made of the same material as the rest of the handle 208, may be made of a different material, or may be made of a combination thereof. Possible materials may include, but are not limited to, rubber, polymer, composite, metal, plastic, foam, etc. Additionally, the gripping portion 209 of the gripping handle 208 may comprise ergonomic finger groves, nubs, a ribbed texture, a honeycombed texture, etc.

Additionally, the back plate 206 may also feature any of a variety of mechanisms or mounts 219 which allow the user to attach a load to the clamp apparatus 202. Such mechanisms 219 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

In the example embodiment shown in FIGS. 3A-3E, on the right side of the front face of the back plate 206 a rectangular block 212 projects at an angle substantially perpendicular to the front face of the back plate 206. The rectangular block 212 need not be rectangular in all embodiments. The rectangular block 212 is coupled to the back plate 206 in any of a variety of ways. The example embodiment employs screws 216, but bolts, welds or any other suitable means could also be utilized. The back plate 206 and rectangular block 212 could also be formed as a continuous part during manufacture. The rectangular block 212 may be generally planar. The rectangular block 212 may also be arced/curved to better accommodate a clamped object 100.

Figure 3A:
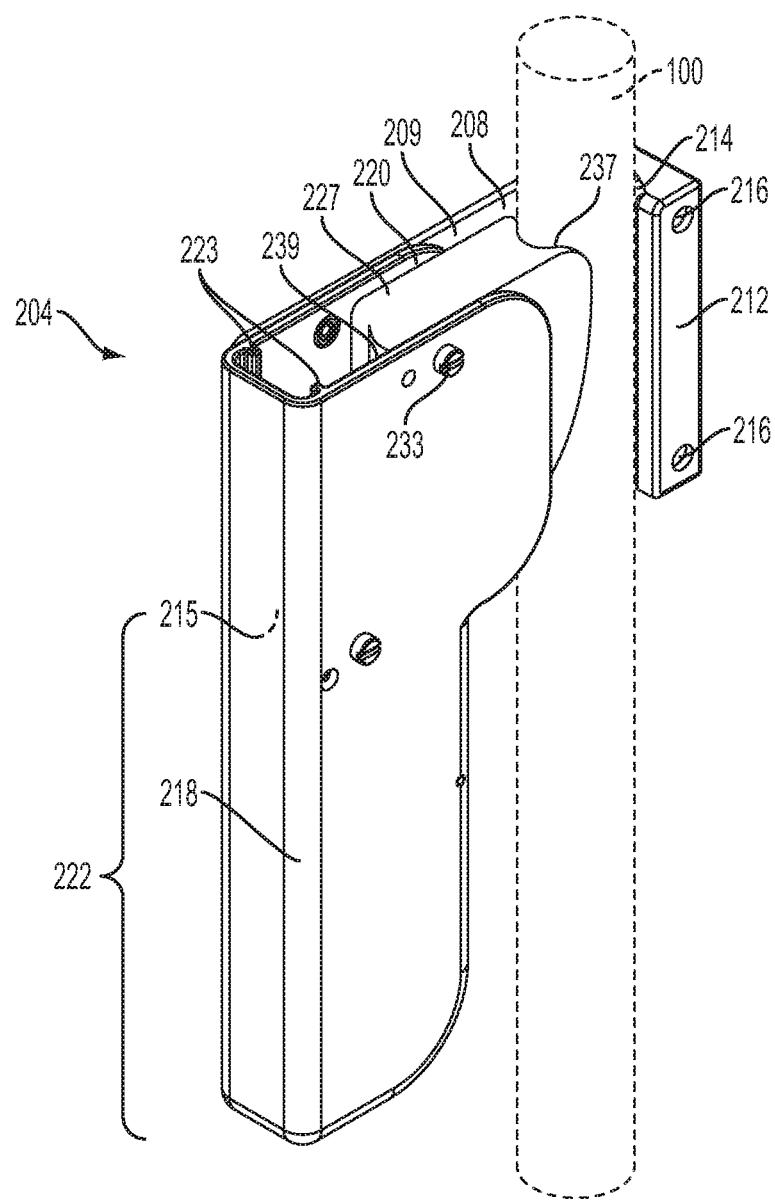

On at least a part of the inward facing side of the rectangular block 212, a gripping surface 214 may be affixed. The gripping surface 214 can engage the clamped object 100. This gripping surface 214 consists of a material chosen for its gripping ability. The gripping surface 214 could be made of a high friction material, a compressible material, a material exhibiting both of these qualities, or any other suitable material. The gripping surface 214 is made of a material which allows a firm grip without the deformation of a clamped object 100. Additionally, the gripping surface 214 may be contoured (as shown in FIGS. 3C-3E). In order to accommodate the contoured gripping surface 214 the inward face of the rectangular block 212 may also be contoured. Though the example embodiments only have one fixed gripping surface 214, it would be conceivable to add additional fixed gripping surfaces to the clamping apparatus 202.

The housing 204 may also comprise a second portion. The second portion of the housing may include a handle sleeve 218. In the example embodiment, the handle sleeve 218 comprises a body which may be entirely hollow (as shown) or have one or more hollow cavities. In the example embodiment shown in FIGS. 3A-3E, the top and a portion of the right side of the handle sleeve 218 are open to a hollow cavity. In alternate embodiments this need not always be the case. At the top of the handle sleeve 218 two rounded ears 220 project off the front and rear faces of the handle sleeve 218 toward the right of the page.

A portion of the handle sleeve 218 may have grip portion 222 to allow for greater ease of use. The gripping portion 222 may be made of the same material as the rest of the housing 204, may be made of a different material, or may be made of a combination thereof. Possible materials may include, but are not limited to, rubber, polymer, composite, metal, plastic, foam, etc. Additionally, the gripping portion 222 may comprise ergonomic finger groves, nubs, a ribbed texture, a honeycombed texture, etc.

In the example embodiment, on at least one or both the interior of the front or/and rear faces of the handle sleeve 218 near the left face of the handle sleeve 218 are tracks 223 which extend at least some portion of the length of the handle sleeve 218. In the embodiment in FIGS. 3A-3E the tracks 223 are raised and run vertical. Other embodiments may differ. For example, it would be conceivable to have a track 223 recessed into the sleeve handle. The track(s) 223 may also be cut into or raised out of the interior of the left face of the handle sleeve 218. In some embodiments, the track 223 may be the rack of a rack and pinion arrangement.

Figure 3B:
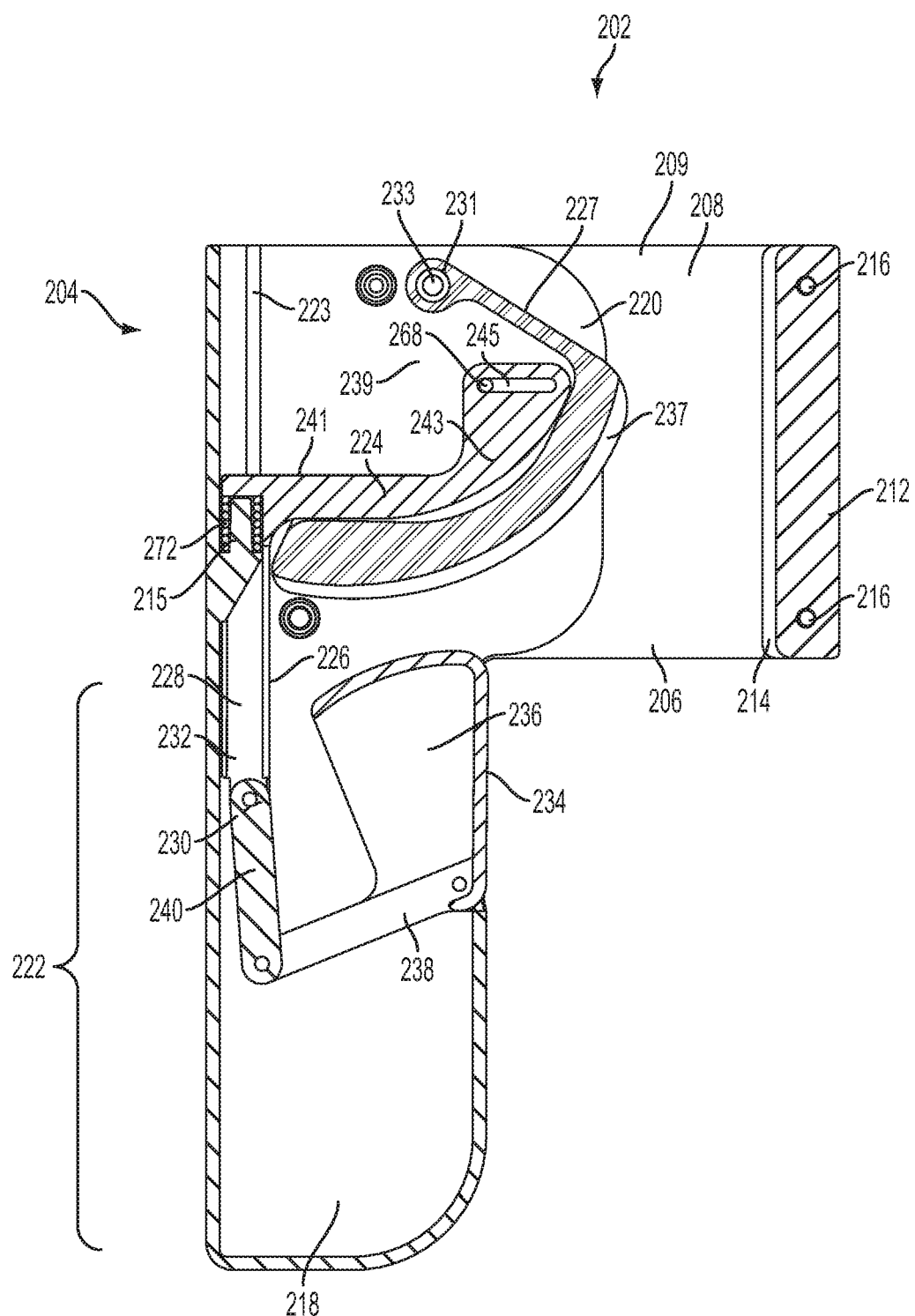
Figure 3C:
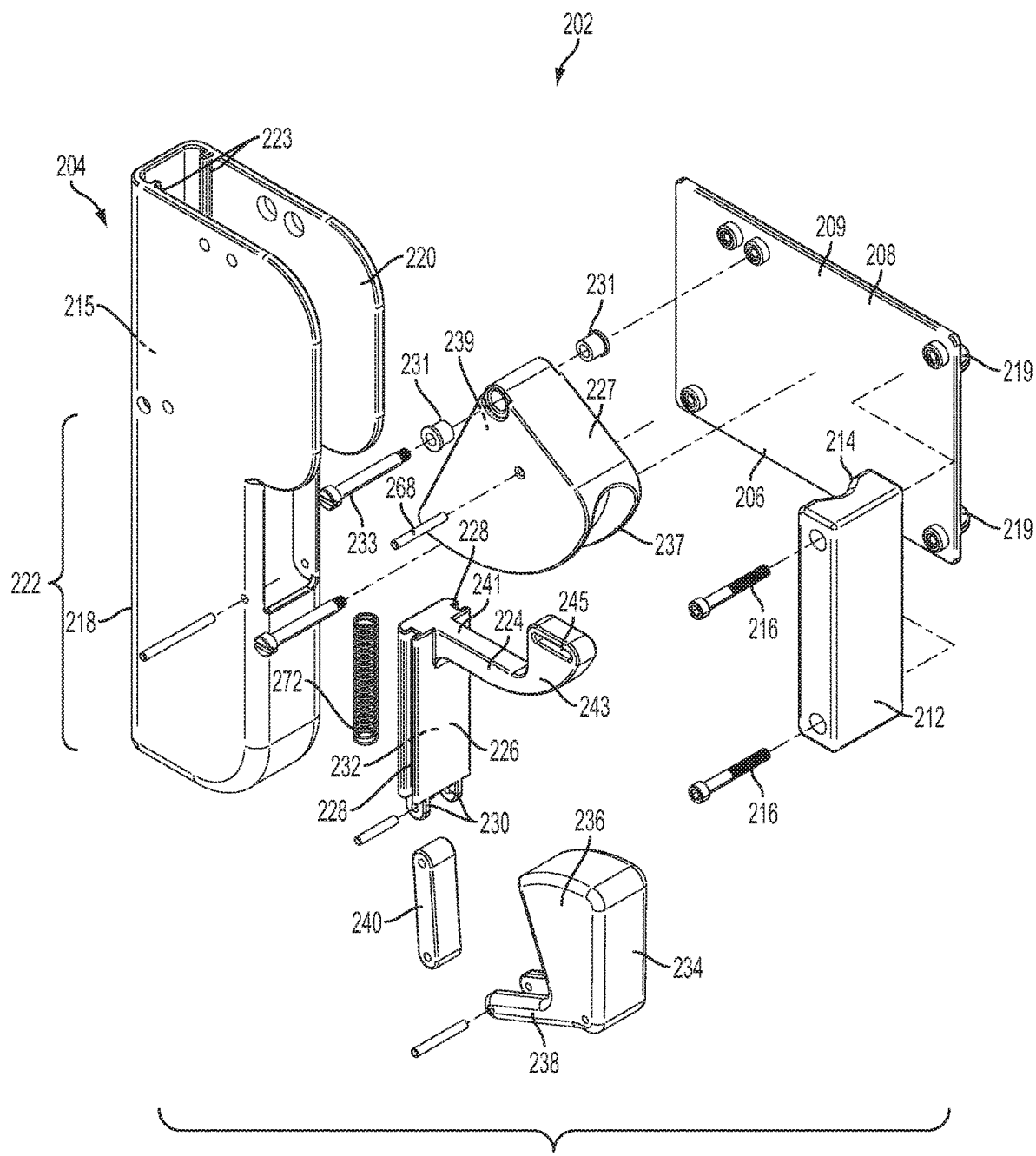
Figure 3D:
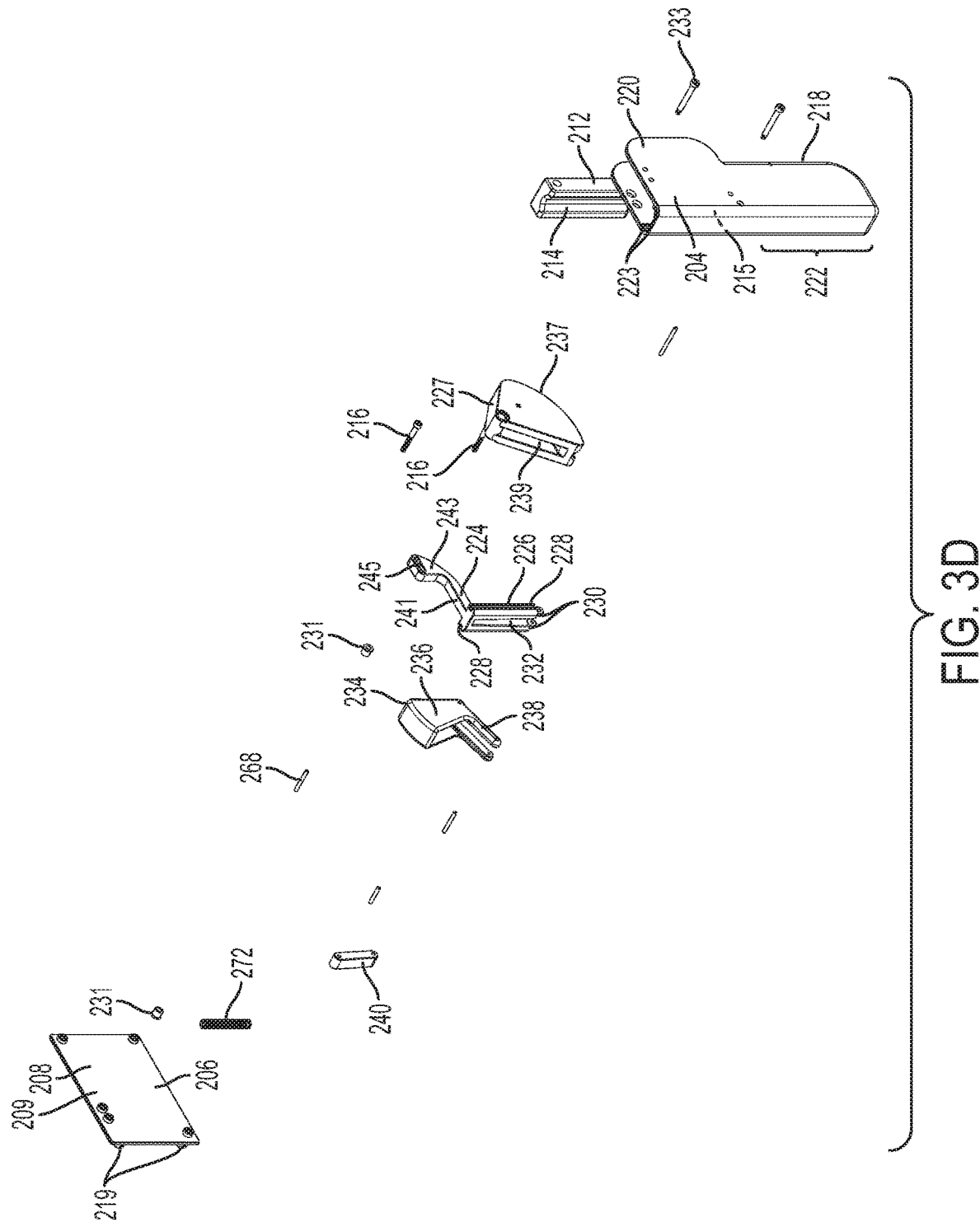

On the left face of the interior cavity, one or more compression spring pocket(s) 215 may be extended out into a hollow cavity as best shown in FIG. 3B. The compression spring pocket(s) 215 may also be extended out from at least one or both the interior of the front or/and rear faces of the handle sleeve 218. The compression spring pocket (s) 215 will be elaborated upon later.

At the top of the handle sleeve 218 a pawl 227 may be pivotally coupled. The pawl 227 may be pivotally coupled by any of a variety of means such as a screw 233 (as shown), pins, etc. Additionally, bushings 231 may be present to provide a bearing surface. The pawl 227 is able to swing about its pivot axis point within the cavity in the handle sleeve 218. The pawl 227 is also able to swing about its pivot out towards the fixed gripping surface 214 on the interior face of the rectangular block 212.

The surface of the pawl 227 facing the fixed gripping surface 214 on the interior face of the rectangular block 212 may be arced as best shown in FIG. 3C. The surface of the pawl 227 facing the fixed gripping surface 214 on the interior face of the rectangular block 212 may further comprise a gripping surface 237. The gripping surface 237 could be made of a high friction material, a compressible material, a material exhibiting both those qualities, or any other suitable material. The gripping surface 237 is made of a material which allows a firm grip without the deformation of a clamped object 100. Additionally, the gripping surface 237 may be contoured (as shown best in FIGS. 3A-3E).

The pawl 227 may be additionally comprised of a trough 239 cut into the pawl 227 essentially along the center plane of the pawl 227 running parallel to the plane of the back plate 206. The trough 239 is shaped such that it is able to accommodate the shape of a lift bar 241. As best shown in FIGS. 3C-3E, the lift bar 241 may comprise a first portion comprising a member 224 which projects into the trough 239 in the pawl 227. The member 224 may be shaped such that at the right end of the member 224 there is a wing like projection 243. Within the wing like projection 243, there may be a slit 245. It should be noted that the slit 144 in FIGS. 2A-2E is at an angle and the slit 245 in FIGS. 3A-3E is substantially horizontal. Alternate embodiments may employ slits oriented at any angle or may employ arced slits. A coupling dowel 268 runs through the slit 245 and into the pawl 227 coupling the lift bar 241 to the pawl 227.

The lift bar 241 may also comprise a second portion in which a member 226 extends toward the bottom of the page at an angle that is substantially perpendicular to the member 224 of the first portion. The member 226 of the second portion has an engagement surface 228 which engages with the track 223 on the interior of the handle sleeve 218. In the shown embodiment, the engagement surface 228 is depicted as a recessed groove. The engagement surface 228 may, however, be raised or take other forms including but not limited to, rollers, ball bearings, etc. In embodiments where the track 223 is the rack of a rack and pinion arrangement, one or more pinion gears capable of engaging the track 223 may be present on the member 226 of the second portion.

The member 226 of the second portion of the lift bar 241 may also have a bracket 230 extending off the bottom surface of the member 226. The bracket 230 need not extend as shown at an angle substantially perpendicular to the bottom surface of the member 226.

The member 226 of the second portion of the lift bar 241 may also be comprised of a groove or grooves 232 recessed into the face of the member 226 which abuts the interior surface of the handle sleeve 218 from which the compression spring pocket(s) 215 extend. The groove 232 is of a size and shape sufficient to fit around the compression spring pocket 215 which projects off the interior of the handle sleeve 218. Additionally, the groove 232 does not run the entire length of the member 226 stopping at least some distance from the top of the member 226. As shown, the diameter of the groove 232 may taper as it extends toward the top of the member 226.

A coil spring 272 is placed in the groove 232 such that one end of the coil spring 272 abuts the bottom of the compression spring pocket 215. The other end of the coil spring 272 abuts the top of the groove 232. Though the shown embodiments use a coil spring 272, other embodiments could conceivably employ any other suitable bias member. A wide variety of suitable bias members may be employed. Examples of suitable bias members include, but are not limited to, a gas spring (using a bladder arrangement, piston type arrangement, etc.), a compression spring made of a compressible, springy material such as rubber, an extension spring, constant force spring, and so on.

In the example embodiment, the coil spring 272 biases the clamp apparatus 202 toward the closed position (FIG. 3A). In the closed position, the coil spring 272 is not compressed. Additionally, the lift bar 241 is at its highest point of travel along the tracks 223 in the handle sleeve 218 of the housing 112. Since the lift bar 241 is coupled to the pawl 227 via the coupling dowel 268, this forces the pawl 227 to be pivoted up and in toward the fixed gripping surface 214. In the closed position, the coupling dowel 268 abuts the right edge of the slit 245.

If a clamped object 100 is present in the example embodiment, the coil spring 272 biases the clamp apparatus 202 to clamp down on the object 100. Depending on the size of the clamped object 100, the lift bar's 241 location on the track 223 will vary. The larger the clamped object 100 the lower the lift bar 241 will be on the track 223. Additionally, the pawl 227 will not be fully rotated up and inward toward fixed gripping surface 214. Instead the distance between the gripping surface 237 of the pawl 227 and the fixed gripping surface 214 will mimic the diameter of the clamped object 100. This also means that the location of the coupling dowel 268 will be somewhat closer to the left of the slit 245.

The clamp apparatus 202 in the example embodiment is designed in such a way as to utilize the force of gravity to increase the clamping force. As gravity pulls on the clamp apparatus 202, especially when a load is attached to the housing 204 the force causes the pawl 227 to want to rotate further up and in towards the fixed gripping surface 214. Since the clamped object 100 is in the way, the pressure of the pawl 227 against the clamped object 100 increases and the clamping apparatus 202 grips the clamped object 100 more vigorously. Furthermore, the clamped object 100 is pushed against the fixed gripping surface 214 with greater force again causing the clamping apparatus 202 to clamp more vigorously to the clamped object 100.

This more vigorous clamping force is accomplished by ensuring that the pawl 227 is constructed and shaped in order to ensure the clamp apparatus 202 will be in static equilibrium with a clamped object 100 when the clamp apparatus 202 is clamped onto a clamped object 100. This may require ensuring that the coefficient of friction of the pawl 227 is greater than the ratio of the vertical distance from the contact point of the pawl 227 on the clamped object 100 to the pivot point of the pawl 227 (said distance hereafter referred to as A) to the horizontal distance from the contact point on the pawl 227 to the pivot point of the pawl 227 (said distance hereafter referred to as B). The compliance and shape of the pawl 227 gripping surface 237 of the pawl 227 also is sufficiently configured.

As shown, the pawl 227 does not have a constant radius from the gripping surface 237 to the pivot point of the pawl 227. If the radius is constant, and the pawl 227, gripping surface 237, or both are relatively compliant, A:B may become less than zero if the pawl 227, gripping surface 237, or both become compressed. If the radius of the pawl 227 constantly increases as best shown in FIG. 3C, this cannot occur. The rate of increase in the radius of the pawl 227 may be chosen so that the ratio A:B does not become too large. This may be done to ensure that the coefficient of friction is not inordinately large.

In embodiments of the pawl 227 where the radius of the pawl 227 is constantly increasing and the pawl 227, gripping surface 237, or both are compliant, as the downward force of gravity acting on the clamp apparatus 202 increases the ratio A:B decreases. As a result, the normal forces present at the contact point of the pawl 227 on the clamped object 100 increase. The vertical reaction force increases as a result. This may create the more vigorous clamping force described above To move the clamp apparatus 202 to the open position shown in the embodiment in FIG. 3B, the user must actuate a trigger 234. The trigger 234 has a button portion 236 which extends at least partially out of the right face of the handle sleeve 218 when the clamp apparatus 202 is in the closed position. Toward the lower right of the button portion 236, the button portion 236 is pivotally coupled to the handle sleeve 218 by any of a variety of means. The button portion 236 may be hollow or solid. Projecting toward the left of the page of along the bottom plane of the button portion 236 of the trigger 234 may be one or more arms 238. The one or more arms 238 may be capable of coupling to a linkage structure 240. The linkage structure 240 also extends up to, and is coupled to, the bracket 230 which extends off the bottom surface of the lift bar 241. As best shown in FIG. 3C-3E, the link structure 240 in the example embodiment is an oblong with rounded edges. In other embodiments, the link structure 240 may take other forms and shapes.

Examples of link structures 240 in other possible embodiments may include, but are not limited to, prismatic joints, any of a variety or springs, etc. It would also be conceivable to forgo the brackets 230 while coupling a camming surface to the trigger 234 thus effectively making the lift bar 214 a cam follower.

In the example embodiment, when the trigger 234 is actuated, it acts as a lever pulling the linkage structure 240 and the lift bar 241 toward the bottom of the page. As the lift bar 241 is pulled down the track 223 on the handle sleeve 218 the coil spring 272 gets compressed. The slit 245 in the wing 243 of the lift bar 241 slides over the coupling dowel 268 until the coupling dowel 268 abuts the left most edge of the slit 245. As a result, the pawl 227 rotates down and away from the fixed gripping surface 214 and into the open position. Releasing the trigger 234 causes the clamping apparatus 202 to return to the closed position as a result of the restoring force of the coil spring 272. In alternate embodiments, a torsion spring may be employed where the button portion 236 of the trigger 234 is pivotally coupled to the handle sleeve 218. The torsion spring may be a substitute for or used in conjunction with the coil spring 272 or other suitable bias member configuration.

Figure 4A:
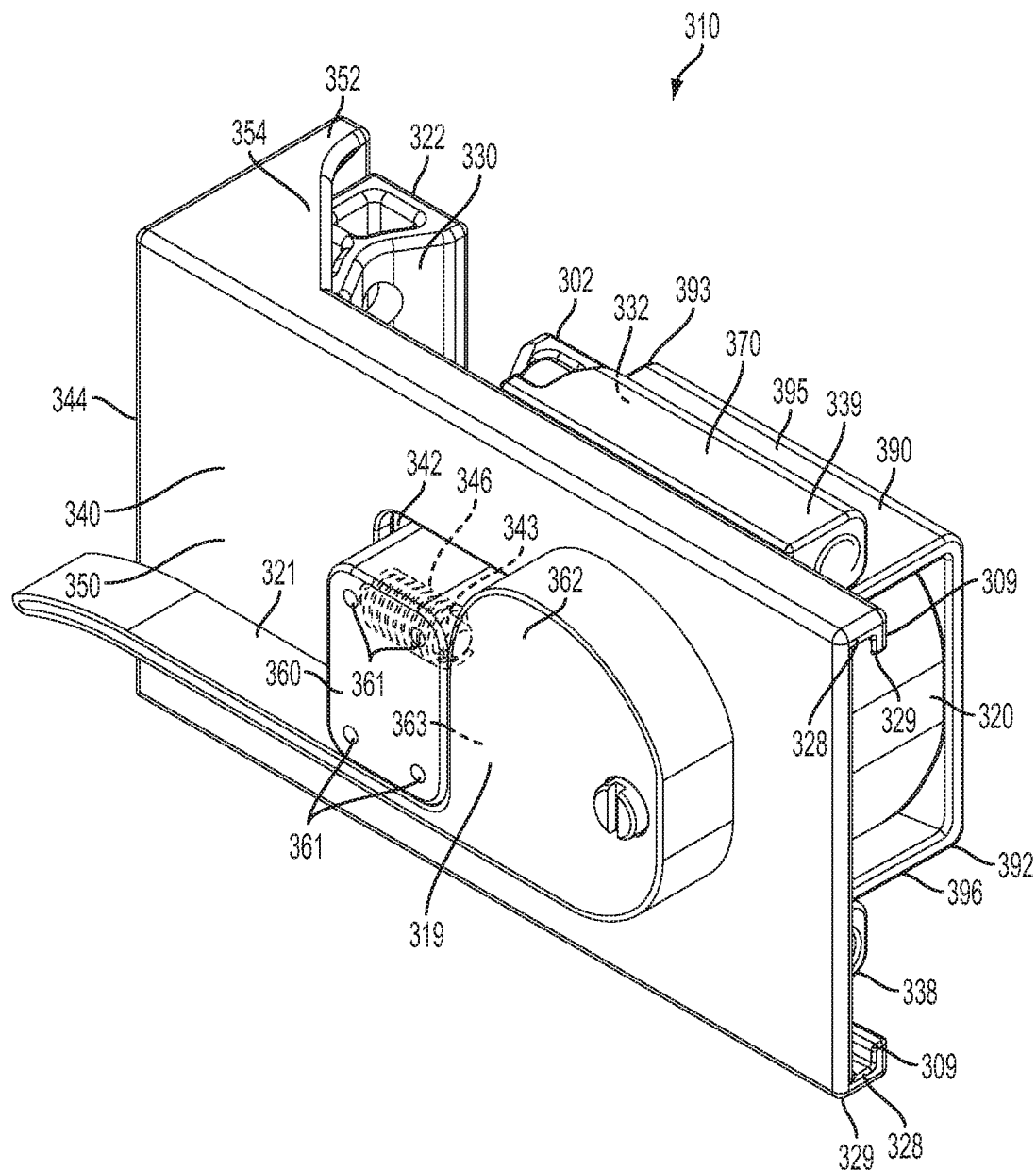
Figure 4B:
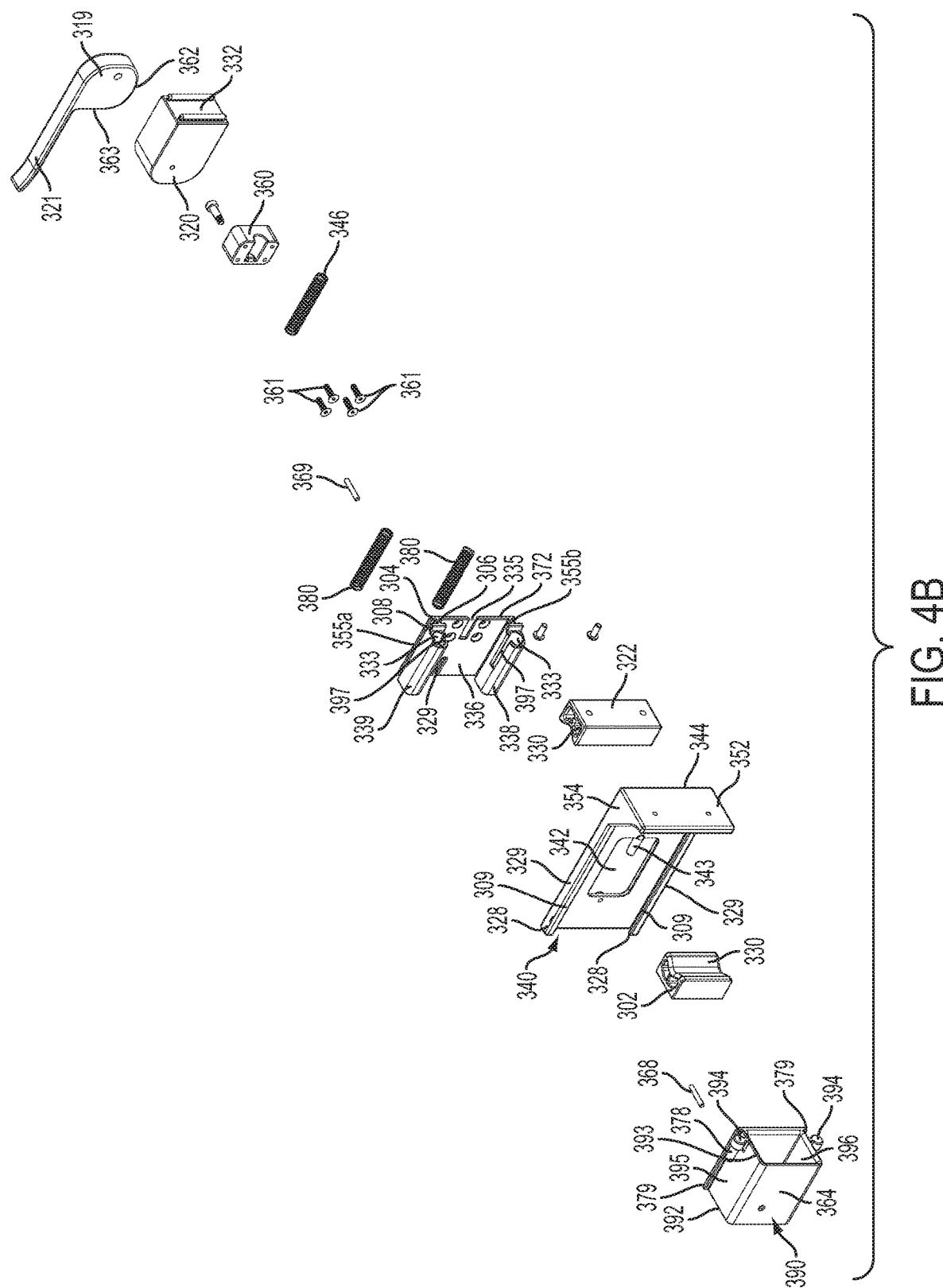
Figure 4D:
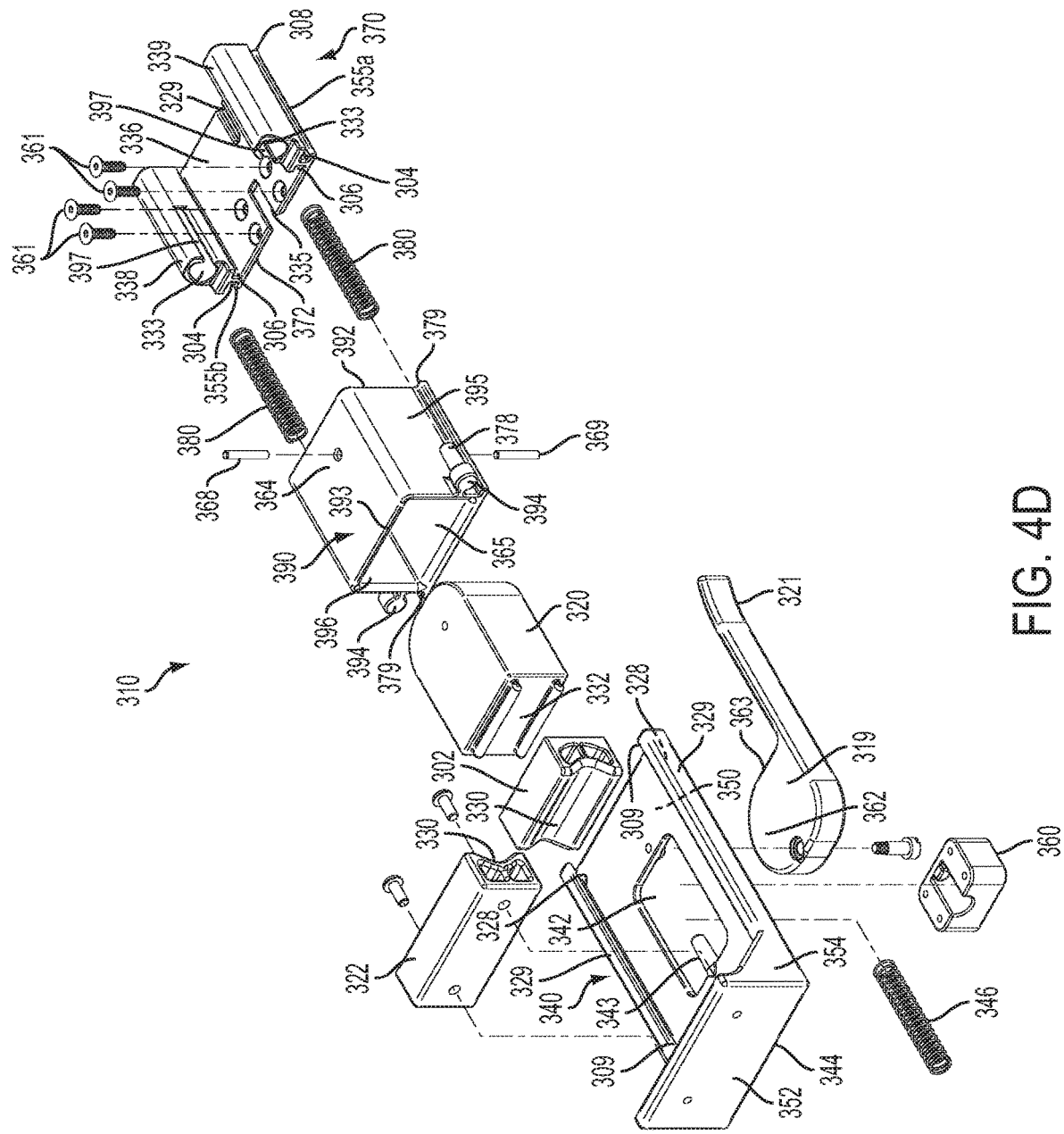

FIG. 4A shows a perspective view of a clamp apparatus 310 in the open position according to one embodiment of the present disclosure. A clamped object 100 may be squeezed between a fixed gripper 322 and a sliding gripper 302. The fixed gripper 322 and sliding gripper 302 may consist of a material chosen for its gripping ability. The fixed gripper 322 and sliding gripper 302 may be made of a material which allows for a firm grip without the deformation of a clamped object 100. The fixed gripper 322 and sliding gripper 302 may be made of a high friction material, a compressible material, a material exhibiting both these qualities, or any other suitable material. Suitable materials may include any suitable elastomeric or non-deformable substance, including but not limited to plastic, rubber, metal, foam, fabric, gel, etc. At least a portion of the fixed gripper 322 and sliding gripper 302 may comprise a roughly semi-circular depression or contour to accommodate a round clamped object 100 such as a pole.

In some embodiments, the fixed gripper 322 and sliding gripper 302 are formed from a relatively inelastic material, but have caps 330 (not shown) that fit substantially over the fixed gripper 322 and sliding gripper 302. The cap 330 may be constructed from any suitable material, including but not limited to, elastic materials such as rubber, plastic, gel, foam, fabric, polyurethane, etc. The caps 330 may be replaceable and removably attached to the fixed gripper 322 and sliding gripper 302.

The fixed gripper 322 may be firmly mounted to the fixed gripper mount end 344 of a guide plate 340. In some embodiments, a gripper support wall 352 is attached to the fixed gripper mount end 344 of the guide plate 340 and provides additional support for the fixed gripper 322. The gripper support wall 352 may optionally be supported by one or more buttresses 354 that span from at least a portion of the guide plate 340 to the gripper support wall 352. In some embodiments, the buttresses 354 may be arched to maximize support.

At least one face of the guide plate 340 may also feature any of a variety of mechanisms 305 (not shown) to attach a load to the clamp apparatus 310. Such mechanisms 305 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

The sliding gripper 302 is mounted to the sliding gripper mount end 332 of a sliding gripper base 320. The position of the sliding gripper base 320 is adjustable to accommodate clamped objects 100 of various dimensions and girths. The sliding gripper base 320 will be elaborated upon later.

In an embodiment of the present disclosure shown in FIG. 4A, the clamp apparatus 310 is depicted in the closed position (though a clamped object 100 is not present). To move the clamp apparatus 310 to the closed position, a user must rotate a handle assembly 319, such that the hand grip 321 of the handle assembly 319 is pointed toward the left of the page as shown in FIG. 4A. This action propels the sliding gripper 302 and all attached structures towards the fixed gripper 322. If a clamped object 100 is present, the sliding gripper 302 will squeeze the clamped object 100 against the fixed gripper 322, thus clamping the clamped object 100.

The handle assembly 319 is rotatably attached to the front face 350 of the guide plate 340. In the exemplary embodiment shown in FIGS. 4A-4D, the handle assembly 319 is disposed on a plane approximately parallel to the plane of the front face 350 of the guide plate 340 regardless of whether the clamp apparatus 310 is in the open or closed position or in transit between an open and closed position. The handle assembly 319 is comprised of a number of portions. At least a one portion of the handle assembly 319 abuts a cam plate 360, which is immovably attached to a pressure plate 370 (pressure plate 370 introduced in subsequent paragraphs). In the depicted exemplary embodiment in FIGS. 4A-4D, the handle assembly 319 comprises a cam 362 positioned to contact the cam plate 360. The rounded, contoured surface of the cam 362 grades into a planate section which spans the length of the hand grip 321.

In some embodiments, hand grip 321 may be made of the same material as the rest of the handle assembly 319, may be made of a different material, or may be made of a combination thereof. Possible materials may include, but are not limited to, rubber, polymer, composite, metal, plastic, foam, etc. The hand grip 321 may also comprise ergonomic finger groves, nubs, a ribbed texture, a honeycombed texture, etc. to facilitate ease of grasping.

Additionally, as shown in the example embodiment in FIGS. 4A-4D the cam 362 may include at least one flat segment 363. Clockwise rotation of handle assembly 319 causes the cam 362 to rotate into the cam plate 360. This displaces the cam plate 360 towards fixed gripper 322. In the closed position, the cam 362 is fully rotated into the cam plate 360 and the flat segment 363 of the cam 362 abuts the right edge (relative to FIG. 4A) of the cam plate 360. Additionally, in the fully closed position, the planate surface of the hand grip 321 may rest against the bottom edge of the cam plate 360. The flat segment 363 of the cam 362 prevents the restoring force from a compressed return spring 346 (which spring loads the cam plate 360) from pushing cam plate 360 back to the open position, and thus may effectively lock the clamp apparatus 310 in the closed position.

To open the clamp apparatus 310, a user rotates the handle assembly 319 counter-clockwise. As the cam 362 releases pressure on the cam plate 360, the compressed return spring 346 causes the cam plate 360 to automatically return back to the open position as the return spring 346 expands back to a relatively uncompressed state.

In the open position (not shown) the cam plate 360 comes to rest against the right edge (in reference to FIG. 4A) of an aperture 342 in the guide plate 340. The aperture 342 is cut through the guide plate 340 at an angle which is substantially perpendicular to the front face 350 of the guide plate 340. On the left vertical edge of the aperture 342 a return spring peg 343 may project into the aperture 342 in a direction substantially parallel to the plane of the front face 350 of the guide plate 340. The return spring peg 343 is slightly smaller in diameter than the return spring 346. The return spring 346, may be seated around the return spring peg 343 (as shown in FIG. 4A). In the open position, the return spring 346 may be slightly compressed to prevent any "slop" and to keep the cam plate 360 against the right edge of the aperture 342.

The cam plate 360 is immovably coupled to a pressure plate 370. In the example embodiment shown in FIGS. 4A-4E, the cam plate is coupled to the pressure plate 370 via screws 361. In other embodiments, the cam plate 360 and pressure plate 370 may be coupled to each other in any number of ways, including, but not limited to welds, bolts, rivets, etc. In some embodiments, they may be formed as a continuous part during manufacture.

Since the cam plate 360 is attached to the pressure plate 370, the pressure plate 370 also moves as the cam 362 of the handle assembly 319 displaces the cam plate 360. When the return spring 346 expands as the clamp apparatus 310 is opened, the pressure plate 370 is also spring loaded to automatically return toward its open orientation. When the clamp apparatus 310 is fully opened, the pressure plate 370 may be approximately flush with the right edge of the guide plate 340 (in reference to FIG. 4A). In the example embodiment shown in FIGS. 4A-4E, the pressure plate 370 may not extend out past the right edge of the guide plate 340 because the cam plate 360 to which it is immovably attached is restricted in movement by the right edge of the aperture 342 in the guide plate 340.

Extending perpendicularly from the center of the left edge 372 of the pressure plate 370 (in reference to FIG. 4D) into the pressure plate 370 is a return spring trough 335. The return spring trough 335 allows the return spring 346 to fit comfortably into the clamp apparatus 310 when the clamp apparatus 310 is fully assembled and operated.

In the example embodiment shown in FIGS. 4A-4D, the pressure plate 370 is slidingly coupled to the guide plate 340 by a tongue-in-groove type association. The top edge 355a and bottom edge 355b (relative to FIGS. 4A-4C) of the pressure plate 370 function as the tongues. The top edge 355a and bottom edge 355b of the guide plate 370 ride along a track 328 which comprises a part of the guide plate 340 structure. In the embodiment depicted, the track 328 is a recessed groove which is cut out of flanges 329 extended off the top and bottom edges of the guide plate 340. The flanges 329 project toward the back of the page (in relation to FIG. 4A) in a direction substantially perpendicular to the plane of the front face 350 of the guide plate 340. As shown, the tracks 328 may be cut into the flanges 329 such that the tracks 328 run substantially parallel to the plane of the front face 350 of the guide plate 340.

The clamp apparatus 310 in the illustrated embodiment in FIGS. 4A-D also comprises a gripper sled 390. The gripper sled 390 may also be coupled to the clamp apparatus 310 by one or a number of tongue-in-groove associations. As shown, the gripper sled 390 may be slidably coupled to the pressure plate 370. Additionally, at least one spring 380 may be disposed between the gripper sled 390 and pressure plate 370 to exert additional clamping force while the clamp apparatus 310 is in the closed position and a clamped object 100 is present.

In an example embodiment, the gripper sled 390 is a generally a hollow, mostly rectangular sleeve open on its right end 392 and left end 393 (relative to FIG. 4A). The sliding gripper base 320 may fit into, hollow interior of the sleeve-like gripper sled 390. Other embodiments may close the left end 393 of the gripper sled 390 and attach the sliding gripper 302 to it such that the left end 393 of the gripper sled 390 performs the function of the sliding gripper base 320.

In the exemplary embodiment shown in FIGS. 4A-4D, the sliding gripper base 320 is immovably coupled inside the hollow interior of the gripper sled 390. This may be accomplished in any number of ways. As shown, the sliding gripper base 320 may be coupled into the gripper sled by a first dowel 368 and a second dowel 369. Other embodiments which employ dowels may use any suitable number of dowels. The first dowel 368 may be inserted through an orifice in the in the back face 364 of the gripper sled 390 into a corresponding orifice in the back face of the sliding gripper base 320 (directions refer to orientation of FIG. 4A). The second dowel 369 may be inserted through an orifice in the front face 365 of the gripper sled 390 into a corresponding orifice in the front face of the sliding gripper base 320.

In the example embodiment shown in FIGS. 4A-4D, the second dowel 369 is not flush with the front face 365 of the gripper sled 390. Instead, at least a portion of the second dowel 369 projects past the front face 365 of the gripper sled 390. At least a part of this portion of second dowel 369 rides along a slit 329 which is cut into the edge of the pressure plate 370 opposite the return spring trough 335. As shown, the slit 329 may be cut into the said edge of the pressure plate 370 at an angle substantially perpendicular to said edge. The interaction of the slit 329 and second dowel 369 effectively restricts the movement of the gripper sled 390. When the second dowel 369 abuts the left end of the slit 329, the second dowel 369 and all attached components may travel no further toward the left of the page (in relation to FIG. 4A).

The gripper sled 390 may also comprise a set of ears 394. As shown in the example embodiment in FIGS. 4A-D, one of the ears 394 may project off the top face 395 of the gripper sled 390 while the other projects off the bottom face 396 of the gripper sled 390. In the embodiment illustrated in FIGS. 4A-4D, each ear 394 comprises a post which supports a round cylinder whose elongate section runs in a direction parallel to the plane of the front face 365 of the gripper sled 390. The ears 394 project off the top face 395 and bottom face 396 of the gripper sled 390 at an angle substantially perpendicular to the top face 395 and bottom face 396 of the gripper sled 390. In alternate embodiments, the shape, thickness, construction, orientation, etc. of the ears 394 may differ. Additionally, some embodiments may comprise a compression spring peg 378 which projects off each ear 394. The compression spring pegs 378 are similar to the return spring peg 343.

In an embodiment of the present disclosure, the top and bottom edges of the front face 365 of the gripper sled 390 may comprise gripper sled tongues 379 which run at least partially along at least one of the top and bottom edges of the front face 365 of the gripper sled 390. In the example embodiment shown in FIGS. 4A-4D, the gripper sled tongues 379 project off the entire length of the top and bottom edges of the front face 365 of the gripper sled 390 and are extensions of the plane of the front face 365 of the gripper sled 390.

Extending from the rear face 336 of the pressure plate 370 and oriented approximately parallel to the return spring trough 335 may be a top spring housing 339, and a bottom spring housing 338. In an exemplary embodiment shown in FIGS. 4A-4D, the top spring housing 339 and bottom spring housing 338 both comprise a raised ridge 304 and a compression spring pocket 333. The raised ridge 304 projects off the rear face 336 of the pressure plate 370 at an angle substantially perpendicular to rear face 336 of the pressure plate 370. The raised ridges 304 run parallel to the top edge 355a and bottom edge 355b of the pressure plate 370. As shown, the raised ridges 304 may span the entire length of the pressure plate 370. The raised ridges 304 function as a post on which the compression spring pockets 333 of the top spring housing 339 and bottom spring housing 338 are coupled. As shown in the example embodiment in FIGS. 4A-4D the compression spring pockets 333 may be elongated along the entire length of the ridges 304.

The compression spring pockets 333 overhang the ridges 304 forming "T" type shapes. The portions of the "T" type shapes facing the lateral center line of the pressure plate 370 form the grooves 306 of a tongue-in-groove arrangement in conjunction with the rear face of the pressure plate 370. The gripper sled tongues 379 are slidably coupled into these grooves 306.

The opposite portions of the "T" type shapes (those distal to the lateral centerline of the pressure plate 370) also form the grooves 308 of another tongue-in-groove type arrangement in conjunction with the rear face of the pressure plate 370. In the embodiment shown in FIGS. 4A-4D, the distal grooves 308 slidably couple around tongues 309 formed by a part of the flanges 329 which are extended off the guide plate 340.

The compression spring pockets 333 may be hollow so as to allow compression springs 380 to be seated inside the compression spring pockets 333. In the embodiment shown in FIGS. 4A-4D, the right end (relative to FIG. 4A) of the compression spring pockets 333 is closed to provide a surface upon which the compression springs 380 may be compressed against. Additionally, the compression spring pockets 333 each feature a slot 397 (best shown in FIG. 4D) which is cut out of the face of the compression spring pockets 333 most proximal to the lateral centerline of the pressure plate 370.

When assembled, as detailed above, a compression spring 380 may be seated in each of the compression spring pockets 333. One end of the compression springs 380 abuts the closed ends of the compression spring pockets 333. The other ends of the compression springs 380 abut the right faces of the ears 394 which protrude off the top face 395 and bottom face 396 of the gripper sled 390. The compression springs 380 fit around the compression spring pegs 378 which may extend from the ears 394 on the gripper sled 390. This helps to keep the compression springs 380 firmly in place during operation and use of the clamp apparatus 310. The compression springs 380 bias the gripper sled 390 and components immovably attached to it (notably sliding gripper 302 and sliding gripper base 320) to the left of the page (relative to FIG. 4A) until the second dowel 369 abuts the left end of the slit 329 and the components may move no further to the left of the page. This ensures that as the handle assembly 319 is actuated, the cam plate 360, pressure plate 370, gripper sled 390, and attached components move together as a unit until the sliding gripper 302 encounters a clamped object 100.

In the shown embodiment in FIGS. 4A-4D, the diameter of the hollow portions of the compression spring pockets 333 is slightly larger than the diameter of the cylinder portion of the ears 394. The slot 397 in the compression spring pockets 333 creates a path for the post portion of ears 394 to travel. When a force sufficient to overcome the bias force of the compression springs 380 is applied, the compression springs 380 begin to compress.

Such a force may be generated when a user rotates the handle assembly 319 and a clamped object 100 is present. As mentioned above, in the embodiment shown in FIGS. 4A-4B, the cam plate 360, pressure plate 370, gripper sled 390 and attached components move together substantially as a unit until the sliding gripper 302 encounters a clamped object 100. When the clamped object 100 comes into contact with the sliding gripper 302, the sliding gripper 302 begins to push the clamped object 100 against the fixed gripper 322. When the force which the clamped object 100 exerts back against the sliding gripper 302 becomes greater than the bias force of the compression springs 380, the sliding gripper 302, sliding gripper base 320, gripper sled 390 and components immovably coupled to the gripper sled 390 stopping moving. The cam plate 360 and pressure plate 370 continue to move toward their closed orientation as the handle assembly 319 rotates to its closed orientation. This causes the compression springs 380 to begin to compress. As the compression springs 380 are compressed the ears 394 slide progressively further into the hollow portions of the compression spring pockets 333 and along the slots 397 of the compression spring pockets 333 until the clamp apparatus 310 reaches its fully closed orientation.

The force exerted by the compressed compression springs 380 on the clamped object 100 through the gripper sled 390 and sliding gripper 302 helps to create a more vigorous gripping force than could otherwise be achieved. Additionally, the restoring force of the compression springs 380 is complimentary to that provided by the return spring 346 when the clamp apparatus 310 is moved to the open position. The compression spring 380 restoring force causes the gripper sled 390 and immovably attached components to return back to their default orientation along slit 329 in the pressure plate 370. The force exerted by the compressed compression springs 380 additionally facilitates opening of the clamp apparatus 310.

In an embodiment of the present disclosure shown in FIGS. 5A-5D, the restoring force from a pair of tensioned springs 409 acts to clamp a clamped object 100 between a fixed gripper 401 and a sliding gripper 403. The sliding gripper 403 can then be locked in place by a ratcheting pawl 476, thus securing clamp apparatus 410 in the clamped position about a clamped object 100.

In an exemplary embodiment, a fixed gripper 401 may be firmly attached to the front face 404 of an approximately rectangular back plate 402. The gripping surface of the fixed gripper 401 is oriented perpendicularly to the front face 404 of the back plate 402. In the embodiment shown in FIGS. 5A-5D, a fixed gripper support wall 452 may be attached to the front face 404 of the back plate 402. As shown, the fixed gripper support wall 452 may project from the left edge (in relation to FIG. 5A) of the back plate 402 in a direction perpendicular to the front face 404 of the back plate 402. Instead of attaching the fixed gripper 401 to front face 404 of the back plate 402, the fixed gripper 401 may be fixedly coupled to the right face (in relation to FIG. 5A) of the fixed gripper support wall 452. This is desirable because the fixed gripper support wall 452 is able to provide additional support for the fixed gripper 401. The fixed gripper support wall 452 may optionally be supported by one or more buttresses 454 that span from at least a portion of the back plate 402 to the fixed gripper support wall 452. In some embodiments, the buttresses 454 may be arched to maximize support.

The fixed gripper 401 may consist of a material chosen for its gripping ability. The fixed gripper 401 may be made of a high friction material, a compressible material, a material exhibiting both these qualities, or any other suitable material. The fixed gripper 401 may be made of a material which allows a firm grip without the deformation of a clamped object 100. Suitable materials may include any suitable elastomeric or non-deformable substance, including but not limited to plastic, rubber, metal, foam, fabric, gel, etc. At least a portion of the fixed gripper 401 may comprise a roughly semi-circular depression or contour to accommodate a round clamped object 100 such as a pole.

In some embodiments, the fixed gripper 401 is formed from a relatively inelastic material, but has a cap 458 (not shown) that fits substantially over the fixed gripper 401. The cap 458 may be constructed from any suitably material, including but not limited to, elastic materials such as rubber, plastic, gel, foam, fabric, polyurethane, etc. The cap 458 may be replaceable and removably attached to the fixed gripper 401.

In some embodiments, in addition to comprising the mounting site for the fixed gripper 401, the support plate 402 also includes an attachment site 418 for a gear assembly and a track-way 412 for a rack plate 420. The gear assembly attachment site 418, track-way 412, and rack plate 420 will be elaborated on in subsequent paragraphs.

In an example embodiment, the sliding gripper 403 is firmly attached to the front face 422 of a rack plate 420 such that the gripping surface of the sliding gripper 403 faces the gripping surface of the fixed gripper 401. As shown in FIGS. 5A-5D, the sliding gripper 403 is coupled to the front face 422 of the rack plate 420 near the edge of the rack plate 420 most proximal to the fixed gripper 401. In some embodiments, the rack plate 420 may have the shape of a quadrilateral, specifically a rectangle. Some embodiments include a sliding gripper support base 421 which may be similar in varying degrees to the fixed gripper support wall 452. The sliding gripper support base 421 may optionally have one or more buttresses 456 that span from at least a portion of the rack plate 420 to the sliding gripper support base 421. In some embodiments, the buttresses 456 may be arched to maximize support.

The sliding gripper 403 may consist of a material chosen for its gripping ability. The sliding gripper 403 may be made of a high friction material, a compressible material, a material exhibiting both these qualities, or any other suitable material. The sliding gripper 403 may be made of a material which allows a firm grip without the deformation of a clamped object 100. Suitable materials may include any suitable elastomeric or non-deformable substance, including but not limited to plastic, rubber, metal, foam, fabric, gel, etc. At least a portion of the sliding gripper 403 may comprise a roughly semi-circular depression or contour to accommodate a round clamped object 100 such as a pole.

In some embodiments, the sliding gripper 403 is formed from a relatively inelastic material, but has a cap 458 (not shown) that fits substantially over the sliding gripper 403. The cap 458 may be constructed from any suitably material, including but not limited to, elastic materials such as rubber, plastic, gel, foam, fabric, polyurethane, etc. The cap 458 may be replaceable and removably attached to the fixed gripper 403.

In the example embodiment shown in FIGS. 5A-5D, the rack plate 420 is roughly rectangular. A handle 430 may project off the edge of the of the rack plate 420 most distal to the fixed gripper 401. The handle 430 may be a part of a "U" shaped member. As shown, the bottom of the "U" shape and at least a portion of each upright of the "U" shape protrude from rack plate 420 forming a void 432. The void 432 is defined by the edge of the rack plate 420 and the protruding sections of the "U" shaped handle 430. A user's finger(s) may easily grip around the bottom of the "U" shape of the handle 430 via this void 432 when a user desires to manipulate the position of the rack plate 420.

In the example embodiment shown in FIGS. 5A-5D, at least a section of the uprights of the "U" shape of the handle 430 couple the handle 430 to the rack plate 420. The uprights of the "U" shape of the handle 430 may project off the top and bottom spans (directions relative to orientation in FIG. 5A) of the perimeter of the front face 422 of the rack plate 420 toward the front of the page at an angle substantially perpendicular to the front face 422 of the rack plate 420. The rack plate 420 and handle 430 may be formed as a continuous part during manufacture. Additionally, the top sections of the uprights of the "U" shape of the handle 430 may comprise the buttresses 456 that span from at least a portion of the rack plate 420 to the sliding gripper support base 421. In alternate embodiments, the handle 430 may be coupled to the rack plate 420 in any of a variety of ways and may take any suitable shape or size.

At least a portion of the handle 430 may be made of a material such as, but not limited to, rubber, polymer, composite, metal, plastic, foam, etc. Additionally, the handle 430 may comprise ergonomic finger groves, nubs, a ribbed texture, a honeycombed texture, etc.

The front face 404 of the back plate 402 may comprise at least one track-way 412 that runs substantially the full length of the width of the back plate 402. In the embodiment shown in FIGS. 5A-5B, twin track-ways 412 on the front face 404 of the back plate 402 run in parallel fashion from the edge of the back plate 402 on which the fixed gripper 401 is affixed to the opposite edge of the back plate 402. The twin track-ways 412 run along planes parallel to the top and bottom edges (in reference to FIG. 5A) of the back plate 402. The track-ways 412 may support and guide the rack plate 420 as the clamp apparatus 410 is moved between its clamped and unclamped orientations.

In the exemplary embodiment shown in FIGS. 5A-5D, each of the track-ways 412 comprise a groove 414 which is recessed into each track-way 412. The groove 414 is recessed into the side of each track-way 412 which faces the other track-way 412. This causes the track-ways 412 to have an "L" shape. The rear face 415 of the rack plate 420 comprises projections 440 which are dimensioned such that they may be received by the groove 414 in the track-ways 412 on the back plate 402. This tongue-in-groove type arrangement slidingly and securely couples the back plate 402 and rack plate 420 together.

The clamp apparatus 410 is biased toward the closed position by at least one extension spring 409. In the embodiment shown in FIGS. 5A-5D, the clamp apparatus 410 comprises two extension springs 409. One end of each extension spring 409 is hooked around an extension spring peg 411a. Each extension spring peg 411a projects toward the front of the page (relative to FIG. 5A) from the back plate 402 at an angle perpendicular to the front face 404 of the back plate 402. The other end of each extension spring 409 is hooked to another extension spring peg 411b. Each extension spring peg 411b projects toward the rear of the page (relative to FIG. 5A) from the rear face 415 of the rack plate 420 and an angle substantially perpendicular to the rear face 415 of the rack plate 420.

The extension spring pegs 411a and 411b may comprise a feature such as a notch to help ensure the extension springs 409 do not come off the extension spring pegs 411a and 411b. In some embodiments, the extension spring pegs 411a and 411b may be substituted for by a variety of different attachment means. In some embodiments, hooks, rings, eye bolts, U bolts, or any other arrangement obvious to one skilled in the art may be used. In other embodiments, the clamp apparatus 410 may not use extension springs 409 and instead use any other type of spring such as, but not limited to, a gas spring using a bladder, piston type arrangement, a compression spring, a compression spring made of a compressible, springy material such as rubber, an extension spring, a constant force spring, etc.

In an example embodiment, the non-tensioned length of the extension springs 409 is somewhat smaller than the distance between a set of extension spring pegs 411a and 411b. This is desirable because it ensures that the rack plate 420 and attached sliding gripper 403 are always biased against the fixed gripper 401 and that there is no "slop" in the clamp apparatus 410. Pulling the rack plate 420 and attached sliding gripper 403 away from the fixed gripper 401 (i.e. toward the open position) thus may tension the extension springs 409, and further spring load the clamp apparatus 410 toward the closed position. When the rack plate 420 is released, the clamp apparatus 410 will automatically default back toward its closed orientation due to the restoring force of the extension springs 409.

In the exemplary embodiment depicted in FIGS. 5A-5D, a user may open the clamp apparatus 410 by pulling the handle 430 as well as the attached rack plate 420 and sliding gripper 403 away from the fixed gripper 401. While the clamp apparatus 410 is held in the open position, a clamped object 100 may be placed in the space between the fixed gripper 401 and the sliding gripper 403. The clamp apparatus 410 may then be allowed to automatically return to the closed position by a user's release of the handle 430.

Other embodiments, including the embodiment shown in FIGS. 5A-5D, may comprise additional features which provide additional clamping force, make the clamp easier to operate, etc. In addition to the tongue-in-groove type arrangement mentioned above, an embodiment of the present disclosure comprises a lockable ratcheting rack and pinion type connection which may additionally be utilized to inform the movement of the rack plate 420.

In some embodiments, a gear assembly attachment site 418 may comprise a projection jutting from the front face 404 of the back plate 402. The gear assembly attachment site 418 is adapted to receive a gear shaft 416. In an example embodiment, the gear shaft 416 is a rod or dowel made of metal, plastic, or other suitably durable material. The gear shaft 416 may allow a pinion gear 450 to freely rotate about the axis of the gear shaft 416. In some embodiments, the gear assembly attachment site 418 may take the shape of a raised ring. In embodiments where the gear assembly attachment site 418 is shaped like a raised ring, the center, open section of the ring may have an internal diameter slightly, though not substantially larger than the diameter of gear shaft 416. The gear shaft 416 may fit securely and non-rotatably within the internal diameter raised ring of the gear assembly attachment site 418. A pinion gear 450 may be placed on the gear shaft 416.

Figure 5A:
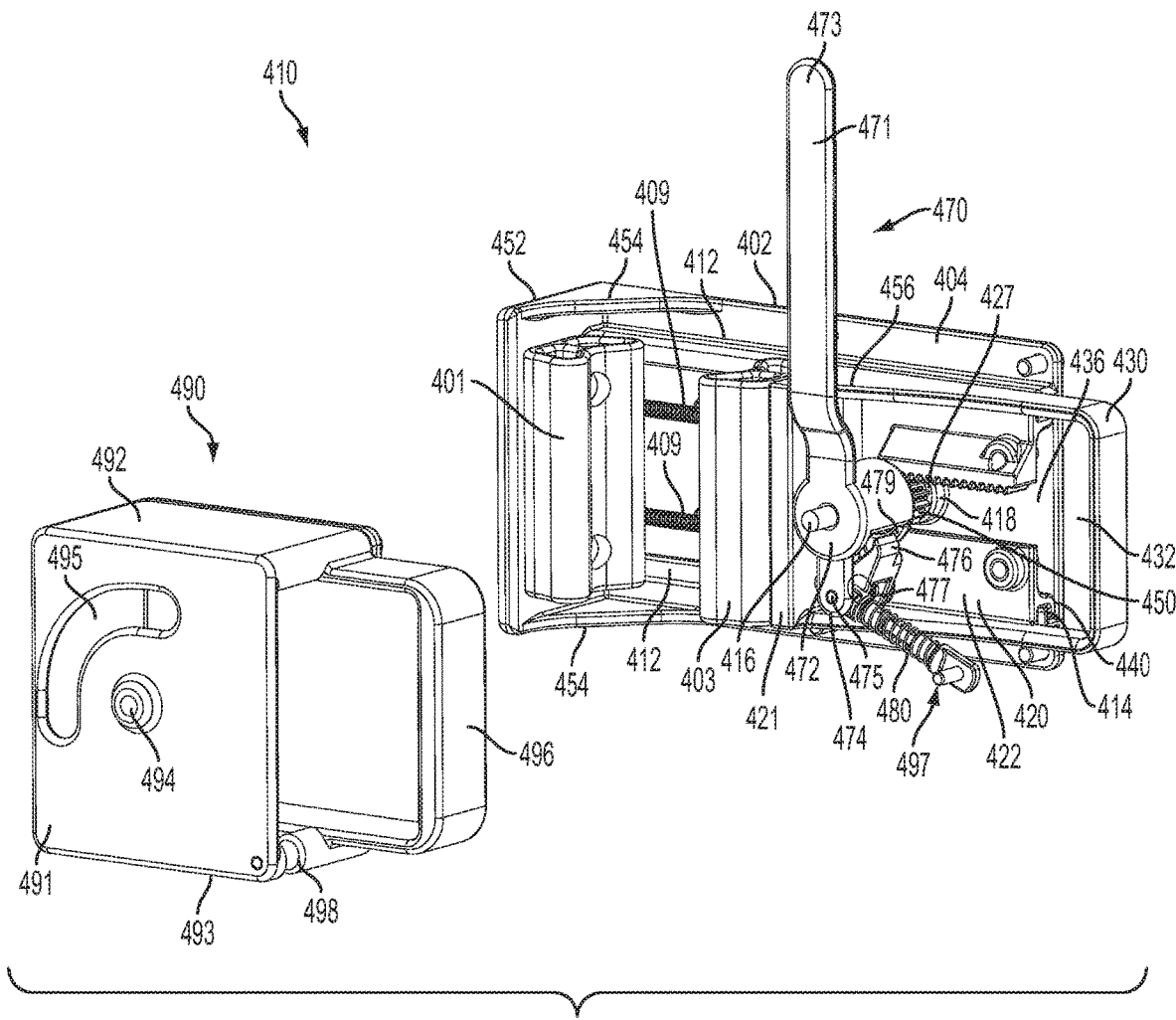
Figure 5C:
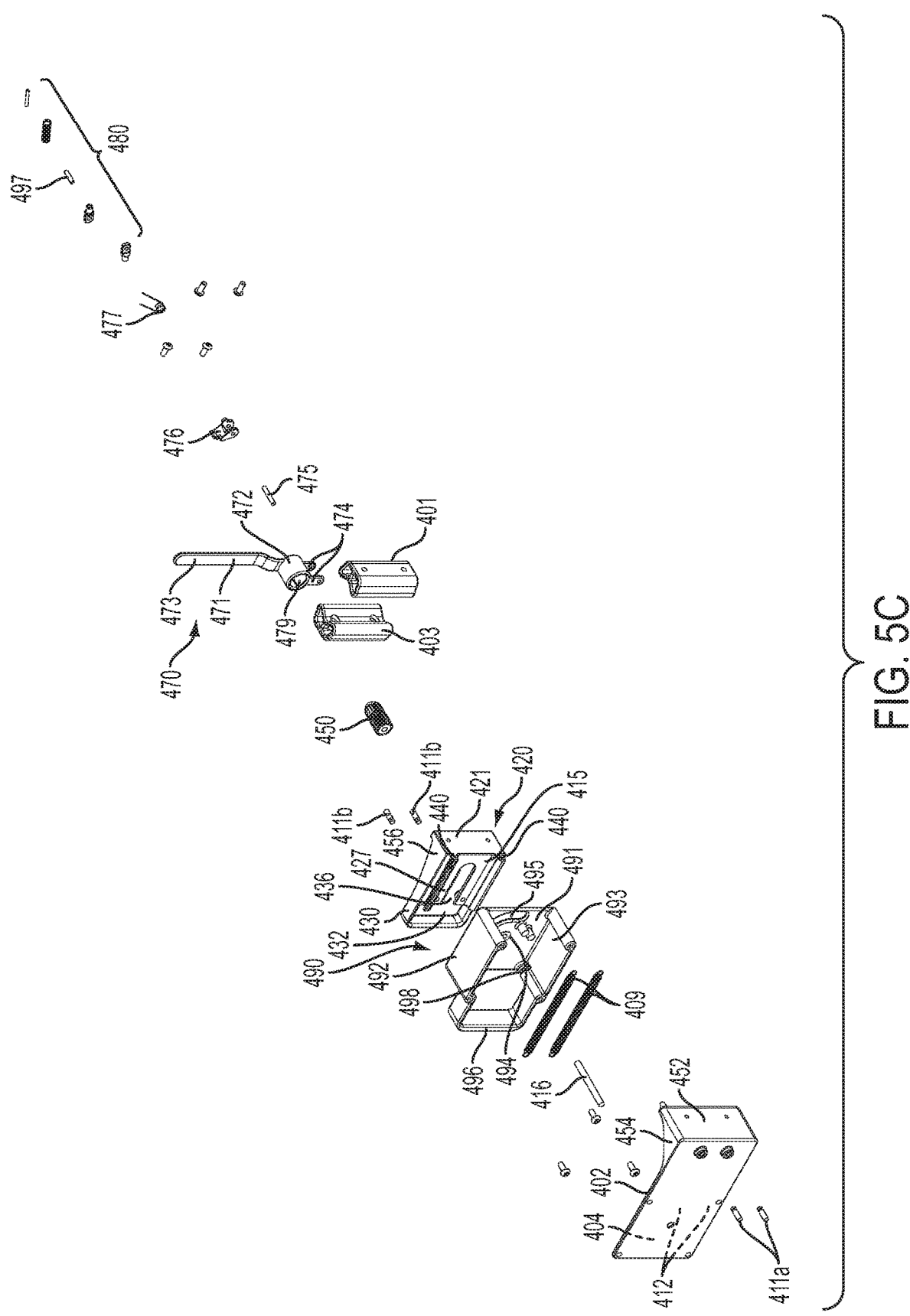
Figure 5D:
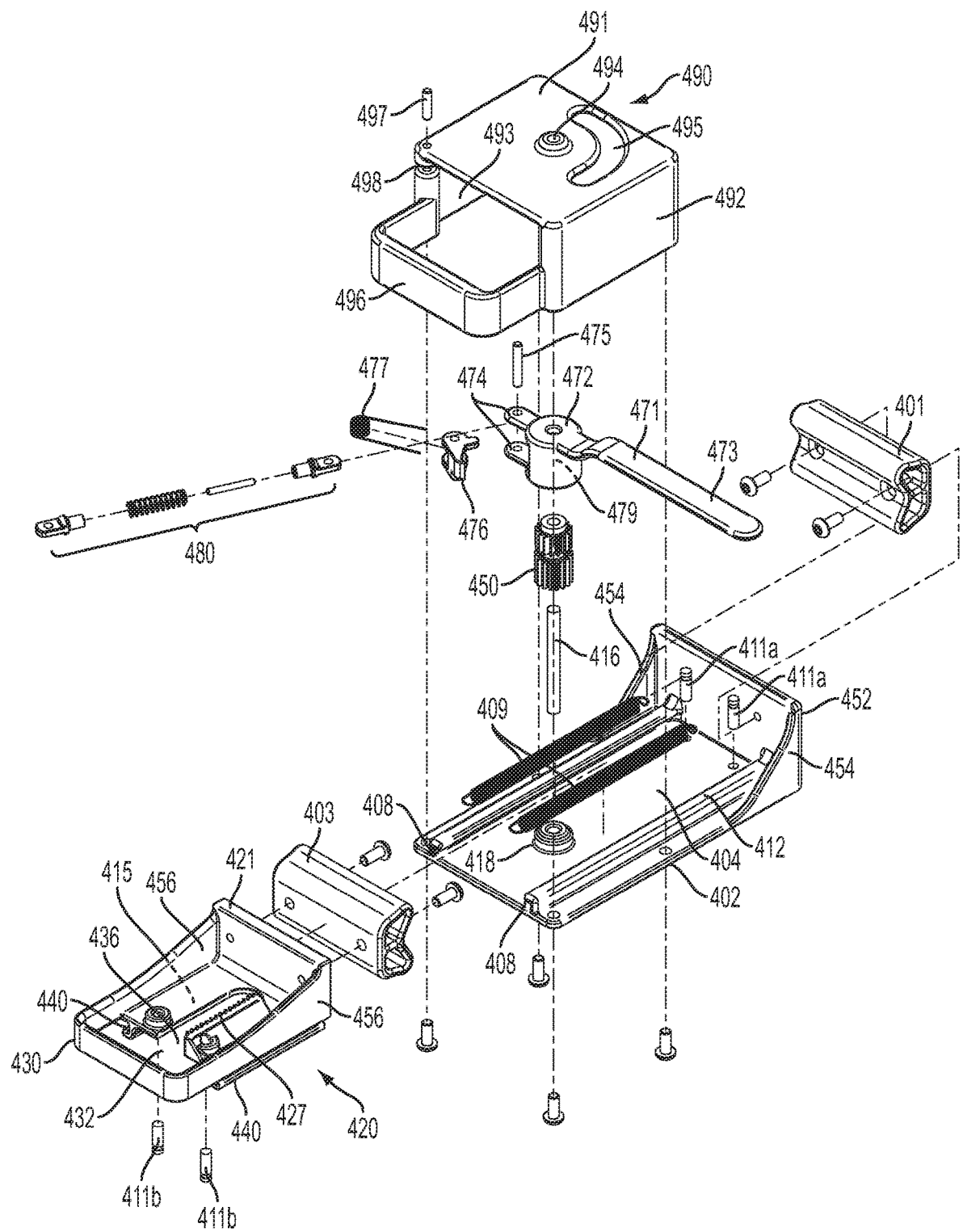

The rack plate 420 may comprise a slot that defines a pinion aperture 436 sized to allow the pinion gear 450 to protrude through the aperture 436 toward the front of the page (relative to FIG. 5A). As shown in the embodiment in FIGS. 5A-5D, a rack 427 is positioned adjacent the aperture 436 such that the teeth of the rack 427 interdigitate with the teeth of the pinion gear 450. Since the teeth of the rack 427 and teeth of the pinion gear 450 interdigitate, the pinion gear 450 rotates about the axis of the gear shaft 416 when the rack plate 420 is moved toward or away from the fixed gripper 401.

The interaction of the teeth of the rack 427 and the teeth of the pinion gear 450 may be exploited via a ratcheting assembly 470 to ratchet the rack plate 420 and attached sliding gripper 403 against a clamped object 100. This is desirable because it allows a user to generate more clamping force than the extension springs 409 alone are capable of generating. The ratcheting assembly 470 may also enable a user to lock the clamp apparatus 410 against a clamped object 100.

As shown in the exemplary embodiment illustrated in FIGS. 5A-5D, the ratcheting assembly 470 comprises a ratcheting lever 471. The ratcheting lever 471 comprises a ratcheting lever hub 472. The ratcheting lever hub 472 may be shaped like a cup which fits over the section of the pinion gear 450 protruding past the rack 427 of the rack plate 420. The front face (relative to FIG. 5A) of the pinion gear 450 may abut the bottom of the cup formed by the ratcheting lever hub 472. The ratcheting lever hub 472 comprises an orifice which may allow the ratcheting lever hub 472 to be slid onto the gear shaft 416. In such embodiments, the gear shaft 416 becomes a fulcrum for the ratcheting lever 471. The ratcheting lever hub 472 may also comprise an opening 479 in the wall of the ratcheting lever hub 472 cup which exposes a number of teeth of the pinion gear 450.

The ratcheting lever 471 may further comprise a ratcheting lever handle 473. In the example embodiment in FIGS. 5A-5D, the ratcheting lever handle 473 acts as the input side of the ratcheting lever 471. The ratcheting lever handle 473 may be grasped by a user and rotated about the axis of the gear shaft 416 to provide an input.

The ratcheting lever handle 473 may be made of the same material as the rest of the ratcheting lever 471, may be made of a different material, or may be made of a combination thereof. Possible materials may include, but are not limited to, rubber, polymer, composite, metal, plastic, foam, etc. Additionally, the ratcheting lever handle 473 may comprise ergonomic finger groves, nubs, a ribbed texture, a honeycombed texture, etc.

The ratcheting lever 471 may further comprise at least two ratcheting lever posts 474 opposite the ratcheting lever handle 473 which function as the output side of the ratcheting lever 471. The ratcheting lever posts 474 extend parallel to each other. One ratcheting lever post 474 is extended from the bottom section of the cup of the ratcheting lever hub 472. The other ratcheting lever post 474 may be extended off the rim section of the cup of the ratcheting lever hub 472. A ratcheting lever dowel 475 may span the distance between the ratcheting lever posts 474. A ratcheting pawl 476 and torsion spring 477 may be positioned on the ratcheting lever dowel 475 between the two ratcheting lever posts 474.

In the exemplary embodiment shown in FIGS. 5A-5D a user provides an input to the ratcheting lever lock 471 by rotating the ratcheting lever handle 473 substantially 90° counter-clockwise (relative to FIG. 5A) from the unlocked position to the locked position. In the unlocked position, the ratcheting lever handle 473 is oriented perpendicular to the top edge (relative to FIG. 5A) of the back plate 402 and the ratcheting pawl 476 is retracted away from the teeth of the pinion gear 450.

As the ratcheting lever handle 473 is rotated to the locked position, the ratcheting pawl 476 rotates into and engages the teeth of the pinion gear 450 through the opening 479 in the ratcheting lever hub 472. The torsion spring 477 applies a force against the ratcheting pawl 476 which keeps it in engagement with the teeth of the pinion gear 450. As a user continues to rotate the ratcheting lever handle 473 the ratcheting pawl 476 catches a tooth of the pinion gear 450 and forces the pinion gear 450 to rotate with the ratcheting lever 471. This rotation of the pinion gear 450 is transmitted to the rack 427 causing the rack 427 and the attached rack plate 420 and sliding gripper 403 to move toward the fixed gripper 401. If a clamped object 100 is present, this movement squeezes the clamped object 100 against the fixed gripper 401 with more clamping force than the tensioned extension springs 409 alone can generate. The ratcheting pawl 476 additionally locks the clamp apparatus 410 into the ratcheted and closed position because the ratcheting pawl 476 obstructs any rotation of the pinion gear 450 in a direction which would result in movement of the rack 427, rack plate 420 and attached sliding gripper 403 toward the open position.

In some embodiments, including the embodiment depicted in FIGS. 5A-5D, the clamp apparatus 410 may comprise a cover 490. In the embodiment shown in FIGS. 5A-5D, the cover 490 has a front plate 491. Extending perpendicularly off the top and bottom of the rear face (directions refer to orientation in FIG. 5A) of the front plate 491 are a top plate 492 and a bottom plate 493. The rear edges of the top plate 492 and the bottom plate 493, which run parallel to the plane of the front plate 491, may be immovably coupled to the cover 490 to the front face 404 of the back plate 403 via screws, or any other suitable fastening method. The right edge (relative to FIG. 5A) of the bottom plate 493 has a cutout 498. A dowel 497 may run from the front plate 491 through the cutout 498.

The front plate 491 of the cover 490 may comprise a second gear assembly attachment site 494. The second gear assembly attachment site 494 may comprise an orifice which has a diameter slightly, though not substantially larger than the diameter of the gear shaft 416. The gear shaft may fit securely and non-rotatably into the orifice of the second gear assembly attachment site 494.

In some embodiments, the front plate 491 may comprise a ratcheting lever handle slot 495 through which the ratcheting lever arm 473 may extend. The ratcheting lever handle slot 495 may arc so as to allow uninhibited travel of the lever handle 473 from the unlocked position to the locked position.

In one embodiment, the cover 490 has a palm support 496. The palm support 496 may be formed as a U-shaped member projecting from the cover 490 in a manner and direction similar to that of the handle 430 of the rack plate 420. The palm support 496 is adapted for use as a carrying handle. The palm support 496 may also be utilized to aid in easy, one-handed opening of the clamp apparatus 410. A user may place the palm support 496 in their palm and grasp the handle 430 by placing their finger(s) in the void 432. By clenching their fist, a user may then transition the clamp apparatus 410 to the open position.

The palm support 496 may be made of the same material as the rest of the cover 490, may be made of a different material, or may be made of a combination thereof. Possible materials may include, but are not limited to, rubber, polymer, composite, metal, plastic, foam, etc. Additionally, the palm support 496 may comprise ergonomic finger groves, nubs, a ribbed texture, a honeycombed texture, etc. to aid in carrying or grasping.

In some embodiments, the clamp apparatus 410 may comprise an over-center linkage 480 to help ensure the ratcheting lever lock 471 stays in a desired position. As shown in the embodiment in FIGS. 5A-5D, the over-center linkage 480 is attached at one end to the dowel 497 running through the cutout 498 in the cover 490. The other end of the over-center linkage 480 is attached to the ratcheting lever dowel 475 adjacent the ratcheting pawl 476 and torsion spring 477. The over-center linkage 480 may bias the ratcheting lever lock 471 to stay in either the unlocked position or locked position. When the over-center linkage 480 is in the over center position the clamp apparatus 410 is kept in the locked position. Before the over-center linkage 480 reaches an over-center position, the clamp apparatus 410 is kept in the unlocked position.

In another example embodiment of the present disclosure shown in FIG. 6A-6G, a sliding gripper 503 is coupled to a sliding gripper base 504 and may be capable of movement towards a fixed gripper 501 mounted on a fixed gripper base 524. As the sliding gripper 503 is displaced towards the fixed gripper 501, a clamped object 100 placed between the fixed gripper 501 and sliding gripper 503 may be clamped between the fixed gripper 501 and sliding gripper 503. As a clamped object 100 is clamped, at least one compression spring 550 compresses. The restoring force of the compressed compression spring 550 supplies additional clamping force as it pushes the sliding gripper 503 against the clamped object 100. An actuator handle latch 584 locks the clamp apparatus 510 in the closed position, safely securing the clamp apparatus 510 and its attached load (for example, a medical device) to a clamped object 100.

The fixed gripper 501 and sliding gripper 503 may be comprised of a material chosen for its gripping ability. The fixed gripper 501 and sliding gripper 503 may be made of high friction materials, compressible materials, materials exhibiting both these qualities, or any other suitable material. The fixed gripper 501 and sliding gripper 503 are made of materials which allow for a firm grip without the deformation of a clamped object 100. Suitable materials may include any suitable elastomeric or non-deformable substance, including but not limited to plastic, rubber, metal, foam, fabric, gel, etc. At least a portion of the fixed gripper 501 and sliding gripper 503 may comprise roughly semicircular depressions or contours to accommodate a round clamped object 100 such as a pole.

Figure 6B:
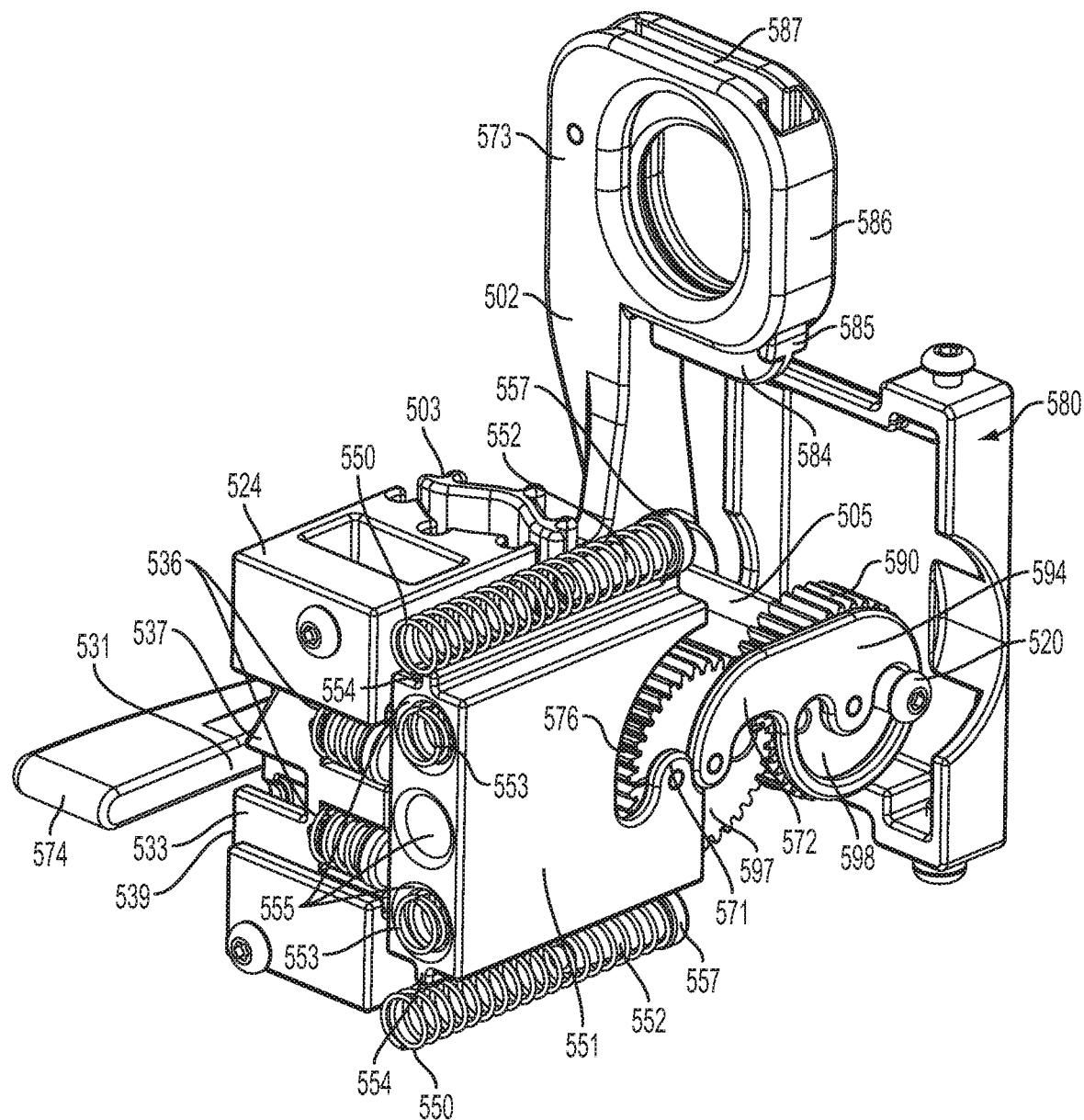
Figure 6C:
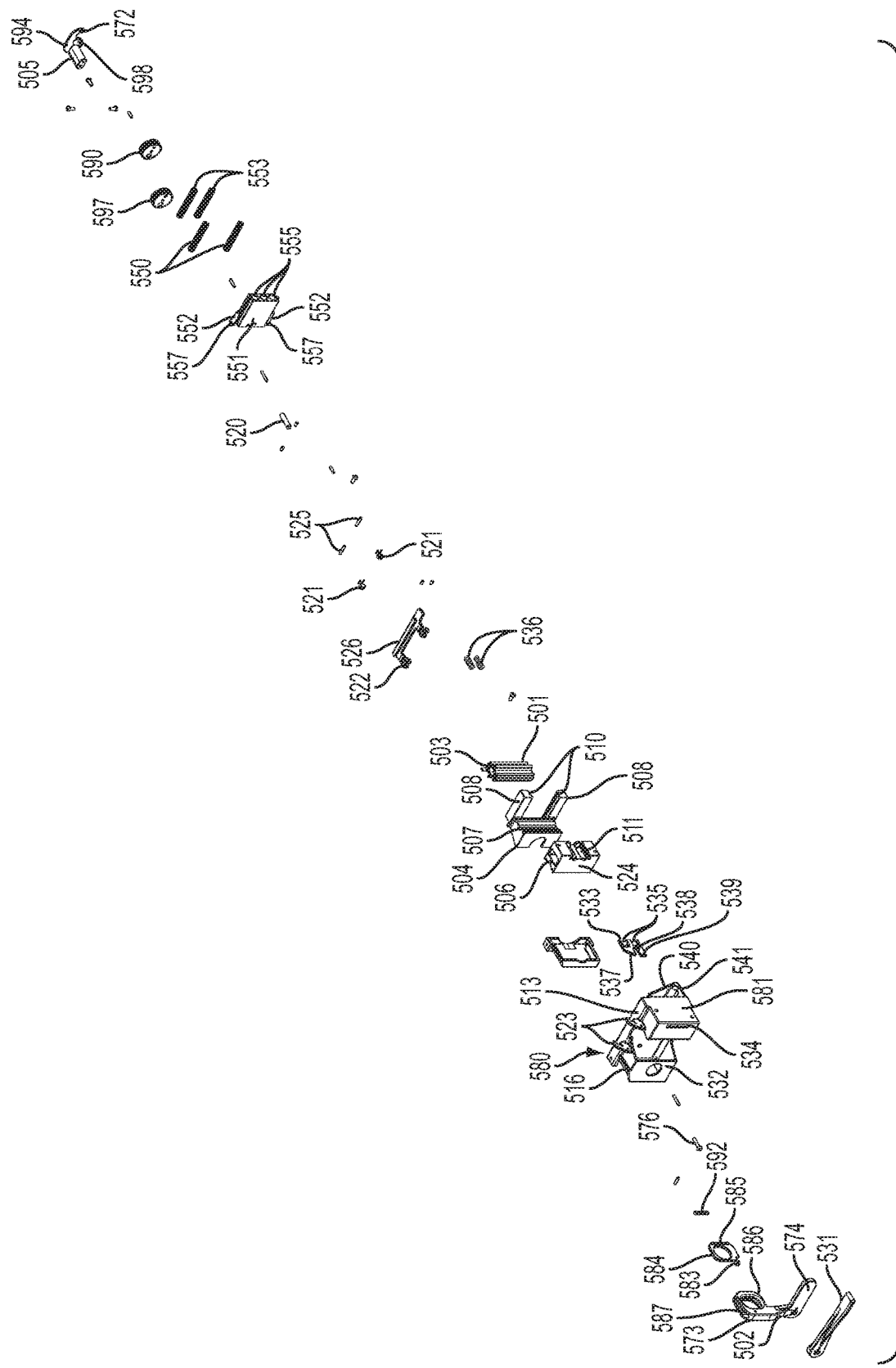

In the example embodiment shown in FIGS. 6A-6G, the fixed gripper 501 is mounted to a fixed gripper base 524. The fixed gripper base 524 comprises a fixed gripper attachment site 506. The fixed gripper attachment site 506, faces the sliding gripper 503. As best shown in FIG. 6E, the fixed gripper attachment site 506 may be a depression dimensioned to fit the contour of the fixed gripper 501. In some embodiments, the fixed gripper attachment site 506 may frictionally retain the fixed gripper 501 by means of a friction fit. In alternate embodiments, the fixed gripper 501 may be coupled to the fixed gripper attachment site 506 by any of a variety of means including, but not limited to, screws, bolts, ultrasonic welds, magnets, adhesive, hook and loop tape, or any other suitable coupling means.

The fixed gripper base 524 may be a substantially rectangular block which fits into a cavity of the housing 580 of the clamp apparatus 510. One side of the fixed gripper base 524 may be fixedly coupled to the right face 581 (relative to FIG. 6A) of the housing 580. The fixed gripper base 524 may be coupled to the right face 581 of the housing 580 by any of a number of means, such as screws, bolts, ultrasonic welds, magnets, adhesive, or any other suitable coupling means. The fixed gripper base 524 may also comprise a strike plate spring bay 511. The strike plate spring bay 511 will be elaborated upon later.

As best shown in FIG. 6F, the sliding gripper base 504 may comprise both a sliding gripper attachment site 507 and a guide rail 508 to guide movement of the sliding gripper 503. The sliding gripper attachment site 507 is located on the face of the sliding gripper base 504 which faces the left of the page (relative to FIG. 6F). As shown in FIG. 6F, the sliding gripper attachment site 507 may be depression dimensioned to fit the contour of sliding gripper 503. In some embodiments, including the embodiment in FIGS. 6A-6G, gripper attachment site 507 may frictionally retain the sliding gripper 503 by means of a friction fit. In alternate embodiments, the sliding gripper 503 may be coupled to the sliding gripper attachment site 507 by screws, bolts, ultrasonic welds, magnets, adhesive, or any other suitable coupling means.

Offset from the sliding gripper attachment site 507 may be at least one guide rail 508. In the example embodiment in FIG. 6A-6G, there are two guide rails 508. The guide rails 508 are offset from the sliding gripper attachment site 507 toward the front of the page (relative to FIG. 6F) and run perpendicular to the face of the sliding gripper base 504 on which the sliding gripper attachment site 507 is disposed. In some embodiments, a guide recess 510 may be defined along/into at least one surface of the guide rail(s) 508. The at least one guide rail 508 and guide recess 510 will be elaborated upon later.

Some embodiments may also include a slider sled 551. In some embodiments, the slider sled 551 is involved in four interrelated functions. First, the slider sled 551 provides a predefined track-way for the guide rails 508 of the sliding gripper base 504. Second, the slider sled 551 may support at least one compression spring 550. The compression spring(s) 550 may ensure that the slider sled 551, sliding gripper base 504 and attached components move together as a unit until the sliding gripper 503 abuts a clamped object 100. When the clamp apparatus 510 is locked in the closed position and the compression spring(s) 550 are compressed, the restoring force exerted by the compressed compression springs 550 provides additional clamping force against a clamped object 100. Third, the slider sled 551 may comprise at least one return spring pocket 555. A return spring 553 may be placed in each of the return spring pocket(s) 555. The return springs 553 may bias the clamp apparatus 510 toward the open position and automatically return the slider sled 551 to the open position when the user actuates the clamp apparatus 510 into the open position. Fourth, the slider sled 551 may comprise a catch 571 which may act as a stop during user actuation of the clamp apparatus 510.

In relation to the first function, the guide recess 510 is sized to fit a complimentary guide projection 554 located on at least one face of the slider sled 551. In the embodiment shown in FIGS. 6A-6G, the guide projections 554 run the length of the top face 558 and bottom face 556 of the slider sled 551. The guide projections 554 may serve as a track-way to direct the slider gripper base 504 as it moves between an open and closed position. In one embodiment, the guide projection(s) 554 are raised ridges running the length of the top face 558 and bottom face 556 and fit into the guide recesses 510 on slider gripper base 504. Alternatively, the guide projection 554 may be located on slider gripper base 504 or the guide rail(s) 508 of the slider gripper base 504 for movement along a guide groove 510 located on slider sled 551. Other embodiments may use other guide configurations.

In some embodiments, the guide rail 508 may be hollow and the guide recess 510 may be a slot which is cut through the guide rail 508 and into the hollow portion of the guide rail 508. The guide rail 508 may be open on one end and a compression spring 550 may be placed into the hollow portion of the guide rail 508 through this opening.

In relation to the second function, at least one of the guide projection(s) 554 on the slider sled 551 may feature a compression spring peg 552 on which one side of a compression spring 550 is seated. In one embodiment, the compression spring peg 552 is an essentially cylindrical structure with an end piece 575 that has a diameter greater than the diameter of its associated compression spring 550. Movement of slider sled 551 relative to the sliding gripper base 504 compresses the compression spring 550 between the end piece 575 and the end wall of the hollow guide rail 508. As the compression spring 550 is compressed, the compression spring peg 552 moves into the hollow of the guide rail(s) 508. Such movement may occur when the clamp apparatus 510 is moved from the open position to the closed position and a clamped object 100 is present. Selection of a compression spring 550 of appropriate elasticity allows the restoring force generated during compression to be sufficient to return the sliding gripper 503 and sliding gripper base 504 to the open position, while at the same time not unduly opposing user actuation of the clamp apparatus 510.

Relative to the third function, in some embodiments, the slider sled 551 may include at least one return spring 553 (best shown in FIG. 6B) which helps to bias the clamp apparatus 510 toward the open position. In the embodiment shown in FIGS. 6A-6G, there are two return springs 553. Each return spring 553 is seated in a return spring pocket 555 which has a diameter slightly larger than that of the return spring 553. Each return spring pocket 555 is recessed into the left face (relative to FIG. 6B) of the slider sled 551. One end of each return spring 553 abuts the bottom of its respective return spring pocket 555. The opposite end of each return spring 533 abuts the inside of the right face 581 (relative to FIG. 6A) of the housing 580 of the clamp apparatus 510. As the slider sled 551 is moved toward the right face 581 of the housing 580 when a user actuates the clamp apparatus 510 toward the closed position, the return springs 553 compress between the bottom of the return spring pockets 555 and the inside of the right face 581 of the housing 580. When a user actuates the clamp apparatus 510 toward the open position, the restoring force exerted by the return springs 553 automatically returns the slider sled 551 to its open orientation.

In the embodiment illustrated in FIGS. 6A-6G, there are three return spring pockets 555 yet only two return springs 553. In some embodiments, including the illustrated embodiment, a user may add additional return springs 553 to the clamp apparatus 510 if such action is deemed desirable.

The fourth, catch function of the slider sled 551 requires a broader description of how a user may actuate the clamp apparatus 510. As shown in FIGS. 6A-6G, the clamp apparatus 510 may comprise an actuator handle 502. User rotation of the actuator handle 502 may generate the force sufficient to actuate the clamp apparatus 510 toward the closed position. The actuator handle 502 is a roughly L-shaped structure comprised of a vertical arm 573 and a horizontal arm 574; both arms merge at a substantially right angle. The actuator handle 502 comprises at least one means for a rotatably attaching the actuator handle 502 to the clamp apparatus 510. In the example embodiment depicted in FIGS. 6A-6G, the actuator handle 502 is coupled to a gear shaft 520 with a screw 576. When the actuator handle 502 is rotated, the gear shaft 520 rotates about its axis.

At rest, the clamp apparatus 510 is biased to the open position. In the open position, the vertical arm 573 of the actuator handle 502 may point toward the bottom of the page as shown in FIG. 6A. The horizontal arm 574 may project toward the left of the page in a manner perpendicular to the vertical arm 573 of the actuator handle 502 as shown in FIG. 6A. To actuate the clamp apparatus 510 to the closed orientation, the actuator handle 502 must be rotated clockwise (in relation to FIG. 6A) substantially a full 180°.

In some embodiments, rotation of actuator handle 502 is converted to the linear motion propelling the sliding gripper 503 towards the fixed gripper 501. Thus, rotation of the actuator handle 502 closes the clamp apparatus 510. As mentioned above, rotation of the actuator handle 502 causes the rotation of a gear shaft 520. In some embodiments, at least one cam gear 590 is driven by the rotation of the gear shaft 520. Optionally, two or more cam gears 590 may be used to best accommodate the specific space and size needs of a particular embodiment of the clamp apparatus 510.

In the embodiment shown in FIGS. 6A-6G, the cam gear 590 is eccentrically attached to the gear shaft 520 at a distance "r" from the cam gear 590 center. In some embodiments an extension linkage 505 may project toward the center of the cam gear 590 from the gear shaft 520. The extension linkage 505 may be coupled into the center of the cam gear 590 to help support rotation of the cam gear 590 as the actuator handle 502 is rotated. Over the approximately 180° of rotation of the actuator handle 502, the cam gear 590 may displace a linear distance of approximately 2"r".

In the exemplary embodiment depicted in FIGS. 6A-6G, linear movement of the cam gear 590 is multiplied and imparted to the sliding gripper 503 through a linkage cam gear 597. The teeth of the linkage cam gear 597 and the teeth of the cam gear 590 interdigitate thus operatively coupling the cam gear 590 to the slider sled 551. In some embodiments, the linkage cam gear 597 is eccentrically coupled to the slider sled 551 at distance "r" from the center of the linkage cam gear 597. In the embodiment shown in FIGS. 6A-6G the linkage cam gear 597 is substantially a mirror image of the cam gear 590. Additionally, the movement of the linkage cam gear 597 mirrors the movement of the cam gear 590. Consequentially, a 180° rotation of the actuator handle 502 creates a linear displacement of 4"r" in the slider sled 551. This causes the sliding gripper base 504 and sliding gripper 503 to displace toward the fixed gripper 501. If a clamped object 100 is present, the slider sled 551 and sliding gripper base 504 move as a unit only until the sliding gripper 503 contacts the clamped object 100. When the sliding gripper 503 contacts the clamped object 100. The compression springs 550 begin to compress per the above description.

In embodiments where a smaller degree of linear displacement may be desirable, either the cam gear 590 or linkage cam gear 597 may not be eccentrically coupled into the clamp apparatus. This would halve the linear displace of slider sled 551. Alternatively, the distance "r" could be increased or decreased to achieve a greater or lesser degree of displacement of the slider sled 551.

The fourth, stop function of the slider sled 551 may prevent the actuator handle 502 from being rotated past the fully open orientation. As best shown in FIG. 6B the slider sled 551 features a catch 571. The catch 571 may be a nub which projects into a claw shaped cutout 576 in the slider sled 551. Other suitable shaped cutouts may alternatively be used. The catch 571 catches a claw shaped prong 572 which extends off a thin disc 594 which is coupled to the center of the cam gear 590. The thin disc 594 may be coupled to the center of the linkage cam gear 597. The thin disc 594 may feature a semi-circle track 598 which the gear shaft 520 may extend through. As the actuator handle 502 is rotated the thin disc 594 and attached prong 572 follow the eccentric motion of the cam gear 590. The position of the gear shaft 520 along the semi-circle track 598 also changes. In the closed position, the gear shaft 520 may be located at the right end of the semi-circle track 598 (relative to FIG. 6B). Also in the closed position, the prong 572 may not intrude into the catch 571 cutout. After 90° of actuator handle 502 rotation toward the open position, the gear shaft 520 is located at the lowest point in the arc of the semi-circle track 598. Consequently, the thin disc 594 and attached prong 572 are at the highest point in their travel and the prong 572 has entered the claw shaped cutout 576 above the nub catch 571. In the fully open position, the gear shaft 520 may be located at the left end of the semi-circle track 598. The prong 572 may fully protrude into the claw shaped cutout 576 and hook around the nub catch 571. In this position, the actuator handle 502 may not be further rotated toward the open direction because the catch 571 blocks any further movement of the prong 572. Additionally, further rotation of the actuator handle 502 is prohibited because the gear shaft 520 is at the end of the semi-circle track 598 and the thin disc 594 blocks any further travel.

In some embodiments, an actuator handle latch 584 functions to operatively prevent the actuator handle 502 from being rotated out of the locked position. The actuator handle latch 584 (best shown in FIG. 6G) may be a roughly rectangular, planar structure. There may be a hole through roughly the center of the actuator handle latch 584. The hole may be large enough to comfortably accommodate a user's finger. Relative to FIG. 6G, the top edge of the actuator handle latch 584 may comprise a latch compression spring peg 583 on which an actuator handle spring 592 may be seated. The bottom edge may comprise projections 585.

In some embodiments, the vertical arm 573 of the actuator handle 502 comprises a latch housing 586. As shown best in FIG. 6G, the latch housing 586 extends perpendicularly from the vertical arm 573 and over the top face 513 of the clamp apparatus 510. The latch housing 586 may comprise a channel 587 sized to fit the actuator handle latch 584, latch compression spring peg 583 actuator handle spring 592 and the projections 585. The channel 587 may be cut along the central plane of the latch housing 586 running perpendicular to the vertical arm 573. The channel 587 guides movement of the actuator handle latch 584. There may be a hole through roughly the center of the actuator latch housing 586 which is large enough to accommodate a user's finger.

The actuator handle latch 584 projects out of the actuator latch housing 586 and against the top face 513 of the housing 580. A dowel 588 may run through the channel 587 above the actuator handle spring 592. The dowel 588 is disposed such that the actuator handle spring 592 may bias the actuator handle latch 584 against the top face of the housing 580.

In the path of the actuator handle latch 584 a ramp 516 is disposed. As the actuator handle 502 is rotated toward the closed position, the actuator handle latch 584 abuts the ramp 516. As the actuator handle 502 continues to rotate toward the closed position, the actuator handle latch 584 rides up the ramp 516. This causes the actuator handle latch 584 to be pushed up the channel 587 and into the actuator latch housing 586 which in turn compresses the actuator handle spring 592 between the dowel 588 and the latch compression spring peg 583. When the actuator handle 502 is in the fully closed position, the actuator handle latch 584 clears the ramp 516 and the restoring force of the spring causes the actuator handle latch 584 to spring back against the top face 513 of the housing 580. This locks the clamp apparatus 510 in the closed position as any movement toward the open position is prevented by the actuator handle latch 584 catching on the lip of the ramp 516. To release the clamp apparatus 510 from the locked position, a user may insert a finger into the hole in the actuator handle latch 584 and latch housing 586 and pull the actuator handle latch 584 back inside the actuator latch housing 586. This allows the actuator handle latch 584 to clear the lip of the ramp 516 thus allowing rotation of the actuator handle 502 toward the open position.

In some embodiments, the horizontal arm 574 of the actuator handle 502, may also comprise a lock/latch feature 531. This lock/latch feature 531 may be present in conjunction with or as a substitute for the actuator latch 584. In embodiments where the horizontal arm 574 comprises a lock/latch feature 531, the front face 532 of the clamp apparatus 510 housing 580 may comprise a slot 534 through which a spring loaded strike plate 533 protrudes. The strike plate 533 (best shown in FIG. 6E) may be roughly planar. The bottom of the strike plate 533 (relative to FIG. 6E) may comprise at least one strike plate spring peg 535 on which a strike plate spring 536 is seated. In the embodiment depicted in FIGS. 6A-6G, there are two strike plate spring pegs 535 and two accompanying strike plate springs 536. The strike plate springs 536 fit inside the strike plate spring bay 511 recessed into the fixed gripper base 524. In some embodiments, the top edge of the strike plate 533 (relative to FIG. 6E) may comprise a ramp portion 537, a trough portion 538, and a post portion 539. The strike plate 533 protrudes from the slot 534. The strike plate 533 may be pushed into the slot 534, in the front face 532 of the housing 580 such that it does not protrude past the surface of the front face 532 of the housing 580. In this position, the strike plate springs 536 are compressed between a portion of the strike plate spring bay 511 and the strike plate spring pegs 535. This spring loads the strike plate 533 to automatically return to its protruding orientation.

As the actuator handle 502 is rotated to the closed position, the horizontal arm 574 of the actuator handle 502 contacts the ramp portion 537 of the strike plate 533. As the horizontal arm 574 is further rotated, it moves to a more elevated section of the ramp portion 537. Since the strike plate springs 536 are not strong enough to cause the horizontal arm 574 to deflect, the strike plate springs 536 compress and the strike plate 533 is pushed into the slot 534 to its non-protruding position. When the horizontal arm 574 passes the top of the ramp portion 537, the restoring force of the strike plate springs 536, causes the strike plate 533 to be pushed back toward its protruding position with the trough portion 538 abutting the horizontal arm 574. This locks the clamp apparatus 510 in the closed position. In this locked position, the horizontal arm 574 cannot be further rotated toward the closed position because the post portion 539 of the strike plate 533 blocks such movement. Additionally, the horizontal arm may not progress toward the open position because it will abut and be restricted in movement by the lip of the ramp portion 537. To unlock the clamp apparatus 510, a user must depress the post portion of the strike plate 533 into the slot 534 and compress the strike plate springs 536. This allows the horizontal arm 574 to clear the lip of the ramp 537 as a user rotates the actuator handle 502 toward the open position.

In some embodiments of the present disclosure, a quick release clip 519 may be used to secure a medical device or other object to the clamp apparatus 510. The quick release clip 519 may comprise a torsion clip 522 and a latch hook 523. In some embodiments of the present disclosure, at least one torsion spring 521 may be used to clip a load for the clamp apparatus 510 between the torsion clip 522 and the latch hook 523. In the example embodiment shown in FIGS. 6A-6G, two latch hooks 523 are firmly attached to the top face 513 of the housing 580. The latch hooks 523 are offset from each other. The hook portions of the latch hooks 523 project toward the back of the page (relative to FIG. 6A). The torsion clip 522 is pivotally attached to the latch hook 523 by a fastening means 525, which may for example be a pin, dowel, cotter pin, bolt, hex bolt, screw, or other means known to one skilled in the art. As shown in FIGS. 6A-6G, the torsion clip 522 may be a relatively planar member which spans the distance between the two latch hooks 523. In some embodiments, at least one surface of torsion clip 522 may comprise a catch 526. The catch 526 may act as a stop for a receiving structure on a medical device or other object. The torsion spring(s) 521 may supplement the catch 526 by biasing the receiving structure into contact with the latch hooks 523. The latch hooks 523 may also couple to a receiving structure on a medical device or other object. Rotation of the torsion clip 522 downwards spring loads each torsion spring 521 so that the torsion clip 522 will automatic pivot to the closed position when released. This is desirable because it causes the quick release clip 519 to automatically adjust to a load, such as medical device or other object, regardless of the size of the receiving structure.

Figure 6D:
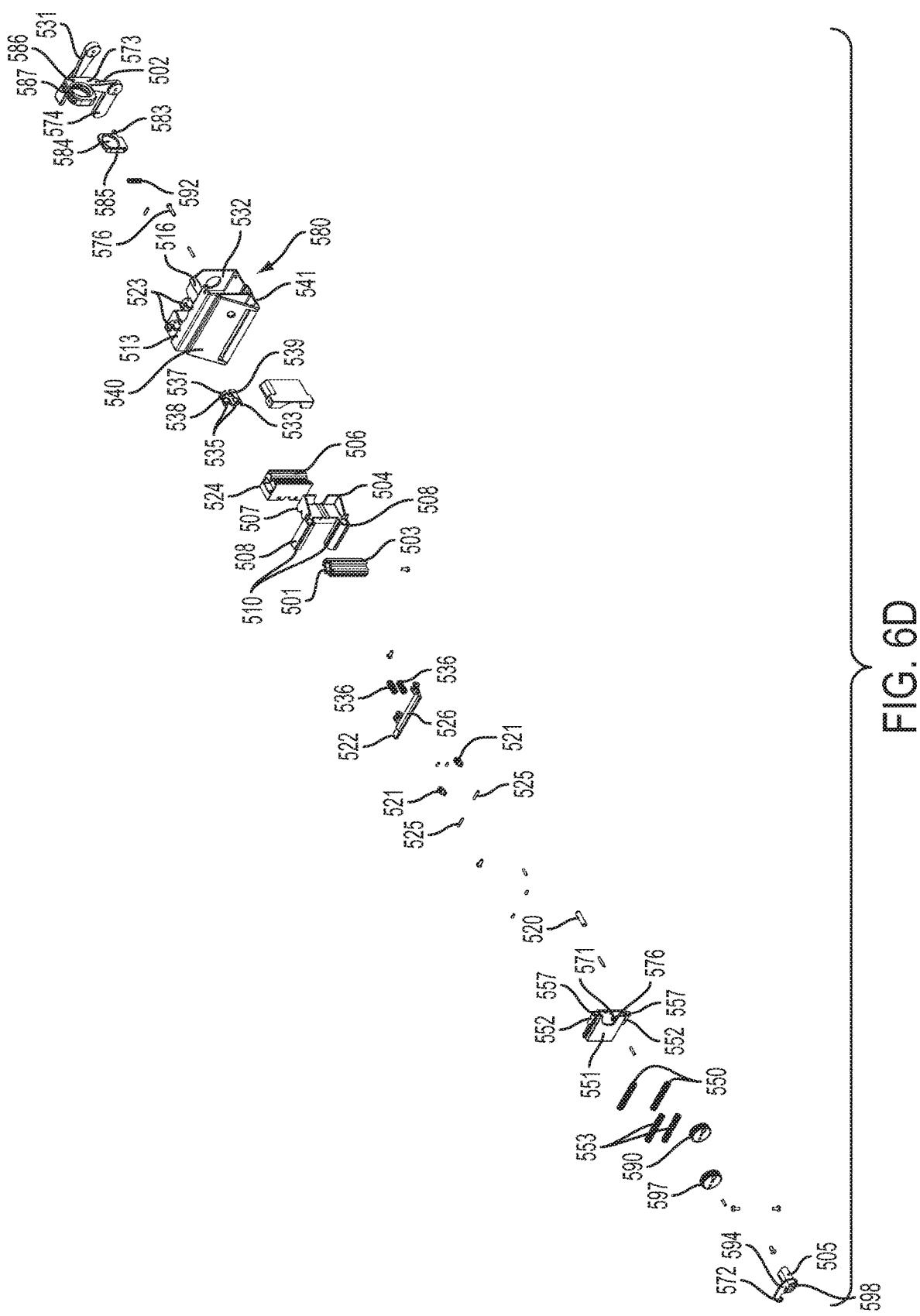

As best shown in FIG. 6D, some embodiments may comprise a rest 540 for a medical device or other object which may be coupled to the clamp apparatus via the quick release clip 519. As shown, the rest 540 may project at an angle from the top face 513 of the housing 580. Extending perpendicularly from the bottom edge of the back face 512 of the housing 580 may be a rest support 541 for the rest 540. The rest support 541 couples the back face 512 of the housing 580 to the rest 540. Additionally, the rest 540 may have various features which help to hold the medical device or other object in place on the rest 540.

The housing 580 or rest 540 may also feature any of a variety of mechanisms 515 (not shown) to attach a load to the clamp apparatus 510. Such mechanisms 515 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

FIGS. 7A-7D show another embodiment of a clamp apparatus 610. The clamp apparatus 610 comprises a first moving jaw 630 and a second moving jaw 632, coupled to move in unison. A clamped object 100 may be clamped between the first moving jaw 630 and the second moving jaw 632 and clamped by the clamp apparatus 610.

Figure 7A:
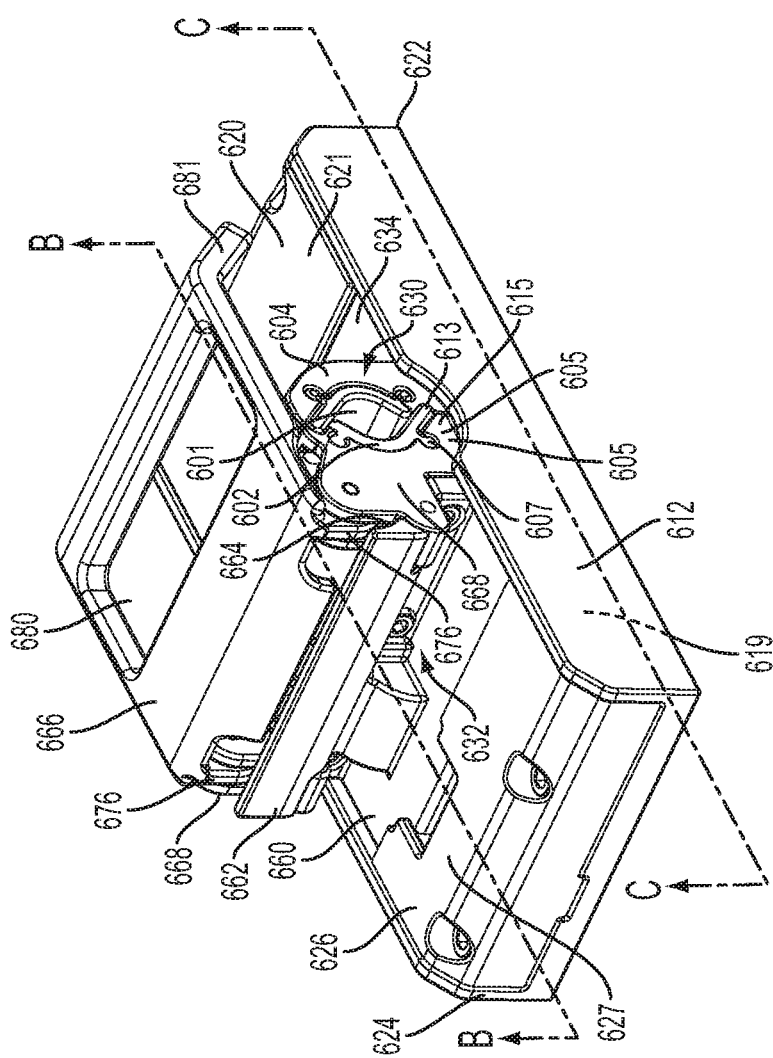
FIGS. 7A-7D show several views of a clamp in accordance with an embodiment of the present disclosure.
Figure 7B:
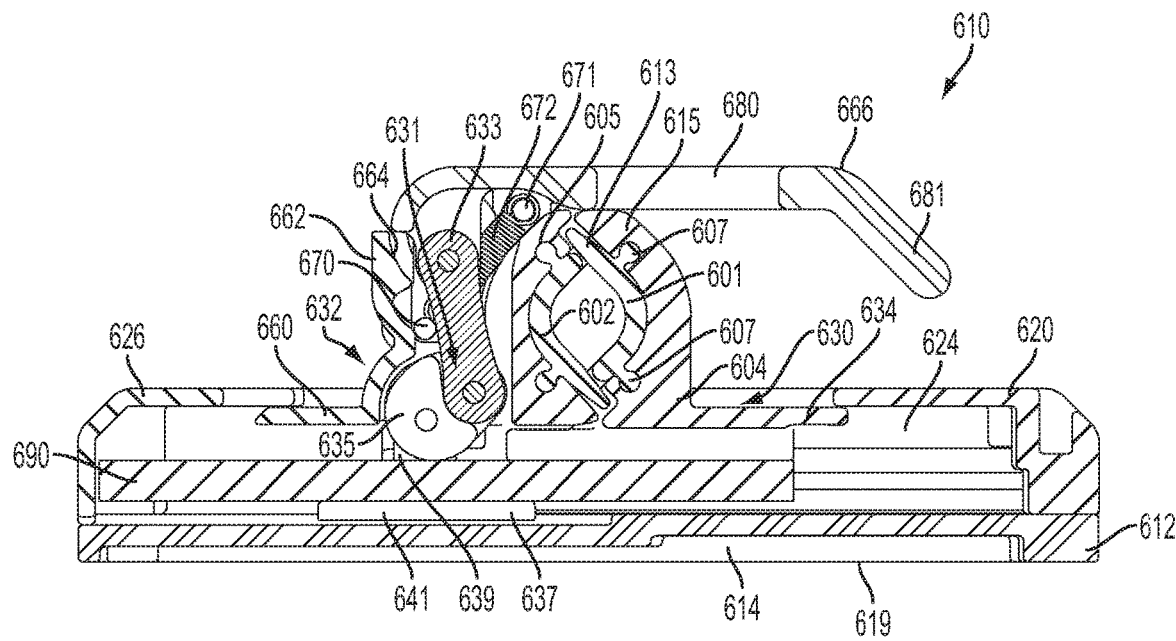
Figure 7C:
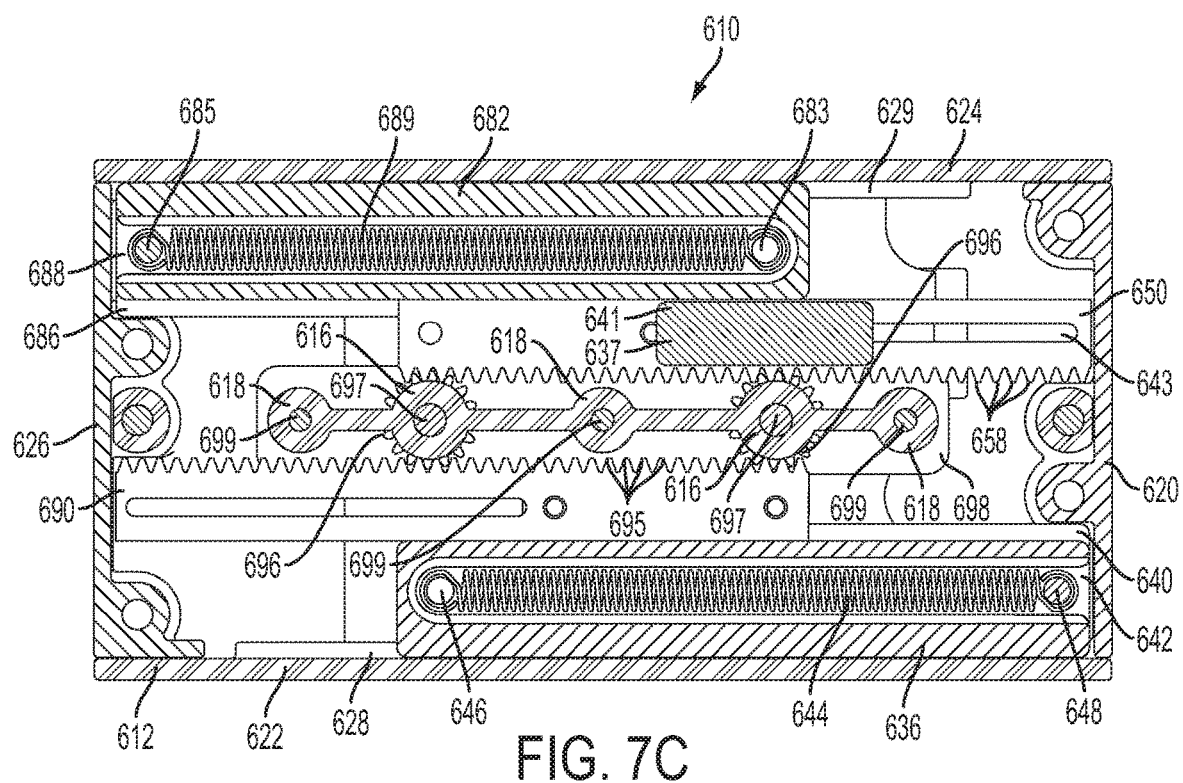

In some embodiments, the clamp apparatus 610 includes a housing 612. As shown in FIGS. 7A-7D, the housing 612 may be shaped like a rectangular tray. The bottom face 614 of the housing 612, may be substantially planar. In some embodiments, the bottom face 614 of the housing 612 may have one or more gear attachment sites 616. The bottom face may also have one or more raised posts 618. The raised posts may comprise a hole sunk substantially into the center of the posts 618. The hole may additionally be tapped to receive the thread of a screw. As shown in FIG. 7A, the gear attachment sites 616 and the raised posts 618 may all be in line with each other. Also as shown, the gear attachment sites 616 and the raised posts 618, may run along the center line of the bottom face 614 running parallel to the front wall 622 and back wall 624 of the housing 612. The gear attachment sites 616 and raised posts 618 will be further elaborated upon later.

At least a portion of the housing 612 may also feature any of a variety of mechanisms 619 (not shown) to attach a load to the clamp apparatus 610. Such mechanisms 619 may include, but are not limited to, brackets, magnets, straps, suction cups, hooks, screws or bolts, a friction fit, etc. This load could be any number of things, especially a medical device (such as an infusion pump, or peristaltic infusion pump), I.V. bag, etc.

As mentioned above, the housing 612 may comprise a front wall 622 and a back wall 624. Relative to FIG. 7D, the front wall 622 projects toward the top of the page from the edge of the bottom face 614 which faces the front of the page. The front wall 622 projects substantially perpendicularly to the plane of the bottom face 614 of the housing 612. The interior face of the front wall 622 may comprise a projecting track section 628 which runs parallel to the top and bottom edges of the front wall 622. The back wall 624 projects toward the top of the page from the edge of the bottom face 614 of the housing 612 which faces the back of the page. The back wall 624 projects perpendicularly to the bottom face 614 of the housing 612. The interior face of the back wall 624 may comprise a projecting track section 629 which runs parallel to the top and bottom edges of the back wall 624.

In the embodiment shown in FIGS. 7A-7D, the right side 620 and left side 626 of the housing 612 are detachable end caps. The right side 620 and left side 626 of the housing 612 may be coupled to the bottom face 614 of the housing 612 via screws, bolts, welds, or any other suitable means. In other embodiments, the right side 620 and left side 626 may be formed as a continuous part of the housing 612 during manufacture. The right side 620 of the housing 612 may have an overhanging flange 621 which overhangs a portion of the bottom face 614 of the housing 612. Similarly, the left side 626 of the housing 612 may have an overhanging flange 627 which overhangs a portion of the bottom face 614 of the housing 612.

In some embodiments, a first gripper 601 and a second gripper 602 are firmly attached to a first bracket 604 and a second bracket 606 respectively. The first bracket 604 and second bracket 606 respectively comprise a part of the first moving jaw 630 and second moving jaw 632. In the example embodiment depicted in FIG. 7A-7D, each of the first bracket 604 and second bracket 606 comprise friction fit features 607. The friction fit features 607 allow the respective grippers 601 and 602 to be coupled to the first bracket 604 and second bracket 606. In other embodiments, the grippers 601 and 602 may be coupled to the first bracket 604 and second bracket 606 by any number of coupling means including, but not limited to, screws, bolts, ultrasonic welds, magnets, adhesive, etc.

The first gripper 601 and second gripper 602 consists of a material chosen for its gripping ability. The first gripper 601 and second gripper 602 may be made of a high friction material, a compressible material, a material exhibiting both these qualities, or any other suitable material. The first gripper 601 and second gripper 602 are made of a material which allows a firm grip without the deformation of a clamped object 100. Suitable materials may include any suitable elastomeric or non-deformable substance, including but not limited to plastic, rubber, metal, foam, fabric, gel, polyurethane, etc. At least a portion of the first gripper 601 and second gripper 602 may comprise roughly semi-circular depressions or contours to accommodate a round clamped object 100 such as a pole. The first gripper 601 and second gripper 602 may be replaceable.

In some embodiments, the first gripper 601 and second gripper 602 may comprise gripper teeth 613 which project from the top and bottom edges of the first gripper 601 and second gripper 602. The gripper teeth 613 may be disposed about the first gripper 601 and second gripper 602 such that they may interdigitate with each other when the clamp apparatus 610 is in the closed position. The gripper teeth 613 allow the first gripper 601 and second gripper 602 to better encompass and hold a clamped object 100 when the clamp apparatus 610 in the closed position. The first bracket 604 and second bracket 606 may comprise bracket teeth 615 which support the gripper teeth 613 on the first gripper 601 and second gripper 602. The bracket teeth 615 may be disposed about the first bracket 604 and second bracket 606 such that they interdigitate with each other similarly to the gripper teeth 613.

The first bracket 604 may have a flange 634 which extends perpendicularly off the face of the first bracket 604 opposite the face to which the first gripper 601 is attached. The flange 634 is shaped and disposed such that it may slide under the overhanging flange 621 of the right side 620 of the housing 612. A polygonal block 636 may be fixedly coupled to the bottom face of the first bracket 604 (relative to FIG. 7D). In the example embodiment depicted in FIGS. 7A-7D, the polygonal block 636 is specifically a long, rectangular block. The short, right and left ends of the long, rectangular block run parallel to the right edge of the flange 634 of the first bracket 604. The long sides of the rectangular block in the example embodiment shown in FIGS. 7A-7D, extend for roughly seventy-five percent of the length of the front wall 622 of the housing 612. This may differ in alternate embodiments. The first bracket 604, first gripper 601, flange 634, and polygonal block 636 collectively may comprise the first moving jaw 630.

One side of the polygonal block 636 may abut the interior face of the front wall 622. The side of the polygonal block 636 which abuts the interior face of the front wall 622 may include a recessed groove 638 which accepts the projecting track section 628 on the interior face of the front wall 622. The projecting track section 628 operatively functions as a guide to inform the movement of the first moving jaw 630.

The side of the polygonal block 636 opposite the recessed groove 638 may include a projecting jaw track section 640. The projecting jaw track section 640 runs substantially parallel to the recessed groove 638. The bottom of the polygonal block 636 may comprise an extension spring trough 642 which is sunk into the bottom face of the polygonal block 636. The extension spring trough 642 also runs parallel to both the recessed groove 638 and projecting jaw track section 640. The bottom of the polygonal block 636 may abut the bottom face 614 of the housing 612.

A first extension spring 644 may be placed in the extension spring trough 642. As shown in the embodiment in FIGS. 7A-7D, the right end (relative to FIG. 7D) of the extension spring 644 may be coupled into the extension spring trough 642 by a first extension spring peg 646. The left end of the extension spring 644 may be coupled to the bottom face 614 of the housing 612 by a second extension spring peg 648. The first extension spring 644 biases the first moving jaw 630 toward the closed position. Moving the first moving jaw 630 from the closed position to the open position extends the first extension spring 644. The restoring force from the first extension spring 644 will automatically cause the first moving jaw 630 to return to the closed position. When a clamped object 100 is present, the restoring force of the first extension spring 644 will cause the first moving jaw 630 to press the first gripper 601 into the clamped object 100, automatically adjusting to the size or girth of the clamped object 100.

In some embodiments, including the embodiment shown in FIGS. 7A-7D, a first rack 650 may additionally be coupled to the bottom of the first moving jaw 630. As shown, the first rack 650 is coupled to the first moving jaw 630 via two screws 652. One screw 652 couples the first rack 650 to the first moving jaw 630 via a screw hole in the flange 634. As shown, the first moving jaw 630 may further comprise a coupling ledge 654 which projects along the plane of the bottom of the first bracket 604. The coupling ledge 654 projects toward the left of the page relative to FIG. 7D. The second screw 652 couples the first rack 650 to the first moving jaw 630 through a screw hole in the coupling ledge 654.

Figure 7D:
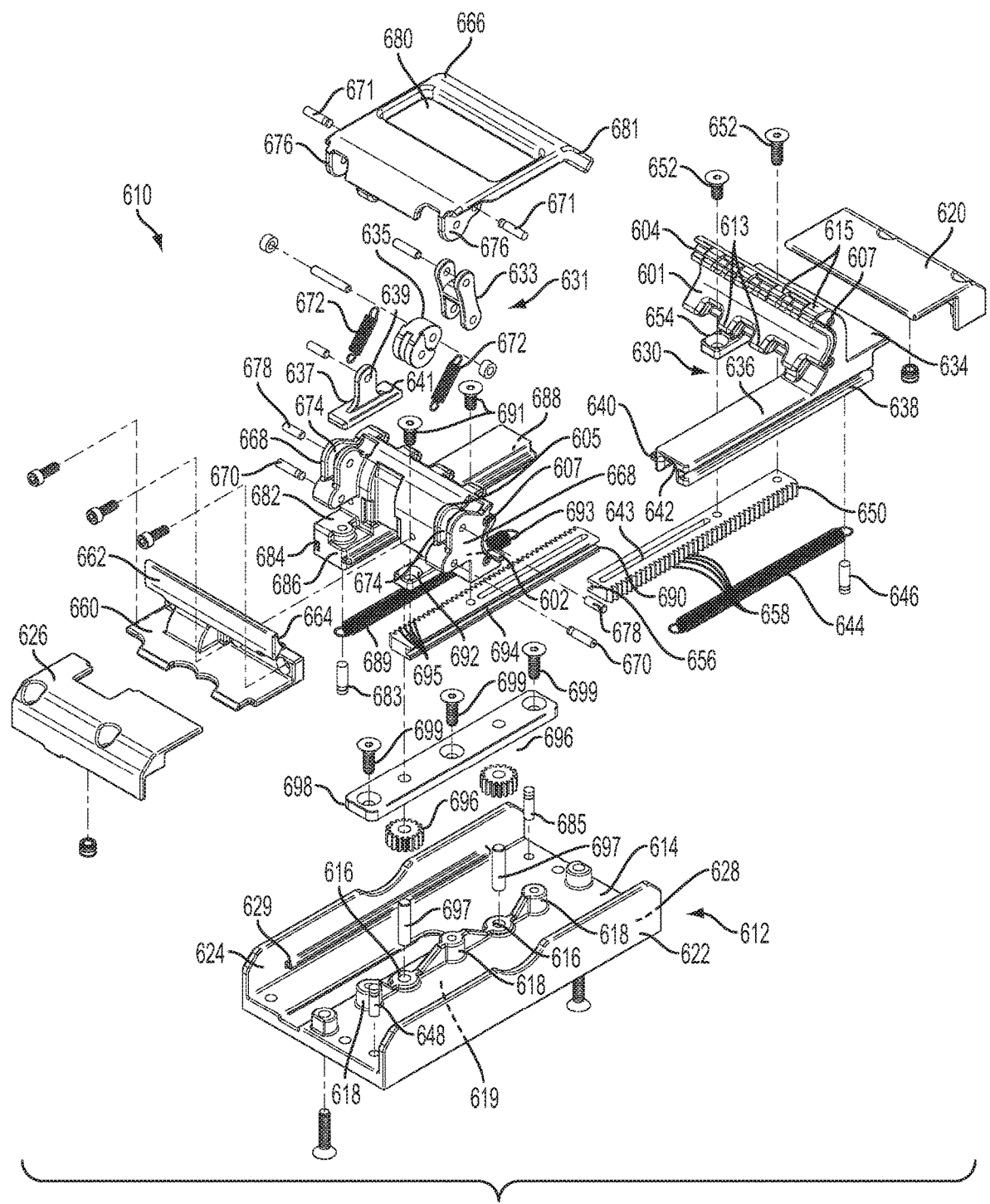

As shown in FIGS. 7A-7D, the first rack 650 has a rack groove 656 recessed into the face of the first rack 650 which faces the back of the page relative to FIG. 7D. The face opposite the rack groove 656 comprises a number of rack teeth 658.

The second moving jaw 632 may be generally similar to the first moving jaw 630. In the embodiment shown in FIGS. 7A-7D, the second moving jaw 632 is similar to the first moving jaw 630 although it comprises some additional or different components. The second bracket 606 may comprise a second flange 660 which extends perpendicularly off the face of the second bracket 606 opposite the face to which the second gripper 603 is attached. As shown in FIGS. 7A-7D, the second flange 660 may be detachable. In embodiments where the second flange 660 may be detachable, the second flange 660 may be coupled to the second bracket 606 via screws, bolts, magnets, adhesive, etc.

The second flange 660 may comprise a handle mechanism cover 662. The handle mechanism cover 662 may be raised off the second flange 660 toward the top of the page. At least one section of the handle mechanism cover 662 may comprise an arcuated segment 664 which faces a pivoting handle 666. The arcuated segment 664 allows the pivoting handle 666 to rotate. The handle mechanism cover 662 helps to keep foreign material and debris from getting inside the clamp apparatus 610. The handle mechanism cover 662 does not abut the second bracket 606. The handle mechanism cover 662 is offset from the second bracket 606 toward the left of the page relative to FIG. 7D. The void created between the second bracket 606 and the handle mechanism cover 662 allows various linkages to couple the pivoting handle 666 to the inner workings of the clamp apparatus 610.

The second bracket 606 may additionally comprise wings 668 which project off the front and back edges of the second bracket 606 toward the handle mechanism cover 662. In the embodiment shown in FIGS. 7A-7D, the wings 668 are not coupled to the handle mechanism cover 662. A handle spring peg 670 extends through the bottom of each wing 668. The handle spring pegs 670 protrude into the void between the second bracket 606 and the handle mechanism cover 662. One end of a handle extension spring 672 may be placed around each handle spring peg 670.

As shown in the embodiment depicted in FIGS. 7A-7D a slit 674 is recessed into the each wing 668 on a plane parallel to the front wall 622 and back wall 624 of the housing 612. The slit 672 may effectively make the top portion of each wing 668 into a coupling bracket to which fins 676 projecting off the pivoting handle 666 may be inserted. A dowel 678 may run through each wing 668 into the slits 674 and through the fins 676 of the pivoting handle 666. The dowels 678 pivotally couple the pivoting handle 666 to the wings 668 of the second bracket 606. The dowels 678 act as the pivot axis for the pivoting handle 666.

The fins 676 of the pivoting handle 666 may also comprise a hole through which a second set of handle spring pegs 671 may extend. The second set of handle spring pegs 671 may protrude into the void between the second bracket 606 and the handle mechanism cover 662. The end of each handle extension spring 672 not connected to the first set of handle spring pegs 670 is connected to the second set of handle spring pegs 671. The handle extension spring 672 thus acts as an over-center linkage and helps keep the pivoting handle 666 in the closed position if the pivoting handle 666 is in the closed position and helps keep the pivoting handle 666 in the open position if the pivoting handle 666 is in the open position.

In the example embodiments shown in FIGS. 7A-7D, the pivoting handle 666 extends toward the right of the page. In some embodiments, including those displayed in FIGS. 7A-7D, the pivoting handle 666 comprises an open section 680 through which a user may place their fingers. The open section 680 of the pivoting handle may be included to allow a user to grasp the pivoting handle 666 more easily. The pivoting handle may also comprise a bent or arced section 681. Again, the bent or arced section of the pivoting handle 666 may make it easier for a user to grasp the pivoting handle 666.

A portion of the bent or arced section 681 of the pivoting handle 666 may be made of the same material as the rest of the pivoting handle 666, may be made of a different material, or may be made of a combination thereof. Possible materials may include, but are not limited to, rubber, polymer, composite, metal, plastic, foam, etc. Additionally, the bent or arced section 681 may comprise ergonomic finger groves, nubs, a ribbed texture, a honeycombed texture, etc. to afford a user greater ease of use.

The second moving jaw 632 may additionally comprise a second polygonal block 682. The second polygonal block 682 may be fixedly coupled to the bottom face of the second bracket 606 (relative to FIG. 7D). In the example embodiment depicted in FIGS. 7A-7D, the second polygonal block 682 is specifically a long, rectangular block. The short, right and left ends of the long, rectangular block run perpendicular to the planes of the front wall 622 and back wall 624 of the housing 612. The long sides of the rectangular block in the example embodiment shown in FIGS. 7A-7D, extend for roughly seventy-five percent of the length of the back wall 624 of the housing 612. This may differ in alternate embodiments.

One side of the second polygonal block 682 may abut the interior face of the back wall 624. The side of the second polygonal block 682 which abuts the interior face of the back wall 624 may include a recessed groove 684 which accepts the projecting track section 629 on the interior face of the back wall 624. The projecting track section 629 operatively functions as a guide to inform the movement of the second moving jaw 632.

The side of the second polygonal block 682 opposite the recessed groove 684 may include a projecting second jaw track section 686. The projecting second jaw track section 686 runs substantially parallel to the recessed groove 684. The bottom of the second polygonal block 682 may comprise a second extension spring trough 688 which is sunk into the bottom face of the second polygonal block 682. The extension spring trough 688 also runs parallel to both the recessed groove 684 and projecting second jaw track section 686. The bottom of the second polygonal block 682 may abut the bottom face 614 of the housing 612.

A second extension spring 689 may be placed in the extension spring trough 688. As shown in the embodiment in FIGS. 7A-7D, the left end (relative to FIG. 7D) of the second extension spring 689 may be coupled into the extension spring trough 688 by a third extension spring peg 683. The right end of the extension spring 689 may be coupled to the bottom face 614 of the housing 612 by a fourth extension spring peg 685. The second extension spring 689 biases the second moving jaw 632 toward the closed position. Moving the second moving jaw 632 from the closed position to the open position extends the second extension spring 689. The restoring force from the second extension spring 689 will automatically cause the second moving jaw 632 to return to the closed position. When a clamped object 100 is present, the restoring force of the second extension spring 689 will cause the second moving jaw 632 to press the second gripper 603 into the clamped object 100, automatically adjusting to the size or girth of the clamped object 100.

In some embodiments, including the embodiment shown in FIGS. 7A-7D, a second rack 690 may additionally be coupled to the bottom of the second moving jaw 632. As shown, the second rack 690 is coupled to the second moving jaw 632 via two screws 691. One screw 691 couples the second rack 690 to the second moving jaw 632 via a screw hole in a ledge 692 which projects under the second flange 660. As shown, the second moving jaw 630 may further comprise an additional ledge 693 which projects along the plane of the bottom of the second bracket 606. The additional ledge 693 projects toward the right of the page relative to FIG. 7D. The second screw 691 couples the second rack 690 to the second moving jaw 632 through a screw hole in the additional ledge 693.

As shown in FIGS. 7A-7D, the second rack 690 has a second rack groove 694 recessed into the face of the second rack 690 which faces the front of the page relative to FIG. 7D. The face opposite the second rack groove 694 comprises a number of second rack teeth 695.

When the clamp apparatus 610 is assembled, the second rack groove 694 fits around and is guided by the projecting jaw track section 640 coupled to the first moving jaw 630. Similarly the rack groove 656 fits around and is guided by the projecting second jaw track section 686. The first rack teeth 658 and the second rack teeth 695 face each other. The first rack 650 and second rack 690 run substantially parallel to each other. The first rack teeth 568 and second rack teeth 695 mesh with teeth on opposite sides of at least one pinion gear 696. The at least one pinion gear 696 may be placed on a gear shaft 697 which runs into the at least one gear attachment site 616 described earlier in the specification. In the embodiment depicted in FIGS. 7A-7D, two pinion gears 696 are present. Each pinion gear 696 is placed on its own gear shaft 697 which in turn runs into its own gear attachment site 616 located on the bottom face 614 of the housing 612. To ensure the pinion gears 696 do not stray off their associated gear shafts 697, the pinion gears 696 may be sandwiched against the back face 614 of the housing 612 by a bar-like plate 698. The bar-like plate 698 is coupled to the raised posts 618 which project off the back face 614 of the housing 612 via screws 699.

Since both the first rack 650 and the second rack 690 mesh with the same pinion gear(s) 696 on opposite sides of said pinion gear(s) 696, any movement of either the first moving jaw 630 or the second moving jaw 632 necessitates movement of the other moving jaw in the opposite direction. If one moving jaw is pulled to the open position, the other moving jaw must then also move to the open position. If one moving jaw retracts toward the closed position, the other moving jaw must then also retract toward the closed position.

The clamp apparatus 610 additionally comprises a tightening/locking mechanism 631. The tightening/locking mechanism 631 may comprise a number of components. In the embodiment depicted in FIGS. 7A-7D, the tightening/locking mechanism 631 comprises a linkage 633, a cam 635, and a cincher 637. The cincher 637 may comprise a post 639 and a flat plate 641. The tightening/locking mechanism 631 may be disposed in the void between the handle mechanism cover 662 and the gripper bracket 605. The linkage 633 is pivotally coupled on one end to the pivoting handle 666. The linkage 633 may be pivotally coupled to the pivoting handle 666 by any means known to one skilled in the art. The other end of the linkage 633 is pivotally coupled to an end of the cam 635. The other end of the cam 635 may comprise a slot which accepts the post 639 of the cincher 637. The cam 635 may be pivotally coupled to the post 639 of the cincher 637 by any means known to one skilled in the art. In the example embodiment, the post 639 of the cincher 637 projects perpendicularly from the flat plate 641 of the cincher 637.

The flat plate 641 of the cincher 637 is disposed under the rack 650 of the first moving gripper 630 when the clamp apparatus 610 is fully assembled. The post 639 of the cincher 637 projects up through a channel 643 which is cut out of the rack 650. The channel 643 may not run the entire length of the rack 650.

In the embodiment shown in FIGS. 7A-7D, as the pivoting handle 666 is pivoted from the open position to the closed position, the linkage 633 also moves. Movement of the linkage 633 causes the cam 635 to rotate. Rotation of the cam 635 causes the cincher 637 to experience linear displacement along the channel 643 of the rack 650. Since the channel 643 does not run the entire length of the rack 650, the post 639 of the cincher 637 abuts the end of the channel 643 and begins to cause linear displacement of the rack 650. Linear displacement of the rack 650 causes both the first moving jaw 630 and second moving jaw 632 to move, cinch down on, and clamp harder on a clamped object 100. In the embodiment shown in FIGS. 7A-7D, the linkage 633 is also an over-center linkage. When the pivoting handle 666 moves all the way to the closed position, the linkage 633 assumes an over-center position. When the linkage 633 assumes this over-center position, the clamp apparatus 610 is effectively locked.

FIGS. 8A-8D show another example embodiment of a clamp apparatus 710. In the clamp apparatus 710 shown in FIGS. 8A-8D, a user rotates a toggle handle 750 to provide the force needed to propel a movable gripper assembly 704 towards a fixed gripper assembly 703 via at least one linkage 770 which may be an over-center linkage.

In some embodiments, such as the embodiment shown in FIGS. 8A-8D, the fixed gripper assembly 703 comprises a fixed gripper cradle 711, a fixed gripper 713, and a fixed gripper base 717. The fixed gripper cradle 711 extends off the top face of the fixed gripper base 717. More specifically, the fixed gripper cradle 711 extends from the right edge (relative to FIG. 8D) of the fixed gripper base 717 at an angle roughly perpendicular to the top face of the fixed gripper base 717 and is fixedly coupled to the fixed gripper base 717.

A fixed gripper 713 is coupled to the face of the fixed gripper cradle 711 which faces the movable gripper assembly 704. The fixed gripper 713 may be coupled to the fixed gripper cradle 711 by any of a variety of coupling means including, but not limited to, screws, bolts, magnets, adhesive, ultrasonic welds, snap fit, friction fit. In some embodiments the fixed gripper 713 may be overmolded onto the fixed gripper cradle 711.

The fixed gripper base 717 may be a roughly rectangular block as shown in FIGS. 8A-8D. The fixed gripper base 717 may comprise a cavity 719 which is dimensioned to fit and surround the gripper sled 705 when the clamp apparatus 710 is in the closed orientation. The fixed gripper base 717 may also comprise at least one buttress 715 which helps to support the fixed gripper cradle 711. The fixed gripper base 717 may comprise one or a number of threaded holes 791. In the embodiment depicted in FIGS. 8A-8D, four screws 714 run through the housing 712 of the clamp apparatus 710 and into corresponding threaded holes 791 in bottom of the fixed gripper base 717. The four screws 714 couple the fixed gripper base 717 to the housing 712. In alternate embodiments, different coupling methods may be employed including, bolts, welds, magnets, adhesive, and any other coupling method known to one skilled in the art. The fixed gripper base 717 may alternatively be a continuous part of the housing 712.

In some embodiments, including the embodiment shown in FIGS. 8A-8D, the movable gripper assembly 704 comprises a movable gripper cradle 706, movable gripper 701, and a gripper sled 705. As shown in FIGS. 8A-8D, the movable gripper cradle 706 extends off the top face of a gripper sled 705. More specifically, the movable gripper cradle 706 extends from the right edge (relative to FIG. 8D) of the gripper sled 705 at an angle roughly perpendicular to the top face of the gripper sled 705 and is fixedly coupled to the gripper sled 705. This may differ in alternate embodiments.

A movable gripper 701 is coupled to the face of the movable gripper cradle 706 which faces the fixed gripper assembly 703. The movable gripper 701 may be coupled to the movable gripper cradle 706 by any of a variety of coupling means including, but not limited to, screws, bolts, magnets, adhesive, ultrasonic welds, snap fit, friction fit.

The movable gripper 701 and fixed gripper 713 may consist of a material chosen for its gripping ability. The movable gripper 701 and fixed gripper 713 may be made of a high friction material, a compressible material, a material exhibiting both these qualities, or any other suitable material. The movable gripper 701 and fixed gripper 713 are made of a material which allows for a firm grip without the deformation of a clamped object 100. Suitable materials may include any suitable elastomeric or non-deformable substance, including but not limited to plastic, rubber, metal, foam, fabric, gel, etc. At least a portion of the movable gripper 701 and fixed gripper 713 may comprise roughly semi-circular depressions or contours to accommodate a round clamped object 100 such as a pole. The movable gripper 701 and fixed gripper 713 may be replaceable.

Figure 8A:
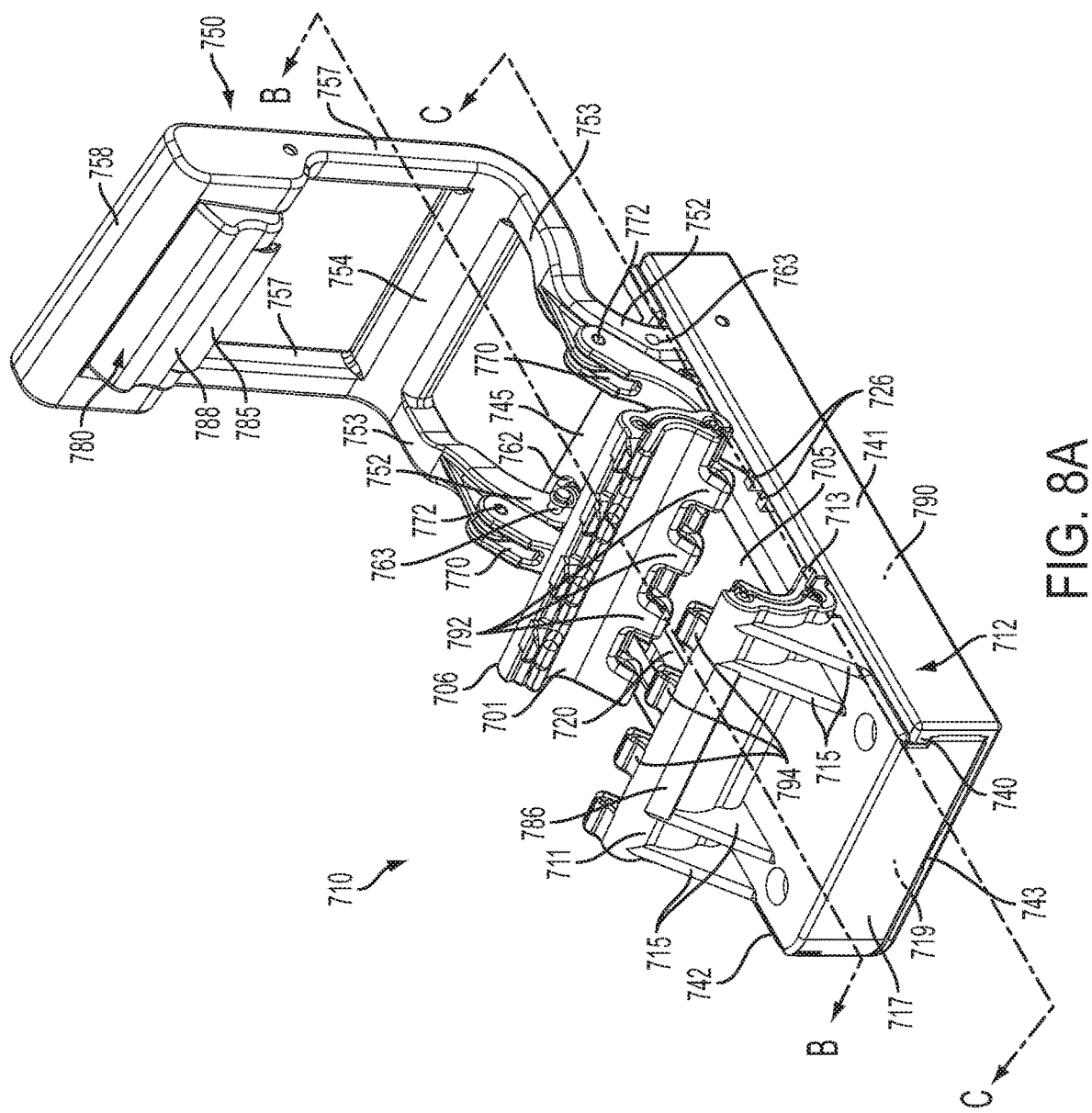
FIGS. 8A-8D show several views of a clamp in accordance with an embodiment of the present disclosure.
Figure 8B:
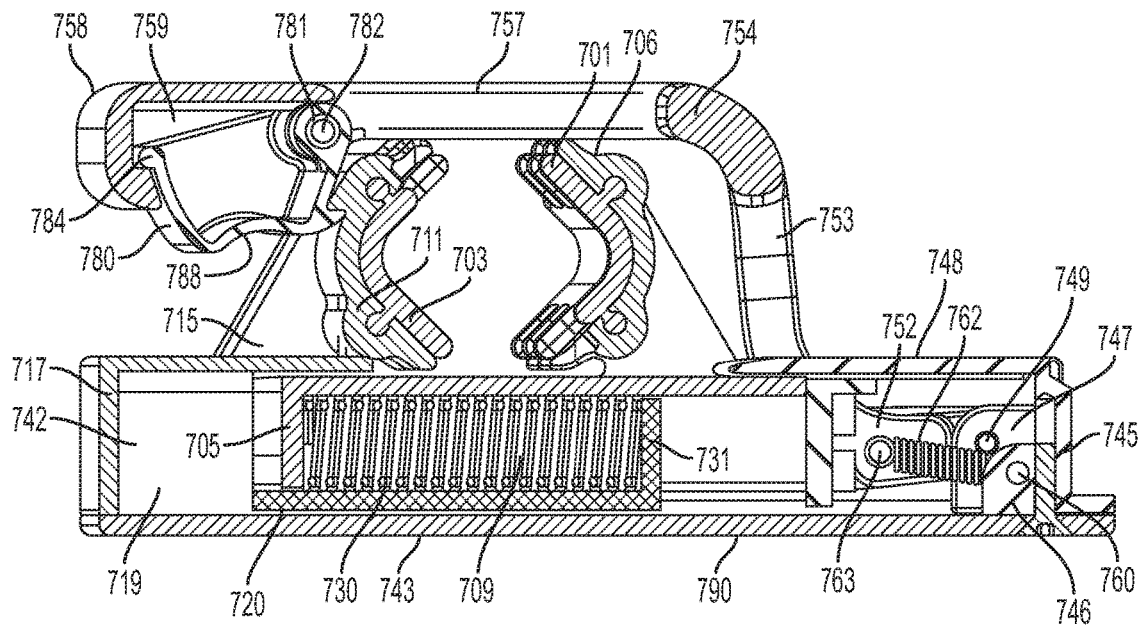
Figure 8C:
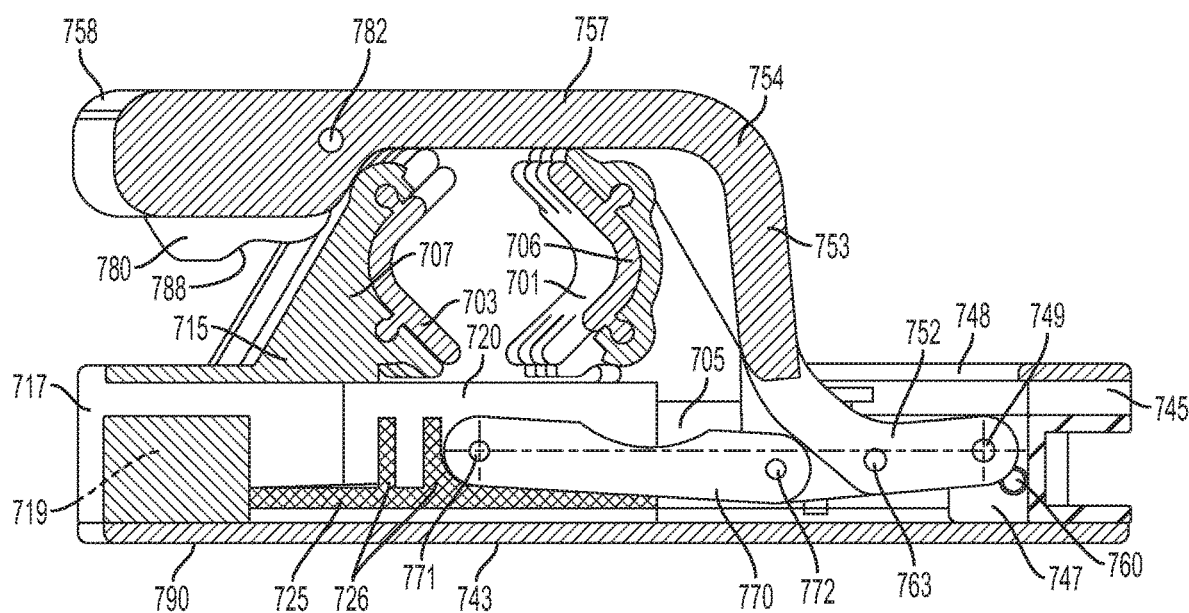

In some embodiments, the movable gripper 701 and fixed gripper 713 may comprise gripper teeth 792 (As shown in FIG. 8A) which project from the top and bottom edges of the movable gripper 701 and fixed gripper 713. The gripper teeth 792 may be disposed about the movable gripper 701 and fixed gripper 713 such that they may interdigitate with each other when the clamp apparatus 710 is in the closed position. The gripper teeth 792 allow the movable gripper 701 and fixed gripper 713 to hold an increased range of clamped object 100 when the clamp apparatus 710 is in the closed position. By disposing the gripper teeth 794 such that they may interdigitate, the movable gripper 701 may move further toward the closed position. The movable gripper cradle 706 and the fixed gripper cradle 711 may comprise cradle teeth 794 which support the gripper teeth 792 on the movable gripper 701 and fixed gripper 713. The cradle teeth 794 may be disposed about the movable gripper cradle 706 and the fixed gripper cradle 711 such that they interdigitate with each other similarly to the gripper teeth 792.

As illustrated in the example embodiment in FIGS. 8A-8D, the gripper sled 705 may be roughly rectangular. The gripper sled 705 may be substantially hollow and open to the hollow on one end. In FIGS. 8A-8D, the gripper sled 705 is hollow, except for a dividing wall 707 (relative to FIG. 8D) which extends from the interior bottom face of the hollow to the interior top face of the hollow. The dividing wall 707 divides the hollow portion of the gripper sled 705 into two spring bays 709 which are roughly equally dimensioned. The gripper sled 705 in FIGS. 8A-8D is open to the hollow on its right end (relative to FIG. 8D). In the embodiment shown in FIGS. 8A-8D a spring 730 is seated in each of the spring bays 709. The spring 730 is a compression spring 730. In a preferred embodiment, the clamp apparatus 710 may be adapted to fit at least one constant force spring 4012 instead of or in addition to the compression spring 730. Constant force springs 4012 may be used in other embodiments such as but not limited to those detailed above. Using a constant force spring 4012 is preferable because it may make the clamp apparatus 710 easier to operate, especially when it is being used to clamp a large/thick object. It may also allow the clamp apparatus 710 to be made more compactly. An alternative embodiment comprising a constant force spring 4012 is shown in FIGS. 8E-8F.

Figure 8D:
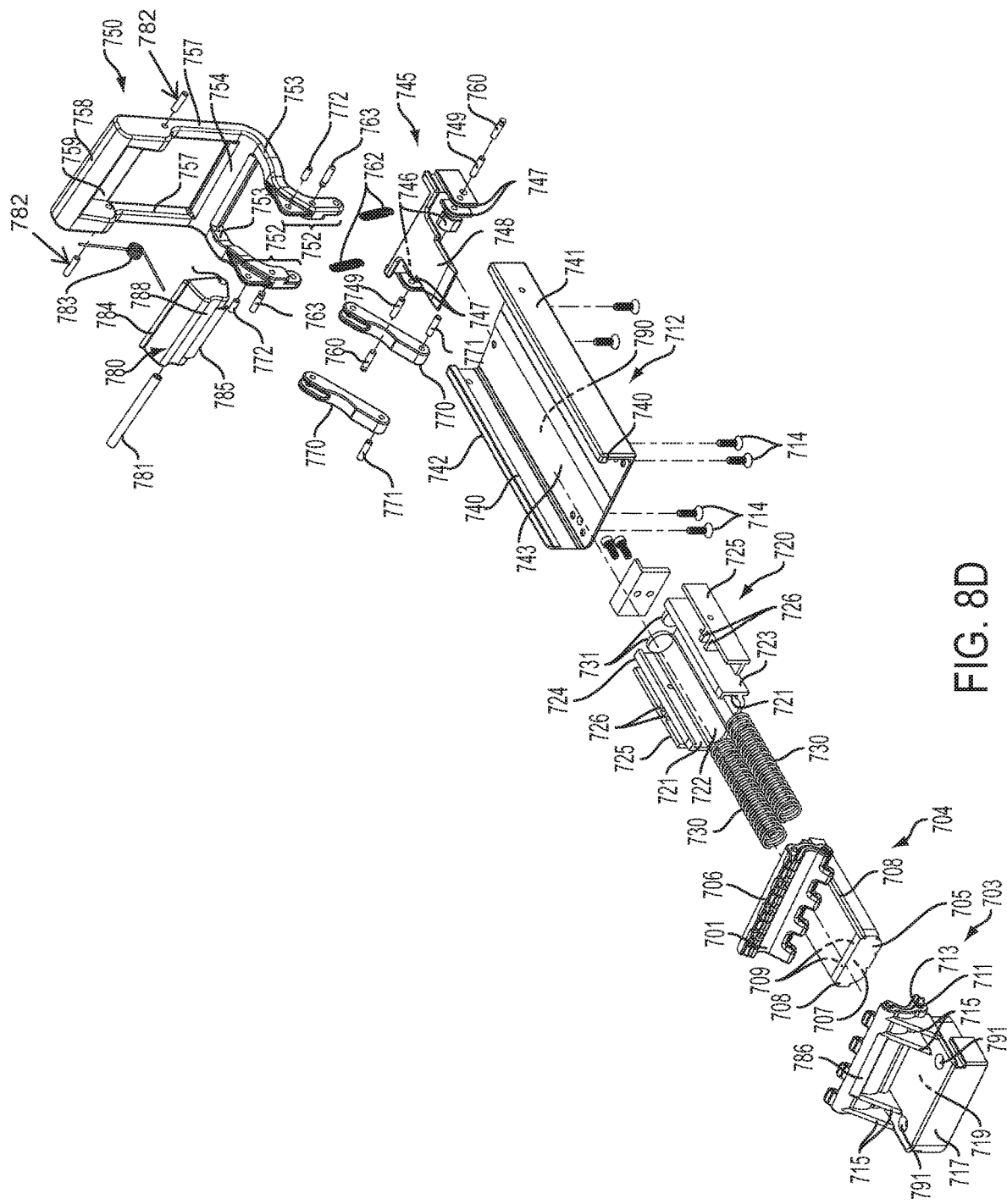
Figure 8E:
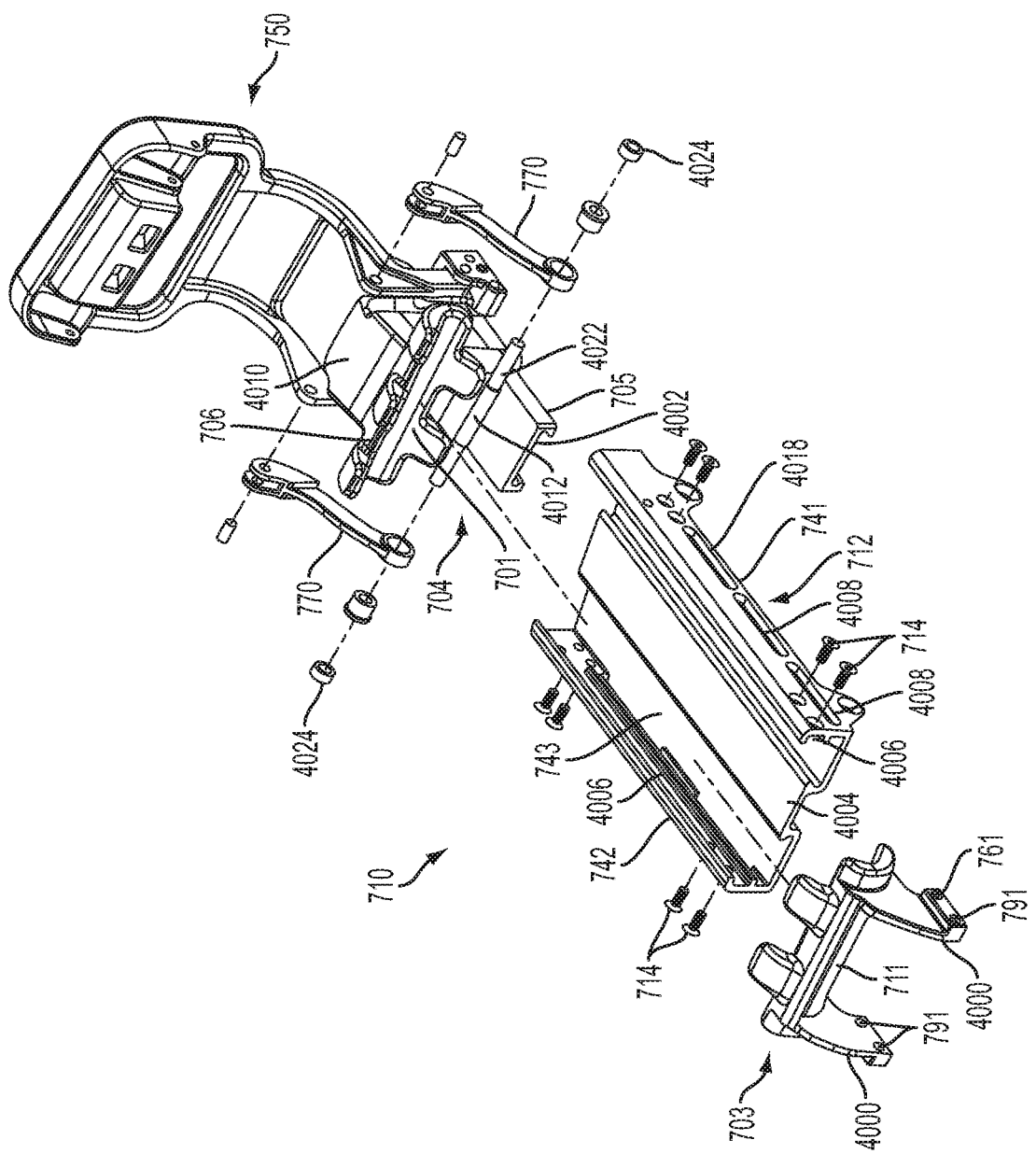
FIGS. 8E-8F show an alternate embodiment of the clamp shown in FIGS. 8A-8D in accordance with an embodiment of the present disclosure.
Figure 8F:
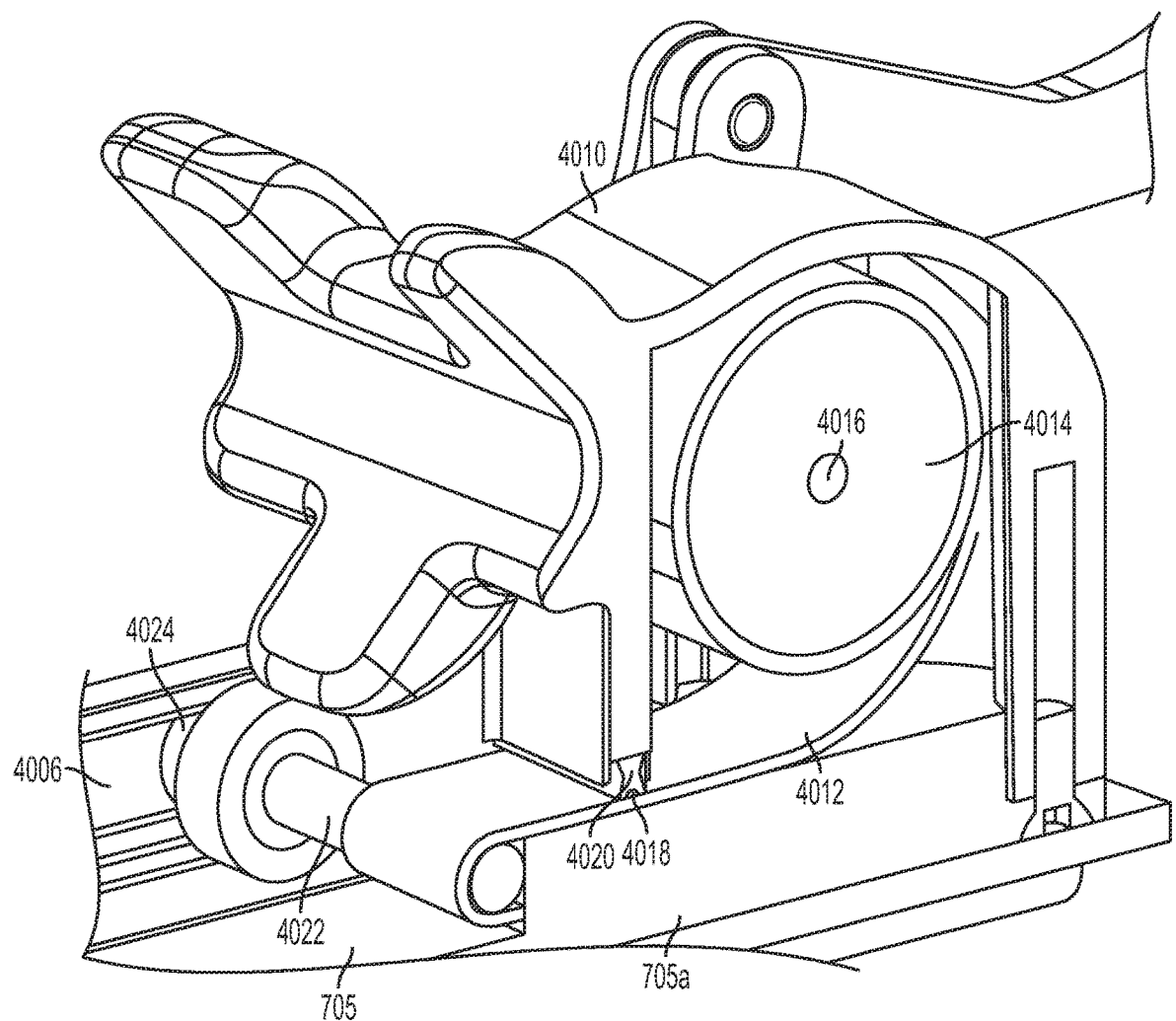

The gripper sled 705 may also comprise sled projecting tracks 708 on its front and back faces (relative to orientation in FIG. 8D). The sled projecting tracks 708 fit into guide grooves 721 on a driven member 720. In the example embodiment shown in FIGS. 8A-8D, the driven member 720 is roughly "U" shaped. The bottom face 722 of the driven member 720 comprises the bottom span of the "U" shape. Projecting perpendicularly from front and back edges (relative to FIG. 8D) of the bottom face 722 of the driven member 720 toward the top of the page are a front upright wall 723 and a back upright wall 724. The front upright wall 723 and back upright wall 724 comprise the upright spans of the "U" shape. The guide grooves 721 run along the surfaces of the front upright wall 723 and back upright wall 724 which face each other.

In some embodiments, the driven member 720 may comprise at least one appendage 725 which extends from either the front upright wall 723 or back upright wall 724. In the exemplary embodiment illustrated in FIGS. 8A-8D, the driven member 720, includes two appendages 725. One appendage 725 extends from the face of the front upright wall 723 opposite the face on which the guide groove 721 of the front upright wall 723 is disposed. The other appendage extends from the face of the back upright wall 724 opposite the face on which the guide groove 721 of the back upright wall 724 is disposed.

The appendages 725 are roughly "L" shaped. One portion of each appendage 725 projects from its corresponding front upright wall 723 or back upright wall 724 at an angle substantially perpendicular to the front upright wall 723 and back upright wall 724. This portion of each appendage 725 comprises the horizontal span of the "L" shape. The vertical span of the "L" shape is formed by a second portion of the appendage 725 which projects toward the top of the page from the distal end of the first portion of the appendage 725 at an angle substantially perpendicular to the first portion of the appendage 725. As shown in FIGS. 8A-8D the one or more appendages may be buttressed by at least one support piece 726. In some embodiments, including the embodiment shown in FIGS. 8A-8D, the one or more appendages may not span the entire length of the front upright wall 723 and back upright wall 724 of the driven member 720. In the shown embodiment, the appendages stop short of the left edge (relative to FIG. 8D) of the driven member 720.

The appendages 725 or a portion of the appendages 725 may fit into and slide along a grooved track 740 on front wall 741 and back wall 742 the housing 712. The bottom of the driven member 720 may ride along the bottom face 743 of the housing 712.

When the clamp apparatus 710 is assembled, the gripper sled 705 fits in the driven member 720 between the front upright wall 723 and back upright wall 724. When the clamp apparatus 710 is not clamped around a clamped object 100 the gripper sled 705 fits in the driven member 720 such that the right and left faces (relative to FIG. 8D) of the gripper sled 705 are flush with the right and left edges of the driven member 720. One end of each compression spring 730 abuts the interior left face (relative to FIG. 8D) of the hollow portion of the gripper sled 705. The other end of each compression spring 730 abuts a compression spring disc 731 which projects toward the top of the page from the right edge (relative to FIG. 8D) of the driven member 720. The compression springs 730 bias the gripper sled 705 to the unclamped position where the gripper sled 705 is flush with the right and left edges (relative to FIG. 8D) of the driven member 720.

When the clamp apparatus 710 is actuated from the open position to a clamped position the driven member 720 moves toward the fixed gripper assembly 703 and the appendages 725 of the driven member 720 slide along the grooved tracks 740 on the housing 712. In turn, this displaces the movable gripper assembly 704 toward the fixed gripper 703 assembly. Until the movable gripper 701 contacts a clamped object 100, the driven member 720 and movable gripper assembly 703 move as a unit. When the movable gripper 701 comes into contact with a clamped object 100, the movable gripper assembly 704 can make no further progress toward the fixed gripper assembly 703 because the clamped object 100 is in the way. The driven member 720 continues to move toward the fixed gripper assembly 703 compressing the compression springs 730 between the interior left wall (relative to FIG. 8D) of the hollow portion of the gripper sled 705 and the compression spring discs 731. The restoring force of the compression springs 730 causes the movable gripper assembly 704 to exert a more vigorous clamping force on the clamped object 100.

When the clamp apparatus 710 is moved from a clamped position toward an open position, the restoring force of the compression springs 730 may automatically spring the clamp apparatus 710 back to the unclamped and open position.

The clamp apparatus 710 may be moved from the open position to the closed position by user actuation of a toggle handle 750. One end of the toggle handle 750 may be pivotally coupled to the housing 712 of the clamp apparatus 710. In the embodiment shown in FIGS. 8A-8D, the toggle handle 750 attaches to the right (relative to FIG. 8D) end cap 745 of the housing 712. As shown, the right end cap 745 projects perpendicularly from the bottom face 743 of the housing 712 toward the top of the page. The right end cap 745 may be fixedly coupled to the housing 712 via screws, bolts, welds, etc. or may be molded as a continuous part of the housing 712.

The right end cap 745 may comprise a number of other features. As shown in FIGS. 8A-8D, the right end cap 745 may comprise a pair of projections 746 which project toward the fixed gripper assembly 703. The projection 746 may extend parallel to the front wall 741 and back wall 742 of the housing 712. Extension spring pegs 760 may protrude from each of the pair of projections 746. In the embodiment depicted in FIGS. 8A-8D, each of the extension spring pegs 760 project substantially perpendicularly from one of the pair of projections 746. One end of an extension spring 762 is placed around each extension spring peg 760. The extension springs 762 will be elaborated upon later.

Extending from the top edge of the right end cap 745 toward the fixed gripper assembly 703 may be a guide piece 748. The guide piece 748 may extend parallel to the plane of the bottom face 743 of the housing 712. The guide piece 748 may overhang the bottom face 743 of the housing 712. As shown, the guide piece 748 in FIGS. 8A-8D, may only extend from the medial section of the top edge of the right end cap 745.

The right end cap 745 may also comprise a pair of U-brackets 747. In the embodiment shown, the U-brackets 747 are disposed on the right end cap 745 such that the uprights of each U-bracket 747 project in the same direction and plane as the pair of projections 746. One of the upright sections of one U-bracket 747 may be flush with the front edge of the right end cap 745 and abut the interior face of the front wall when the clamp apparatus 710 is assembled. One of the upright sections of the other U-bracket 747 may be flush with the back edge of the right end cap 745 and abut the interior face of the back wall 742 of the housing 712 when the clamp apparatus 710 is assembled. The other upright of each U-bracket 747 may be offset from the first upright of each U-bracket 747 such that it nearly abuts the extension spring pegs 760. The bottom span of the U-bracket 747 may be formed by a face of the right end cap 745. In alternate embodiments, the number, location, and orientation of projections 746, U-brackets 747, extension spring pegs 760, and extension springs 762 may differ.

In the embodiment shown in FIGS. 8A-8D, the toggle handle 750 is pivotally coupled into the U-brackets 747. As shown, this is accomplished by means of dowel pins 749 which run through the U-brackets 747 and into the coupling spans 752 of the toggle handle 750. The toggle handle 750 in the exemplary embodiment may be divided up into a number of sections. As indicated above, the toggle clamp may have one or more coupling spans 752 to which other components of the clamp apparatus 710 may be coupled. Relative to FIG. 8D, the coupling spans 752 are two vertical spans. As shown, the coupling spans 752 are offset from each other. Extending toward the right of the page from the each coupling span 752 at an angle roughly perpendicular to each coupling span 752 may be a horizontal span 753. The horizontal spans 753 may be joined by a strut 754. In some embodiments, the strut 754 may complete the toggle handle 750. In the illustrated embodiment in FIGS. 8A-8D, the toggle handle 750 comprises additional sections. Projecting off the strut 754 vertically toward the top of the page (relative to FIG. 8D) are two extension spans 757. The extension spans 757 may be connected together by a handle grip 758 which a user may grasp when actuating the toggle handle 750.

At least a portion of the handle grip 758 may be made of the same material as the rest of the toggle handle 750, may be made of a different material, or may be made of a combination thereof. Possible materials may include, but are not limited to, rubber, polymer, composite, metal, plastic, foam, fabric, etc. Additionally, the handle grip 758 may comprise ergonomic finger groves, nubs, a ribbed texture, a honeycombed texture, etc. to facilitate ease of grasping and gripping.

In addition to the coupling spans 752 coupling the toggle handle 750 to the clamp apparatus 710, the coupling spans 752 may also comprise a pair of handle extension spring pegs 763. In the example embodiment shown in FIGS. 8A-8D, one of the pair of handle extension spring pegs 763 projects perpendicularly from each coupling span 752 of the toggle handle 750. In the example embodiment in FIGS. 8A-8D, the handle extension spring pegs 763 project from the surface of each coupling span 752 which faces the opposite coupling span 752. The end of the each extension spring 762 not seated on the first pair of extension spring pegs 760 is seated around one of the pair of handle extension spring pegs 763. In the example embodiment in FIGS. 8A-8D, the extension springs 762 act as over-center springs. When the toggle handle 750 is in the open position, the extension springs 762 bias the toggle handle 750 to stay in the open position. When the toggle handle 750 is in the closed position, the extension springs 762 move to an over-center position and bias the toggle handle 750 to stay in the closed position.

The coupling spans 752 of the toggle handle 750 may additionally couple to linkages 770. In the example embodiment in FIG. 8A-8D, one end of each linkage 770 is pivotally coupled to the driven member 720. As shown, one linkage 770 is pivotally coupled between the front upright wall 723 of the driven member 720 and the vertical span of the appendage 725 which extends off the front upright wall 723 of the driven member 720. Also as shown in FIGS. 8A-8D, the other linkage 770 is pivotally coupled between the back upright wall 724 of the driven member 720 and the vertical span of the appendage 725 which extends off the back upright wall 724 of the driven member 720. In the example embodiment in FIGS. 8A-8D, a dowel 771 is used to pivotally couple the linkages 770 to the driven member 720.

The other end of each linkage 770 pivotally couples to the top of one of the coupling spans 752 of the toggle handle 750. The linkage 770 and coupling spans 752 may be pivotally coupled by means of a coupling dowel pin 772. Any other suitable coupling means may also be used.

When the clamp apparatus 710 is actuated, the coupling span 752 of the toggle handle 750 and the linkages 770 collectively may act as an over-center linkage. To actuate the toggle handle 750 a user may grasp the handle grip 758 of toggle handle 750. The user may then rotate the toggle handle 750 substantially a full 90° counter-clockwise from the orientation of the handle toggle handle 750 shown in FIG. 8A. In some embodiments, the sufficient degree of rotation may be larger or smaller (e.g. 95°). As the toggle handle 750 is rotated, the linkage 770 and coupling span 752 which comprise the over-center linkage move toward the center position. This pushes the driven member 720 and movable gripper assembly 704 as detailed above. Slightly before the toggle handle 750 has been rotated a full 90° counter-clockwise, the linkage 770 and coupling span 752 comprising the over-center linkage reach the center position. When the linkage and coupling span 752 comprising the over-center linkage reach the center position a large force is generated on the moveable gripper assembly 704 by applying only a small force to the toggle handle 750. When the toggle handle 750 is rotated the full 90° counter-clockwise, the linkage 770 and the coupling span 752 comprising the over-center linkage reach an over-center position which keeps the toggle handle 750 and clamp apparatus 710 in the closed and clamped position and acts as a passive latch. This clamping action makes actuation of the clamp apparatus 710 easy for the user while also providing a sufficiently strong clamping force.

In some embodiments, the toggle handle 750 comprises a toggle handle latch 780 that operatively secures the toggle handle 750 and clamp apparatus 710 in the closed and clamped position. The toggle handle latch 780 may be disposed on the handle grip 758 of the toggle handle 750 such that it fits in a concavity 759 in the handle grip 758. The toggle handle latch 780 may be pivotally coupled to the handle grip 758 and may be pivotable between an advanced and a retracted position. In some embodiments a pivot pin bearing 781 runs the length of the toggle handle latch 780. In the embodiment shown in FIGS. 8A-8D, the pivot pin bearing 781 runs along the bottom edge of the toggle handle latch 780. A pivot pin 782 may pivotally couple the toggle handle latch 780 to the handle grip 758 by running through the pivot pin bearing 781 and into at least part of the handle grip 758.

In some embodiments, including the embodiment illustrated in FIGS. 8A-8D, the toggle handle latch 780 may be adapted such that a torsion spring 783 may be slid over at least a portion of the pivot pin bearing 781. The torsion spring 783 may bias the toggle handle latch 780 to the advanced position. When the toggle handle latch 780 is pivoted toward the retracted position, the torsion spring 783 is spring loaded such that the restoring force of the torsion spring 783 causes the toggle handle latch 780 to automatically pivot back to the advanced position. In the advanced position, the toggle handle latch 780 is in its most protruding position. In the retracted position, the toggle handle latch 780 is pushed into the concavity 759 such that it protrudes minimally from the handle grip 758.

In some embodiments, the toggle handle latch 780 may comprise a stop surface 784 along at a part of at least one face of the toggle handle latch 780. The stop surface 784 catches on a part of the concavity 759 in the handle grip 758 and ensures the torsion spring 783 cannot eject the toggle handle latch 780 out of the concavity 759.

The toggle handle latch 780 may also comprise a latch projection 785. The latch projection 785 in the example embodiment depicted in FIGS. 8A-8D runs substantially the full length of the toggle handle latch 780 and projects off the toggle handle latch 780 toward the bottom of the page (relative to FIG. 8D). This may differ in alternative embodiments.

In some embodiments, the left face (relative to FIG. 8D) of the fixed gripper cradle 711 comprises a ramp catch 786 for the latch projection 785 of the toggle handle latch 780. The catch 786 in alternative embodiments need not comprise a ramp. The catch 786 may take any other suitable form.

In the example embodiment in FIGS. 8A-8D, as the toggle handle 750 and toggle handle latch 780 are rotated toward the closed position, the latch projection 785 of the toggle handle latch 780 abuts the catch 786 ramp. As the toggle handle 750 continues to rotate toward the closed position, the latch projection 785 of the toggle handle latch 780 rides up the catch 786 ramp. This causes the toggle handle latch 780 to be pivoted into the retracted position, i.e. into the concavity 759 of the handle grip 758. In turn, this twists the torsion spring 783 and stores mechanical energy in the torsion spring 783. When the toggle handle 750 is in the fully closed position, the latch projection 785 of the toggle handle latch 780 clears the catch 786 ramp and the restoring force of the torsion spring 783 causes the toggle handle latch 780 to spring back to the advanced position. This locks the clamp apparatus 710 in the closed position as any movement toward the open position is prevented by the latch projection 785 of the toggle handle latch 780 catching on the lip of the catch 786 ramp.

To rotate the toggle handle 750 back toward the open position and/or unclamp the clamp apparatus 710, a user must manually push in the toggle handle latch 780 to the retracted position. This allows the latch projection 785 of the toggle handle latch 780 to clear the lip of the catch 786 ramp, thus allowing rotation of the toggle handle 750 toward the open position.

In some embodiments, the toggle handle latch 780 may have various contours which provide an ergonomic benefit to the user as a user tries to depress the toggle handle latch 780 to the retracted position when opening the clamp apparatus 710. In the embodiment shown in FIGS. 8A-8D, the toggle handle latch 780 comprises a valley 788 which may better accommodate a user's fingertips as they pivot the toggle handle latch 780 into the retracted position. In other embodiments there may be additional ergonomic contours which supplement or replace the valley 788.

In some embodiments, the housing 712 of the clamp apparatus 710 may also feature any of a variety of mechanisms 790 (not shown) to attach a load to the clamp apparatus 710. Such mechanisms may include, but are not limited to, brackets, magnets, straps, suction cups, hooks, screws, bolts, a friction fit, etc. This load could be any number of things, especially a medical device (such as an infusion pump, or peristaltic infusion pump), I.V. bag, etc.

In some embodiments, the clamp apparatus 710 may be adapted such that the fixed gripper assembly and 703 movable gripper assembly 704 may be oriented obliquely to the right and left ends (relative to FIG. 8D) of the housing 712. In embodiments where the gripper assemblies 703 and 704 are oriented obliquely, any load attached to the clamp apparatus 710 by any of the variety of mechanisms 790 detailed above would be at an angle oblique to a clamped object 100 clamped in the clamp apparatus 710. Such an orientation may be helpful in accommodating the needs of a load attached to the clamp apparatus 710 through any of the variety of mechanisms 790 described in the preceding paragraph.

FIGS. 8E-8F show an alternative embodiment of the example clamp apparatus 710 shown in FIGS. 8A-8D. As shown, the alternative embodiment of the clamp apparatus 710 shown in FIG. 8E comprises a fixed gripper assembly 703 similar to the fixed gripper assembly 703 shown in FIGS. 8A-8D. The fixed gripper assembly 703 in FIG. 8E is somewhat simplified and allows the clamp apparatus 710 to have a more open concept which facilitates ease of cleaning. The fixed gripper assembly 703 in FIG. 8E does not include a fixed gripper base 717 as it does in FIGS. 8A-8D. The fixed gripper assembly in FIG. 8E features two support legs 4000. Each support leg 4000 may be coupled to the left (relative to FIG. 8E) face of the fixed gripper cradle 711. The support legs 4000 may be coupled to the fixed gripper cradle 711 at an angle which is substantially perpendicular to the left face of the fixed gripper cradle 711. In some embodiments, including the embodiment shown in FIG. 8E, the support legs 4000 may be formed as a continuous part of the fixed gripper cradle 711*b*.

One support leg 4000 may coupled to the fixed gripper cradle 711 near the front edge of the fixed gripper cradle 711. The second support leg 4000 may be coupled to the fixed gripper cradle 711 near the back edge of the fixed gripper cradle 711. The support legs 4000 are slightly arched in the example embodiment shown in FIG. 8E. As shown, the width of the support legs 4000 may gradually decrease as the support legs 4000 extend toward the bottom of the page. The bottom of the support legs 4000 may be substantially parallel to the direction of elongation of the housing 712.

As shown in the example embodiment in FIG. 8E, the threaded holes 791 which are located in the fixed gripper base 717 in FIGS. 8A-8D may be disposed at the bottom of the support legs 4000. The threaded holes 791 may extend through the bottom of the support legs 4000 in a direction substantially perpendicular to the front and back faces of each support leg 4000. As shown, four screws 714 may run through the housing 712 of the clamp apparatus 710 and into the corresponding threaded holes 791 in the bottom of the support legs 4000 thereby coupling the fixed gripper assembly 703 to the housing 712.

As shown, the alternative embodiment of the clamp apparatus 710 shown in FIGS. 8E-8F comprises a movable gripper assembly 704 similar to the movable gripper assembly 704 shown in FIGS. 8A-8D. As shown, the movable gripper assembly 704 comprises a gripper sled 705. The gripper sled 705 may be roughly planate and rectangular. The gripper sled 705 in FIGS. 8E-8F is roughly planate and rectangular though one end of the rectangular gripper sled 705 is rounded. The gripper sled 705 may comprise a dovetail cutout 4002 as shown in FIG. 8E. The gripper sled 705 may be extruded.

The dovetail cutout 4002 of the gripper sled 705 may be sized to accommodate and slide along a dovetail projection 4004 on the housing 712 of the clamp apparatus 710. As shown in the example embodiment in FIG. 8E, the dovetail projection 4004 in the housing 712 may run roughly parallel with the front wall 741 and back wall 742 of the housing 712. The dovetail projection 4004 on the housing 712 may run along the medial portion of the bottom face 743 of the housing 712.

As shown in FIG. 8E, the housing 712 may include roller tracks 4006. As shown, the roller tracks 4006 are similar to the grooved tracks 740 shown in FIGS. 8A-8D. The roller tracks of the housing 712 will be further elaborated on later. The housing 712 may also include any number of housing voids 4008. The housing voids 4008 may be cut into the housing 712 or may be created during manufacture of the housing 712. The housing voids 4008 help to keep debris and unwanted matter from accumulating in and on the clamp apparatus 710. The housing voids 4008 may also aid in making the clamp apparatus 710 easier to clean. In some embodiments, the housing 712 may be extruded. In such embodiments, the clamp 710 may be extruded from any suitable material.

The movable gripper assembly 704 may comprise a number of additional components in addition to the gripper sled 705. Projecting perpendicularly from the top face of the gripper sled 705 on the right (relative to FIG. 8E) of the gripper sled 705 there may be a spring housing 4010. The spring housing 4010 may project in a direction that is substantially perpendicular to the top face of the gripper sled 705. The spring housing 4010 may be dimensioned such that the sides of the spring housing 4010 are flush with the edges of the gripper sled 705. The spring housing 4010 may be coupled to the gripper sled 705 by any of a variety of fastening means.

In some embodiments, the movable gripper cradle 706 may be coupled to the left side (relative to FIG. 8E) of the spring housing 4010. In such embodiments, the movable gripper cradle 706 may be coupled to the spring housing 4010 by any suitable fastener. In the example embodiment, the movable gripper cradle 706 is made as a continuous part of the spring housing 4010. As shown, the movable gripper cradle 706 is disposed on the spring housing 4010 such that it is at substantially the same height as the fixed gripper cradle 703.

As shown in the cross section of the clamp apparatus 710 in FIG. 8F, the spring housing 4010 is substantially hollow. Within the hollow portion of the spring housing 4010 a constant force spring 4012 is housed. In some embodiments, there may be more than one constant force spring 4012 housed in the spring housing 4010. The constant force spring 4012 in some example embodiments may be a rolled ribbon of spring steel. The constant force spring 4012 may be a laminar spring. In some embodiments, the constant force spring 4012 may be a triple laminar spring. In some embodiments, the constant force spring 4012 may be an approximately 191b constant force spring 4012. Use of a constant force spring 4012 provides many benefits over other varieties of bias members as detailed above.

As shown, the constant force spring 4012 may be disposed about a mandrel 4014 which is capable of rotating about the axis of an axle 4016. In the example embodiment, the mandrel 4014 is a solid spindle. In other embodiments, the mandrel 4014 may not be solid. In some embodiments, the mandrel 4014 may be a hollow cylinder. In some embodiments, the mandrel 4014 may be mostly hollow and comprise a number of supporting spokes. The axle 4016 may span across the hollow section of the spring housing 4010. The axle 4016 may extend in a direction substantially perpendicular to the front wall 741 and back wall 742 of the housing 712 shown in FIG. 8E.

In the example embodiment in FIG. 8F, the gripper sled 705 features a raised section 705a. The raised section 705a of the gripper sled 705 projects off the gripper sled 705 toward the top of the page in manner substantially perpendicular to the rest of the gripper sled 705. As shown, a small gap 4018 may be left between the top of the raised portion 705a of the gripper sled 705 and the bottom of the left side of the spring housing 4010. The constant force spring 4012 may extend out of the spring housing 4010 through the small gap 4018.

To help keep debris and other matter from entering the spring housing 4010, spring housing sealing member 4020 may be placed at the bottom of the left side of the spring housing 4010. As shown in the example embodiment in FIG. 8F, a part of the spring housing sealing member 4020 may be seated in a cavity recessed into the bottom face of the left side of the spring housing 4010. The spring housing sealing member 4020 may be made of a deformable material. As the constant force spring 4012 is advanced and retracted out of and back into the spring housing 4010 during operation of the clamp apparatus 710, the spring housing sealing member 4020 blocks any debris or other matter on the constant force spring 4012 from being pulled into the spring housing 4010 as the constant force spring 4012 retracts back into the spring housing 4010.

One end of the constant force spring 4012 may be located exterior to the spring housing 4010 at all times. The end of the constant force spring 4012 located exterior to the spring housing 4010 may be fixedly coupled to a roller axle 4022. By pulling the roller axle 4022 toward the left of the page (relative to FIG. 8F) the constant force spring 4012 is unwound and spooled out of the spring housing 4010. If the roller axle 4022 is released, the restoring force of the constant force spring 4012 will cause the roller axle 4022 to be biased back to the position shown in FIG. 8F. The constant force spring 4012 will also retract back into the spring housing 4010.

A roller 4024 may be seated on each end of the roller axle 4022. One of the rollers 4024 is visible in FIG. 8F. The rollers 4024 are capable of rotation about the axis of the roller axle 4022. As shown in FIGS. 8E-8F, the rollers 4024 may ride and roll along the roller tracks 4006 on the front wall 741 and back wall 742 of the housing 712.

Referring back to FIG. 8E, the linkages 770 extending from the toggle handle 750 may be coupled onto the roller axle 4022. As such, the roller axle 4022 functions similarly to the driven member 720 in FIGS. 8A-8D and may be referred to as an alternative driven member. When the clamp apparatus 710 is actuated from the open position to a clamped position via rotation of the toggle handle 750, the roller axle 4022 moves toward the fixed gripper assembly 703 and the rollers 4024 on the roller axle 4022 slide along the roller tracks 4006 on the housing 712. In turn, this displaces the movable gripper assembly 704 toward the fixed gripper 703 assembly. Until the movable gripper 701 contacts a clamped object 100, the roller axle 4022 and movable gripper assembly 703 move as a unit. When the movable gripper 701 comes into contact with a clamped object 100, the movable gripper assembly 704 can make no further progress toward the fixed gripper assembly 703 because the clamped object 100 is in the way. The roller axle 4022 continues to move toward the fixed gripper assembly 703. This causes the constant force spring 4012 to be pulled out of the spring housing 4010. The restoring force of the constant force spring 4012 causes the movable gripper assembly 704 to exert a more vigorous clamping force on the clamped object 100.

When the clamp apparatus 710 is moved from a clamped position toward an open position by rotation of the toggle handle 750, the restoring force of the constant force spring 4012 may automatically spring the clamp apparatus 710 back to the unclamped and open position.

Figure 8G:
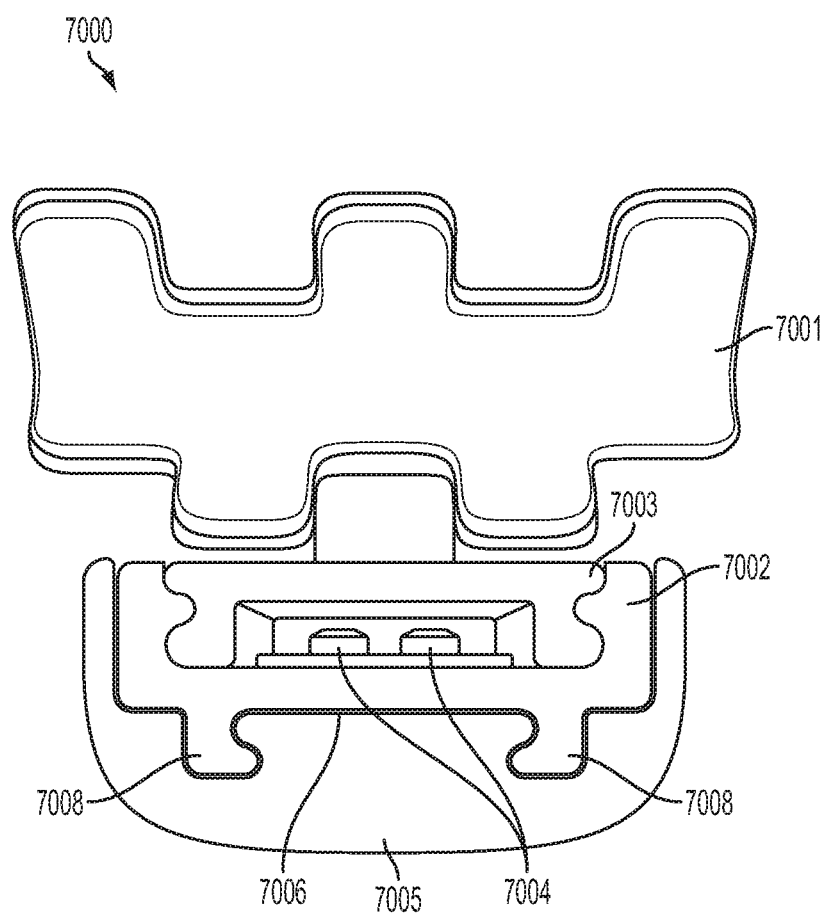
FIG. 8G shows an alternate embodiment of a moveable gripper assembly with a housing in accordance with an embodiment of the present disclosure.

FIG. 8G shows an alternate embodiment of a moveable gripper assembly 7000 with a housing 7005 in accordance with an embodiment of the present disclosure. The moveable gripper assembly 7000 may be similar to the moveable gripper assembly shown in FIG. 8F. The moveable gripper assembly 7000 includes a moveable gripper 7001, a driven member 7002, and a gripper sled 7003 with a housing 7005. The driven member 7002 is guided via guide members 7008 along a track 7006. Note that the contact force spring (e.g., spring 4012 as shown in FIG. 8F) is secured to the driven member 7002 by fasteners 7004.

A Rack Apparatus

Figure 9A:
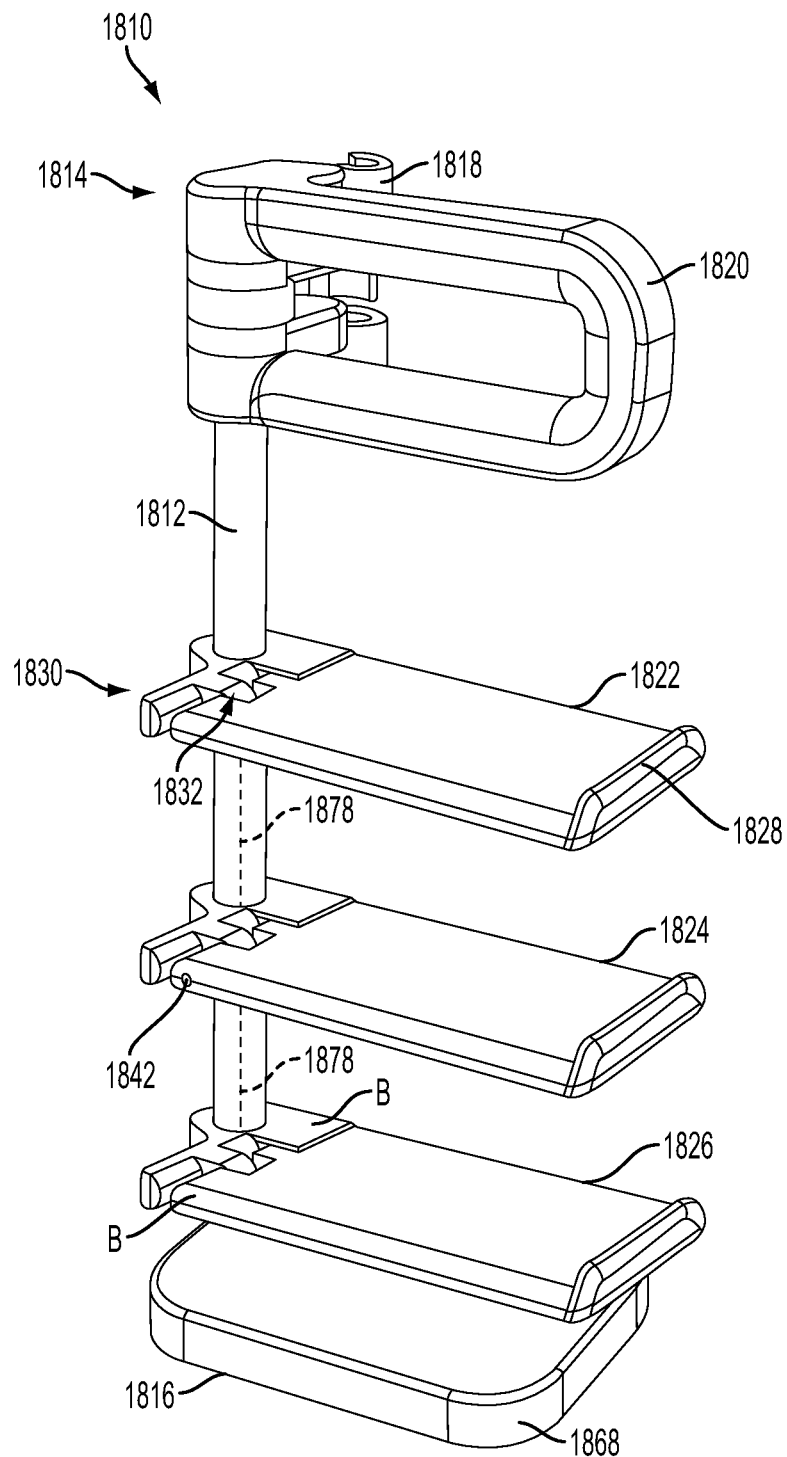
FIG. 9a is a perspective view of an exemplary embodiment of a rack apparatus in accordance with an embodiment of the present disclosure.

FIG. 9a depicts one exemplary embodiment of a rack 1810. The rack 1810 includes a cylindrically-shaped support pole 1812. A clamp assembly 1814 may be attached to a first end portion of the support pole 1812. The clamp assembly 1814 may further include a clamp mechanism 1818 and an elongated, U-shaped handle 1820 that may be oriented perpendicularly to the longitudinal axis of the support pole 1812. The clamp assembly 1814 and the clamp mechanism 1818 may be configured to removably couple with a support structure such as an IV pole. As should be appreciated by those having ordinary skill in the art, any number of clamp mechanisms may be used to accomplish this objective, including the clamp mechanisms described below and above. The handle 1820 enables the rack 1810 and any received medical devices to be carried as unit from one location to another. In certain embodiments, the handle 1820 may serve as a means to actuate the clamp mechanism 1818. One such embodiment could include a handle 1820 that shares an axis of rotation with a clamp mechanism 1818, wherein the clamp mechanism 1818 includes at least one fixed gripper and at least one mobile gripper that may be coupled to the handle 1820. Actuation of the clamp mechanism 1818 may be achieved by rotating the handle 1820 in a first direction such that the at least one mobile gripper rotates towards the at least one fixed gripper and a support structure therebetween. The at least one mobile gripper and the at least one fixed gripper may be secured in a clamped position by a latch or any other means known in the relevant art when the aforementioned grippers exert a sufficient clamping force on the support structure. Rotating the handle 1820 in a second, opposite direction may rotate the at least one mobile gripper away from the at least one fixed gripper, and the clamp mechanism 1818 may be decoupled from the support structure when the at least one mobile gripper is sufficiently far from the support structure.

Figure 9B:
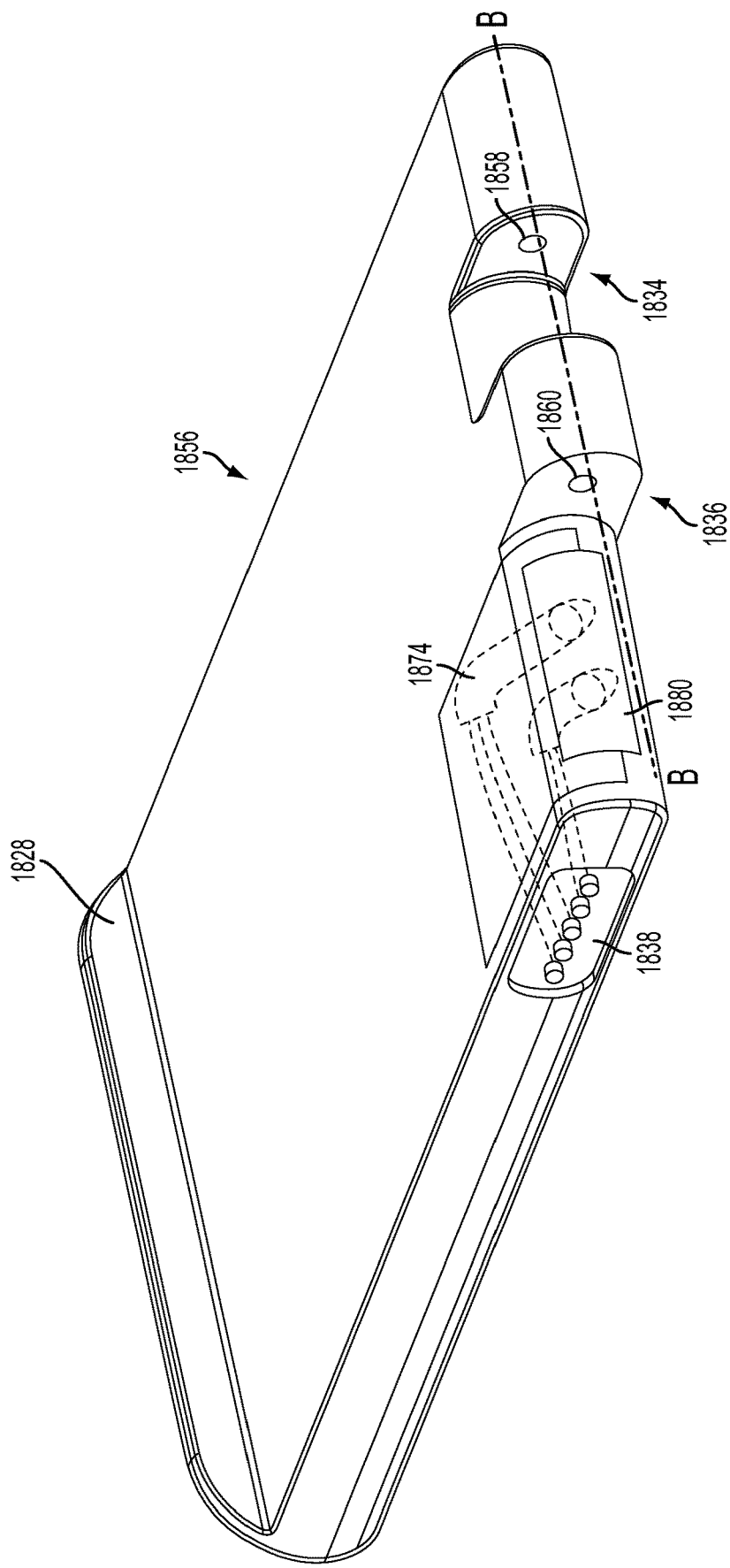
FIG. 9b is a perspective view of an exemplary embodiment of a device mount, like those depicted in FIG. 9a, wherein the device mount includes a support plate that is adapted to receive a medical device in accordance with an embodiment of the present disclosure.

A variety of medical device mounts may be disposed between the first end and a second end of the support pole 1812. FIGS. 9a and 9b depict an exemplary embodiment where the mounts may be elongated support plates that extend perpendicularly to the support pole 1812. FIG. 9a depicts a rack 1810 having a first support plate 1822, a second support plate 1824, and a third support plate 1826. FIG. 9b depicts an embodiment of an individual support plate 1856. The support plate 1856 may be sized to receive and support a medical device. Examples of medical devices that may be received by the support plate 1856 include syringe pumps, infusion pumps, dialysis machines, pill dispensers, and chemotherapy devices. A first end portion of the support plate 1856 may be coupled to the support pole 1812 using a joint member 1830. The support plate 1856 may include a first support plate projection 1834 and a second support plate projection 1836 that may interface with the joint member 1830 (see FIG. 9C) to facilitate coupling. To more securely receive and retain a medical device, the support plate 1856 may include a flange 1828 that extends upwardly from a second end portion of the support plate 1856.

To reduce the need to run power cables from electrical outlets to each individual medical device, each support plate 1856 may include a mount connector 1838 that may be adapted to transmit electrical power to a received medical device. In certain embodiments, the mount connector 1838 may also be adapted to enable signals to be communicated between two or more medical devices and thus provide each medical device with a network connection.

Figure 9C:
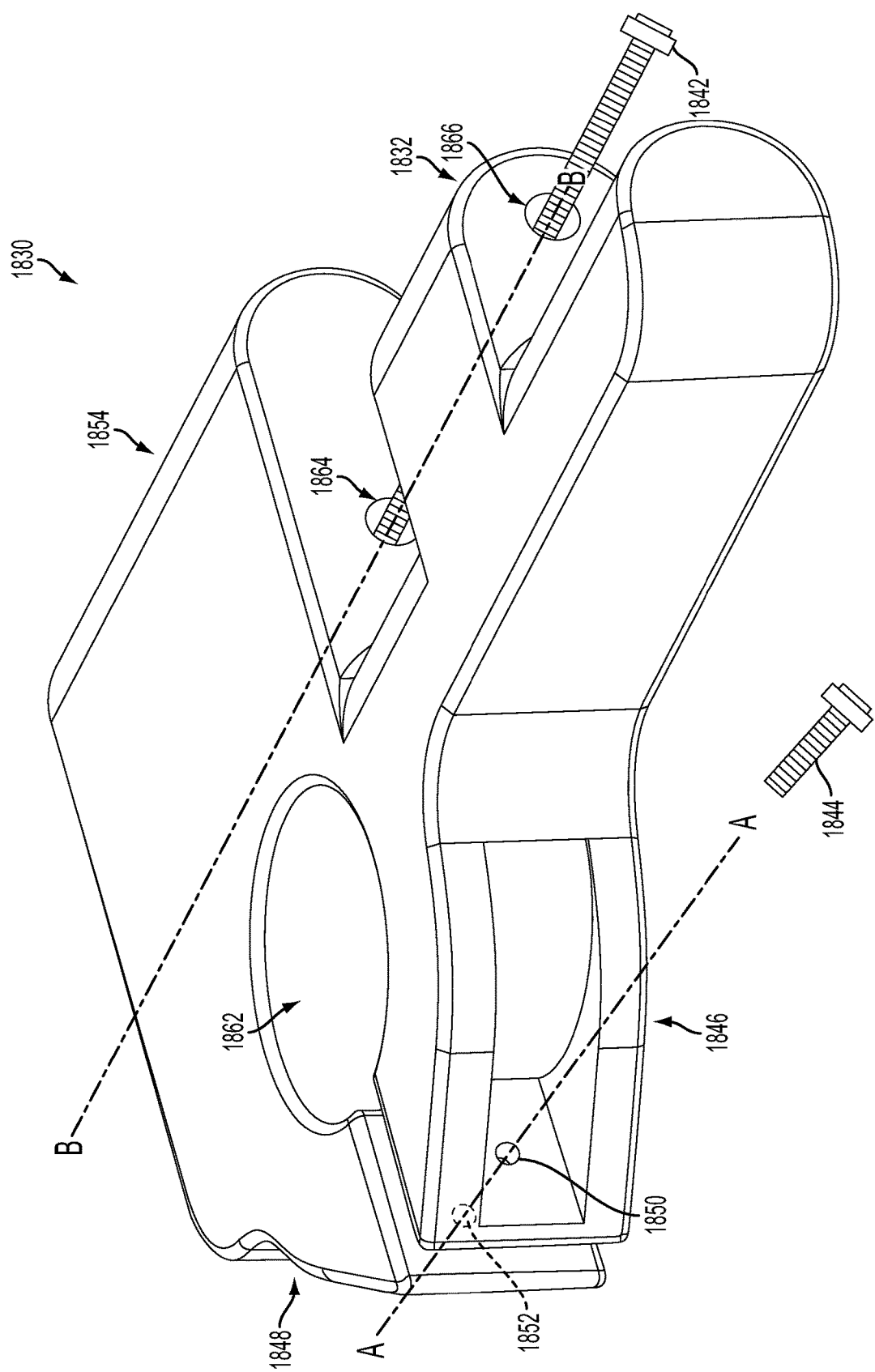
FIG. 9c is a perspective view of an exemplary embodiment of a joint member that is adapted to couple with the embodiment of a device mount that is depicted in FIG. 9b in accordance with an embodiment of the present disclosure.

In the embodiment depicted in FIG. 9a, a corresponding number of joint members 1830 couple each of the support plates 1822, 1824, 1826 to the support pole 1812. Each joint member 1830 may be configured to receive a support plate 1856 such that the joint member 1830 enables the received support plate 1856 to rotate around a longitudinal axis of the support pole 1812. FIG. 9c depicts an exemplary joint member 1830 that permits rotation around a longitudinal axis of the support pole 1812. The joint member 1830 may include a joint member aperture 1862 that is sized to receive the support pole 1812. The joint member 1830 may be rotated and re-secured to the support pole 1812 by loosening a threaded screw 1844, rotating the exemplary joint member 1830 and a received support plate 1856 to the desired position, and retightening the threaded screw 1844.

As depicted in FIG. 9c, the exemplary joint member 1830 may include a first clamping arm 1846 and a second clamping arm 1848, each having an inner surface that forms a portion of the joint member aperture 1862. The first and the second clamping arms 1846, 1848 may further include a first threaded aperture 1850 and a second threaded aperture 1852 respectively. The first threaded aperture 1850 and the second threaded aperture 1852 may be aligned along a line A-A and each may be sized to receive the threaded screw 1844. As will be understood by persons having ordinary skill in the art, rotating the threaded screw 1844 in a first direction, generally clockwise, may pull the first and the second clamping arms 1846, 1848 towards one another and enable the joint member aperture 1862 to exert a predominantly horizontal force against a received support pole 1812 such that the received support pole 1812 may support against the force of gravity the weight of the joint member 1830, the received support plate 1856, and any received medical devices. Turning the threaded screw 1844 in a second, opposite, and generally counter-clockwise direction may push the first and the second clamping arms 1846, 1848 apart and may reduce the force applied to the support pole 1812 by the joint member aperture 1862 and may enable the joint member 1830 to be rotated about the support pole 1812.

In addition, the joint member 1830 may be hingably coupled with a received support plate 1856, and the joint member 1830 may be placed in one of a vertical or a horizontal orientation such that the received support plate 1856 (eg. 1822, 1824, 1826 in FIG. 9a) can rotate in a transverse plane or a longitudinal plane of the support pole 1812. FIGS. 9b and 9c respectively depict an embodiment of the present disclosure wherein a support plate 1856 and a joint member 1830 are configured to be hingably coupled, and wherein the resulting hinged joint may be placed in a substantially horizontal orientation such that the support plate 1856 may rotate in a longitudinal plane of the support pole 1812. FIG. 9a depicts an embodiment wherein the rack 1810 includes three of this type of coupling mechanism. Alternatively, a support plate 1856 or other type of medical device mount may be fixedly and rigidly coupled to the support pole 1812 in different embodiments.

In the embodiment depicted in FIG. 9b, the support plate 1856 may include a first support plate projection 1834 and a second support plate projection 1836 that extend in substantially parallel directions from a first end portion of the support plate 1856. The first support plate projection 1834 and the second support plate projection 1836 respectively include a first support plate aperture 1858 and a second support plate aperture 1862 that may be aligned along a line B-B, and wherein each is sized to receive a pin 1842.

In the embodiment depicted in FIG. 9c, the joint member 1830 may include a first joint member projection 1832 and a second joint member projection 1856 that extend in substantially parallel directions. The first joint member projection 1832 and the second joint member projection 1856 may respectively include a first joint member aperture 1864 and a second joint member aperture 1866 that may be aligned along a line B-B, and wherein each is sized to receive a pin 1842.

To hingably couple the support plate 1856 to the joint member 1830 as depicted in FIG. 9a, the first and the second support plate projections 1834, 1836 and the first and the second joint member projections 1832, 1856 may be respectively sized and disposed on the support plate 1856 and joint member 1830 such that the respective projections 1832, 1834, 1836, 1856 are capable of interleaving. The apertures 1864, 1866 of the joint member 1830 are configured to align with the apertures 1860, 1858 of the support plate 1856 such that all four apertures 1858, 1862, 1864, 1866 will align along the line B-B when the four projections 1832, 1834, 1836, 1856 are interleaved. When properly aligned, a pin 1842 may be inserted through and retained in the four apertures 1858, 1862, 1864, 1866 such that the joint member 1830 retains the support plate 1856. As will be understood by persons having ordinary skill in the art, a number of methods are available to maintain the position of the support plate 1856 about the pin 1842. In certain embodiments, the friction between the interleaved projections 1832, 1834, 1836, 1856 and/or the friction between the pin 1842 and the four apertures 1858, 1862, 1864, 1866 in which the pin 1842 is disposed may be sufficient to maintain the position of the support plate 1856 about the pin 1842. Any other structure may secure the joint member 1830 to the support plate 1856 known to one of ordinary skill in the relevant art.

In other embodiments, the position of the support plate 1856 about the pin 1842 may be maintained at one of several predefined positions by a detent pin (not shown) that is capable of engaging one of several detents (not shown) in an inner joint member projection. The detents may be annularly inscribed at several positions about the pin 1842. In embodiments having such detents, a detent pin aperture may retain the detent pin and be disposed in an outer support plate projection so as to enable the detent pin to selectively engage any one of the detents in the inner joint member projection. Once a healthcare provider engages the detent pin with the appropriate detent, the detent and the detent pin can prevent the support plate 1856 from rotating out of the selected position.

In particular embodiments, like the embodiment depicted in FIG. 9a, the weight of multiple received medical devices may cause the rack 1810 to become unbalanced and begin to rotate about the point where the clamp mechanism 1818 couples with a support structure like an IV pole. To mitigate this type of rotation, a base member 1816 may be employed that exerts a stabilizing force on the support structure. As depicted in FIG. 9a, the base member 1816 may comprise an elongated housing 1868 that is coupled to a second end portion of the support pole 1812 and that extends perpendicularly to the support pole 1812. The base member 1816 may include a rounded notch 1840 that is configured to abut a substantially cylindrical support structure. The notch 1840 may be disposed on the elongated housing 1868 such that the base member 1816 and the clamp mechanism 1818 position the support pole 1812 in spaced relation to and substantially parallel to an elongated, cylindrical support structure like an IV pole. In other embodiments, the base member may comprise a second clamp assembly like the clamp assembly 1814 that may be coupled to the first end of the support pole 1812.

An advantage of the exemplary embodiment depicted in FIG. 9a, is that the base member 1816 and the elongated housing 1868 can serve other functions in addition to providing a counterbalancing force to the rack 1810. For example, the elongated housing 1868 may serve as a bedside surface on which a healthcare provider may temporarily store items that are needed to care for a patient. In another embodiment, the elongated housing 1868 could also be configured to receive a medical device and include the same features as a support plate 1856, such as a mount connector 1838 that is configured to provide one or both of electrical power and a network connection to a received medical device. In embodiments where the base member 1816 does not include an elongated housing 1868, the base member

1816 may nevertheless be configured to receive, power, and provide a network connection to an additional medical device.

Figure 9D:
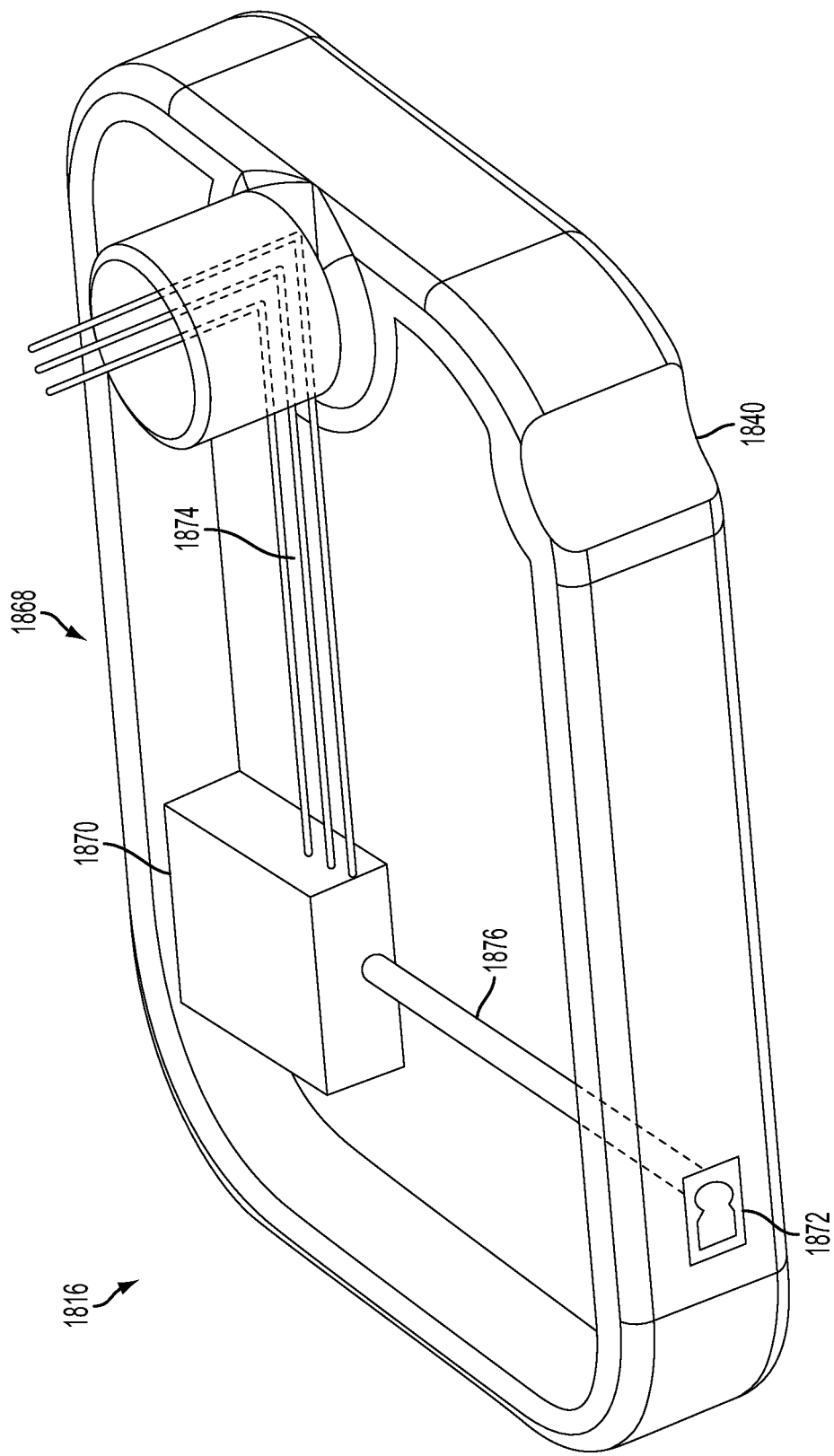
FIG. 9d is a perspective view of an exemplary embodiment of a base member that includes a power system that is configured to transmit power to at least one device mount like the embodiment depicted in FIG. 9b in accordance with an embodiment of the present disclosure.

Another advantage of the exemplary embodiment depicted in FIG. 9a and the exemplary base member 1816 depicted in FIG. 9d is that the elongated housing 1868 may provide space to contain certain elements of a power system. FIG. 9d depicts an exemplary power system that includes a power supply 1870, a power connector 1872, power transmission cables 1874, and a main power cable 1876. As discussed above, embodiments that include a power system may have the advantage of reducing the number of cables that are needed to power the received medical devices. Rather than having to run a separate power cable from an electrical outlet to each medical device, a single power cable may be connected from an electrical outlet to a power connector 1872 that is preferably located on the elongated housing 1868 of the base member 1816. A main power cable 1876 may then deliver power to a power supply 1870. The power supply 1870 may be configured to convert balanced or unbalanced AC current to direct current and provide the desired voltage and amperage for any received medical devices. A respective power transmission cable 1874 may be used to transmit electrical power from the power supply 1870 to a respective mount connector 1838 and a received medical device. The power transmission cables 1874 may provide one more DC voltages for use by any received medical devices. In certain embodiments, the respective power transmission cable 1874 may operatively run from a power supply 1870, up through a hollow support pole 1812, and may be operatively distributed to the respective mount connector 1838. Each of the support plates 1856 may include a mount connector 1838 and receive a respective power transmission cable 1874 that enables the mount connector 1838 to supply electrical power to a received medical device. In some embodiments, a common power bus may be positioned within a hollow support pole 1812 that receives power from the power transmission cables 1874; each mount connector 1838 may be electrically coupled to the power bus.

In addition to supplying power to a received medical device, the exemplary mount connector 1838 depicted in FIG. 9b may be configured to provide a network connection to a received medical device. In embodiments that are capable of receiving two or more medical devices, it may be advantageous to enable the received medical devices to communicate with one another. For example, a patient may require a regime of several different drugs that are administered by respective syringe pumps. Enabling the rack 1810 to transmit signals between network-capable syringe pumps may allow for each syringe pump to know how much of which drugs were delivered by the other syringe pumps in the rack 1810 network. To achieve this objective, exemplary embodiments like the embodiment depicted in FIG. 9a may include a central bus 1878 that is operatively coupled to the support pole 1812. Each of the support plates 1856 may include a support-plate bus 1880 that operatively interfaces with the central bus 1878 and that is coupled to a mount connector 1838.

In some embodiments, each received medical device may broadcast its data over the central bus 1878. In other embodiments a turn-based communication scheme may be used by the received medical devices to communicate with each other using the central bus 1878. In yet additional embodiments, a carrier-sense, multiple-access with optional collision avoidance communication scheme may be used by the medical devices when communicating via the central bus 1878.

Yet another advantage of the exemplary embodiment of the rack 1810 depicted in FIG. 9a and the exemplary base member 1816 depicted in FIG. 9d is that the elongated housing 1868 may optionally include provisions, such as casters and the like, for coupling with two or more wheels. In addition to the handle 1820, wheels may allow the rack 1810 to be more easily moved from one location to another, particularly when transporting multiple received medical devices. As should be understood by persons having ordinary skill in the art, wheels may be coupled to the elongated housing 1868 by any number of well-known means. In addition, two or more wheels may be coupled to a wheel assembly structure that enables the wheels to be coupled to or decoupled from the elongated housing 1868 as a group. In other exemplary embodiments, the support pole 1812 may include provisions for mounting two or more wheels or a wheel assembly.

Figure 9E:
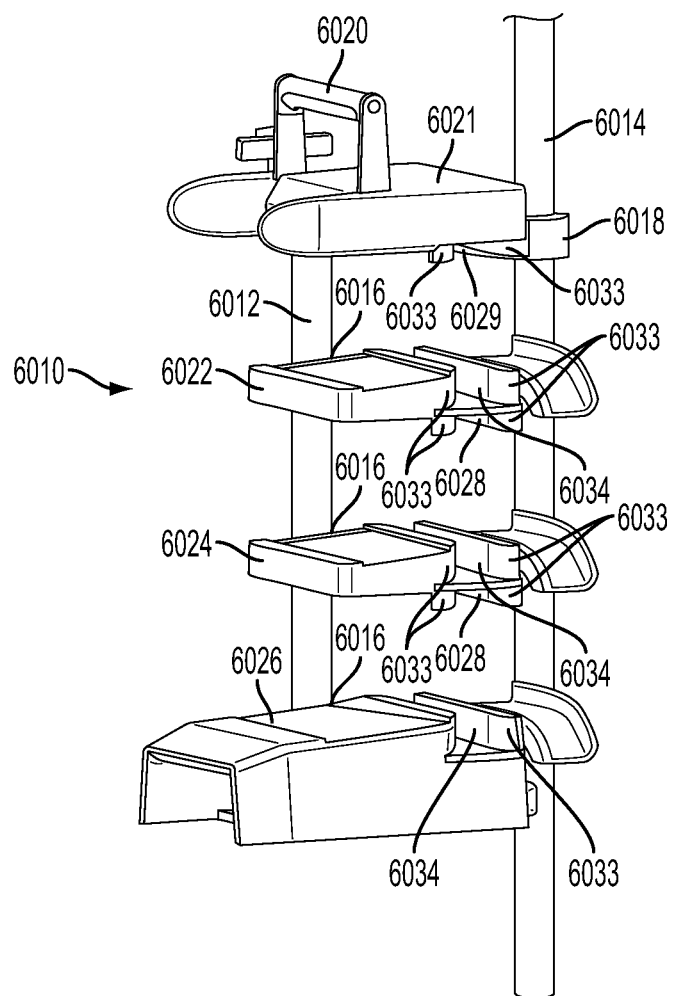
FIG. 9e depicts a perspective view of another exemplary embodiment of a rack apparatus in accordance with an embodiment of the present disclosure.

FIG. 9e depicts one exemplary embodiment of a rack 6010. The rack 6010 includes a cylindrically-shaped support pole 6012. A clamp mechanism 6018 and a U-shaped handle 6020 on a handle plate 6021 may be oriented perpendicularly to the longitudinal axis of the support pole 6012. The clamp mechanism 6018 may be configured to removably couple with a support structure 6014 such as an IV pole. As should be appreciated by those having ordinary skill in the art, any number of clamp mechanisms 6018 may be used to accomplish this objective, including the clamp mechanisms described below and above. The handle 6020 enables the rack 6010 and any received medical devices to be carried as unit from one location to another. In certain embodiments, the handle 6020 may serve as a means to actuate the clamp mechanism 6018. One such embodiment could include a handle 6020 that shares an axis of rotation with a clamp mechanism 6018, wherein the clamp mechanism 6018 includes at least one fixed gripper and at least one mobile gripper that may be coupled to the handle 6020. Actuation of the clamp mechanism 6018 may be achieved by rotating the handle 6020 in a first direction such that the at least one mobile gripper rotates towards the at least one fixed gripper and a support structure 6014 therebetween. The at least one mobile gripper and the at least one fixed gripper may be secured in a clamped position by a latch or any other means known in the relevant art when the aforementioned grippers exert a sufficient clamping force on the support structure 6014. Rotating the handle 6020 in a second, opposite direction may rotate the at least one mobile gripper away from the at least one fixed gripper, and the clamp mechanism 6018 may be decoupled from the support structure 6014 when the at least one mobile gripper is sufficiently far from the support structure 6014.

A variety of medical device mounts may be disposed between the first end and a second end of the support pole 6012. FIG. 9e depicts an exemplary embodiment where the mounts may be elongated support plates that extend perpendicularly to the support pole 6012. FIG. 9e depicts a rack 6010 having a first support plate 6022, a second support plate 6024, and a third support plate 6026. The first support plate 6022, second support plate 6024, and third support plate 6026 may be sized to receive and support a medical device such as any of those described above. One end portion of each of the first support plate 6022, a second support plate 6024, and a third support plate 6026 may be coupled to the support pole 6012 via a joint member 6016. The joint member 6016 may be similar to the joint member 1830 described above.

The third support plate 6026 may perform the same function as the base member 1816 and elongate housing 1868 in FIGS. 9*a-d*. In some embodiments, the third support plate 6026 may also house elements of a power system like the power system described above and may include a mount connector 6038 (best shown in FIG. 10E) that is configured to provide one or both of electrical power and a network connection to a received medical device. As described above in relation to FIGS. 9*a-d* the first support plate 6022, second support plate 6024, and third support plate 6026 may each include a mount connector 6038.

As shown in FIG. 9*e*, the first support plate 6022, a second support plate 6024, and a third support plate 6026 each may include a first guide trough 6034 and a second guide trough 6028. As shown, the third support plate 6026 only includes a first guide trough 6034. As shown, the handle plate 6021 also includes a handle plate guide trough 6029. The guide troughs 6026, 6034, 6029 may also include guide rails 6033. The guide rails 6033 may be the sides of the guide troughs 6026, 6034, 6029, or may be projections which project off the first support plate 6022, second support plate 6024, and third support plate 6026 or handle plate 6021. In embodiments where the guide rails 6033 are projections, the guide rails 6033 may define the sides of the guide troughs 6026, 6034, 6029. As in the exemplary embodiment in FIG. 9*e*, the ends of the guide rails 6033 may bow out or angle out away from the longitudinal axis of the guide troughs 6026, 6034, 6029. This may allow a medical device to be easily and sightlessly slid into the guide troughs 6026, 6034, 6029 and docked on the supports plates 6022, 6024, 6026. In some embodiments, the medical device may include a feature or features such as a flanges 6062 (see FIG. 10*d*) which may be sized to fit within the guide troughs 6026, 6034, 6029.

As will be understood by persons having ordinary skill in the art, the racks 1810, 6010 and their components can be made from a variety of rigid, engineering materials. Possible materials include aluminum alloys, stainless steel alloys, steel alloys, and engineering polymers. In addition, a variety of coatings may be applied to the racks 1810, 6010 and their components. Many of the possible coatings may provide a means of reducing the likelihood of cross-contamination. Cross-contamination may pose a serious health risk to young and old patients and patients with weakened immune systems. Optionally, an antibacterial, an antiviral, or an antimicrobial coating may be applied to the structural components of the racks 1810, 6010 to kill or inhibit the growth bacteria, viruses, fungi, and various other microorganisms. Exemplary coatings may include copper, copper particles, silver, silver particles, or other materials that have antibacterial, antiviral, or antimicrobial properties.

Rack Systems

Figure 10A:
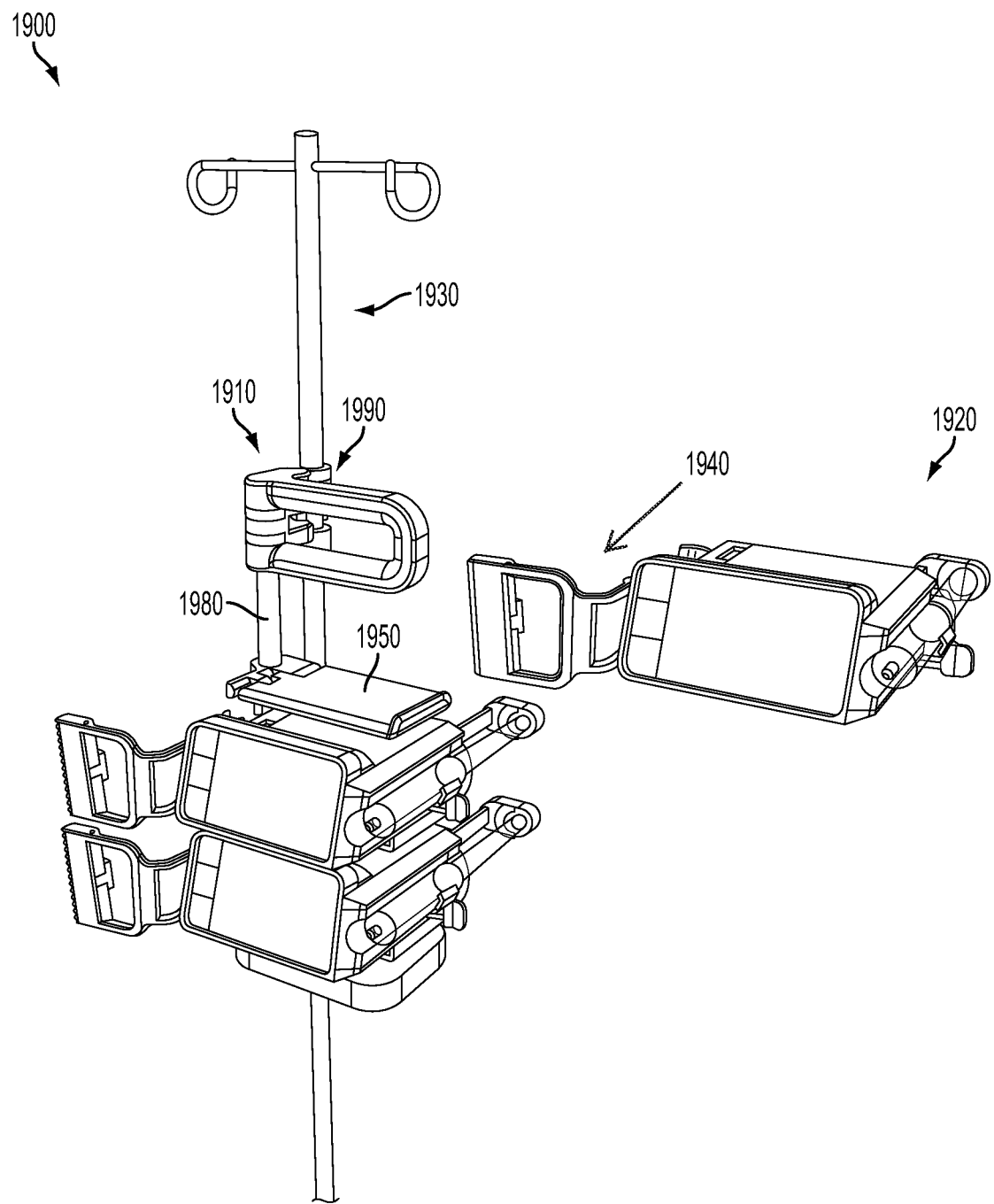
FIG. 10a is a perspective view of an exemplary embodiment of a rack system, wherein the embodiment of a rack depicted in FIG. 9a includes a support pole adapted to couple with the clamp of a medical device in accordance with an embodiment of the present disclosure.

FIG. 10*a* shows an exemplary rack system 1900. The exemplary embodiment of a rack 1810 depicted in FIG. 9*a* may be one element of a rack system 1900 shown in FIG. 10*a*. Another element of the rack system 1900 may be a device that includes a mounting mechanism that is configured to couple with the rack, such as a clamp mechanism like any one of those described above. It should be understood that the exemplary embodiment depicted in FIG. 9*a* is but one embodiment of a rack that may be used in the rack system, and alternative embodiments of the rack and mounting mechanism may depart, perhaps substantially, from the exemplary embodiments described herein.

Figure 10B:
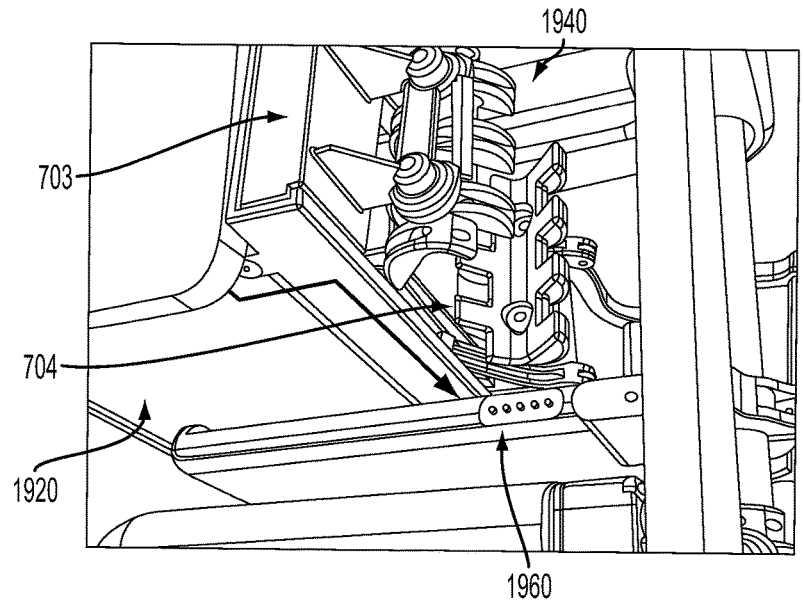
FIG. 10b is a close-up, perspective view of the exemplary embodiment of a rack system depicted in FIG. 10a, wherein the rack embodiment includes a mount connector that may couple to a device connector when the medical device couples with the support pole in accordance with an embodiment of the present disclosure.
Figure 10C:
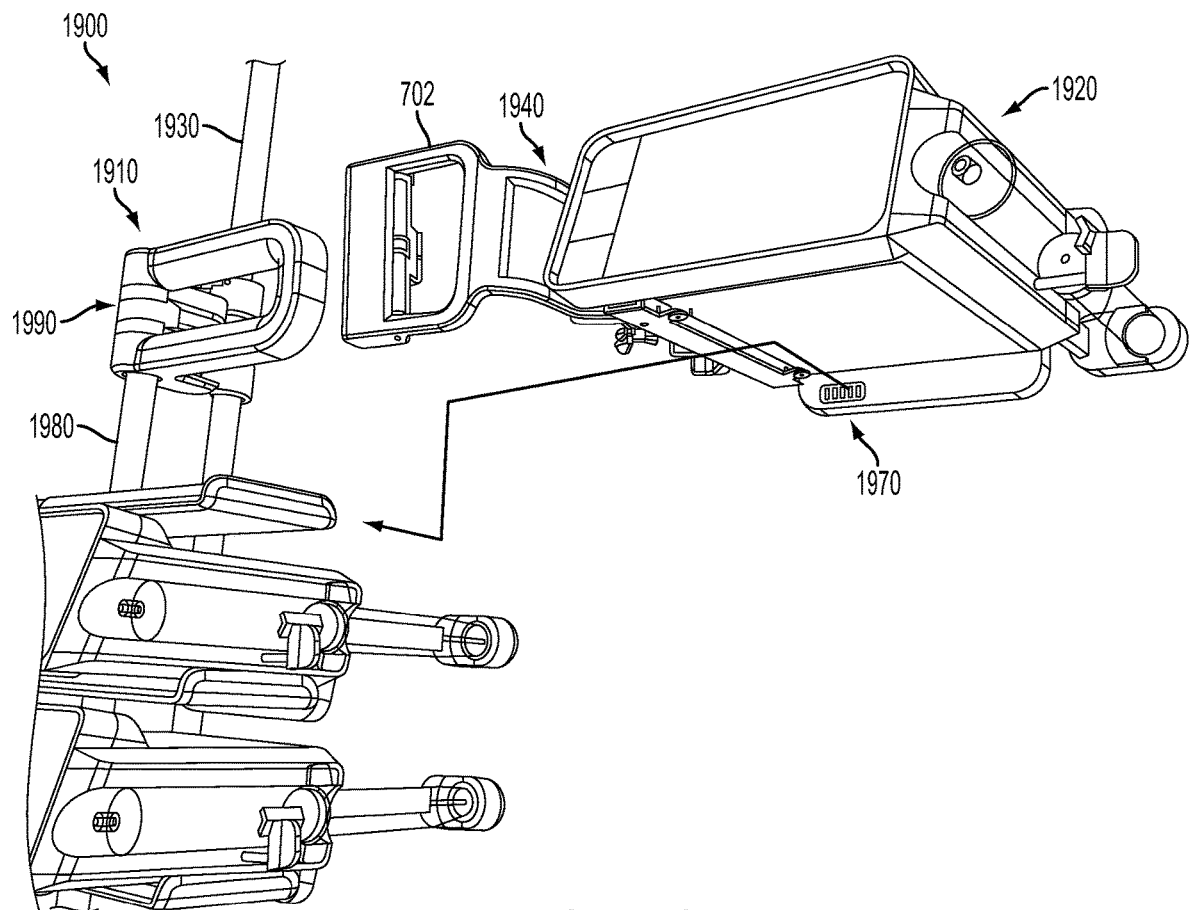
FIG. 10c is another alternate perspective view of the exemplary embodiment of a rack system depicted in FIG. 10a, wherein an embodiment of a medical device includes an embodiment of a device connector that may couple to a mount connector, like the embodiment depicted in FIG. 10b, when the medical device couples with the support pole in accordance with an embodiment of the present disclosure.

FIG. 10*a* depicts an embodiment of a rack system 1900 comprising a rack 1910 that is substantially the same as the rack 1810 embodiment described above and depicted in FIGS. 9*a-d*, a medical device 1920 that may be received by a support plate 1950 of the rack 1910, and a clamp mechanism 1940 that is coupled to a first side of a medical device 1920 and that is adapted to securely couple the medical device 1920 to the rack 1910. FIG. 10*b* depicts the same embodiment as FIG. 10*a* but from a different perspective. FIG. 10*b* includes a view of the clamp mechanism 1940, described in detail below, and a mount connector 1960 that is disposed on the support plate 1950. FIG. 10*c* is yet another perspective of the embodiment depicted in FIGS. 10*a* and 10*b* and includes a view of a device connector 1970 that is disposed on the medical device 1920. The mount connector 1960 and the device connector 1970 are preferably disposed on the support plate 1950 and the medical device 1920 respectively so that they are operatively aligned and capable of coming into contact when the clamp mechanism 1940 couples the medical device 1920 to the rack 1910.

In a preferred embodiment of the rack system 1900, the clamp mechanism 1940 may be a mechanism like the embodiment depicted in FIGS. 8*a*-8*d* or described in relevant portions of the specification above. The clamp mechanism 1940 may latch onto the support pole 1980 depicted in FIGS. 10*a*-10*c*.

As should be evident from the description of the above embodiment of a clamp mechanism 1940, actuating the clamp mechanism 1940 to couple an attached medical device 1920 to a support pole 1980 has a first phase and a second phase. Refer now to FIGS. 8*a*-8*d* and FIGS. 10*a*-10C. In the first phase, user rotation of the handle 702 may move the driven member 710 and the slidably attached mobile gripper 704 towards the fixed gripper 703 until the girth of the support pole 1980 arrests the movement of the mobile gripper 704. Thus, the first phase ends when the fixed gripper 703 and the mobile gripper 704 contact the support pole 1980. In the second phase, continued rotation of the handle 702 may continue to drive the driven member 710 towards the fixed gripper 703 and bias the compression spring 730 because the driven member 710 may continue to move independently of the mobile gripper 704. Therefore, the second phase enables the user to increase the clamping force and ensure that the medical device 1920 is securely coupled to the rack 1910.

In some embodiments, the medical device may be a monitoring client (e.g., a tablet computer) to monitor the operation of the other medical devices (e.g., via wireless communications such as WiFi or Bluetooth, for example). The monitoring client may have a serial interface to connect to the connector 1960 (see FIG. 10B).

Referring now to FIGS. 10*a*-10*c*, the rack system 1900 may be best employed where a patient requires treatment with a coordinated regime of drugs, particularly where the drugs are to be administered by syringe pumps. Because syringe pumps are capable of continuously or discretely delivering precise quantities of fluid over a period of time, syringe pumps are well-suited to administering a regime of different drugs at predefined times. Computerized and networked syringe pumps may allow such a regime to be administered automatically. Embodiments of the present disclosure, like the embodiment of a rack system 1900 depicted in FIGS. 10*a-c*, may enable a healthcare provider to quickly setup a group of networked syringe pumps to administer such a regime of drugs.

For example, a healthcare provider may quickly couple the clamp assembly 1990 to a support structure 1930, such as an IV pole, and connect the rack 1910 to a source of electrical power. If no syringe pumps or other devices are already coupled to the rack 1910, the healthcare provider may proceed to couple the required syringe pumps to the rack 1910 one at a time. The healthcare provider may couple each syringe pump to the rack 1910 by placing a portion of each syringe pump on one of the support plates 1950 such that the support plate 1950 bares at least a portion of the weight of the syringe pump, allowing the healthcare provider to more easily maneuver the syringe pump into position. Once the support pole 1980 is positioned between the fixed gripper 703 (see FIGS. 8*a*-8*d*) and the mobile gripper 702 (see FIGS. 8*a*-8*d*) and once the mount connector 1960 and the device connector 1970 are in general alignment, the healthcare provider may rotate the handle 702 through the first phase of operation. During the first phase of operation, the device clamp-mechanism 1940 may automatically adjust to the size of the support pole 1980 and the mount connector 1960 and the device connector 1970 may be brought into contact with one another. The healthcare provider may secure the syringe pump to the rack 1910 by continuing to rotate the handle 702 through the second phase of operation, and the healthcare provider may repeat the procedure for as many syringe pumps as may be desired. Thus, the healthcare provider may provide each syringe pump with electrical power and a network connection to other syringe pumps without having to run multiple power and network cables that may complicate the setup procedure and clutter the environment around the patient. Moreover, any one of the syringe pumps may be decoupled from the rack 1910, or another syringe pump may be coupled to the rack 1910, without having to detach or attach any additional cables. When treatment is complete, certain syringe pumps may remain coupled to the rack 1910 and continue to treat the patient while others may be decoupled, again without having to detach any additional cables, and used to treat a different patient. Alternatively, a healthcare provider could transport the entire rack system 1900 and any syringe pumps coupled thereto by decoupling the rack 1910 from the support structure 1930. A rack 1910 that includes a handle 1820 and/or wheels may make transporting the rack system 1900 and medical devices 1920 easier in this scenario.

Figure 10D:
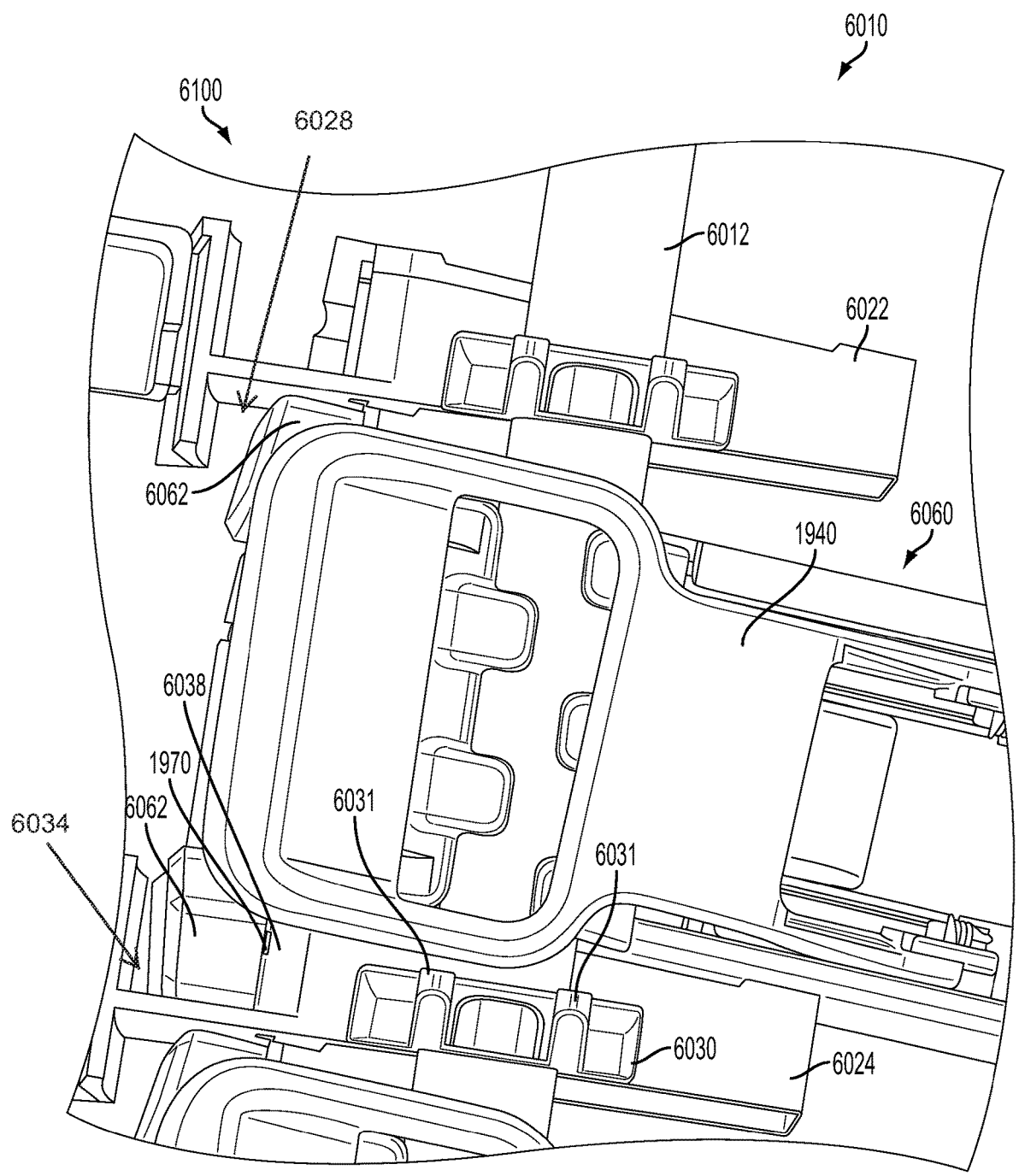
FIG. 10d is a perspective view of an exemplary embodiment of a rack system including the embodiment of a rack depicted in FIG. 9e in accordance with an embodiment of the present disclosure.

FIG. 10*d* shows a view of another embodiment of a rack system 6100 including the rack 6010 embodiment shown in FIG. 9*e*. A medical device, which for exemplary purposes is shown as an infusion pump 6060, is in place on the rack 6010. As shown, the flanges 6062 of the infusion pump 6060 are disposed within the guide troughs 6028, 6034 of the first support plate 6022 and second support plate 6024, respectively. A clamp mechanism 1940 is included on the infusion pump 6060 and is shown clamped around the support pole 6012. Additionally, as shown in FIG. 10*d*, the joint members 6030 of the support plates 6022, 6024, 6026 may include functional protrusions 6031. In the example embodiment, the functional protrusions 6031 are hooks or hangers. The functional protrusions 6031 may, for example, be used to hang various cabling, lines, or IV bags.

Figure 10E:
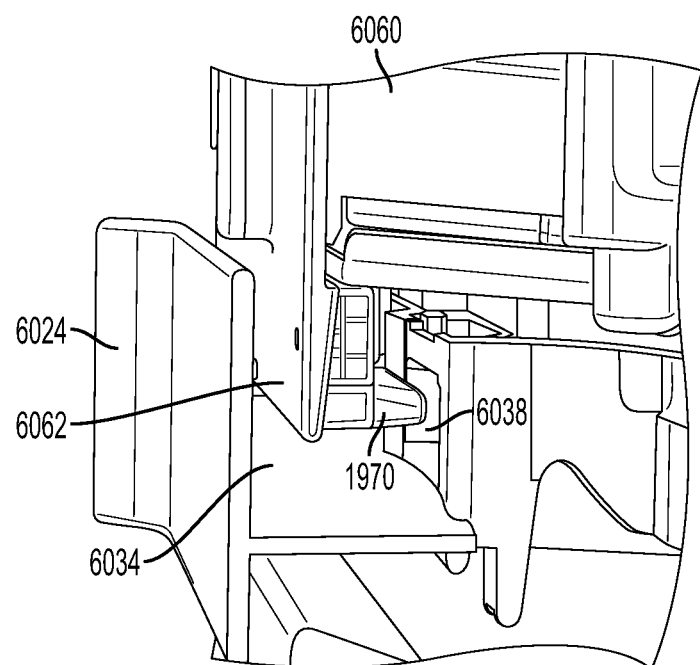
FIG. 10e is a close-up perspective view of an example infusion pump with a flange in place in the guide trough of a support plate of the example rack embodiment depicted in FIG. 9e in accordance with an embodiment of the present disclosure.

FIG. 10*e* depicts an infusion pump 6060 with a flange 6062 which is in place within a guide trough 6034 of the second support plate 6024. As shown, the infusion pump 6060 includes a device connector 1970 and the second support plate 6024 includes a mount connector 6038. The mount connector 6038 may be included in the side wall of the guide trough 6034. The device connector 1970 and the mount connector 6038 are not in contact with one another in FIG. 10*e*. Additionally, the flange 6062 of the infusion pump 6060 is relatively loose within the guide trough 6034. As mentioned above, any or all of the support plates 6022, 6024, 6026 may include mount connectors 6038 which may or may not be similarly disposed.

Referring now back to FIG. 10*d*, the device connector 1970 and the mount connector 6038 are shown in contact with one another. Additionally, the flanges 6062 of the infusion pump 6060 are well retained within the guide troughs 6034, 6028 of the support plates 6022, 6024. In order to bring the device connector 1970 and the mount connector 6038 into contact and firmly retain the flanges 6062 within the guide troughs 6034, 6028 it may be needed to, in some specific embodiments, actuate the clamp mechanism 1940 to the clamped position.

In FIG. 10*e*, the clamp mechanism 1940 (not shown) is not in the clamped position. When the clamp mechanism 1940 is not in the clamped position, the flanges 6062 of the infusion pump 6060 may be easily moved around within the guide troughs 6034, 6028. This may be helpful in inserting the infusion pump 6060 and in aligning the device connector 1970 and mount connector 6038. The clamp mechanism 1940 may then be actuated as described above into the clamped position. This action may drive the device connector 1970 and the mount connector 6038 into contact and cause the flanges 6062 to cinch up against a side wall of the guide troughs 6028, 6034 thus retaining the infusion pump 6060 on the rack 6010.

The healthcare provider may repeat the procedure for as many infusion pumps 6060 or medical devices as may be desired. Thus, the healthcare provider may provide each infusion pump 6060 or medical device with electrical power and a network connection to other infusion pumps 6060 or medical devices without having to run multiple power and network cables that may complicate the setup procedure and clutter the environment around the patient. Moreover, any one of the infusion pumps 6060 or medical devices may be decoupled from the rack 6010, or another infusion pump 6060 or medical device may be coupled to the rack 6010, without having to detach or attach any additional cables. When treatment is complete, certain infusion pumps 6060 or medical devices may remain coupled to the rack 6010 and continue to treat the patient while others may be decoupled, again without having to detach any additional cables, and used to treat a different patient. Alternatively, a healthcare provider could transport the entire rack 6010 and any infusion pump 6060 or medical devices coupled thereto by decoupling the rack 6010 from a support structure 6014 (see FIG. 9*e*). A rack 6010 that includes a handle 6020 and/or wheels may make transporting the rack 6010 and infusion pumps 6060 or medical devices easier in this scenario.

Protective Mechanisms

Figure 11A:
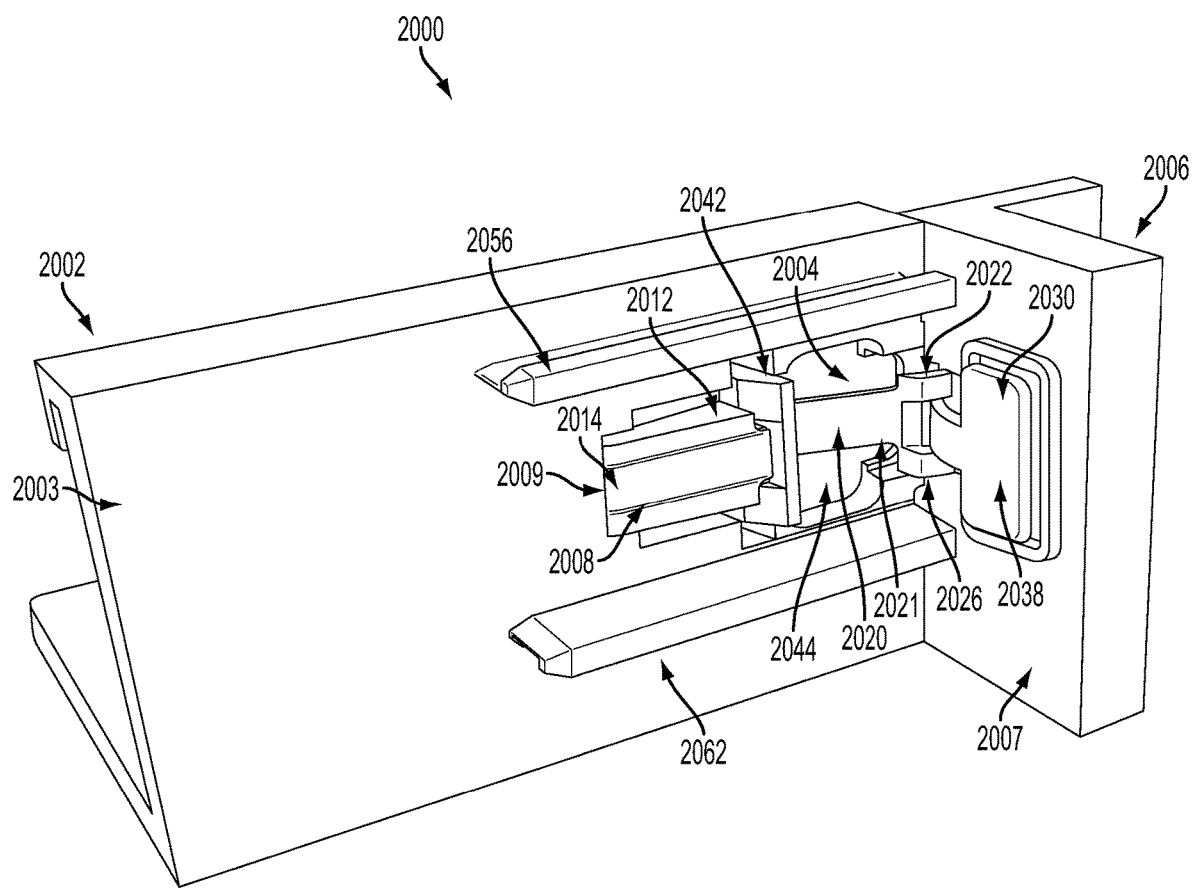
FIG. 11a depicts an embodiment of a pivotable cover mechanism in accordance with an embodiment of the present disclosure.
Figure 12A:
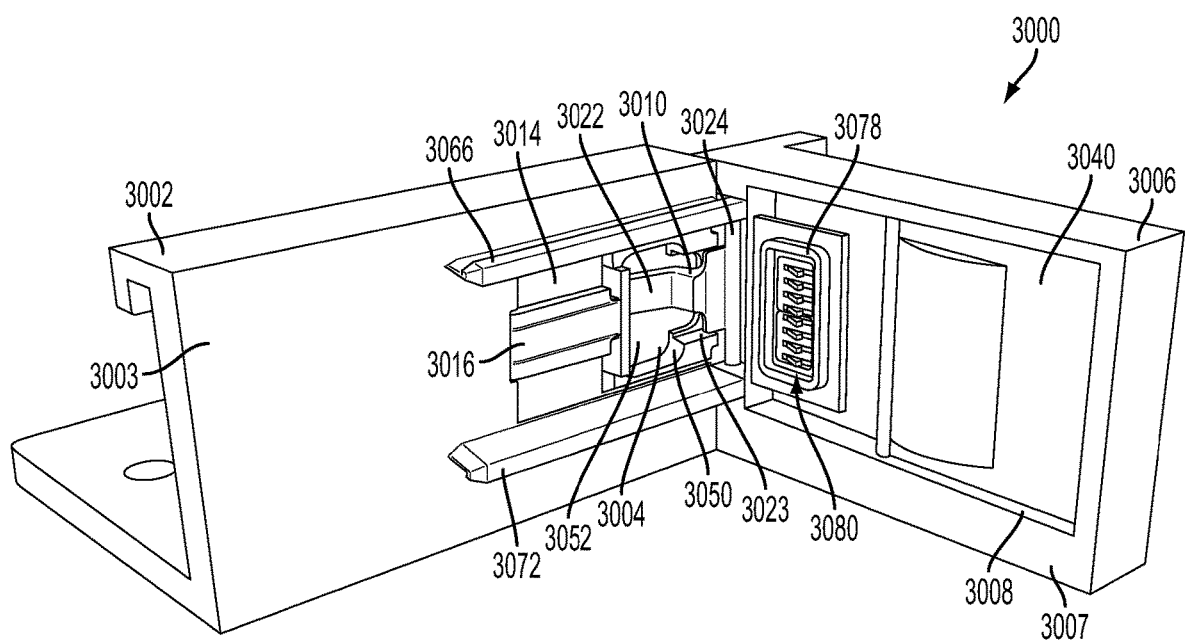
FIG. 12a depicts a view of an embodiment of a clamshell mechanism wherein the cover member is in a non-protective position in accordance with an embodiment of the present disclosure.

In addition, the medical device mounts of the rack 1810, 1910, 6010 may each include a protective mechanism that may protect the mount connector when not in use and during cleaning. For example, the mount connector 2068, 3078 may be covered by a pivotable-cover mechanism 2000 or a clamshell mechanism 3000. FIG. 11*a* depicts an embodiment of a pivotable-cover mechanism 2000. FIG. 12*a* depicts an embodiment of a clamshell mechanism 3000. In the embodiments depicted in FIGS. 11*a* and 12*a* of the pivotable-cover and clamshell mechanisms 2000, 3000 respectively, coupling an electronic device, such as syringe pump, to the mechanism may automatically reveal the mount connector 2068, 3078 and allow the mount connector 2068, 3078, to interface with the connector of the received electronic device.

Pivotable-Cover Mechanism & Clamshell Mechanism: Common Components

In the embodiments of the present disclosure depicted in FIGS. 11a and 12a, the pivotable-cover mechanism 2000 and the clamshell mechanism 3000 may utilize similar components to receive an electronic device and initiate steps to reveal the respective mount connector 2068, 3078. However, the two mechanisms 2000, 3000 are only two of many possible embodiments to complete the process of revealing the mount connector 2068, 3078. The two example mechanisms 2000, 3000 may respectively include a guide member 2002, 3002, a first rail projection 2056, 3066 and a second rail projection 2062, 3072. The first rail projection 2056, 3066 and the second rail projection 2062, 3072 may be disposed on a guide member face 2003, 3003, and run in parallel to one another along a longitudinal axis of the guide member 2002, 3002 such that the first and the second rail projections 2056, 3066, 2062, 3072 are capable of aligning the connector of a received device with the mount connector of the protective mechanisms 2068, 3078.

The pivotable-cover mechanism 2000 and the clamshell mechanism 3000 may also each include a backstop member 2006, 3006 having a backstop member face 2007, 3007 to which the mount connector 2068, 3078 may be coupled. The backstop member face 2007, 3007 may be approximately perpendicular to the guide member face 2003, 3003. The first and the second rail projections 2056, 3066, 2062, 3072 may extend to the backstop member face 2007, 3007 such that the first and the second rail projections 2056, 3066, 2062, 3072 are long enough to support and stabilize a received electronic device. The mount connector 2068, 3078 may be coupled to the backstop member face 2007, 3007 such that the mount connector 2068, 3078 is operatively positioned to interface with the connector of a received electronic device. The protective mechanisms 2000, 3000 may also include a bus 2072, 3082 that is operatively coupled to the respective mount connector 2068, 3078. In preferred embodiments of the two protective mechanisms 2000, 3000, the mount connector 2068, 3078 may be coupled to the backstop member face 2007, 3007 such that the mount connector 2068, 3078 is positioned between the first and the second rail projections 2056, 3066, 2062, 3072.

To provide a mechanism for initiating the process of revealing the mount connector 2068, 3078, the pivotable-cover mechanism 2000 and the clamshell mechanism 3000 may respectively include an actuation member 2008, 3010 that is pivotally coupled to the guide member 2002, 3002 at a first, stationary pivot 2010, 3012, wherein the first, stationary pivot 2010, 3012 may be disposed between the backstop member face 2007, 3007 and a first end of the guide member 2002, 3002. The actuation member 2008, 3010 may include a sloped portion 2012, 3014 that extends from the first, stationary pivot point 2010, 3012 towards the mount connector 2068, 3078. The sloped portion 2012, 3014 may further include a sloped face 2014, 3016, wherein the sloped face 2014, 3016 may be configured such that it may slope upwardly and out of the plane of the guide member face 2003, 3003 from the first, stationary pivot 2010, 3012 towards the mount connector 2068, 3078. Thus, the sloped portion 2012, 3014 may protrude from the plane of the guide member 2002, 3002 when the actuation member 2008, 3010 is in a first position and the mount connector 2068, 3078 is covered. To reveal the mount connector 2068, 3078, the actuation member 2008, 3010, the sloped portion 2012, 3014, and the sloped face 2014, 3016 may pivot about the first, stationary pivot 2010, 3012 in a first direction from the first position to a second position. When the actuation member 2008, 3010 is in the second position and the mount connector 2068, 3078 is uncovered, the sloped face 2014, 3016 may lie substantially in the plane of the guide member 2002, 3002.

Figure 11B:
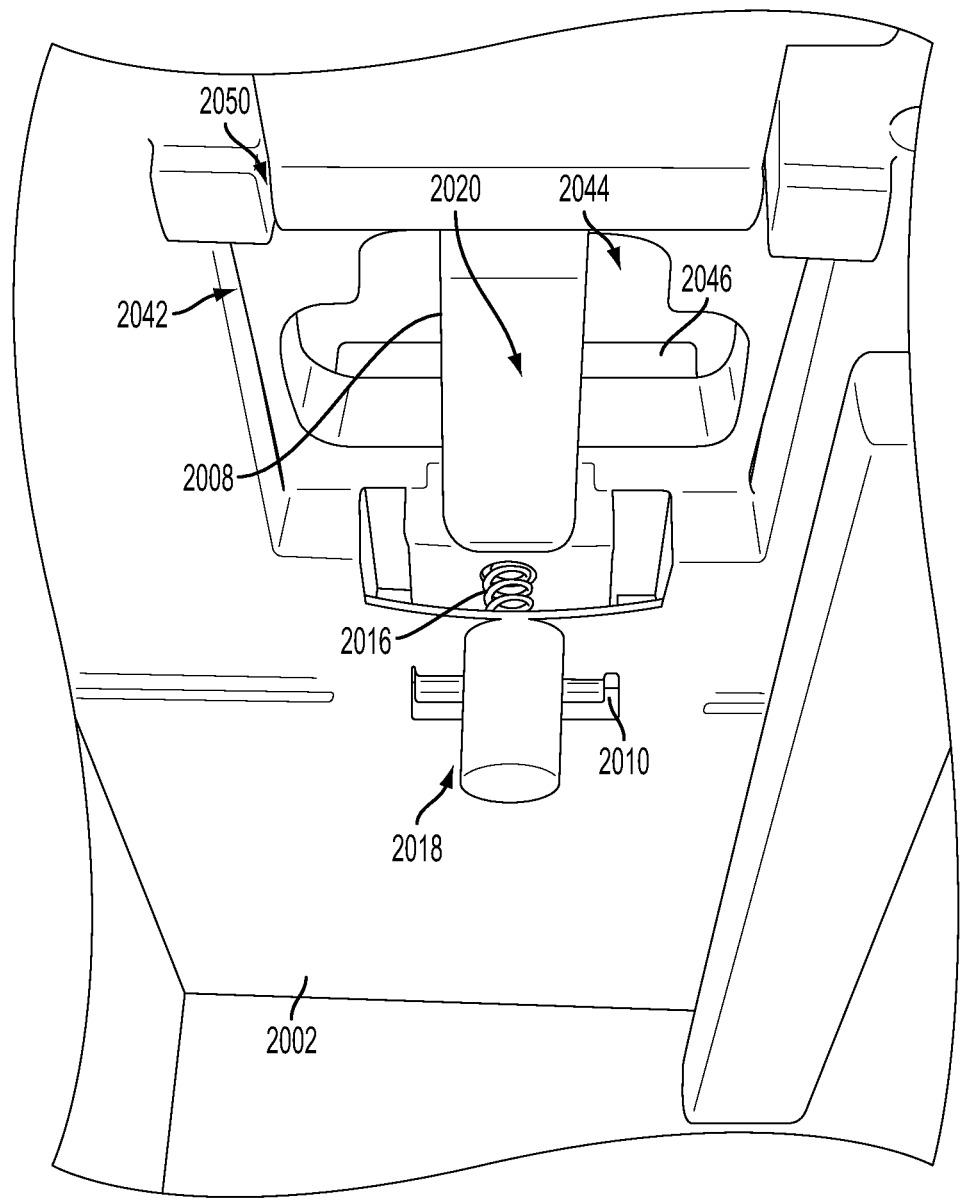
FIG. 11b depicts an actuation spring of an example embodiment of the pivotable-cover mechanism depicted in FIG. 11a acting on the sloped portion of an actuation member, wherein the actuation spring is disposed in an actuation spring pocket in accordance with an embodiment of the present disclosure.
Figure 11C:
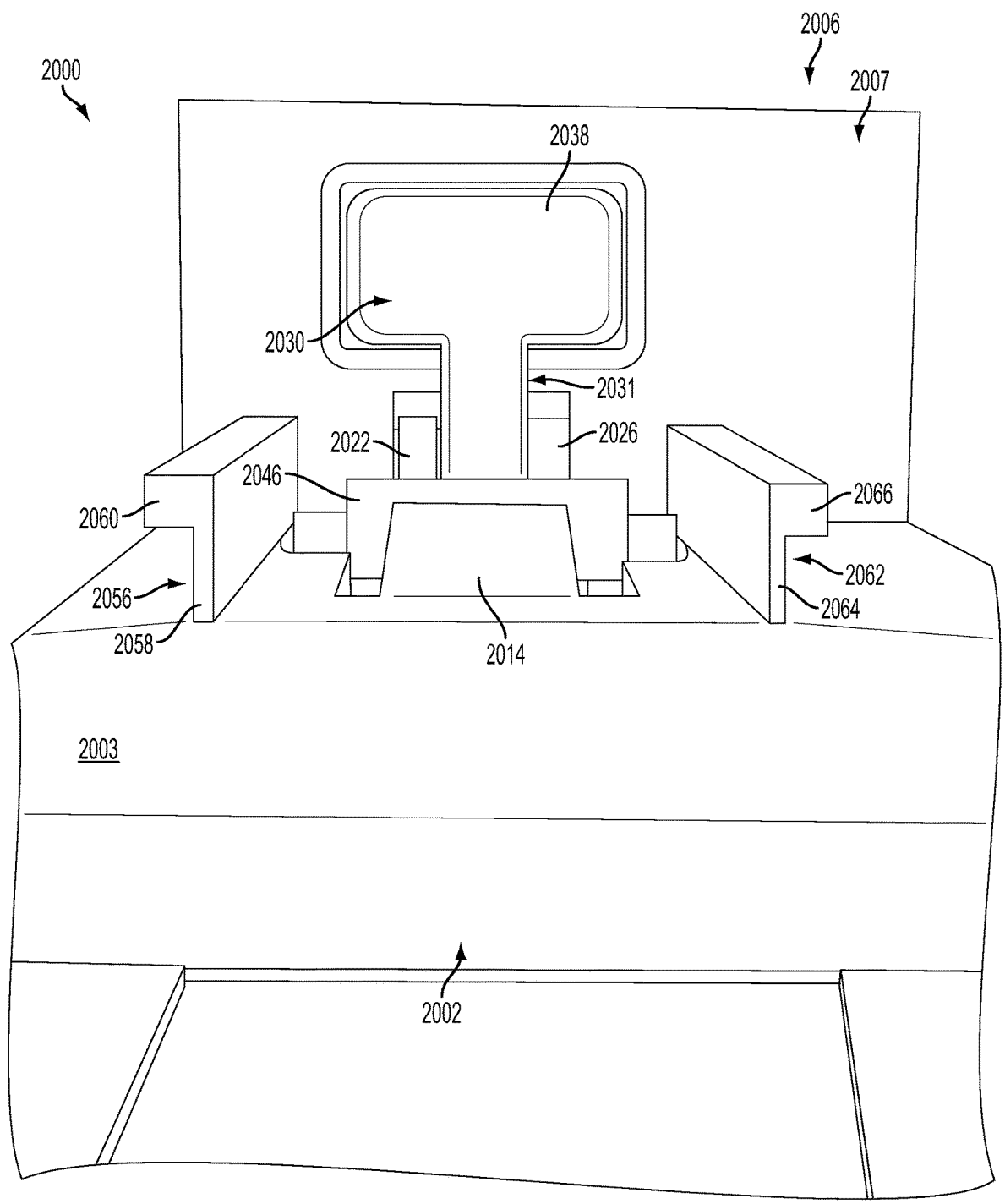
FIG. 11c depicts an example embodiment of the pivotable-cover mechanism wherein a mount connector is covered by a protective member in accordance with an embodiment of the present disclosure.

In addition, actuation springs 2016, 3018 may provide a mechanism for biasing the actuation members 2008, 3010 such that the actuation members 2008, 3010 may automatically return to the first position. To house the actuation springs 2016, 3018, the guide members 2002, 3002 may include an actuation spring pocket 2018, 3020. In certain embodiments, the actuation springs 2016, 3018 and the actuation spring pockets 2018, 3020 may be disposed on the guide members 2002, 3002 such that the actuation springs 2016, 3018 may be coupled to and exert a biasing force on the sloped portion 2012, 3014 of the actuation member 2008, 3010. FIG. 11b depicts the actuation spring 2016 of an embodiment of the pivotable-cover mechanism 2000 acting on the sloped portion 2012 of the actuation member 2008, wherein the actuation spring 2016 is disposed in the actuation spring pocket 2018. The clamshell mechanism 3000 may be similarly configured.

The pivotable-cover mechanism 2000 and the clamshell mechanism 3000 may also respectively include a latch member 2042, 3050 that may be configured to latch onto a received electronic device when the latch member 2042, 3050 is in a latched position. The latch member 2042, 3050 may be disposed within an aperture or a guide member recess 2004, 3004 defined by the guide member 2002, 3002. In addition, the guide member recess 2004, 3004 and the latch member 2042, 3050 may be adapted to extend below a portion of the backstop member 2006, 3006 such that a first end portion of the latch member 2042, 3050 may be adjacent to the sloped portion 2012, 3014 of the actuation member 2008, 3010, and a second, opposite end portion of the latch member 2042, 3050 may be disposed within the guide member recess 2004, 3004 on the opposite side of the backstop member 2006, 3006.

To allow a user to selectively engage or disengage the latch member 2042, 3050, the latch member 2042, 3050 may be adapted to pivot about a third, stationary pivot 2050, 3060. To latch onto a received electronic device, the latch member 2042, 3050 may include a latch projection 2046, 3054 disposed on a first end portion of the latch member 2042, 3050 and adapted to protrude from the guide member face 2003, 3003 when the latch member 2042, 3050 is in the latched position. The latch member 2042, 3050 may also include a latch member aperture 2044, 3052 through which the actuation member 2008, 3010 may pass, and thus, the latch member aperture 2044, 3052 may be sized and adapted to allow the actuation member 2008, 3010 to pivot through its full range of motion without interference from the latch member 2042, 3050.

Like the actuation member 2008, 3010, the latch member 2042, 3050 may be adapted such that a biasing force automatically returns the latch member 2042, 3050 to the latched position. Thus, a latch member spring 2048, 3056 may be disposed within a latch member spring pocket 2049, 3058 operatively defined by the guide member 2002, 3002 or the backstop member 2006, 3006. In a preferred embodiment, the backstop member 2006, 3006 defines the latch member spring pocket 2049, 3058 such that the latch member spring 2048, 3056 may exert a downward force on the latch member 2042, 3050 between the third, stationary pivot 2050, 3060 and the second end portion of the latch member 2042, 3050. To position the latch member projection 2046, 3054 at a desired height above the guide member face 2003, 3003, the backstop member 2006, 3006 may be operatively sized and disposed on the guide member 2002, 3002 such that the backstop member 2006, 3006 may arrest pivotal movement of the latch member 2042, 3050 at the correct position relative to the guide member face 2003, 3003. An alternative mechanism may include at least one arrester projection operatively disposed within the guide member recess 2004, 3004 and adapted to do the same. In a preferred embodiment, a first arrester projection 2052, 3062 (not shown) and a second arrester projection 2054, 3064 (not shown) may be disposed on opposite sides of the guide member recess 2004, 3004 between the third, stationary pivot point 2050, 3060 and the second end portion of the latch member 2042, 3050, wherein the first and second arrester projections 2052, 2054, 3062, 3064 are capable of exerting a normal moment of force to counteract the moment of force that the latch member spring provides 2048, 3056.

As will be understood by persons having ordinary skill in the art, the pivotable-cover and clamshell mechanisms 2000, 3000 and their components can be made from a variety of rigid, engineering materials. Possible materials include aluminum alloys, stainless steel alloys, steel alloys, and engineering polymers. In addition, a variety of coatings may be applied to the mechanisms 2000, 3000 and their components. Many of the possible coatings provide a means of reducing the likelihood of cross-contamination. Cross-contamination may pose a serious health risks to young and old patients and patients with weakened immune systems. Optionally, one or more of an antibacterial, an antiviral, or an antimicrobial coating may be applied to the structural components of the pivotable-cover and clamshell mechanisms 2000, 3000 to kill or inhibit the growth bacteria, viruses, fungi, and various other microorganisms. Exemplary coatings may include copper, copper particles, silver, silver particles, or other materials that have antibacterial, antiviral, or antimicrobial properties.

A Pivotable-Cover Mechanism

While both the pivotable-cover mechanism 2000 and the clamshell mechanism 3000 may include the aforementioned elements to receive an electronic device and initiate the steps to reveal the mount connector 2068, 3078, the pivotable-cover mechanism 2000 and the clamshell mechanism 3000 employ additional, different mechanical linkages to complete the task.

Figure 11D:
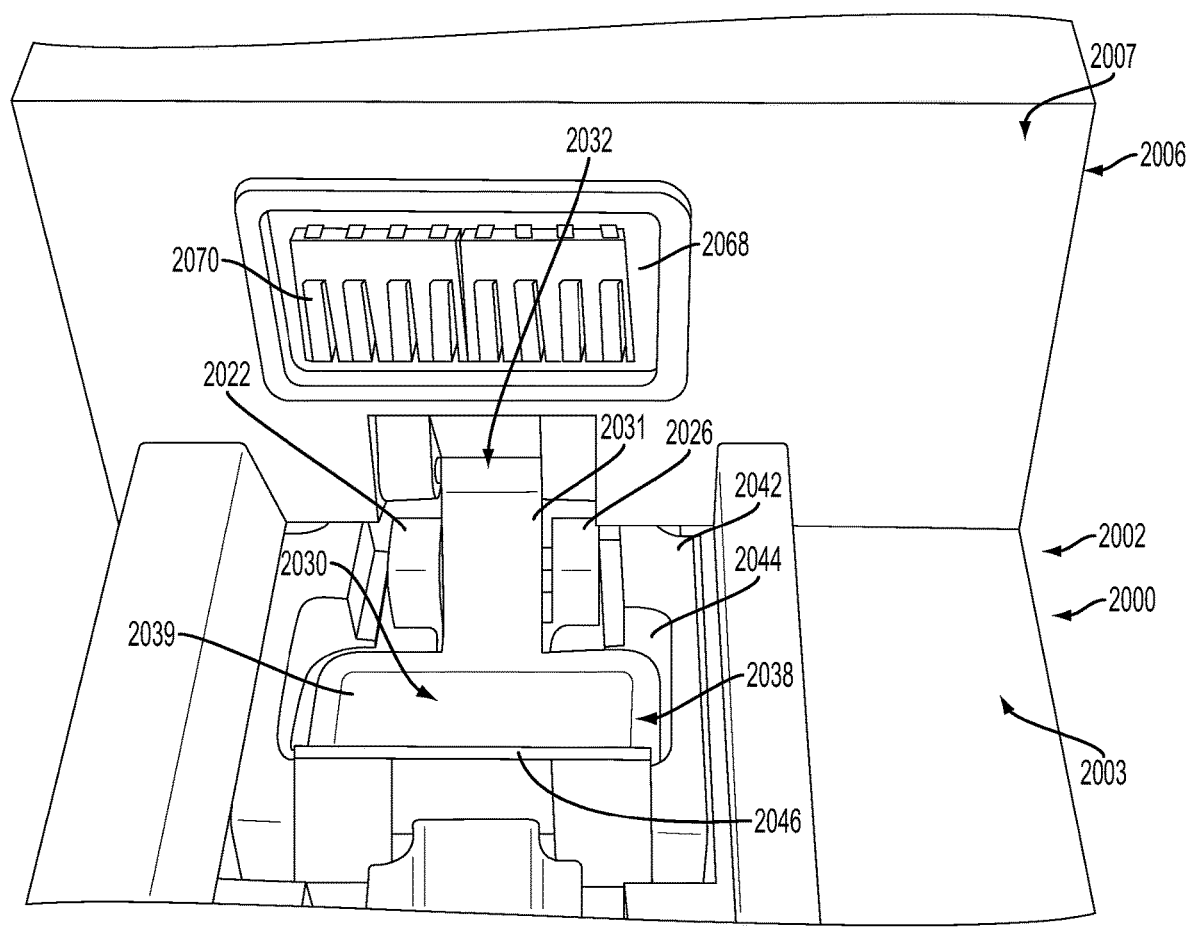
FIG. 11d depicts an embodiment of a pivotable cover mechanism wherein the protective member is in a non-protective position in accordance with an embodiment of the present disclosure.
Figure 11E:
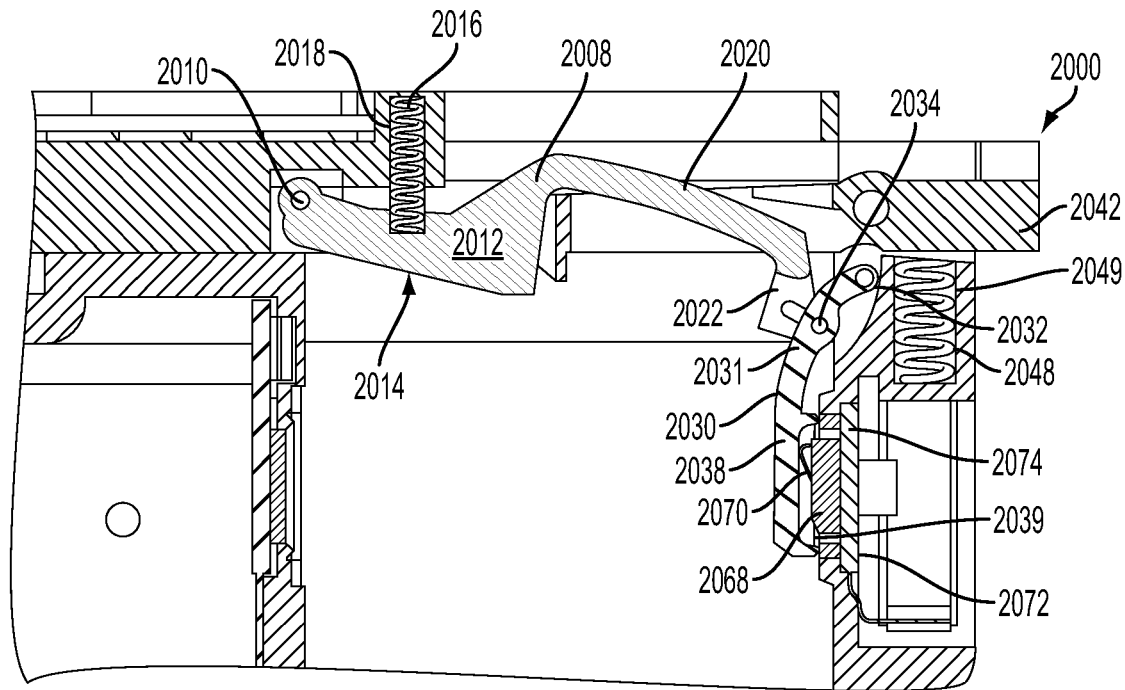
FIGS. 11e-i depict several cross-sectional views of an embodiment of a pivotable cover mechanism in accordance with an embodiment of the present disclosure.

FIGS. 11a-11i depict an exemplary embodiment of the pivotable-cover mechanism 2000. FIGS. 11a and 11e depict an embodiment of the pivotable-cover mechanism 2000 wherein the mount connector 2068 is covered by a protective member 2030. FIG. 11e depicts a cross-section of the pivotable-cover mechanism 2000 wherein the mechanism has received an electronic device, the actuation member 2008 is in the second position, and the mount connector 2068 is uncovered. In addition, FIG. 11e depicts a number portions that may comprise the actuation member 2008, including: the sloped portion 2012, a bridge portion 2020, a first channeled projection 2022, and a second channeled projection 2026. FIG. 11d more clearly shows the first and second channeled projections 2022, 2026 and the gap between them.

Figure 11F:
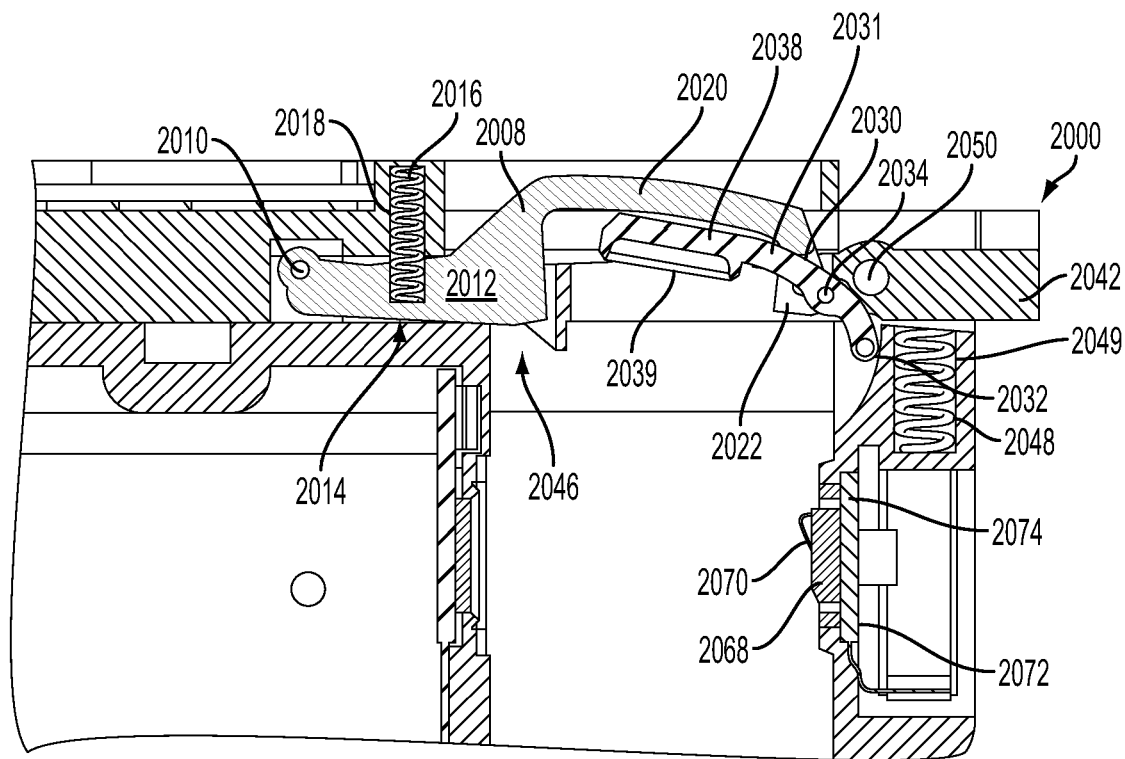
Figure 11G:
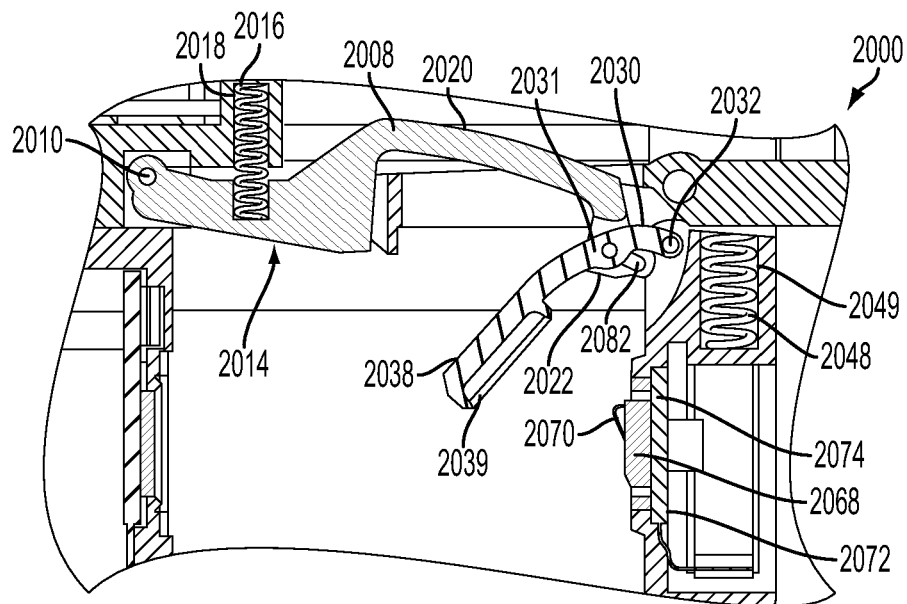
Figure 11H:
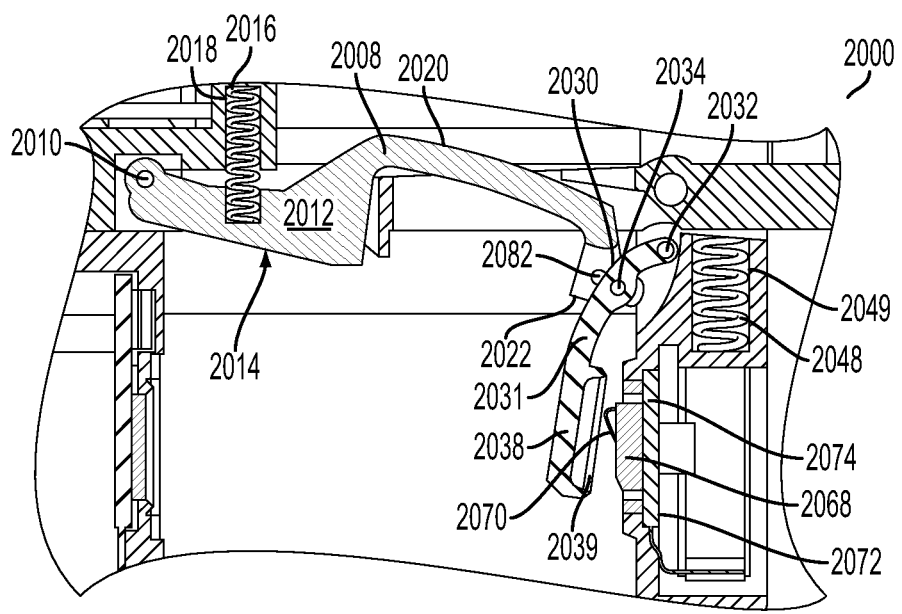
Figure 11I:
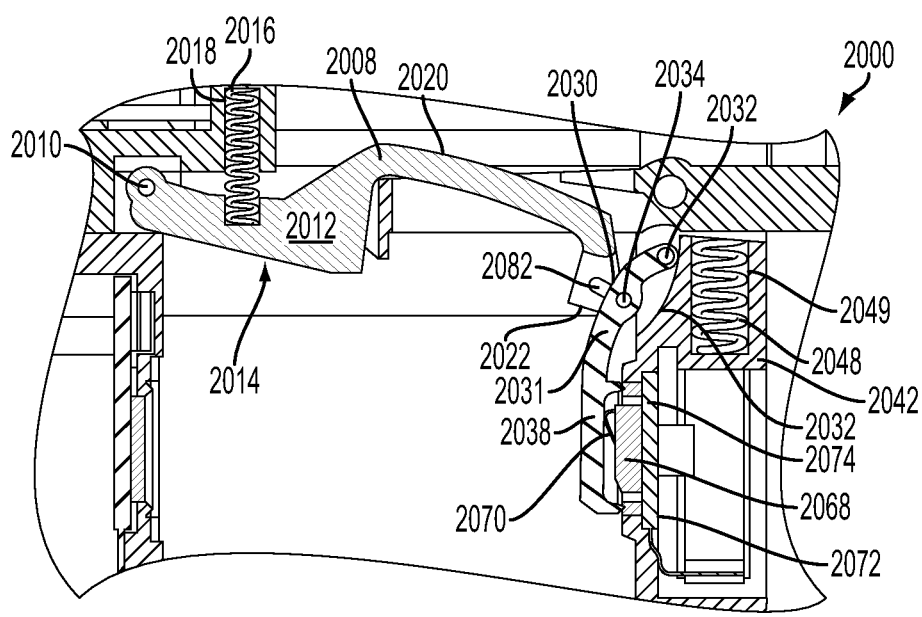

The protective member 2030 of the pivotable-cover mechanism 2000 may be pivotally coupled to either the backstop member 2006 or the guide member 2002 at a second, stationary pivot 2032. As depicted in FIG. 11f, the protective member 2030 is coupled to the backstop member 2006 in this particular embodiment. The third, stationary pivot 2050 lies on the guide member 2002 immediately above the second, stationary pivot 2032. Additionally, the protective member 2030 may comprise a cover portion 2038 and a stem portion 2031 that couples the cover portion 2038 to the backstop member 2006. The cover portion 2038 may be configured to cover the mount connector 2068. The protective member 2030 may also include first and second actuation projections 2034, 2036 (not shown) wherein the first and second actuation projections 2034, 2036 are adapted to respectively engage the first channel 2024 and the second channel 2028 of the first and second channeled projections 2022, 2026 of the actuation member 2008. Therefore, the first and second channeled projections 2022, 2026 may be shaped and sized such that the pivotal moment of the actuation member 2008 from the first position to the second position may pivot the protective member 2030 from a protective position, wherein the cover portion 2038 covers the mount connector 2068, to a non-protective position, wherein the protective member 2030 is disposed within the guide member recess 2004. Consequently, the bridge portion 2020 of the actuation member 2008 may be curved between the sloped portion 2012 and the first and second channeled projections 2022, 2026 to allow the protective member 2030 to nest within the actuation member 2008 when the protective member 2030 is in the non-protective position. FIGS. 11e-11i depict the positions of the actuation member 2008 and the protective member 2030 as they move from their respective positions when the mount connector 2068 is uncovered and in contact with the connector of an electronic device (FIG. 11e) to their respective positions when the mount connector 2068 is covered (FIG. 11i).

In addition, the pivotable-cover mechanism 2000 may include a latch member 2042 having a latch member aperture 2044 adapted to operatively receive a portion of the protective member 2030 when the protective member 2030 is in the non-protective position. FIG. 11d depicts the protective member 2030 in the non-protective position and shows the latch member aperture 2044 receiving the cover portion 2038 of the protective member 2030. FIG. 11d also depicts the stem portion 2031 of the protective member 2030 disposed between the first and second channeled projections 2022, 2026.

To protect the mount connector 2068 during cleaning and normal maintenance, the pivotable-cover mechanism 2000 may include a compliant gasket 2074 configured to, when the protective member 2030 is in the protective position, mechanically seal the mount connector 2068 within a cover portion recess 2039 defined by a perimeter rib 2040 of the cover portion 2038. In an exemplary embodiment depicted in FIG. 11k, the compliant gasket 2074 may encompass and abut the mount connector 2068. In a preferred embodiment, the actuation spring 2016, acting through the actuation member 2008, may bias the protective member 2030 such that the protective member 2030 may automatically return to the protective position. Consequently, the spring force of the actuation spring 2016 may enable the perimeter rib 2040 to contact and compress the compliant gasket 2074 when the protective member 2030 is the protective position. Thus, the perimeter rib 2040 may create mechanical seal with the compliant gasket 2074. FIG. 11k depicts an exemplary embodiment of the pivotable-cover mechanism 2000 wherein the perimeter rib 2040 has created a mechanical seal with the compliant gasket 2074.

As will be appreciated by persons having ordinary skill in the art, the compliant gasket 2074 may be made of any suitably compliant material; such materials may include, but are not limited to, isobutylene, natural rubber, neoprene, styrene butadiene, and silicone. In addition, the compliant gasket material may be chosen so that the compliant gasket 2074 is capable of resisting corrosion from solvents ordinarily used for cleaning device surfaces.

Figure 11J:
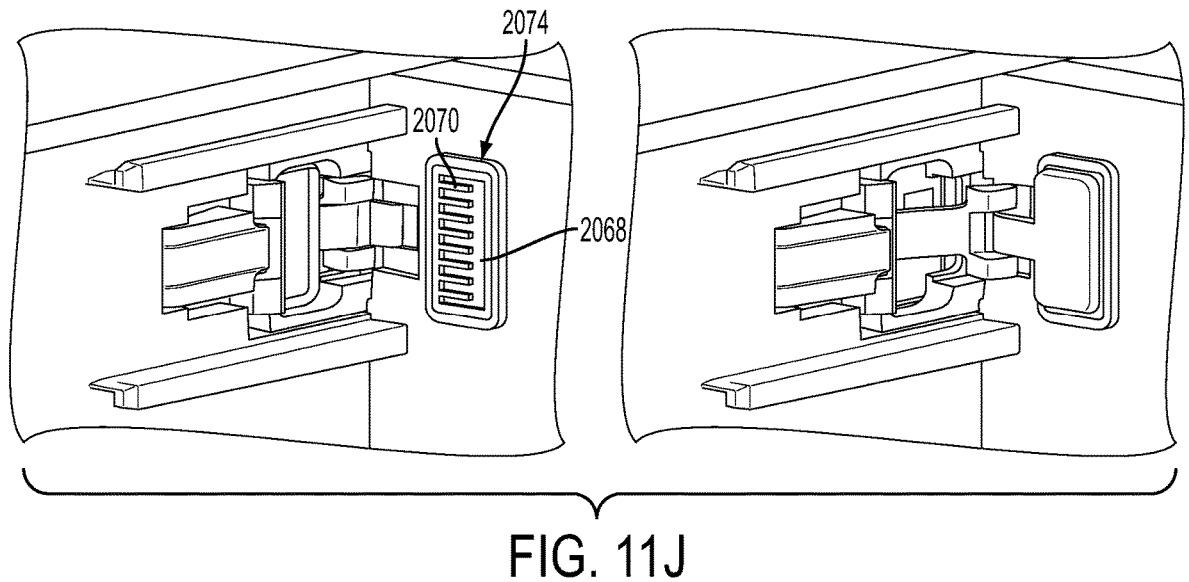
FIG. 11j depicts a view of an example embodiment of the pivotable cover mechanism, wherein the protective member is shown in a protective and a non-protective position and wherein the mount connector is of a type having multiple spring contacts in accordance with an embodiment of the present disclosure.
Figure 11K:
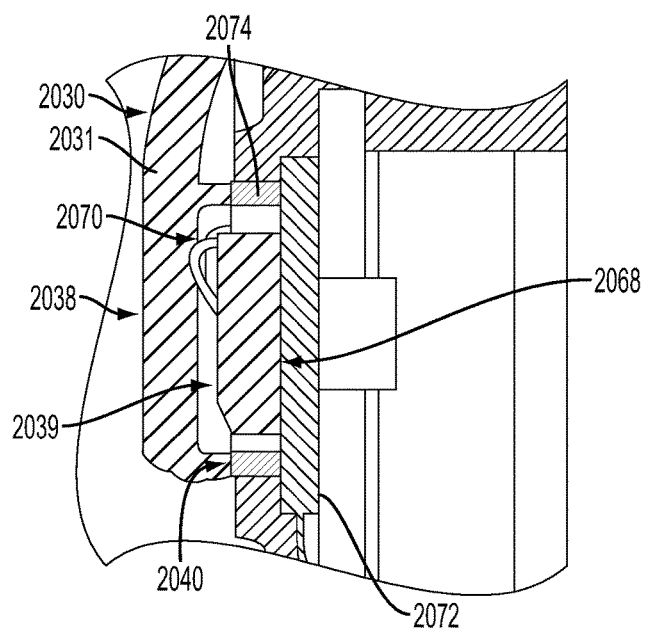
FIG. 11k depicts a cross-sectional view of part of the pivotable cover mechanism, wherein the mount connector is of a type having multiple spring contacts in accordance with an embodiment of the present disclosure.

FIGS. 11*j* and 11*k* depict an embodiment of the present disclosure, wherein the mount connector 2068 is of a type having multiple spring contacts 2070. To protect the spring contacts 2070 when the cover portion 2038 covers the mount connector 2068, the cover portion recess 2039 may include a compressible material, including but not limited to a polyurethane foam, disposed within the cover portion recess 2039 and adapted to receive the spring contacts 2070.

A Clamshell Mechanism

Whereas the protective member 2030 of the pivotable-cover mechanism 2000 is capable of pivoting towards the guide member 2002 to expose the mount connector 2068, the clamshell mechanism 3000 includes a cover member 3040 that is capable of pivotally sliding across the backstop member face 3007 to expose the mount connector 3078.

Figure 12B:
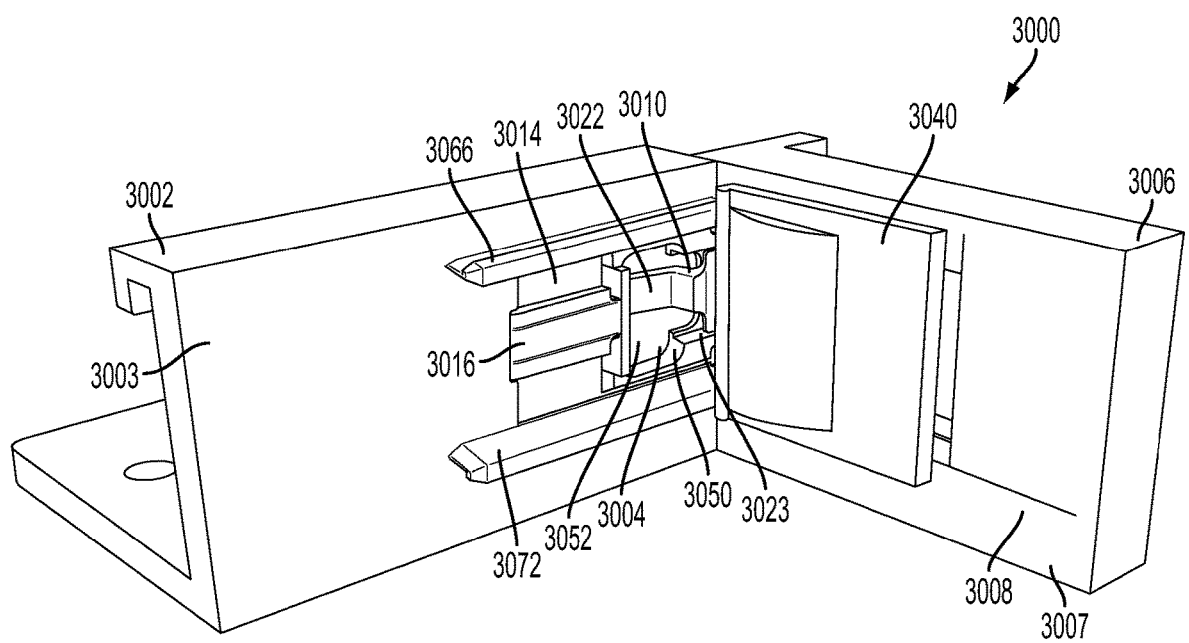
FIG. 12b depicts a view of an embodiment of a clamshell mechanism wherein the cover member is in a protective position in accordance with an embodiment of the present disclosure.

FIG. 12*a* depicts an exemplary embodiment of the clamshell mechanism 3000, wherein the cover member 3040 is in a non-protective position and the mount connector 3078 is exposed. FIG. 12*b* depicts the same embodiment of the clamshell mechanism 3000, wherein the cover member 2040 is in a protective position and the mount connector 3078 is covered.

Figure 12C:
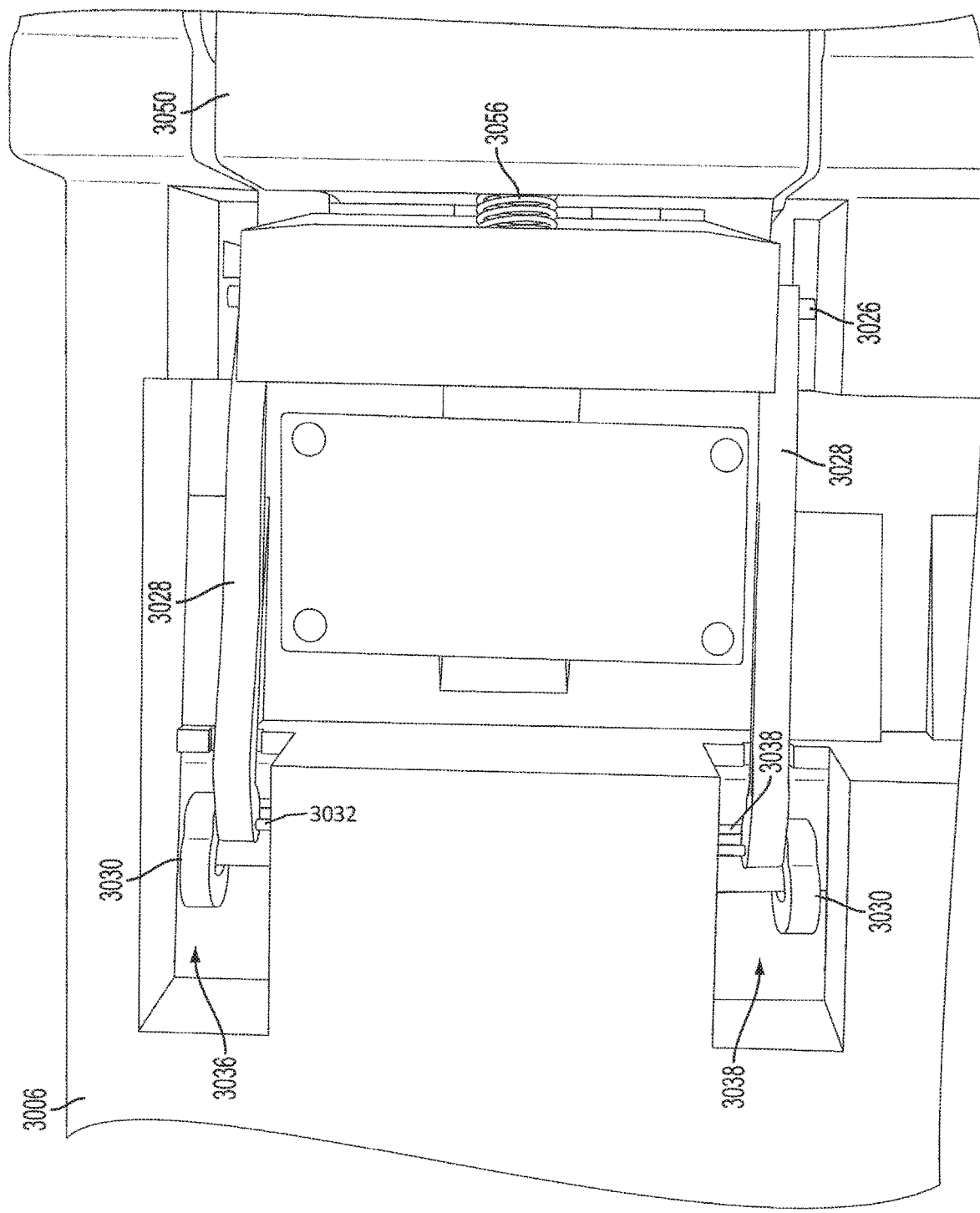
FIG. 12c depicts a close-up perspective view of a part of an embodiment of a clamshell mechanism in accordance with an embodiment of the present disclosure.

To pivotally slide the cover member 3040 across the backstop member face 3007, the clamshell mechanism 3000 may include at least one first link-member 3028 and at least one second link-member 3030 to enable movement of the actuation member 3010 to pivotally slide the cover member 3040. In the embodiment of the clamshell mechanism 3000 depicted in FIG. 12*a*, the actuation member 3010 includes a sleeve portion 3024 that is coupled to the bridge portion 3022 and that is opposite to the sloped portion 3014. FIG. 12*c* depicts an embodiment having a pair of first-link members 3028 that are pivotally coupled at respective first end portions to the sleeve portion 3024 of the actuation member 3010 at a first moveable pivot 3026. In addition, the pair of first link-members 3028 of the embodiment depicted in FIG. 12*c* are pivotally coupled at respective second end portions to respective first end portions of a pair of second link-members 3030 at a second moveable pivot 3032. As should be understood by persons having ordinary skill in the art, the backstop member 3006 is adapted to and coupled to the guide member 3002 so as to enable the at least one first link-member 3028 to couple with the actuation member 3010 and pass behind the backstop member face 3007. Moreover, the backstop member 3006 may be adapted to enable the at least one first and second link-members 3028, 3030 to move through their respective ranges of motion without interference from the backstop member 3006.

By way of movement of the at least one second link-member 3030, the cover member 3040 may pivotally slide across the backstop member face 3007 to reveal the mount connector 3078. In the embodiment of the clamshell mechanism 3000 depicted in FIGS. 12*d*-12*h*, the respective first end portions of the pair of second link-members 3030 are coupled to respective second end portions of the pair of first link-members 3028 at the second moveable pivot 3032 and to the backstop member 3006 at a stationary clamshell pivot 3034. FIGS. 12*d*-12*h* also depict the pair of second link-members 3030, wherein respective second end portions of the pair of second link-members 3030 are coupled to the cover member 3040 at a third moveable pivot 3042. In addition, the backstop member 3006 defines first and second pass-thru apertures 3036, 3038, depicted in FIGS. 12*i* and 12*j*, through which the pair of second-link members 3030 respectively pass to couple with the cover member 3040.

The first and second pass-thru apertures 3036, 3038 may be respectively shaped and sized so as to enable the pair of second link-members 3030 to move through their respective ranges of motion without interference from the backstop member 3006.

As the clamshell mechanism 3000 progresses through the stages of uncovering the mount connector 3078 depicted in FIGS. 12*e*-12*h*, movement of the actuation member 3010 in a first direction from a first position to a second position may cause the cover member 3040 to move from a protective position, wherein the mount connector 3078 is covered, to a non-protective position, wherein the mount connector 3078 is uncovered. During the uncovering process, pivotal movement of the actuation member 3010 in the first direction may cause the pair of first link-members 3028 to pivot slightly about the first moveable pivot 3026 and to move in a substantially translational direction towards the guide member 3002. In turn, the substantially translational movement of the pair of first link-members 3026 may cause the second moveable pivot 3032 to transit a plane that is parallel to the guide member face 3003 and that passes through the stationary clamshell pivot 3034. In doing so, the second moveable pivot 3032 may move from a first position to a second position, wherein the second moveable pivot 3032 is closer to the guide member 3002 in the second position than in the first position. Movement of the second moveable pivot 3032 from the first position to the second position may thereby cause the pair of second link-members 3030 to pivot about the stationary clamshell pivot 3034 and pivotally slide the cover member 3040 from the protective position to the non-protective position. The reverse process, depicted in the progression of figures from FIG. 12*h* to FIG. 12*e*, may be used to cover the mount connector 3078.

Like the pivotable-cover mechanism 2000, an actuation spring 3018 may be used to bias the clamshell mechanism 3000 so that the actuation member 3010 automatically returns to the first position under the force of the actuation spring 3018, and acting through the at least one first link-member 3028 and the at least one second link-member 3030, the actuation member 3010 may thereby cause the cover member 3040 to automatically return to the protective position.

To house the cover member 3040 when it is in the non-protective position, the backstop member may define a backstop member recess 3008 that the cover member 3040 may pivotally slide into as it pivotally slides across the backstop member face 3007 and exposes the mount connector 3078. FIGS. 12*e*-12*h* depict the progression of the cover member 3040 as it uncovers the mount connector 3078 and slides into the backstop member recess 3008. As depicted in FIGS. 12*e*-12*h*, the deepest portion of the backstop member recess 3008 may be an end portion that is furthest from the guide member 3002, and the backstop member recess 3008 may slope from the deepest portion towards the backstop member face 3007. The backstop member recess 3008 may be shaped and sized such that the cover member 3040 lies below the plane of the backstop member face 3007 when the cover member 3040 is in the non-protective position. In addition, the backstop member recess 3008 may be shaped and sized such that the cover member 3040 may surround and cover the mount connector 3078 when the cover member is in the protective position.

Figure 12D:
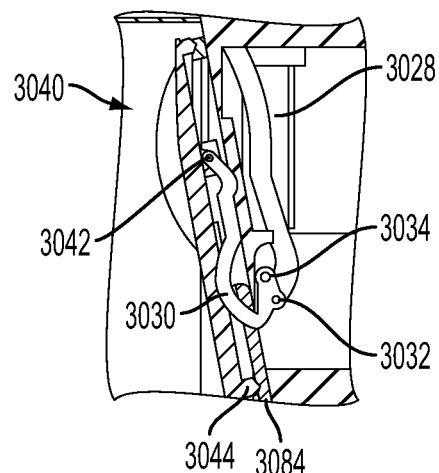
FIG. 12d depicts a cross sectional view of a clamshell mechanism wherein the cover member includes a perimeter rib in accordance with an embodiment of the present disclosure.
Figure 12E:
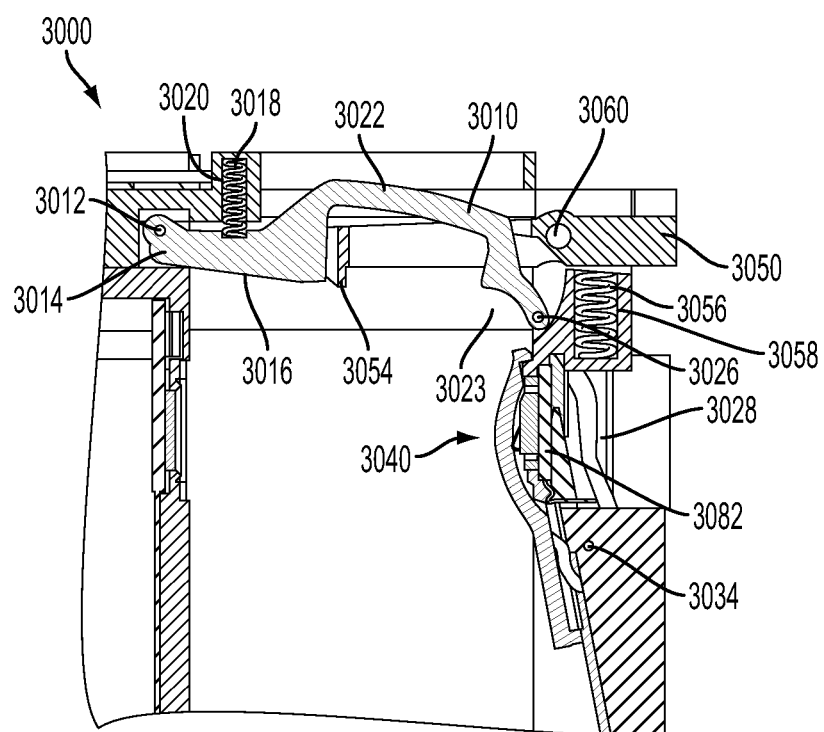
Figure 12I:
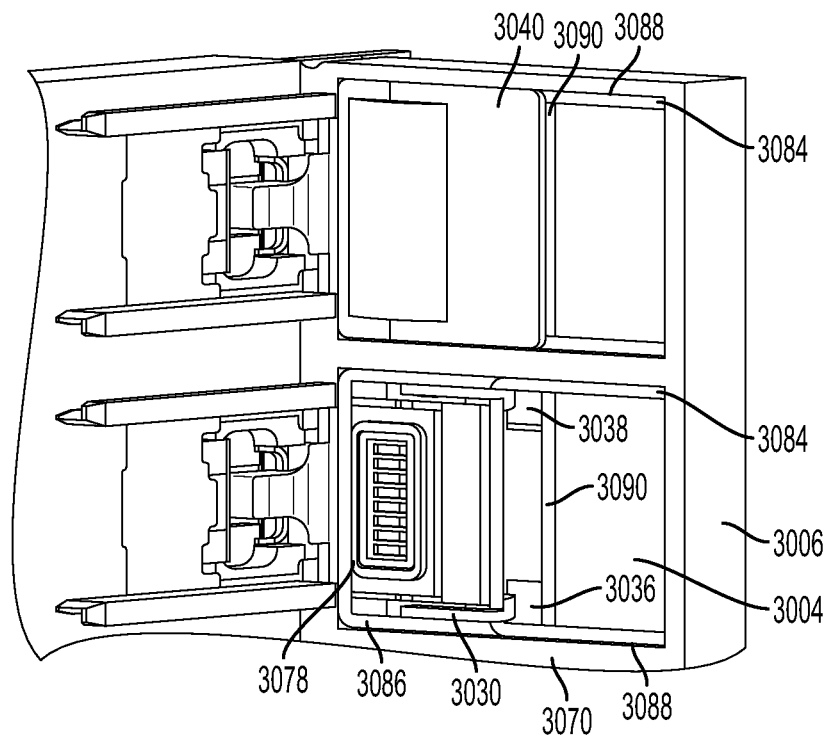
FIG. 12i-j depict a number of views an exemplary embodiment of a series of the clamshell mechanisms with compliant gasket systems in accordance with an embodiment of the present disclosure.
Figure 12J:
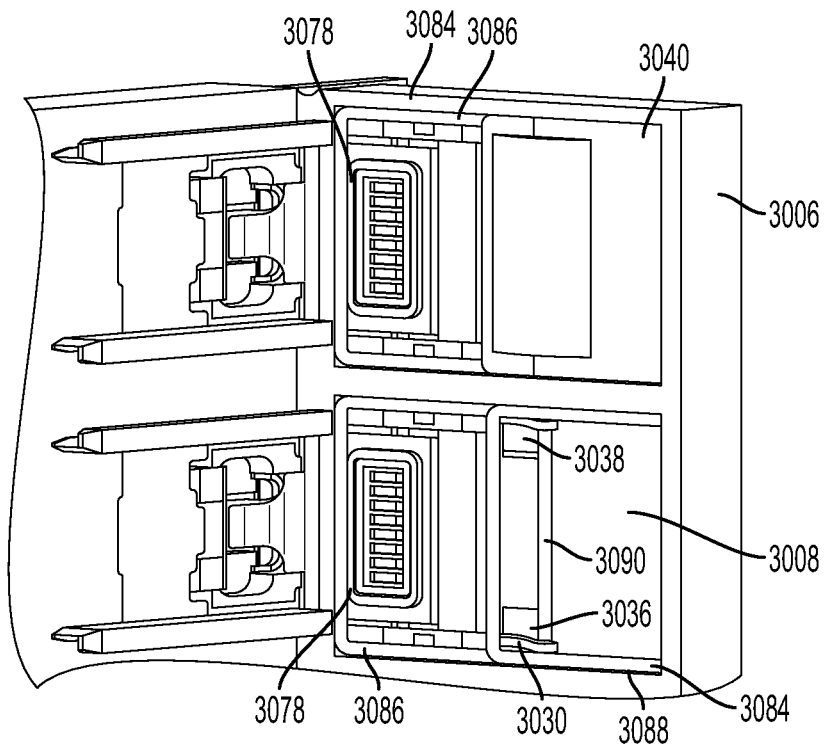

The clamshell mechanism 3000 may also include a compliant gasket system 3084 designed to protect the mount connector 3078, wherein the compliant gasket system 3084 includes a first gasket portion 3086, a second gasket portion 3088, and a transitional gasket portion 3090. The second gasket portion 3088 may mirror the first gasket portion 3086 and may be disposed on an opposite side of the transitional gasket portion 3090. FIGS. 12*i* and 12*j* depict an exemplary embodiment of a series of the clamshell mechanisms 3000 with compliant gasket systems 3084. FIG. 12*i* depicts the cover member 3040 in relation to the compliant gasket system 3084 when the cover member 3040 is in the protective position. In contrast, FIG. 12*j* depicts the cover member 3040 in relation to the compliant gasket system 3084 when the cover member 3040 is in the non-protective position. As depicted in FIG. 12*d*, the cover member 3040 may include a perimeter rib 3044 that may be shaped and sized such that, when cover member 3040 is in the protective position, the perimeter rib 3044 may compress the first gasket portion 3086 and a portion of the transitional gasket portion 3090. Likewise, FIG. 12*j* depicts the mechanical seal created by the perimeter rib 3044 (see FIG. 12*d*) the second gasket portion 3088, and a portion of the transitional gasket portion 3090. In both of FIGS. 12*i* and 12*j*, the perimeter rib 3044 compresses respective portions of the transitional gasket portion 3090 such that the first and second pass-thru apertures 3036, 3038 are within the mechanical seal created by the perimeter rib 3044 and the compliant gasket system 3084. The first and second pass-thru apertures 3036, 3038 may be contained with the mechanical seal to protect at least the first and second pairs of link-members 3028, 3030 against the threat of contamination from foreign matter, particularly during cleaning of the clamshell mechanism 3000.

Like the compliant gasket 2074 of the pivotable-cover mechanism 2000, the compliant gasket system 3084 of the clamshell mechanism 3000 may be made of any suitably compliant material; such materials may include, but are not limited to, isobutylene, natural rubber, neoprene, styrene butadiene, and silicone. In addition, the compliant gasket material may be chosen so that the compliant gasket system 3084 is capable of resisting corrosion from solvents ordinarily used for cleaning device surfaces.

Additionally, and like the pivotable-cover mechanism 2000, the mount connector 3078 of the embodiment depicted in FIGS. 12*a*-12*j* may be of a type having multiple spring contacts 3080. Moreover, the cover member 3040 may likewise include a compliant material, such as but not limited to a polyurethane foam, that may be shaped and sized to receive and protect the spring contacts 3080 when the cover member 3040 is in the protective position.

A System for Receiving a Device

The aforementioned pivotable-cover or clamshell mechanisms 2000, 3000 may be an embodiment of a protective mechanism 5002 that is a first element of a system for receiving a device 5000. A second element of the system for receiving a device 5000 may be a receivable device 5020 that may include a device connector 5022 and a means for being received by the protective mechanism 5002, such as the pivotable-cover or clamshell mechanisms 2000, 3000.

Figure 13A:
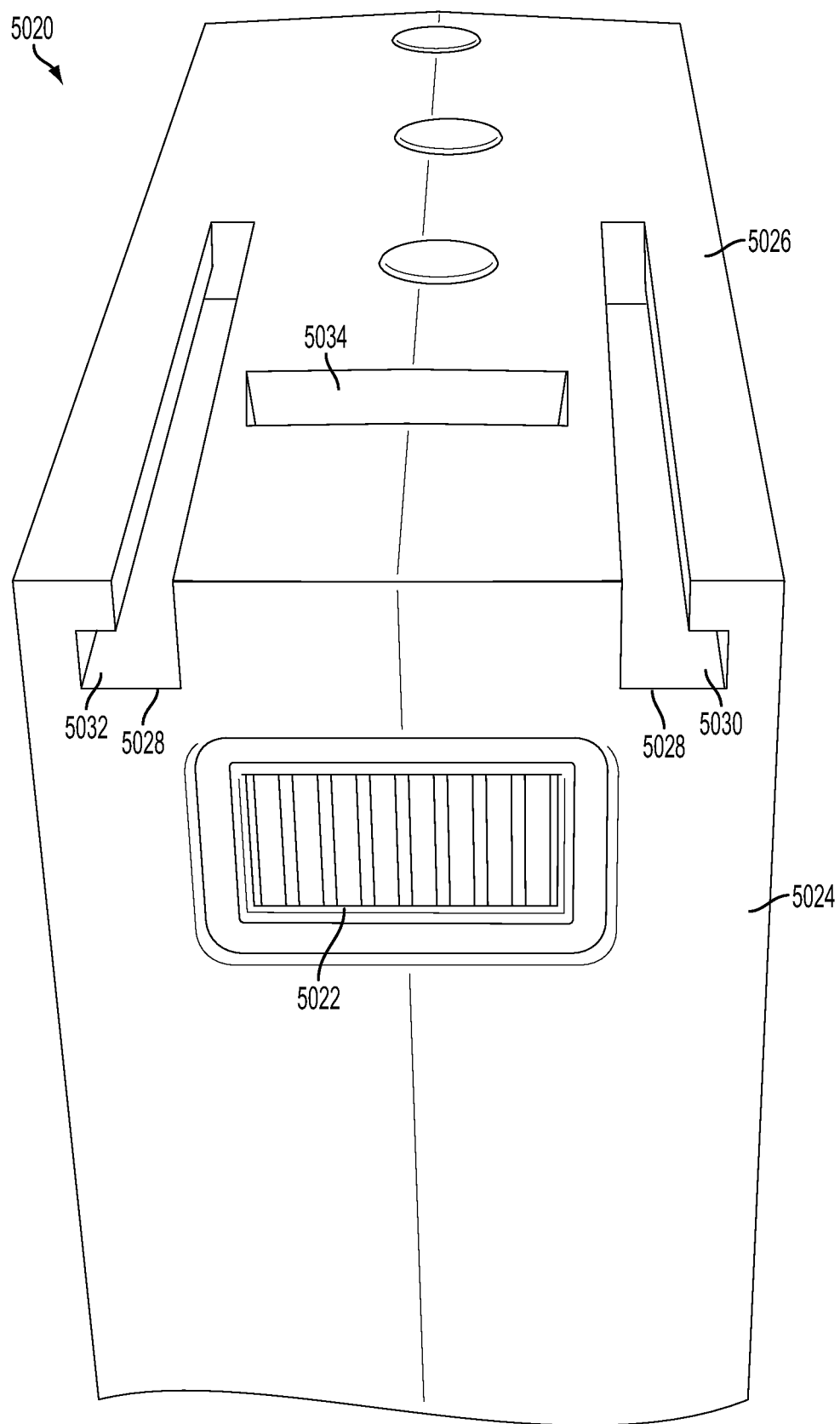
FIG. 13a depicts an embodiment of an example receivable device in accordance with an embodiment of the present disclosure.

FIG. 13*a* depicts an exemplary embodiment of a receivable device 5020, wherein the receivable device includes a device connector 5022 that is disposed on a first face 5024 of the receivable device 5020 such that the device connector 5022 is adapted to interface with a mechanism connector 5004 like the respective mount connectors 2068, 3078 of the pivotable-cover and clamshell mechanisms 2000, 3000.

Figure 13B:
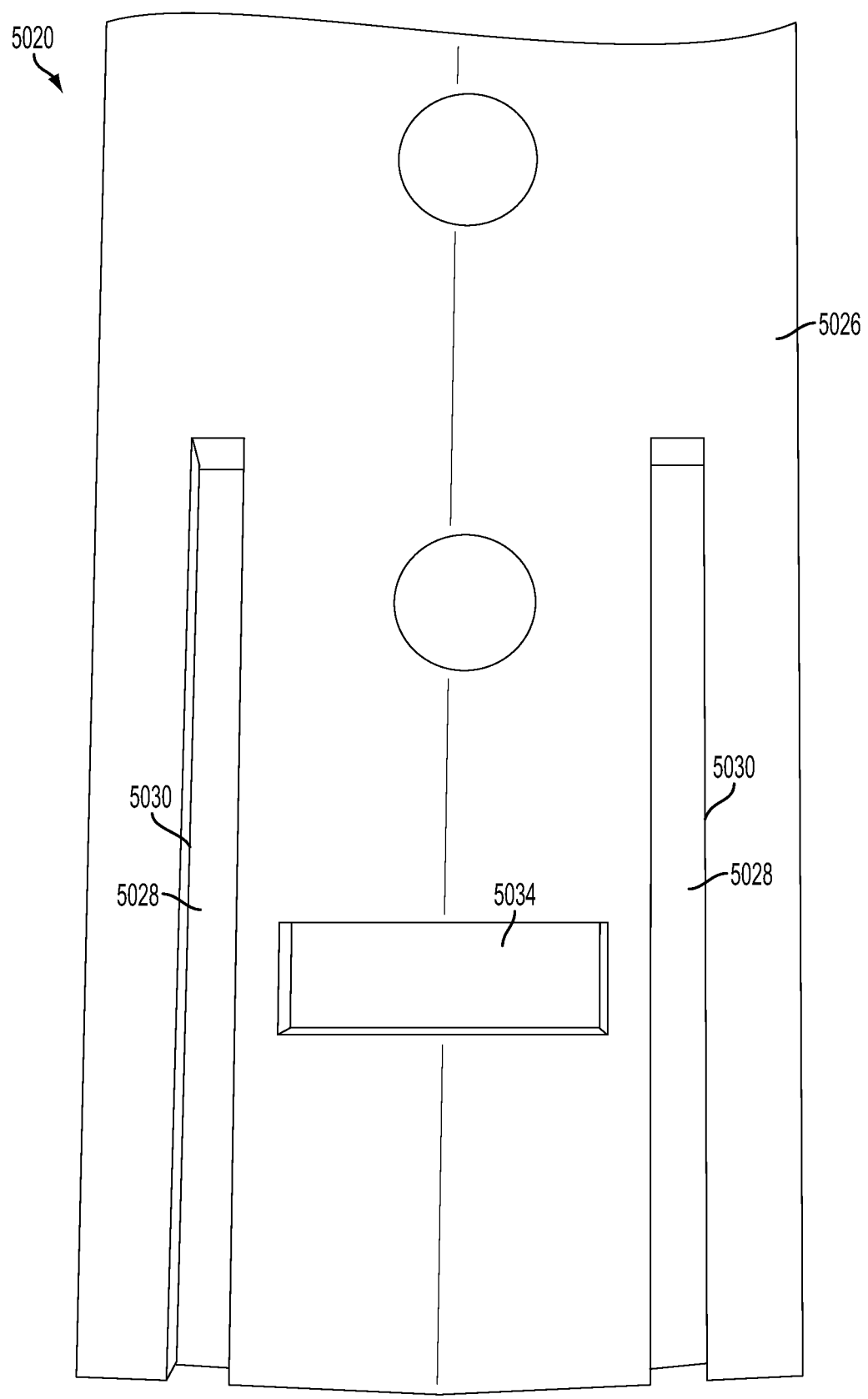
FIG. 13b depicts an example embodiment of a receivable device that includes first and second channels and a latch recess in accordance with an embodiment of the present disclosure.

To receive the receivable device 5020, the protective mechanism 5002 may include at least one rigid member 5008 disposed on a guide member 5006. The at least one rigid member 5008 may be similar to the respective first and second rail projections 2056, 3066, 2062, 3072 of the pivotable-cover and clamshell mechanisms 2000, 3000 as described herein. The receivable device 5020 may include at least one channel 5028 defined by a second face 5026 of the receivable device 5020 and each of the at least one channel 5028 may be adapted to receive a respective at least one rigid member 5008 of the protective mechanism 5002. In embodiments of the protective mechanism 5002 that include respective first and second rail projections 2056, 3066, 2062, 3072 like those of the pivotable-cover and clamshell mechanisms 2000, 3000, the at least one channel 5028 may comprise a first channel 5030 adapted to receive the respective first rail projection 2056, 3066 and a second channel 5032 adapted to receive the respective second rail projection 2062, 3072. FIGS. 13*a* and 13*b* depict an embodiment of the receivable device 5020 that includes the aforementioned first and second channels 5030, 5032 that are adapted to receive the respective first and second rail projections 2056, 3066, 2062, 3072 of the pivotable-cover and clamshell mechanisms 2000, 3000.

Figure 13C:
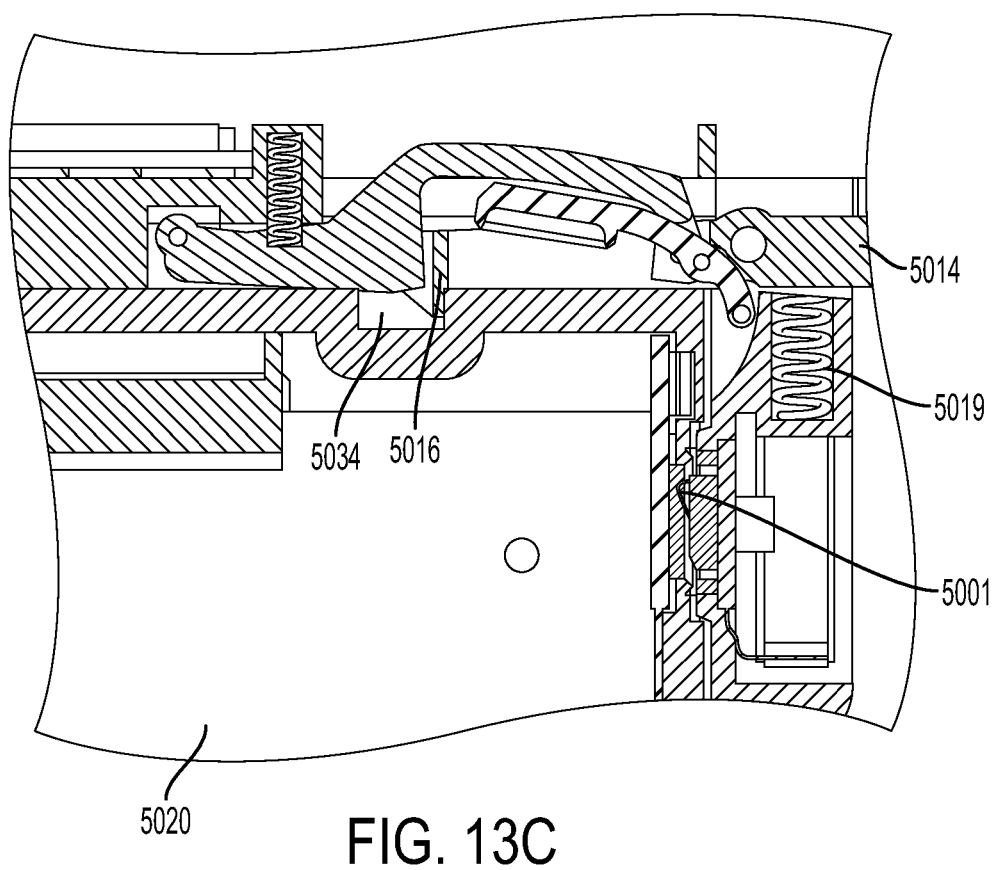
FIG. 13c depicts a cross-section view of the example pivotable cover mechanism of FIG. 11a wherein a latch member projection is in engagement with a latch recess of an example embodiment of a receivable device in accordance with an embodiment of the present disclosure.

To secure the receivable device 5020 in place after the protective mechanism 5002 receives the receivable device 5020, the protective mechanism 5002 may include a latch member 5014 having a latch member projection 5016 that engages a latch recess 5034 defined by the second face 5026 of the receivable device 5020. FIGS. 13*a* and 13*b* depict an exemplary embodiment having a latch recess 5034, and FIG. 13*c* depicts how the latch member projection 5016 may engage the latch recess 5034 to secure a received receivable device 5020. Additionally, the protective mechanism 5002 may include any of the features discussed above with respect to the pivotable-cover and clamshell mechanisms 2000, 3000; such features may include, but are not limited to, a latch member spring 2048, 3056 and latch member aperture 2044, 3052, for example.

Figure 13D:
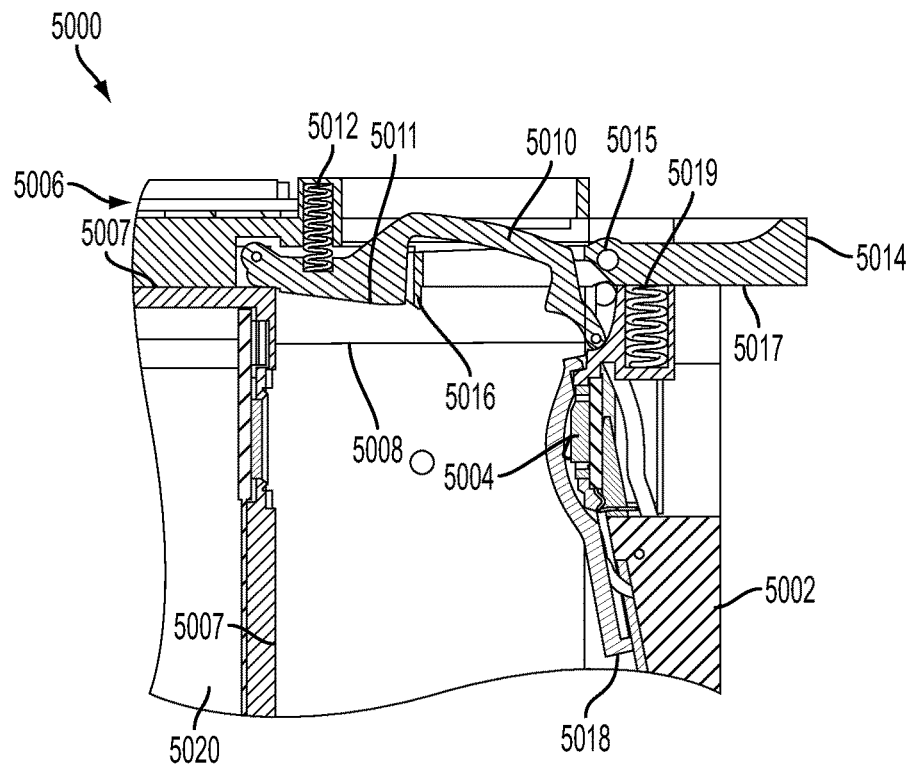
FIG. 13d-g depict a number of cross-section views of an example receivable device and the example clamshell mechanism of FIG. 12a wherein the progression of FIGS. 13d-g demonstrates how receiving a receivable device may cause a clamshell mechanism to automatically reveal a mechanism connector in accordance with an embodiment of the present disclosure.
Figure 13E:
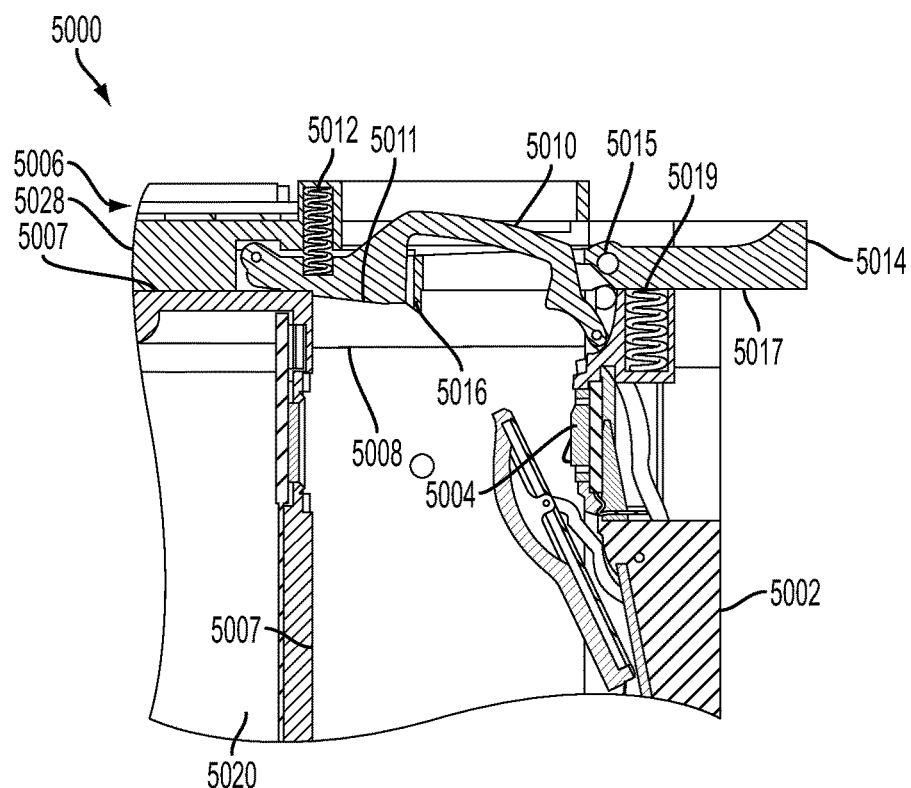
Figure 13F:
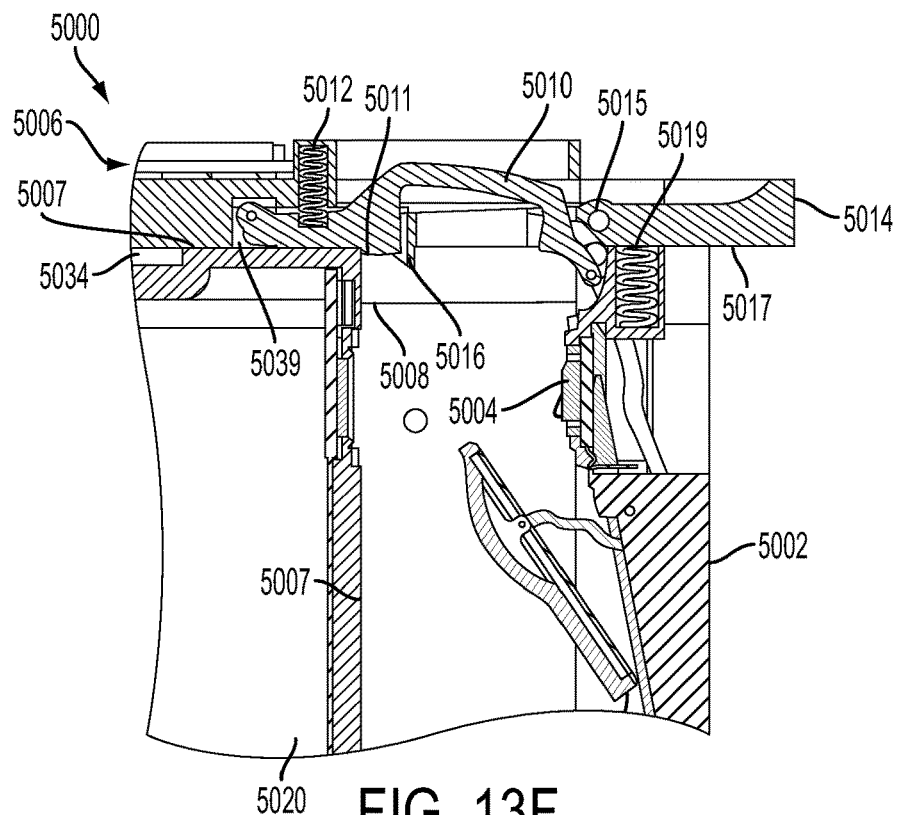

When used in combination, the receivable device 5020 may cause the protective mechanism 5002 to automatically reveal the mechanism connector 5004 as the protective mechanism 5002 receives the receivable device 5020, thereby allowing the mechanism connector 5004 and the device connector 5022 to interface with each other. For example, the progression of FIGS. 13*d*-13*g* demonstrates how receiving a receivable device 5020 may cause the clamshell mechanism 3000 to automatically reveal a mechanism connector 5004. As each of the at least one rigid member 5010 of the a respective protective mechanism slides within a corresponding at least one channel 5028 of the receivable device 5020, the receivable device 5020 engages the sloped face 5011 of the actuation member 5010 as it slides towards the backstop member face 5007 and mechanism connector 5004 (FIG. 13*d*). As the receivable device 5020 continues to slide toward the backstop member face 5007, the receivable device 5020 may begin to pivot the actuation member 5010 in a first direction from a first position to a second position (FIGS. 13*e* and 13*f*). As described above with respect to the pivotable-cover and clamshell mechanisms 2000, 3000, or other embodiment of the protective mechanism 5002, this pivotal movement of the actuation member 5010 may cause the cover member 5018 to reveal the mechanism connector 5004. The receivable device 5020 may slide toward the backstop member face 5007 until it is in a received position where it contacts the backstop member face 5007 and the device connector 5022 interfaces with the mechanism connector 5004 (FIG. 13*g*).

Figure 13G:
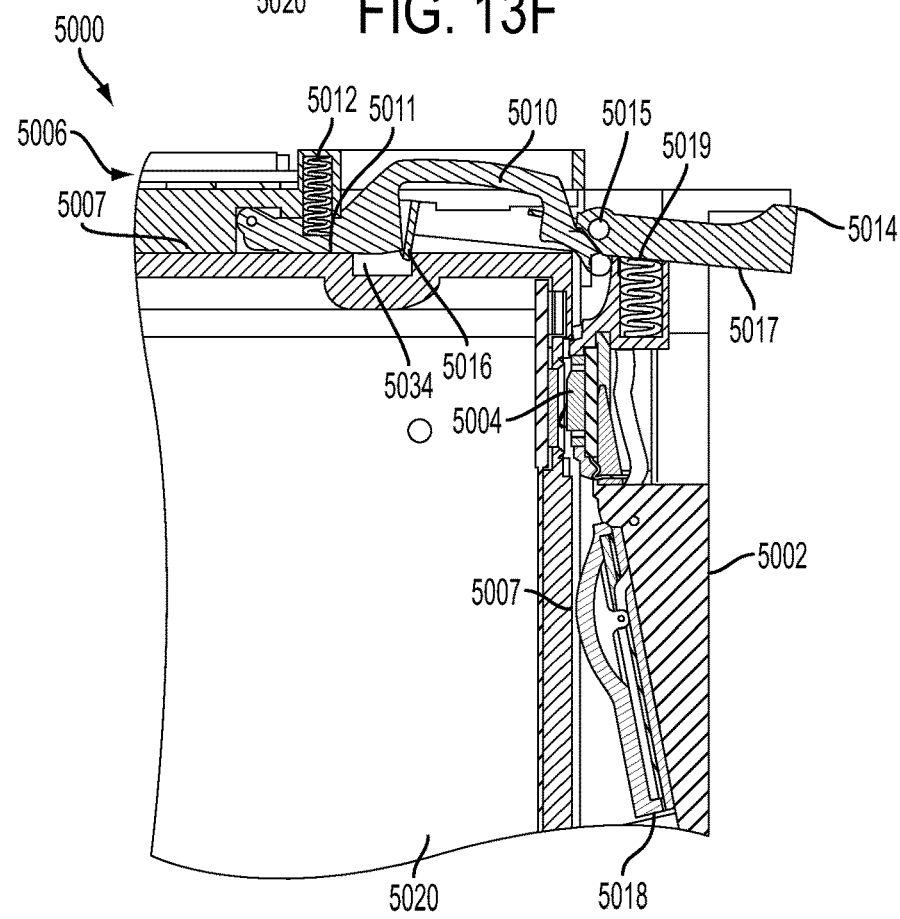

The progression from FIG. 13*g* to FIG. 13*d* depicts the reverse process wherein decoupling the receivable device 5020 from the protective mechanism 5002 may cause the actuation member 5010 to pivot from the second position to the first position under the force of an actuation spring 5012 and thereby cover the mechanism connector 5004.

As should be understood by persons having ordinary skill in the art, the at least one protective mechanism 5002 may be designed such that the cover member 5020 is capable of pivoting from the protective position to the non-protective position as the receivable device 5020 slides towards the backstop member face 5007 and the mechanism connector 5004. The pivotable-cover and clamshell mechanisms 2000, 3000 described above are but two exemplary embodiments wherein the mechanical linkages and the constituent components are shaped and sized so as to pivot or otherwise move through their respective ranges of motion while the receivable device 5020 causes the actuation member 5010 to pivot as the receivable device 5020 coupled or decouples with a protective mechanism 5002.

When the receivable device 5020 is in the received position, the latch member 5014 of the respective protective mechanism 5002 may pivot to a latched position such that the latch member projection 5016 engages the latch recess 5034 defined by a second face of the receivable device 5020. In a preferred embodiment of the system for receiving a device 5000, the latch recess 5034 may be disposed on the first face of the receivable device 5020 such that it is between the first channel 5030 and the second channel 5032. Like the sloped face 5011, the latch member projection 5016 may slope away from the plane of the guide member 5006 and towards the backstop member face 5007 such that the receivable device 5020 may cause the latch member projection 5016 and latch member 5014 to pivot out of the way as the receivable device 5020 slides towards the backstop member face 5007. As described above with respect to the pivotable-cover and clamshell mechanisms 2000, 3000 a latch spring 5019 may be used to automatically restore the latch member 5014 to the latched position when the receivable device 5020 is in the received position.

To decouple the receivable device 5020 from the protective mechanism 5002, pivoting the latch member 5014 away from the latched position may cause the latch member projection 5016 to disengage from the latch recess 5034 and allow the receivable device 5020 to slide in the opposite direction away from the backstop member face 5007 and the mechanism connector 5004. Pivoting the latch member 5014 away from the latched position may be achieved by manually pulling on a latch member release tab 5017 that is disposed on an opposite end portion of the latch member 5014 with respect to the latch member projection 5016. Where the latch member release tab 5017 is on an opposite side of the latch member pivot point 5015 with respect to the latch member projection 5016, pulling towards the mechanism connector 5004 causes the latch member projection 5016 to disengage from the latch recess 5034.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A protective mechanism comprising:
a guide member;
a connector;
an actuation member configured to have a first end portion and a second end portion, the first end portion of the actuation member pivotally coupled to the guide member;
a cover member pivotally coupled to the guide member and configured to interact with the actuation member so as to pivot to uncover the connector when the actuation member pivots in a first direction and to pivot to cover the connector when the actuation member pivots in a second direction;
first and second rail projections, the first rail projection disposed approximately parallel to and in spaced relation to the second rail projection, wherein the rail projections are disposed in spaced relation to the actuation member to guide a medical device to interact with the actuation member to pivot the cover member to uncover the connector prior to the medical device engaging with the connector; and
a first compliant gasket coupled to a backstop member, wherein the cover member includes a perimeter rib adapted to seal against the first compliant gasket when the actuation member is in a first position and the connector is covered by the cover member.

2. The protective mechanism of claim 1, wherein the backstop member is disposed on a guide member face of the guide member, the backstop member is approximately perpendicular to the guide member face.

3. The protective mechanism of claim 1, wherein the connector is disposed on the backstop member.

4. The protective mechanism of claim 3, wherein the backstop member further comprises a backstop member face, said backstop member face having a recess configured to receive at least a portion of the cover member therein.

5. The protective mechanism of claim 3, wherein the first backstop member further comprises a backstop member face, said backstop member face including an aperture configured to receive at least a portion of the cover member therethrough.

6. The protective mechanism of claim 1, wherein the cover member uncovers the connector when the actuation member pivots in the first direction to the first position and in the second direction to a second position, said first direction opposite said second direction and when in the second direction the cover member covers the connector.

7. The protective mechanism of claim 1, further comprising a second compliant gasket coupled to the backstop member.

8. The protective mechanism of claim 1, wherein an aperture is defined in the guide member, said aperture configured to receive at least a portion of the actuation member.

9. The protective mechanism of claim 1, wherein the guide member defines a recess disposed on a guide member face of the guide member, the recess of the guide member configured to receive a portion of the actuation member.

10. The protective mechanism of claim 1, further comprising a latch member configured to have a first end portion and a second end portion, the latch member pivotally coupled to the guide member at a pivot point between the first and the second end portions of the latch member.

11. The protective mechanism of claim 10, wherein an aperture is defined in the latch member between the first end portion of the latch member and the pivot point, the aperture of the latch member configured to receive a portion of the actuation member.

12. The protective mechanism of claim 10, wherein the latch member includes a latch projection disposed on the first end portion of the latch member, the latch projection configured to protrude from a guide member face of the guide member when the latch member is in a latched position.

13. The protective mechanism of claim 10, further comprising at least one arrester projection coupled to the guide member and disposed in spaced relation to the pivot point of the latch member such that the at least one arrester projection arrests movement of the latch member when the latch member pivots to a latched position.

14. The protective mechanism of claim 1, wherein the protective mechanism is configured to protect the connector when operatively gripping the medical device to engage the connector.

15. The protective mechanism of claim 1, wherein the connector is configured to interface with a monitoring client.

16. A protective mechanism comprising:
a guide member;
a connector;
an actuation member configured to have a first end portion and a second end portion, the first end portion of the actuation member pivotally coupled to the guide member;
a cover member pivotally coupled to the guide member and configured to interact with the actuation member so as to pivot to uncover the connector when the actuation member pivots in a first direction and to pivot to cover the connector when the actuation member pivots in a second direction;
a first compliant gasket coupled to a backstop member;
a second compliant gasket coupled to the backstop member; and
first and second rail projections, the first rail projection disposed approximately parallel to and in spaced relation to the second rail projection, wherein the rail projections are disposed in spaced relation to the actuation member to guide a medical device to interact with the actuation member to pivot the cover member to uncover the connector prior to the medical device engaging with the connector; and
wherein the cover member includes a perimeter rib adapted to seal against the second compliant gasket when the actuation member is in a second position and the connector is uncovered.

17. A protective mechanism comprising:
a guide member having a guide member face;
a connector;
an actuation member configured to have a first end portion and a second end portion, the first end portion of the actuation member pivotally coupled to the guide member;
a cover member pivotally coupled to the guide member and configured to interact with the actuation member so as to pivot to uncover the connector when the actuation member pivots in a first direction and to pivot to cover the connector when the actuation member pivots in a second direction;
first and second rail projections, each including a respective web portion and a respective head portion, the respective web portion configured to couple the respective head portion to the guide member face, wherein the rail projections are disposed in spaced relation to the actuation member to guide a medical device to interact with the actuation member to pivot the cover member to uncover the connector prior to the medical device engaging with the connector.

18. The protective mechanism of claim 17, further comprising a first compliant gasket coupled to a backstop member, said first compliant gasket configured to encompass the connector.

19. The protective mechanism of claim 18, wherein the cover member includes a perimeter rib adapted to seal against the first compliant gasket when the actuation member is in a first position and the connector is covered by the cover member.

20. A protective mechanism comprising:
a guide member having a guide member face;
a connector;
an actuation member configured to have a first end portion and a second end portion, the first end portion of the actuation member pivotally coupled to the guide member;
a cover member pivotally coupled to the guide member and configured to interact with the actuation member so as to pivot to uncover the connector when the actuation member pivots in a first direction and to pivot to cover the connector when the actuation member pivots in a second direction; and
first and second rail projections, the first rail projection disposed approximately parallel to and in spaced relation to the second rail projection, wherein the rail projections are disposed in spaced relation to the actuation member to guide a medical device to interact with the actuation member to pivot the cover member to uncover the connector prior to the medical device engaging with the connector, wherein:

the actuation member includes a sloped face, the sloped face defines a sloped portion of the actuation member such that a cross-sectional area of the sloped portion of the actuation member increases from the first end portion of the actuation member to a point between the first and the second end portions of the actuation member where the sloped face ends, when the actuation member is in a first position, the sloped face protrudes from a plane of the guide member face, and when the actuation member is in a second position, the sloped face lies substantially in the plane of the guide member face.

21. The protective mechanism of claim 20, further comprising at least one actuation spring, wherein:

each of the least one actuation spring has a respective first end and a respective second end, wherein:

the respective first end of the at least one actuation spring is coupled to the actuation member, the respective second end of the at least one actuation spring is coupled to the guide member, and the at least one actuation spring is configured to bias the actuation member to the first position.

22. An apparatus comprising:

a guide member having a guide member face;

a connector coupled to the apparatus;

an actuation member configured to have a first end portion and a second end portion, the first end portion of the actuation member pivotally coupled to the guide member;

a protective member configured to have a first end portion and a second end portion, the first end portion of the protective member pivotally coupled to the guide member, the second end portion of the protective member including a cover portion configured to cover the connector, the protective member adapted to engage with the actuation member and first and second rail projections, the first rail projection disposed approximately parallel to and in spaced relation to the second rail projection, wherein the rail projections are disposed in spaced relation to the actuation member to guide a medical device to interact with the actuation member to pivot the protective member to uncover the connector prior to the medical device engaging with the connector, wherein:

the cover portion includes a perimeter rib adapted to seal against a compliant gasket when the actuation member is in a protective position and the connector is covered by the cover portion, pivotal movement of the actuation member in a first direction from a first position to a second position causes the protective member to pivot from the protective position to a non-protective position, thereby uncovering the connector, and pivotal movement of the actuation member in a second, opposite direction from the second position to the first position causes the protective member to pivot from the non-protective position to the protective position, to thereby cover the connector.

23. The apparatus of claim 22, wherein the apparatus is configured to protect the connector when operatively gripping the medical device to engage the connector.

24. The apparatus of claim 22, wherein the connector is configured to interface with a monitoring client.

25. A protective mechanism comprising:

a guide member;

a connector;

an actuation member configured to have a first end portion and a second end portion, the first end portion of the actuation member pivotally coupled to the guide member;

a cover member pivotally coupled to the guide member and configured to interact with the actuation member so as to pivot to uncover the connector when the actuation member pivots in a first direction and to pivot to cover the connector when the actuation member pivots in a second direction;

a latch member configured to have a first end portion and a second end portion, the latch member pivotally coupled to the guide member at a pivot point between the first and the second end portions of the latch member; and first and second rail projections, the first rail projection disposed approximately parallel to and in spaced relation to the second rail projection, wherein the rail projections are disposed in spaced relation to the actuation member to guide a medical device to interact with the actuation member to pivot the cover member to uncover the connector prior to the medical device engaging with the connector; and at least one latch spring, wherein:

each of the at least one latch spring has a respective first end and a respective second end, the respective first end of the at least one latch spring is coupled to the guide member, the respective second end of the at least one latch spring is coupled to the latch member at a respective point between the pivot point and the second end portion of the latch member, and the at least one latch spring is configured to bias the latch member to a latched position.

* * * * *